US009586899B2

(12) United States Patent
Plouvier et al.

(10) Patent No.: US 9,586,899 B2
(45) Date of Patent: Mar. 7, 2017

(54) SYNTHETIC PROCESS FOR AMINOCYCLOHEXYL ETHER COMPOUNDS

(71) Applicant: Cardiome Pharma Corp., Vancouver (CA)

(72) Inventors: Bertrand M. C. Plouvier, Vancouver (CA); Doug Ta Hung Chou, Vancouver (CA); Grace Jung, New Westminster (CA); Lewis Siu Leung Choi, Burnaby (CA); Tao Sheng, Westwood, MA (US); Anthony G. M. Barrett, London (GB); Marco S. Passafaro, Thayngen (CH); Martin Kurz, Schaffhausen (CH); Daniel Moeckli, Schlatt (CH); Pirmin Ulmann, Dachsen (CH); Alfred Hedinger, Thayngen (CA)

(73) Assignee: Cardiome Pharma Corp., Vancouver, BC (CA)

( * ) Notice: Subject to any disclaimer, the term of this patent is extended or adjusted under 35 U.S.C. 154(b) by 23 days.

(21) Appl. No.: 14/818,166

(22) Filed: Aug. 4, 2015

(65) Prior Publication Data
US 2015/0336887 A1    Nov. 26, 2015

Related U.S. Application Data

(62) Division of application No. 13/612,559, filed on Sep. 12, 2012, now Pat. No. 9,115,081, which is a division of application No. 11/719,737, filed as application No. PCT/US2005/042262 on Nov. 18, 2005, now Pat. No. 8,692,002.

(60) Provisional application No. 60/629,526, filed on Nov. 18, 2004, provisional application No. 60/705,716, filed on Aug. 3, 2005.

(51) Int. Cl.
| C07D 207/12 | (2006.01) |
| C07D 207/273 | (2006.01) |
| C07C 213/02 | (2006.01) |
| C07C 231/12 | (2006.01) |
| C07C 269/06 | (2006.01) |

(52) U.S. Cl.
CPC ....... *C07D 207/12* (2013.01); *C07D 207/273* (2013.01); *C07C 213/02* (2013.01); *C07C 231/12* (2013.01); *C07C 269/06* (2013.01); *C07C 2101/14* (2013.01)

(58) Field of Classification Search
CPC .................................................. C07D 207/12
See application file for complete search history.

(56) References Cited

U.S. PATENT DOCUMENTS

| 4,282,388 A | 8/1981 | Draber et al. |
| 4,684,728 A | 8/1987 | Möhring et al. |
| 5,032,687 A | 7/1991 | Diehl et al. |
| 5,215,919 A | 6/1993 | Miya et al. |
| 5,728,873 A | 3/1998 | Kleemiss et al. |
| 5,846,514 A | 12/1998 | Foster et al. |
| 6,503,921 B2 | 1/2003 | Naicker et al. |
| 6,613,739 B1 | 9/2003 | Naicker et al. |
| 6,617,475 B2 | 9/2003 | Studer et al. |
| 6,939,878 B2 | 9/2005 | Naicker et al. |
| 7,053,087 B1 | 5/2006 | Beatch et al. |
| 7,056,942 B2 | 6/2006 | Hildesheim et al. |
| 7,057,053 B2 | 6/2006 | Beatch et al. |
| 7,101,877 B2 | 9/2006 | Bain et al. |
| 7,259,184 B2 | 8/2007 | Beatch et al. |
| 7,345,087 B2 | 3/2008 | Beatch et al. |
| 7,524,879 B2 | 4/2009 | Beatch et al. |
| 7,534,790 B2 | 5/2009 | Bain et al. |
| 7,705,036 B2 | 4/2010 | Chou et al. |
| 7,754,897 B2 | 7/2010 | Jung et al. |
| 7,786,119 B2 | 8/2010 | Cheu et al. |
| 7,875,611 B2 | 1/2011 | Bain et al. |
| 7,977,373 B2 | 7/2011 | Choi et al. |
| 8,008,342 B2 | 8/2011 | Beatch et al. |
| 8,022,098 B2 | 9/2011 | Chou et al. |
| 8,058,304 B2 | 11/2011 | Choi et al. |
| 8,618,311 B2 | 12/2013 | Jung et al. |
| 8,692,002 B2 | 4/2014 | Plouvier et al. |
| 9,006,460 B2* | 4/2015 | Limanto ............ C07D 207/12 548/556 |
| 2003/0073617 A1 | 4/2003 | Li et al. |
| 2003/0130170 A1 | 7/2003 | Li et al. |
| 2003/0186400 A1 | 10/2003 | Asako et al. |
| 2004/0049049 A1 | 3/2004 | Jurayj et al. |

(Continued)

FOREIGN PATENT DOCUMENTS

| CA | 710830 A | 6/1965 |
| DE | 27 53 556 A1 | 6/1979 |

(Continued)

OTHER PUBLICATIONS

Adam et al., "Spectral and Chemical Properties of Dimethyldioxirane as Determined by Experiment and ab Initio Calculations," *J. Org. Chem.* 52(13): 2800-2803, 1987.

Alimardanov et al., "Use of DOE for Rapid Development of a Red-Al Reduction Process for the Synthesis of 3,4-Isopropylidenedioxypyrrolidine Hydrotosylate," *Organic Process Research & Development* 8(6): 834-837, 2004.

Anderson et al., "Sulfonation with Inversion by Mitsunobu Reaction: An Improvement on the Original Conditions," *J. Org. Chem.* 61(22): 7955-7958, 1996.

Anderson et al., "The preparation of β-substituted amines from mixtures of epoxide opening products via a common aziridinium ion intermediate," *Tetrahedron*: Asymmetry 10: 2655-2663,1999.

(Continued)

*Primary Examiner* — Matthew Coughlin
(74) *Attorney, Agent, or Firm* — Seed IP Law Group LLP

(57) ABSTRACT

Methods for the preparation of stereoisomerically substantially aminocyclohexyl ether compounds such as trans-(1R, 2R)-aminocyclohexyl ether compounds and/or trans-(1S, 2S)-aminocyclohexyl ether compounds as well as various intermediates and substrates are disclosed.

24 Claims, 47 Drawing Sheets

(56) References Cited

U.S. PATENT DOCUMENTS

| | | |
|---|---|---|
| 2004/0082043 A1 | 4/2004 | Yadav et al. |
| 2006/0094880 A9 | 5/2006 | Barrett et al. |
| 2007/0190156 A1 | 8/2007 | Beatch et al. |
| 2009/0069404 A1 | 3/2009 | Czarnik |
| 2010/0152464 A1 | 6/2010 | Plouvier et al. |
| 2010/0273724 A1 | 10/2010 | Cheu et al. |
| 2011/0207730 A1 | 8/2011 | Bain et al. |
| 2012/0271057 A9 | 10/2012 | Jung et al. |

FOREIGN PATENT DOCUMENTS

| | | |
|---|---|---|
| EP | 0 014 263 B1 | 8/1980 |
| EP | 0 317 780 B1 | 5/1989 |
| ES | 475575 A1 | 2/1979 |
| WO | WO 96/23894 A1 | 8/1996 |
| WO | WO 97/33552 A1 | 9/1997 |
| WO | WO 99/50225 A1 | 10/1999 |
| WO | WO 00/23023 A1 | 4/2000 |
| WO | WO 01/96335 A1 | 12/2001 |
| WO | WO 03/105756 A2 | 12/2003 |
| WO | WO 2004/014973 A2 | 2/2004 |
| WO | WO 2004/098525 A2 | 11/2004 |
| WO | WO 2004/099137 A1 | 11/2004 |
| WO | WO 2004098525 A2 * | 11/2004 ............ A61K 31/40 |
| WO | WO 2005/016242 A2 | 2/2005 |
| WO | WO 2005/094897 A2 | 10/2005 |
| WO | WO 2005/097087 A2 | 10/2005 |
| WO | WO 2005/113011 A2 | 12/2005 |
| WO | WO 2006/088525 A1 | 8/2006 |
| WO | WO 2006/138673 A2 | 12/2006 |

OTHER PUBLICATIONS

Asunskis and Shechter, "Reactions of Conjugated Nitro Olefins with Phosphoranes and with Dimethylsulfoxonium Methylide to Give Ylides and Nitrocyclopropanes, Respectively," *J. Org. Chem.* 33(3): 1164-1168, 1968.

Augy-Dorey et al., "Synthesis of Carbocyclic Analogues of Lipid X," *Tetrahedron* 49(36): 7997-8006, 1993.

Bodenan et al., "Acid-Catalyzed Ring Opening of 2-Substituted Aziridines with Alcohols," *Synthesis*: 288-292, Mar. 1992.

Bogatskii et al., "Effect of Polymethylene- and Polyhydroxyethylene-bis-(2-Amino-1,3-Diazepinium) Iodides on Cell and Model Membranes," *Byulleten' Éksperimental'noi Biologii i Meditsiny* 94(8): 52-54, Aug. 1982 [English translation included from the Department of Chemistry of Macrocyclic Complexones, Physicochemical Institute, Academy of Sciences of the Ukrainian SSR, Odessa, pp. 1071-1074.]

Brown and Krishnamurthy, "Forty Years of Hydride Reductions," *Tetrahedron* 35(64): 567-607, 1979.

Brown et al., "The Direct and Enantioselective Organocatalytic α-Oxidation of Aldehydes," *J. Am. Chem. Soc.* 125(36): 10808-10809, 2003.

Bryce and Gardiner, "Stereospecific Synthesis of the Cyclopenta[e]phenanthridine Ring System: Tetracyclic and Pentacyclic Analogues of *Cephalotaxus* Alkaloids," *Tetradedron* 44(2): 599-612, 1988.

Carter et al., "Towards phase-transfer catalysts with a chiral anion: inducing asymmetry in the reactions of cations," *Tetrahedron: Asymmetry* 14: 1995-2004, 2003.

Cassidei et al., "Oxygen-17 and Carbon-13 Identification of the Dimethyldioxirane Intermediate Arising in the Reaction of Potassium Caroate with Acetone," *J. Org. Chem.* 52(4): 699-700, 1987.

Chelucci et al., "Synthesis of 1-Substituted 2-[(2S)-2-Pyrrolidinyl]pyridine from L-Proline," *Synthesis*: 1121-1122, Dec. 1990.

Chiu et al., "Molecular dynamics computations and solid state nuclear magnetic resonance of the gramicidin cation channel," *Biophys. J.* 60: 974-978, Oct. 1991.

Christoffers et al., "Synthesis, resolution, and absolute configuration of trans-1-amino-2-dimethylaminocyclohexane," *Tetrahedron* 57: 1765-1769, 2001.

Curci et al., "Selective Oxidation of O-Isopropylidene Derivatives of Diols to 2-Hydroxy Ketones Employing Dioxiranes," *Tetrahedron Letters* 37(1): 115-118, 1996.

Curtis and Walker, "Quantification of arrhythmias using scoring systems: an examination of seven scores in an in vivo model of regional myocardial ischaemia," *Cardiovascular Research* 22: 656-665, 1988.

D'Accolti et al., "Selective Oxidation of Optically Active sec,sec-1,2-Diols by Dioxiranes. A Practical Method for the Synthesis of Homochiral α-Hydroxy Ketones in High Optical Purity," *J. Org. Chem.* 58(14): 3600-3601, 1993.

Daverio and Zanda, "Enantioselective reductions by chirally modified alumino- and borohydrides," *Tetradron: Asymmetry* 12: 2225-2259, 2001.

Engman and Cava, "BIS(p-Methoxyphenyl)telluroxide, a Novel Organotellurium Aldol Catalyst," *Tetrahedron Letters* 22(52): 5251-5252, 1981.

Fráter et al., "Regioselective Synthesis of (±)-Gabaculine Hydrochloride," *Tetrahedron Letters* 25(3): 281-284, 1984.

Godchot and Mousseron, "Sur le dédoublement du 2-aminocyclohexanol en ses antipodes optiques," *Bull. Soc. Chim. Fr.* 51: 1277-1282, 1932.

Gonzaléz-Sabín et al., "Chemoenzymatic preparation of optically active β-amino-cyclohexanols and their application in the enantioselective addition of diethylzinc to benzaldehyde," *Tetrahedron: Asymmetry* 15: 1335-1341, 2004.

Greenwald, "PEG drugs: an overview," *Journal of Controlled Release* 74: 159-171, 2001.

Hamon and Tuck, "Asymmetric Synthesis of (S)-1-Methyl-2-cylohexen-l-ol, a Constituent of the Aggregation Pheromone of *Dendroctonus pseudotsugae*," *Tetrahedron* 56: 4829-4835, 2000.

Hayashi et al., "Asymmetric Ring Opening Reactions of Symmetrical N-Acylaziridines with Thiols Catalyzed by Chiral Dialkyl Tartrate—Diethylzinc Complexes," *Tetrahedron* 52(23): 7817-7832, 1996.

Henrot et al., "Aminoacids as Chiral Synthons: Preparation of Enantiomerically Pure (R) and (S) Malic Acids and Its Application to the Synthesis of 3-Hydroxy 4-Butanolide," *Synthetic Communications* 16(2): 183-190, 1986.

Higuchi and Shiobara, "Quantitative Determination of Nifedipine in Human Plasma by Selected Ion Monitoring," *Biomedical Mass Spectrometry* 5(3): 220-223, 1978.

Howard and Walker, "Electrical Stimulation Studies with Quinacainol, a Putative 1C Agent, in the Anaesthetised Rat," *Proc. West. Pharmacol. Soc.* 33: 123-127, 1990.

Iida et al., "Synthesis of $^{13}$C-Labelled Compounds having a Urea Unit, and Observation of $^{13}$C-Isotope Effect in Their Infrared Spectra," *J. Labelled Cpd. Radiopharm.* XXXIX(1): 69-77, 1997.

Jacobsen, "Asymmetric Catalysis of Epoxide Ring-Opening Reactions," *Acc. Chem. Res.* 33(6): 421-431, 2000.

Johansen et al., "Synthesis of carbon-14 and stable isotope labelled NN414: a potent potassium channel opener," *J. Labelled Cpd. Radiopharm.* 47: 127-138, 2004.

Joshi et al., "Enantioselective Ring Cleavage of meso-Epoxides with B-Halodiisopinocampheylboranes," *J. Am. Chem. Soc.* 110: 6246-6248, 1988.

Kahl et al., "Radioimmunoassay for the Calcium Release Channel Agonist Ryanodine," *Analytical Biochemistry* 218: 55-62, 1994.

Kepler et al., "Synthesis of 5,5-Diphenylhydantoin-2,4,5-$^{13}$C$_3$," *Journal of Labelled Compounds* 10(4): 683-687, Oct.-Dec. 1974.

Kinugasa et al., "Desymmetrization of meso-1,2-Diols via Chiral Lewis Acid-Mediated Ring-Cleavage of 1,3-Dioxolane Derivatives," *J. Am. Chem. Soc.* 119(38): 9067-9068, 1997.

Kodukulla et al., "Synthesis, Chemical Transformation and Antimicrobial Activity of a Novel Class of Nitroolefins: 1,3-Diaryl-2-nitroprop-1-enes," *Synthetic Communications* 24(6): 819-832, 1994.

Kubo et al., "A Facile Synthesis of 1,2,3,4-Tetrahydroisoquinolines Through Cyclization of O-N-Acetals," *Synthesis*: 824-827, Sep. 1987.

(56) References Cited

OTHER PUBLICATIONS

Liu and Yao, "One-pot synthesis of trans-β-alkylstyrenes," *Tetrahedron Letters* 42: 6147-6150, 2001.
Luurtsema et al., "Synthesis and PET-Studies of (R)- and (S)-[$^{11}$C]Verapamil for Measuring PGP Function in MDR1A(+/+)/B(+/+) and MDR1A(−/−)/B(−/−) Mice," *J. Labelled Cpd. Radiopharm.* 44(Suppl. I): S313-S315, 2001.
Maestro et al., "Enzymatic resolution of (±)-trans-2-aminocyclohexanol and (±)-trans-2-aminocyclopentanol," *Tetrahedron: Asymmetry* 8(18): 3153-3159, 1997.
Martichonok and Whitesides, "Stereoselective α-Sialylation with Sialyl Xanthate and Phenylsulfenyl Triflate as a Promotor," *J. Org. Chem.* 61(5): 1702-1706, 1996.
Martinelli et al., "Selective monosulfonylation of internal 1,2-diols catalyzed by di-*n*-butyltin oxide," *Tetrahedron Letters* 41: 3773-3776, 2000.
Martínez et al., "Highly Enantioselective Ring Opening of Epoxides Catalyzed by (salen)Cr(III) Complexes," *J. Am. Chem. Soc.* 117(21): 5897-5898, 1995.
Matsumoto et al., "Diastereoselective Synthesis of a Key Intermediate for the Preparation of Tricyclic β-Lactam Antibiotics," *Tetrahedron Letters* 40: 5043-5046, 1999.
Matsunaga et al., "Catalytic Enantioselective *meso*-Epoxide Ring Opening Reaction with Phenolic Oxygen Nucleophile Promoted by Gallium Heterobimetallic Multifunctional Complexes," *J. Am. Chem. Soc.* 122(10): 2252-2260, 2000.
McCleland et al., "Mechanistic Studies of the Zirconium—Triisopropanolamine-Catalyzed Enantioselective Addition of Azide to Cyclohexene Oxide," *J. Org. Chem.* 63(19): 6656-6666, 1998.
McGraw-Hill, Notes for Chapter 15: Alcohols, Biols and Thiols, obtained from the WayBackMachine with an archive date of Oct. 30, 2002, 4 pages.
Mello et al., "Enzymic Regioselectivity in the Hydroxylation of Cholesterol Catalyzed by a Membrane-Spanning Metalloporphyrin," *J. Org. Chem.* 53(16): 3891-3893, 1988.
Mello et al., "Oxidations by Methyl(trifluoromethyl)dioxirane. 2. Oxyfunctionalization of Saturated Hydrocarbons," *J. Am. Chem. Soc.* 111(17): 6749-6757, 1989.
Momiyama and Yamamoto, "Catalytic Enantioselective Synthesis of α-Aminooxy and α-Hydroxy Ketone Using Nitrosobenzene," *J. Am. Chem. Soc.* 125(20): 6038-6039, 2003.
Mottet et al., "A Simple and Efficient Preparation of Propargylic β-Keto Esters through Transesterification," *J. Org. Chem.* 64(4): 1380-1382, 1999.
Moustafa et al., "Comparative Study on the para-Metabolic Oxidation of Phenytoin and Decadeuteriophenytoin," *Arzneim.-Forsch/Drug Res.* 40(II, 10): 1076-1078, 1990.
Mowry and Butler, "Fumaronitrile," *Organic Syntheses, Coll.* 4: 486, 1963, 3 pages.
Murray and Jeyaraman, "Dioxiranes: Synthesis and Reactions of Methyldioxiranes," *J. Org. Chem.* 50(16) 2847-2853, 1985.
Nachtsheim and Frahm, "Die asymmetrische Synthese von cis-1R,2R- und cis-1S,2S-2-Arylcyclohexanaminen," *Arch. Pharm. (Weinheim)* 322(4): 187-197, Apr. 1989.
Nagai, "Optical Rotatory Dispersion of Nitrobenzene Derivatives. VII. Application of Modified Curtius Rearrangement for Determining the Free Carboxylic Position in Some Partial Esters of 3-Nitrophthalic and 4-Nitrohemimellitic Acid," *Chem. Pharm. Bull.* 23(8): 1841-1844, 1975.
Nagel and Nedden, "Preparative and Structural Chemistry of Chiral 3-(Diphenylphosphanyl)-pyrrolidines and Their Palladium(II) Complexes," *Chem. Ber./Recueil* 130: 385-397, 1997.
Nakamura et al., "Recent developments in asymmetric reduction of ketones with biocatalysts," *Tetrahedron: Asymmetry* 14(60): 2659-2681, 2003.
Nakamura et al., "Chemistry and biology of khafrefungin. Large-scale synthesis, design, and structure-activity relationship of khafrefungin, an antifungal agent," *Org. Biomol. Chem.* 1: 3362-3376, 2003.
Nakane et al., "7-Oxabicyclo[2.2.1]heptyl Carboxylic Acids as Thromboxane A$_2$ Antagonists: Aza ω-Chain Analogues," *J. Med. Chem.* 33(9) 2465-2476, 1990.
Naylor et al., "4-[(Alkylylamino)methyl]furo[3,2-*c*]pyridines: A New Series of Selective κ-Receptor Agonists," *Journal of Medicinal Chemistry* 37(14): 2138-2144, 1994.
Ohkuma et al., "Stereoselective Hydogenation of Simple Ketones Catalyzed by Ruthenium(II) Complexes," *Journal of Organic Chemistry* 61(15): 4872-4873, 1996.
Ohtaka and Kajiwara, "Synthesis of [$^{13}$C$_2$]nifedipine," *J. Labelled Cpd. Radiopharm.* 46: 1177-1179, 2003.
Pallavicini et al., "Resolution of 5-hydroxymethyl-2-oxazolidinone by preferential crystallization and investigations on the nature of the racemates of some 2-oxazolidinone derivatives," *Tetrahedron: Asymmetry* 15: 1659-1665, 2004.
Paquette et al., "Systematic Analysis of the Intramolecular Competition Associated with the Ring Closing Metathesis of Ene-Diene Systems of Differing Chain Length with a Pair of Ruthenium Catalysts," *Helvetica Chimica Acta* 85: 3033-3051, 2002.
Pasumansky and Singaram, "Recent Advances in the Chemistry of Lithium Aminoborohydrides," *AldrichimicaActa* 38(2): 61-65, 2005.
Paterson et al., "Total Synthesis of the Microtubule-Stabilizing Agent (—)-Laulimalide," *Organic Letters* 3(20): 3149-3152, 2001.
Raiford and Fox, "Condensation of Vanillin Substitution Products with Nitromethane," *J. Org. Chem.* 9: 170-174, 1944.
Rampe et al., "Deuterated analogs of verapamil and nifedipine. Synthesis and biological activity," *Eur. J. Med. Chem.* 28: 259-263, 1993.
Rao et al., "Cycloaddition of citral dienamines to β-nitrostyrenes: A stereochemical consideration," *Indian Journal of Chemistry* 29B: 207-214, Mar. 1990.
Schaus et al., "Practical Synthesis of Enantiopure Cyclic 1,2-Amino Alcohols via Catalytic Asymmetric Ring Opening of Meso Epoxides," *J. Org. Chem.* 62(12): 4197-4199, 1997.
Schlichter and Frahm, "Asymmetric Reductive Amination of Cycloalkanones, XIII: Enantioselective Amidoamination: A New Regiospecific Strategy for the Synthesis of Chiral Cyclohexane-1,2-diamino-Derivatives," *Arch. Pharm. (Weinheim)* 326: 429-436, 1993.
Srebnik et al., "Chiral Synthesis via Organoboranes 23. Enantioselective Ring Opening of *meso*-Epoxides with B-Halodiisopinocampheylboranes. The First General Synthesis of Optically Active 1,2-Halohydrins," *Israel Journal of Chemistry* 29: 229-237, 1989.
Tasker et al., "Potent and Selective Non-Benzodioxole-Containing Endothelin-A Receptor Antagonists," *J. Med. Chem* 40(3): 322-330, 1997.
Toshima and Tatsuta, "Recent Progress in O-Glycosylation Methods and Its Application to Natural Products Synthesis," *Chem. Rev.* 93(4): 1503-1531, 1993.
Tsuda et al., "A stereocontrolled construction of 2-azido-2-deoxy-1,2-trans-β-glycosidic linkages utilizing 2-azido-2-deoxyglycopyranosyl diphenyl phosphates," *Tetrahedron Letters* 44: 6453-6457, 2003.
Tuck et al., "A Simple Procedure for the Deuteriation of Phenols," *J. Labelled Cpd. Radiopharm.* 43: 817-823, 2000.
Urban et al., "Process Research and Large-Scale Synthesis of a Novel 5,6-Dihydro-(9H)-pyrazolo[3,4-c]-1,2,4-triazolo[4,3-*a*]pyridine PDE-IV Inhibitor," *Organic Process Research & Development* 5(6): 575-580, 2001.
Ursini et al., "Enzymatic Method of Preparation of Optically Active trans-2-Amino Cyclohexanol Derivatives," *Synthetic Communications* 29(8): 1369-1377, 1999.
Varma et al., "Microwave-Assisted Henry Reaction: Solventless Synthesis of Conjugated Nitroalkenes," *Tetrahedron Letters* 38(29): 5131-5134, 1997.
Ward, "Chiral Separations," *Anal. Chem.* 74(12): 2863-2872, Jun. 15, 2002.
Wimalasena and May, "Mechanistic Studies on Dopamine β-Monooxygenase Catalysis: N-Dealkylation and Mechanism-

(56) References Cited

OTHER PUBLICATIONS

Based Inhibition by Benzylic-Nitrogen-Containing Compounds. Evidence for a Single-Electron-Transfer Mechanism," *J. Am. Chem. Soc. 109*(13): 4036-4046, 1987.
Yadav et al., "Efficient Enantioselective Reduction of Ketones with *Daucus carota* Root," *J. Org. Chem. 67*(11): 3900-3903, 2002.

\* cited by examiner

SYNTHETIC PROCESS FOR AMINOCYCLOHEXYL ETHER COMPOUNDS

CROSS REFERENCE TO RELATED APPLICATIONS

This application is a divisional application of U.S. patent application Ser. No. 13/612,559, filed Sep. 12, 2012 (now pending); which is a divisional application of U.S. patent application Ser. No. 11/719,737, filed Mar. 1, 2010 (now U.S. Pat. No. 8,692,002); which is a national stage application, filed under 35 U.S.C. §371, of International Application No. PCT/US2005/042262, accorded an international filing date of Nov. 18, 2005; which claims the benefit under 35 U.S.C. §119(e) of U.S. Provisional Patent Application No. 60/629,526, filed Nov. 18, 2004, and U.S. Provisional Patent Application No. 60/705,716, filed Aug. 3, 2005; all of which applications are incorporated herein by reference in their entireties.

FIELD OF INVENTION

The present invention is generally directed toward a method for the preparation of stereoisomerically substantially aminocyclohexyl ether compounds such as trans-(1R,2R)-aminocyclohexyl ether compounds and/or trans-(1S,2S)-aminocyclohexyl ether compounds as well as various intermediates and substrates involved. The present invention is also generally directed toward a method for the preparation of stereoisomerically substantially pure cis-aminocyclohexyl ether compounds such as cis-(1R,2S)-aminocyclohexyl ether compounds and/or cis-(1S,2R)-aminocyclohexyl ether compounds as well as various intermediates and substrates involved. The compounds prepared by methods of the present invention are useful for treating medical conditions or disorders, including for example, cardiac arrhythmia, such as atrial arrhythmia and ventricular arrhythmia.

BACKGROUND OF THE INVENTION

Arrhythmia is a variation from the normal rhythm of the heart beat and generally represents the end product of abnormal ion-channel structure, number or function. Both atrial arrhythmias and ventricular arrhythmias are known. The major cause of fatalities due to cardiac arrhythmias is the subtype of ventricular arrhythmias known as ventricular fibrillation (VF). Conservative estimates indicate that, in the U.S. alone, each year over one million Americans will have a new or recurrent coronary attack (defined as myocardial infarction or fatal coronary heart disease). About 650,000 of these will be first heart attacks and 450,000 will be recurrent attacks. About one-third of the people experiencing these attacks will die of them. At least 250,000 people a year die of coronary heart disease within 1 hour of the onset of symptoms and before they reach a hospital. These are sudden deaths caused by cardiac arrest, usually resulting from ventricular fibrillation.

Atrial fibrillation (AF) is the most common arrhythmia seen in clinical practice and is a cause of morbidity in many individuals (Pritchett E. L., N. Engl. J. Med. 327(14):1031 Oct. 1, 1992, discussion 1031-2; Kannel and Wolf, Am. Heart J. 123(1):264-7 Jan. 1992). Its prevalence is likely to increase as the population ages and it is estimated that 3-5% of patients over the age of 60 years have AF (Kannel W. B., Abbot R. D., Savage D. D., McNamara P. M., N. Engl. J. Med. 306(17):1018-22, 1982; Wolf P. A., Abbot R. D., Kannel W. B. Stroke. 22(8):983-8, 1991). While AF is rarely fatal, it can impair cardiac function and is a major cause of stroke (Hinton R. C., Kistler J. P., Fallon J. T., Friedlich A. L., Fisher C. M., American Journal of Cardiology 40(4): 509-13, 1977; Wolf P. A., Abbot R. D., Kannel W. B., Archives of Internal Medicine 147(9):1561-4, 1987; Wolf P. A., Abbot R. D., Kannel W. B. Stroke. 22(8):983-8, 1991; Cabin H. S., Clubb K. S., Hall C., Perlmutter R. A., Feinstein A. R., American Journal of Cardiology 65(16):1112-6, 1990).

WO99/50225 discloses a class of aminocyclohexylether compounds as useful in the treatment of arrhythmias. Some of the new aminocyclohexylether compounds have been found to be particularly effective in the treatment and/or prevention of AF. However, synthetic methods described in WO99/50225 and elsewhere were non-stereoselective and led to mixture of stereoisomers (see e.g., FIGS. 1-3). As active pharmaceutical compounds, it is often desirable that drug molecules are in stereoisomerically substantially pure form. It may not be feasible or cost effective if the correct stereoisomer has to be isolated from a mixture of stereoisomers after a multi-step synthesis. Therefore, there remains a need in the art to develop method for the preparation of stereoisomerically substantially pure trans-aminocyclohexyl ether compounds as well as method for the preparation of stereoisomerically substantially pure cis-aminocyclohexyl ether compounds.

Although WO 2003/105756 describes a method of stereoselectively preparing a trans-1,2, di-substituted cycloalkane, the method disclosed therein requires a trans-1R,2R di-substituted cycloalkane. In an alternate embodiment, disclosed is a method that requires reacting a cis-2-substituted cycloalkanol with a galactose derivative. These requirements may not be generally feasible and/or amenable to large scale manufacture processes. The present invention generally does not have such limitations.

SUMMARY OF THE INVENTION

The present invention is directed to stereoselective synthesis of certain aminocyclohexyl ether compounds.

Accordingly, in one aspect, this invention is directed to a method for stereoselectively making a compound of formula (7):

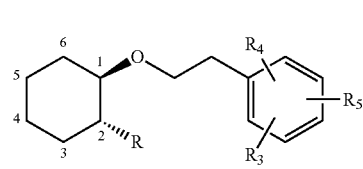

(7)

or a pharmaceutically acceptable salt, ester, amide, complex, chelate, clathrate, solvate, polymorph, metabolite or prodrug thereof, wherein R is —C(O)R$_{14}$ where R$_{14}$ is C$_7$-C$_{12}$aralkoxy or C$_1$-C$_6$alkoxy, —C(O)N(R$_6$)R$_7$ where R$_6$ and R$_7$ are each independently hydrogen, acetyl, methanesulfonyl or C$_1$-C$_6$ alkyl; or R is —OR$_{15}$ where R$_{15}$ is hydrogen, C$_1$-C$_6$alkyl or C$_7$-C$_{12}$aralkyl; or R is —OS(O)$_2$R$_{16}$ where R$_{16}$ is C$_1$-C$_6$alkyl or an optionally substituted aryl; or R is —N(R$_1$)R$_2$ where R$_1$ and R$_2$ are each independently selected from hydrogen, C$_1$-C$_8$alkyl, C$_3$-C$_8$alkoxyalkyl, C$_1$-C$_8$hydroxyalkyl, C$_8$-C$_{12}$aralkoxycarbonyl and C$_7$-C$_{12}$aralkyl; or R$_1$ and R$_2$ are each independently selected from C$_3$-C$_8$alkoxyalkyl, $C_1$-$C_8$hydroxyalkyl, and $C_7$-$C_{12}$aralkyl; or $R_1$ and $R_2$, when taken together with the nitrogen atom to which they are directly attached, form a ring denoted by formula (I):

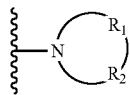

(I)

wherein the ring of formula (I) is formed from the nitrogen as shown as well as three to nine additional ring atoms independently selected from the group consisting of carbon, nitrogen, oxygen, and sulfur; where any two adjacent ring atoms may be joined together by single or double bonds, and where any one or more of the additional carbon ring atoms may be substituted with one or two substituents selected from the group consisting of hydrogen, hydroxy, $C_1$-$C_3$hydroxyalkyl, oxo, $C_2$-$C_4$acyl, $C_1$-$C_3$ alkyl, $C_2$-$C_4$alkylcarboxy, $C_1$-$C_3$alkoxy, $C_7$-$C_{12}$aralkoxy, and $C_1$-$C_{20}$alkanoyloxy, or may be substituted to form a spiro five- or six-membered heterocyclic ring containing one or two heteroatoms selected from the group consisting of carbon, nitrogen, oxygen, and sulfur; or any two adjacent additional carbon ring atoms may be fused to a $C_3$-$C_8$carbocyclic ring, and any one or more of the additional nitrogen ring atoms may be substituted with substituents selected from the group consisting of hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached, form a bicyclic ring system comprising 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl; and $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$, where $R_6$, $R_7$, $R_8$, and $R_9$ are each independently selected from hydrogen, acetyl, methanesulfonyl or $C_1$-$C_6$ alkyl; or $R_3$, $R_4$ and $R_5$ are independently hydrogen, hydroxy or $C_1$-$C_6$ alkoxy; with the proviso that $R_3$, $R_4$ and $R_5$ cannot all be hydrogen at the same time; which method comprises reacting a compound of formula (5):

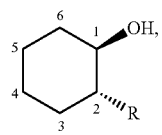

(5)

wherein R is as defined above, with a compound of formula (6):

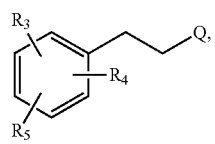

(6)

wherein $R_3$, $R_4$ and $R_5$ are as defined above and Q is a leaving group, under suitable conditions such that upon reaction of the compound of formula (5) with the compound of formula (6), the stereochemical configuration of the carbon at the 1-position in the compound of formula (5) is retained in the resulting compound of formula (7).

In another aspect, this invention is directed to a method for stereoselectively making a compound of formula (8):

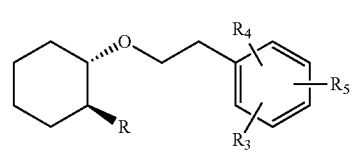

(8)

or a pharmaceutically acceptable salt, ester, amide, complex, chelate, clathrate, solvate, polymorph, metabolite or prodrug thereof, wherein R is —$C(O)R_{14}$ where $R_{14}$ is $C_7$-$C_{12}$aralkoxy or $C_1$-$C_6$alkoxy, —$C(O)N(R_6)R_7$ where $R_6$ and $R_7$ are each independently hydrogen, acetyl, methanesulfonyl or $C_1$-$C_6$ alkyl; or R is —$OR_{15}$ where $R_{15}$ is hydrogen, $C_1$-$C_6$alkyl or $C_7$-$C_{12}$aralkyl; or R is —$OS(O)_2R_{16}$ where $R_{16}$ is $C_1$-$C_6$alkyl or an optionally substituted aryl; or R is —$N(R_1)R_2$ where $R_1$ and $R_2$ are each independently selected from hydrogen, $C_1$-$C_8$alkyl, $C_3$-$C_8$alkoxyalkyl, $C_1$-$C_8$hydroxyalkyl, $C_8$-$C_{12}$aralkoxycarbonyl and $C_7$-$C_{12}$aralkyl; or $R_1$ and $R_2$ are each independently selected from $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached, form a ring denoted by formula (I):

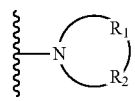

(I)

wherein the ring of formula (I) is formed from the nitrogen as shown as well as three to nine additional ring atoms independently selected from the group consisting of carbon, nitrogen, oxygen, and sulfur; where any two adjacent ring atoms may be joined together by single or double bonds, and where any one or more of the additional carbon ring atoms may be substituted with one or two substituents selected from the group consisting of hydrogen, hydroxy, $C_1$-$C_3$hydroxyalkyl, oxo, $C_2$-$C_4$acyl, $C_1$-$C_3$ alkyl, $C_2$-$C_4$alkylcarboxy, $C_1$-$C_3$alkoxy, $C_7$-$C_{12}$aralkoxy, and $C_1$-$C_{20}$alkanoyloxy, or may be substituted to form a Spiro five- or six-membered heterocyclic ring containing one or two heteroatoms selected from the group consisting of carbon, nitrogen, oxygen, and sulfur; or any two adjacent additional carbon ring atoms may be fused to a $C_3$-$C_8$carbocyclic ring, and any one or more of the additional nitrogen ring atoms may be substituted with substituents selected from the group consisting of hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached, form a bicyclic ring system comprising 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl; and $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —CHF$_2$, —SO$_2$N(R$_8$)R$_9$, —OCF$_3$, C$_2$-C$_7$alkanoyloxy, C$_1$-C$_6$alkyl, C$_1$-C$_6$alkoxy, C$_7$-C$_{12}$aralkoxy, C$_2$-C$_7$alkoxycarbonyl, C$_1$-C$_6$thioalkyl, aryl or —N(R$_6$)R$_7$, where R$_6$, R$_7$, R$_8$, and R$_9$ are each independently selected from hydrogen, acetyl, methanesulfonyl or C$_1$-C$_6$ alkyl; or R$_3$, R$_4$ and R$_5$ are independently hydrogen, hydroxy or C$_1$-C$_6$ alkoxy; with the proviso that R$_3$, R$_4$ and R$_5$ cannot all be hydrogen at the same time; which method comprises reacting a compound of formula (5):

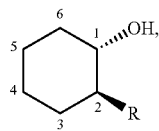

(4)

wherein R is as defined above, with a compound of formula (6):

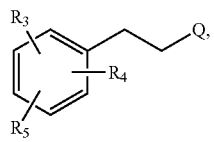

(6)

wherein R$_3$, R$_4$ and R$_5$ are as defined above and Q is a leaving group, under suitable conditions such that upon reaction of the compound of formula (4) with the compound of formula (6), the stereochemical configuration of the carbon at the 1-position in the compound of formula (4) is retained in the resulting compound of formula (8).

In another aspect, this invention is direct to a method of making a compound of formula (73):

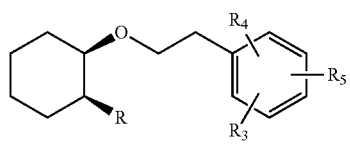

(73)

or a pharmaceutically acceptable salt, ester, amide, complex, chelate, clathrate, solvate, polymorph, metabolite or prodrug thereof, wherein R is —C(O)R$_{14}$ where R$_{14}$ is C$_7$-C$_{12}$aralkoxy or C$_1$-C$_6$alkoxy, —C(O)N(R$_6$)R$_7$ where R$_6$ and R$_7$ are each independently hydrogen, acetyl, methanesulfonyl or C$_1$-C$_6$ alkyl; or R is —OR$_{15}$ where R$_{15}$ is hydrogen, C$_1$-C$_6$alkyl or C$_7$-C$_{12}$aralkyl; or R is —OS(O)$_2$R$_{16}$ where R$_{16}$ is C$_1$-C$_6$alkyl or an optionally substituted aryl; or R is —N(R$_1$)R$_2$ where R$_1$ and R$_2$ are each independently selected from hydrogen, C$_1$-C$_8$alkyl, C$_3$-C$_8$alkoxyalkyl, C$_1$-C$_8$hydroxyalkyl, C$_8$-C$_{12}$aralkoxycarbonyl and C$_7$-C$_{12}$aralkyl; or R$_1$ and R$_2$ are each independently selected from C$_3$-C$_8$alkoxyalkyl, C$_1$-C$_8$hydroxyalkyl, and C$_7$-C$_{12}$aralkyl; or R$_1$ and R$_2$, when taken together with the nitrogen atom to which they are directly attached, form a ring denoted by formula (I):

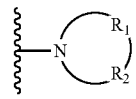

(I)

wherein the ring of formula (I) is formed from the nitrogen as shown as well as three to nine additional ring atoms independently selected from the group consisting of carbon, nitrogen, oxygen, and sulfur; where any two adjacent ring atoms may be joined together by single or double bonds, and where any one or more of the additional carbon ring atoms may be substituted with one or two substituents selected from the group consisting of hydrogen, hydroxy, C$_1$-C$_3$hydroxyalkyl, oxo, C$_2$-C$_4$acyl, C$_1$-C$_3$ alkyl, C$_2$-C$_4$alkylcarboxy, C$_1$-C$_3$alkoxy, C$_7$-C$_{12}$aralkoxy, and C$_1$-C$_{20}$alkanoyloxy, or may be substituted to form a spiro five- or six-membered heterocyclic ring containing one or two heteroatoms selected from the group consisting of carbon, nitrogen, oxygen, and sulfur; or any two adjacent additional carbon ring atoms may be fused to a C$_3$-C$_8$carbocyclic ring, and any one or more of the additional nitrogen ring atoms may be substituted with substituents selected from the group consisting of hydrogen, C$_1$-C$_6$alkyl, C$_2$-C$_4$acyl, C$_2$-C$_4$hydroxyalkyl and C$_3$-C$_8$alkoxyalkyl; or R$_1$ and R$_2$, when taken together with the nitrogen atom to which they are directly attached, form a bicyclic ring system comprising 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl; and R$_3$, R$_4$ and R$_5$ are independently bromine, chlorine, fluorine, carboxy, hydrogen, hydroxy, hydroxymethyl, methanesulfonamido, nitro, cyano, sulfamyl, trifluoromethyl, —CHF$_2$, —SO$_2$N(R$_8$)R$_9$, —OCF$_3$, C$_2$-C$_7$alkanoyloxy, C$_1$-C$_6$alkyl, C$_1$-C$_6$alkoxy, C$_7$-C$_{12}$aralkoxy, C$_2$-C$_7$alkoxycarbonyl, C$_1$-C$_6$thioalkyl, aryl or —N(R$_6$)R$_7$, where R$_6$, R$_7$, R$_8$, and R$_9$ are each independently selected from hydrogen, acetyl, methanesulfonyl or C$_1$-C$_6$ alkyl; or R$_3$, R$_4$ and R$_5$ are independently hydrogen, hydroxy or C$_1$-C$_6$ alkoxy; with the proviso that R$_3$, R$_4$ and R$_5$ cannot all be hydrogen at the same time; which method comprises reacting a compound of formula (71):

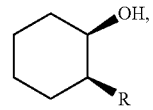

(71)

wherein R is as defined above, with a compound of formula (6):

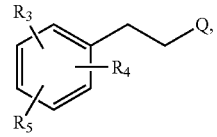

(6)

wherein R$_3$, R$_4$ and R$_5$ are as defined above and Q is a leaving group, under suitable conditions such that upon reaction of the compound of formula (71) with the compound of formula (6), the stereochemical configuration of the carbon at the 1-position in the compound of formula (71) is retained in the resulting compound of formula (73).

In another aspect, this invention is directed to a method of making a compound of formula (74):

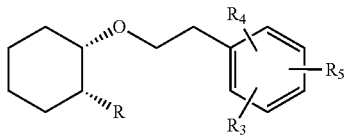
(74)

or a pharmaceutically acceptable salt, ester, amide, complex, chelate, clathrate, solvate, polymorph, metabolite or prodrug thereof, wherein R is —C(O)$R_{14}$ where $R_{14}$ is $C_7$-$C_{12}$aralkoxy or $C_1$-$C_6$alkoxy, —C(O)N($R_6$)$R_7$) where $R_6$ and $R_7$ are each independently hydrogen, acetyl, methanesulfonyl or $C_1$-$C_6$ alkyl; or R is —O$R_{15}$ where $R_{15}$ is hydrogen, $C_1$-$C_6$alkyl or $C_7$-$C_{12}$aralkyl; or R is —OS(O)$_2$$R_{16}$ where $R_{16}$ is $C_1$-$C_6$alkyl or an optionally substituted aryl; or R is —N($R_1$)$R_2$ where $R_1$ and $R_2$ are each independently selected from hydrogen, $C_1$-$C_5$alkyl, $C_3$-$C_8$alkoxyalkyl, $C_1$-$C_8$hydroxyalkyl, $C_8$-$C_{12}$aralkoxycarbonyl and $C_7$-$C_{12}$aralkyl; or $R_1$ and $R_2$ are each independently selected from $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached, form a ring denoted by formula (I):

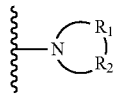
(I)

wherein the ring of formula (I) is formed from the nitrogen as shown as well as three to nine additional ring atoms independently selected from the group consisting of carbon, nitrogen, oxygen, and sulfur; where any two adjacent ring atoms may be joined together by single or double bonds, and where any one or more of the additional carbon ring atoms may be substituted with one or two substituents selected from the group consisting of hydrogen, hydroxy, $C_1$-$C_3$hydroxyalkyl, oxo, $C_2$-$C_4$acyl, $C_1$-$C_3$ alkyl, $C_2$-$C_4$alkylcarboxy, $C_1$-$C_3$alkoxy, $C_7$-$C_{12}$aralkoxy, and $C_1$-$C_{20}$alkanoyloxy, or may be substituted to form a spiro five- or six-membered heterocyclic ring containing one or two heteroatoms selected from the group consisting of carbon, nitrogen, oxygen, and sulfur; or any two adjacent additional carbon ring atoms may be fused to a $C_3$-$C_8$carbocyclic ring, and any one or more of the additional nitrogen ring atoms may be substituted with substituents selected from the group consisting of hydrogen, $C_1$-$C_6$alkyl, $C_2$-$C_4$acyl, $C_2$-$C_4$hydroxyalkyl and $C_3$-$C_8$alkoxyalkyl; or $R_1$ and $R_2$, when taken together with the nitrogen atom to which they are directly attached, form a bicyclic ring system comprising 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl; and $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —CHF$_2$, —SO$_2$N($R_8$)$R_9$, —OCF$_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —N($R_6$)$R_7$, where $R_6$, $R_7$, $R_8$, and $R_9$ are each independently selected from hydrogen, acetyl, methanesulfonyl or $C_1$-$C_6$ alkyl; or $R_3$, $R_4$ and $R_5$ are independently hydrogen, hydroxy or $C_1$-$C_6$ alkoxy; with the proviso that $R_3$, $R_4$ and $R_5$ cannot all be hydrogen at the same time; which method comprises reacting a compound of formula (72):

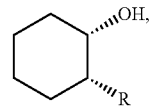
(72)

wherein R is as defined above, with a compound of formula (6):

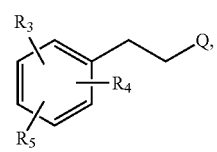
(6)

wherein $R_3$, $R_4$ and $R_5$ are as defined above and Q is a leaving group, under suitable conditions such that upon reaction of the compound of formula (72) with the compound of formula (6), the stereochemical configuration of the carbon at the 1-position in the compound of formula (72) is retained in the resulting compound of formula (74).

In another aspect, this invention is directed to a method for stereoselectively making an aminocyclohexyl ether of the following formula (79), formula (80) or formula (81):

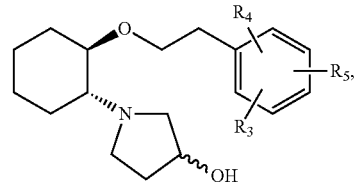
(79)

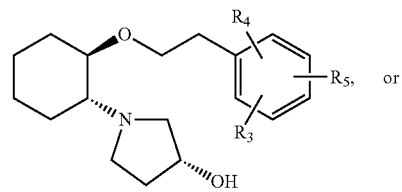
(80)

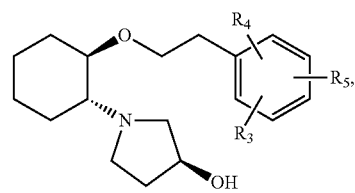
(81)

wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —CHF$_2$, —SO$_2$N($R_8$)$R_9$, —OCF$_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or $N(R_6)R_7$ where $R_6$, $R_7$, $R_8$, and $R_9$, are each independently hydrogen, acetyl, methanesulfonyl or $C_1$-$C_6$alkyl; or $R_3$, $R_4$ and $R_5$ are independently hydrogen, hydroxy or $C_1$-$C_6$alkoxy; with the proviso that $R_3$, $R_4$ and $R_5$ cannot all be hydrogen at the same time; which method comprises:

(a) reacting a compound of formula (75):

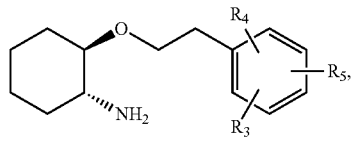
(75)

where $R_3$, $R_4$ and $R_5$ are as defined above, with a compound of formula (82), a compound of formula (83) or a compound of formula (84):

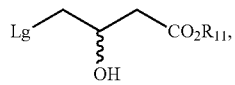
(82)

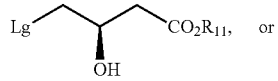  or
(83)

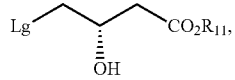
(84)

wherein each Lg is independently a leaving group and each $R_{11}$ is $C_1$-$C_6$alkyl, under suitable conditions to form a compound of formula (85), a compound of formula (86) or a compound of formula (87), respectively:

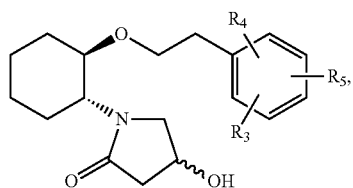
(85)

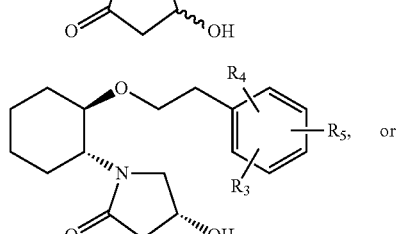  or
(86)

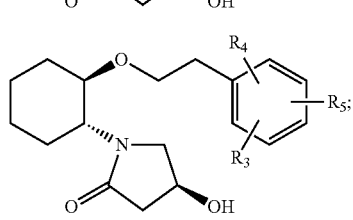
(87)

or reacting a compound of formula (75) with a compound of formula (88), a compound of formula (89) or a compound of formula (90):

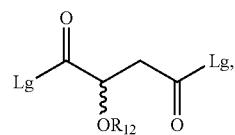
(88)

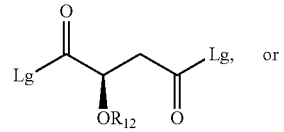  or
(89)

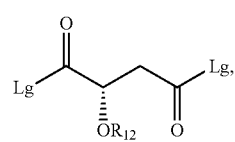
(90)

wherein each Lg is independently a leaving group and each $R_{12}$ is $C_2$-$C_4$acyl or $C_2$-$C_{12}$aralkyl, under suitable conditions to form a compound of formula (91), a compound of formula (92) or a compound of formula (93), respectively:

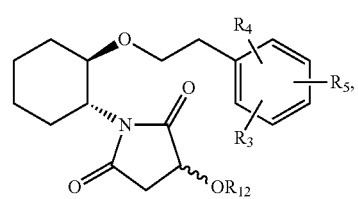
(91)

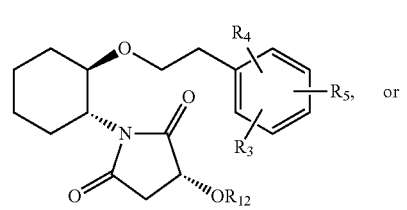  or
(92)

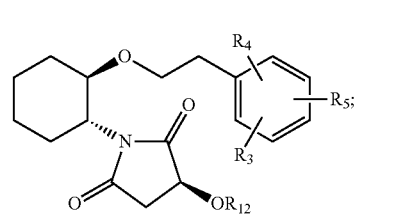
(93)

or reacting a compound of formula (75) with a compound of formula (94), a compound of formula (95) or a compound of formula (96):

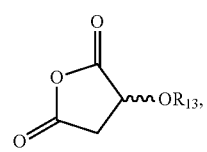
(94)

(95)
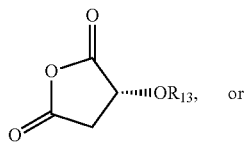
or

(96)
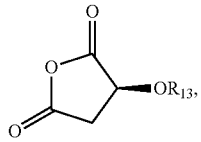

wherein each $R_{13}$ is $C_2$-$C_4$acyl or $C_2$-$C_{12}$aralkyl, under suitable conditions to form a compound of formula (97), a compound of formula (98) or a compound of formula (99), respectively;

(97)
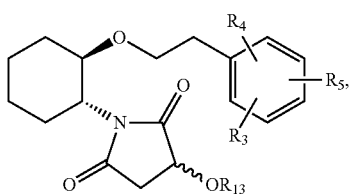

(98)
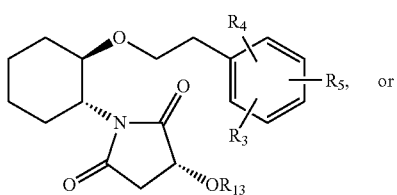
or

(99)
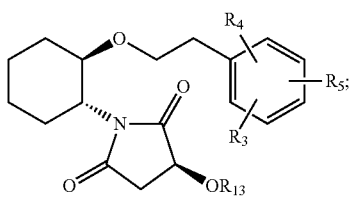

and (b) reducing the compound of formula (85), the compound of formula (91) or the compound of formula (97) formed in step (a) under suitable conditions to form a compound of formula (79) as set forth above; or reducing the compound of formula (86), the compound of formula (92) or the compound of formula (98) formed in step (a) under suitable conditions to form a compound of formula (80) as set forth above; or reducing the compound of formula (87), the compound of formula (93) or the compound of formula (99) formed in step (a) under suitable conditions to form a compound of formula (81) as set forth above.

In another aspect, this invention is directed to a method for stereoselectively making an aminocyclohexyl ether of the following formula (100), formula (101) or formula (102):

(100)

(101)
or (102)

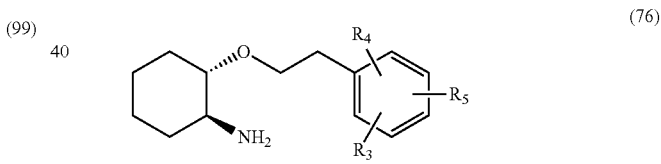

wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or $N(R_6)R_7$ where $R_6$, $R_7$, $R_8$, and $R_9$, are each independently hydrogen, acetyl, methanesulfonyl or $C_1$-$C_6$alkyl; or $R_3$, $R_4$ and $R_5$ are independently hydrogen, hydroxy or $C_1$-$C_6$alkoxy; with the proviso that $R_3$, $R_4$ and $R_5$ cannot all be hydrogen at the same time; which method comprises:

(a) reacting a compound of formula (76):

(76)

where $R_3$, $R_4$ and $R_5$ are as defined above, with a compound of formula (82), a compound of formula (83) or a compound of formula (84):

(82)
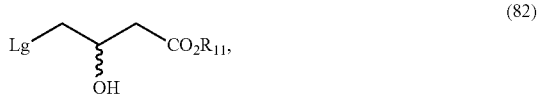

(83)
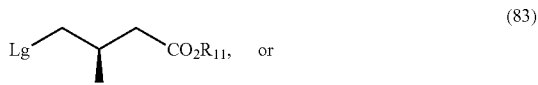
or

(84)

wherein each Lg is independently a leaving group and each $R_{11}$ is $C_1$-$C_6$alkyl, under suitable conditions to form a compound of formula (103), a compound of formula (104) or a compound of formula (105), respectively:

(103)
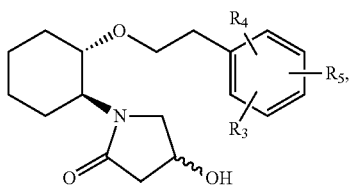

(104)
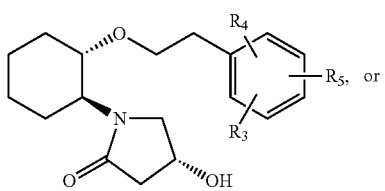
or (105)
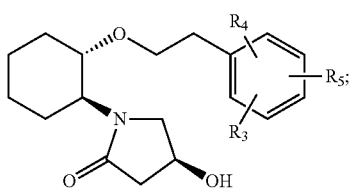

or reacting a compound of formula (76) with a compound of formula (88), a compound of formula (89) or a compound of formula (90):

(88)
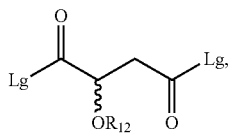

(89)
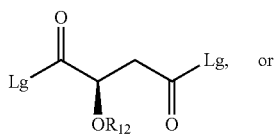
or

(90)
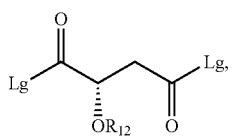

wherein each Lg is independently a leaving group and each $R_{12}$ is $C_2$-$C_4$acyl or $C_7$-$C_{12}$aralkyl, under suitable conditions to form a compound of formula (106), a compound of formula (107), or a compound of formula (108), respectively:

(106)
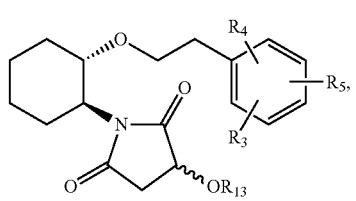

-continued (107)
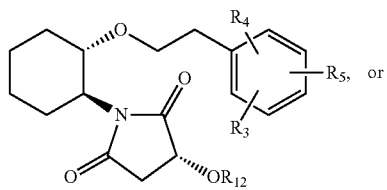
or (108)
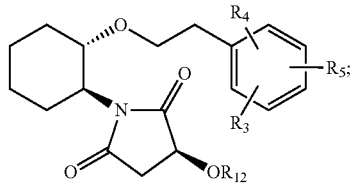

or reacting a compound of formula (76) with a compound of formula (94), a compound of formula (95) or a compound of formula (96):

(94)
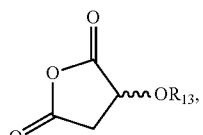

(95)
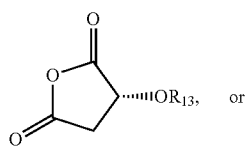
or

(96)
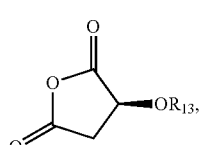

wherein each $R_{13}$ is $C_2$-$C_4$acyl or $C_7$-$C_{12}$aralkyl, under suitable conditions to form a compound of formula (109), a compound of formula (110) or a compound of formula (111), respectively:

(109)

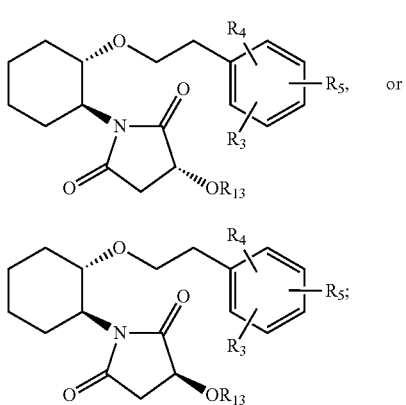

and (b) reducing the compound of formula (103), the compound of formula (106) or the compound of formula (109) formed in step (a) under suitable conditions to form a compound of formula (100) as set forth above; or reducing the compound of formula (104), the compound of formula (107) or the compound of formula (110) formed in step (a) under suitable conditions to form a compound of formula (101) as set forth above; or reducing the compound of formula (105), the compound of formula (108) or the compound of formula (111) formed in step (a) under suitable conditions to form a compound of formula (102) as set forth above.

In another aspect, this invention is directed to a method for stereoselectively making an aminocyclohexyl ether of the following formula (112), formula (113) or formula (114):

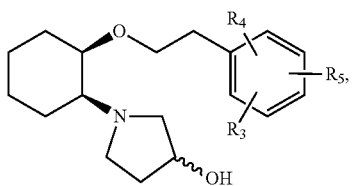

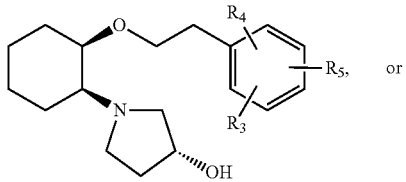

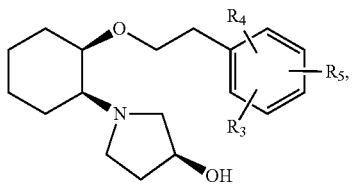

wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or $N(R_6)R_7$ where $R_6$, $R_7$, $R_8$, and $R_9$, are each independently hydrogen, acetyl, methanesulfonyl or $C_1$-$C_6$alkyl;

or $R_3$, $R_4$ and $R_5$ are independently hydrogen, hydroxy or $C_1$-$C_6$alkoxy; with the proviso that $R_3$, $R_4$ and $R_5$ cannot all be hydrogen at the same time; which method comprises:

(a) reacting a compound of formula (77):

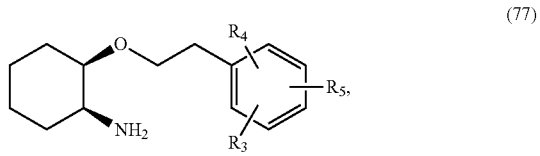

where $R_3$, $R_4$ and $R_5$ are as defined above, with a compound of formula (82), a compound of formula (83) or a compound of formula (84):

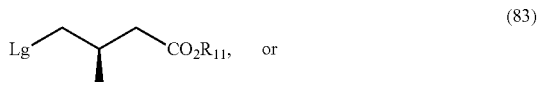

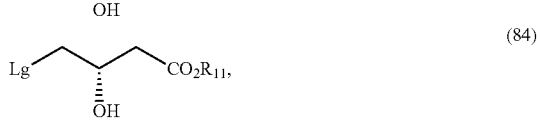

wherein each Lg is independently a leaving group and each $R_{11}$ is $C_1$-$C_6$alkyl, under suitable conditions to form a compound of formula (115), a compound of formula (116) or a compound of formula (117), respectively:

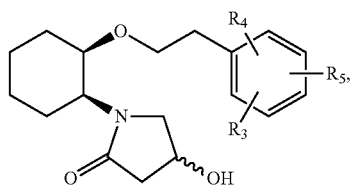

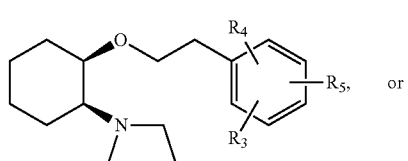

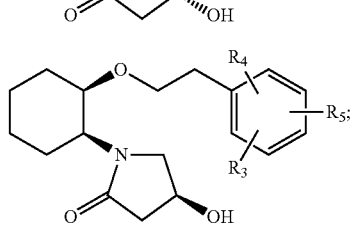

or reacting a compound of formula (77) with a compound of formula (88), a compound of formula (89) or a compound of formula (90):

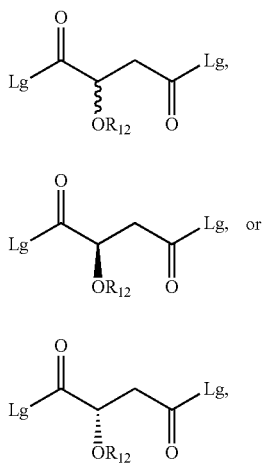

(88)

(89)

(90)

wherein each Lg is independently a leaving group and each $R_{12}$ is $C_2$-$C_4$acyl or $C_7$-$C_{12}$aralkyl, under suitable conditions to form a compound of formula (118), a compound of formula (119), or a compound of formula (120), respectively:

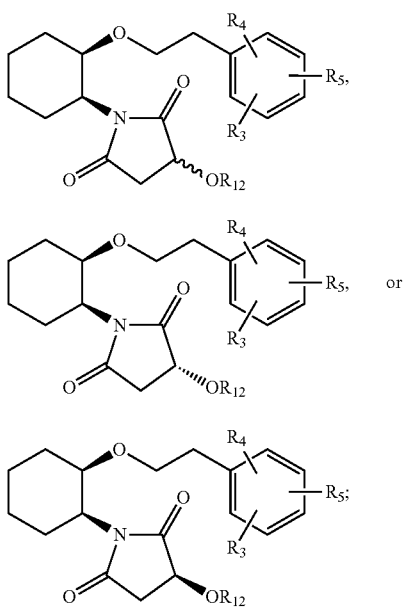

(118)

(119)

(120)

or reacting a compound of formula (77) with a compound of formula (94), a compound of formula (95) or a compound of formula (96):

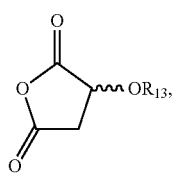

(94)

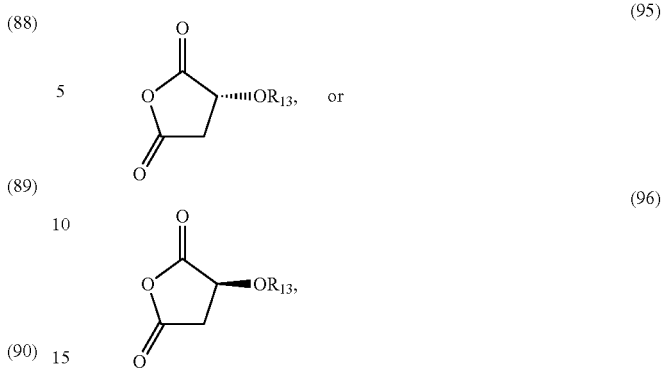

(95)

(96)

wherein each $R_{13}$ is $C_2$-$C_4$acyl or $C_7$-$C_{12}$aralkyl, under suitable conditions to form a compound of formula (121), a compound of formula (122) or a compound of formula (123), respectively:

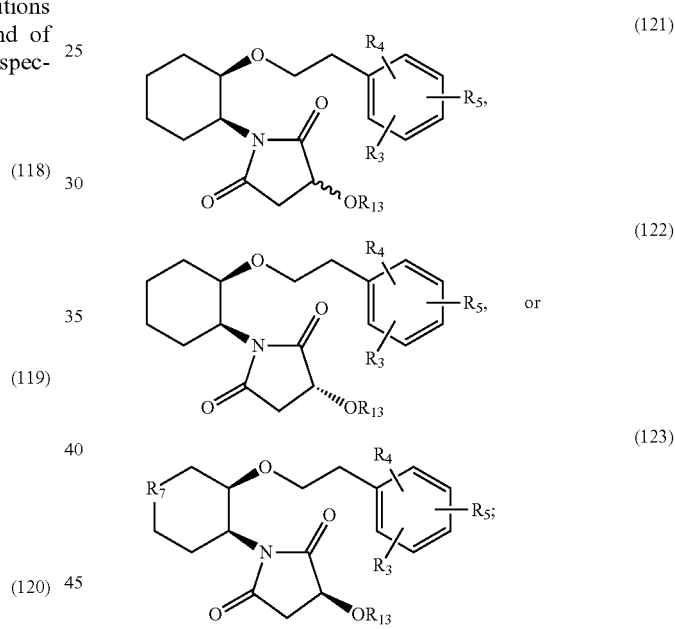

(121)

(122)

(123)

and (b) reducing the compound of formula (115), the compound of formula (118) or the compound of formula (121) formed in step (a) under suitable conditions to form a compound of formula (112) as set forth above; or reducing the compound of formula (116), the compound of formula (119) or the compound of formula (122) formed in step (a) under suitable conditions to form a compound of formula (113) as set forth above; or reducing the compound of formula (117), the compound of formula (120) or the compound of formula (123) formed in step (a) under suitable conditions to form a compound of formula (113) as set forth above.

In another aspect, this invention is directed to a method for stereoselectively making an aminocyclohexyl ether of the following formula (124), formula (125) or formula (126):

(124)

[Structure 124]

(125)

[Structure 125]

(126)

[Structure 126]

wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or $N(R_6)R_7$ where $R_6$, $R_7$, $R_8$, and $R_9$, are each independently hydrogen, acetyl, methanesulfonyl or $C_1$-$C_6$alkyl; or $R_3$, $R_4$ and $R_5$ are independently hydrogen, hydroxy or $C_1$-$C_6$alkoxy; with the proviso that $R_3$, $R_4$ and $R_5$ cannot all be hydrogen at the same time; which method comprises:
(a) reacting a compound of formula (78):

(78)

[Structure 78]

where $R_3$, $R_4$ and $R_5$ are as defined above, with a compound of formula (82), a compound of formula (83) or a compound of formula (84):

(82)

[Structure 82]

(83)

[Structure 83]

(84)

[Structure 84]

wherein each Lg is independently a leaving group and each $R_{11}$ is $C_1$-$C_6$alkyl, under suitable conditions to form a compound of formula (127), a compound of formula (128) or a compound of formula (129), respectively:

(127)

[Structure 127]

(128)

[Structure 128]

(129)

[Structure 129]

or reacting a compound of formula (78) with a compound of formula (88), a compound of formula (89) or a compound of formula (90):

(88)

[Structure 88]

(89)

[Structure 89]

(90)

[Structure 90]

wherein each Lg is independently a leaving group and each $R_{12}$ is $C_2$-$C_4$acyl or $C_7$-$C_{12}$aralkyl, under suitable conditions to form a compound of formula (130), a compound of formula (131), or a compound of formula (132), respectively:

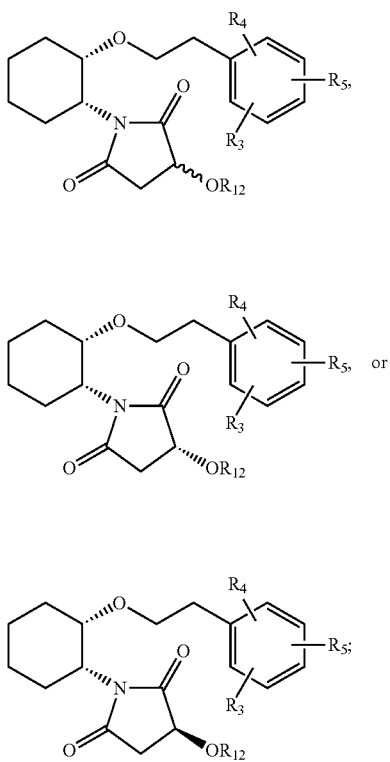

or reacting a compound of formula (78) with a compound of formula (94), a compound of formula (95) or a compound of formula (96):

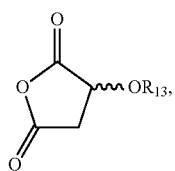

(94)

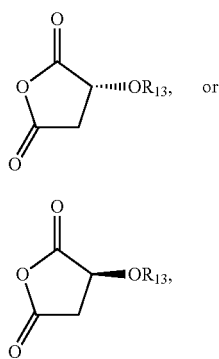

wherein each $R_{13}$ is $C_2$-$C_4$acyl or $C_7$-$C_{12}$aralkyl, under suitable conditions to form a compound of formula (133), a compound of formula (134) or a compound of formula (135), respectively:

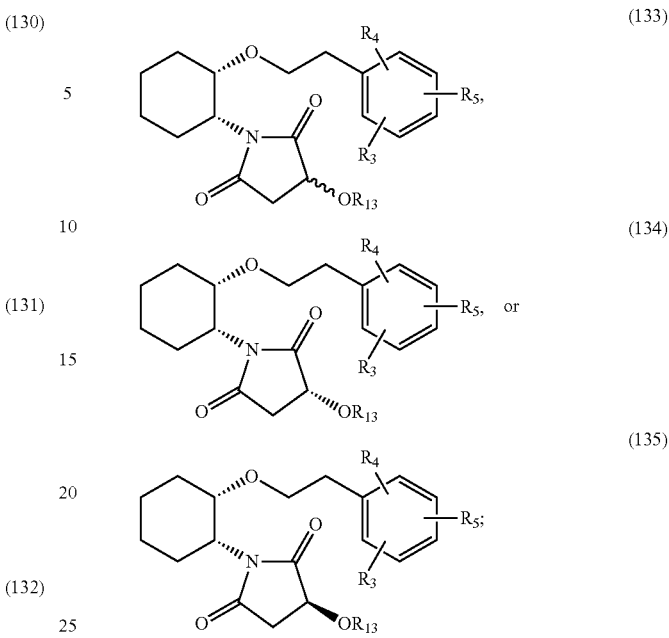

and (b) reducing the compound of formula (127), the compound of formula (130) or the compound of formula (133) formed in step (a) under suitable conditions to form a compound of formula (124) as set forth above; or reducing the compound of formula (128), the compound of formula (131) or the compound of formula (134) formed in step (a) under suitable conditions to form a compound of formula (125) as set forth above; or reducing the compound of formula (129), the compound of formula (132) or the compound of formula (135) formed in step (a) under suitable conditions to form a compound of formula (126) as set forth above.

It is also contemplated that individual steps of the methods described for making intermediates in any of the reaction sequences are part of the invention described herein.

DETAILED DESCRIPTION OF THE INVENTION

Figure 1:
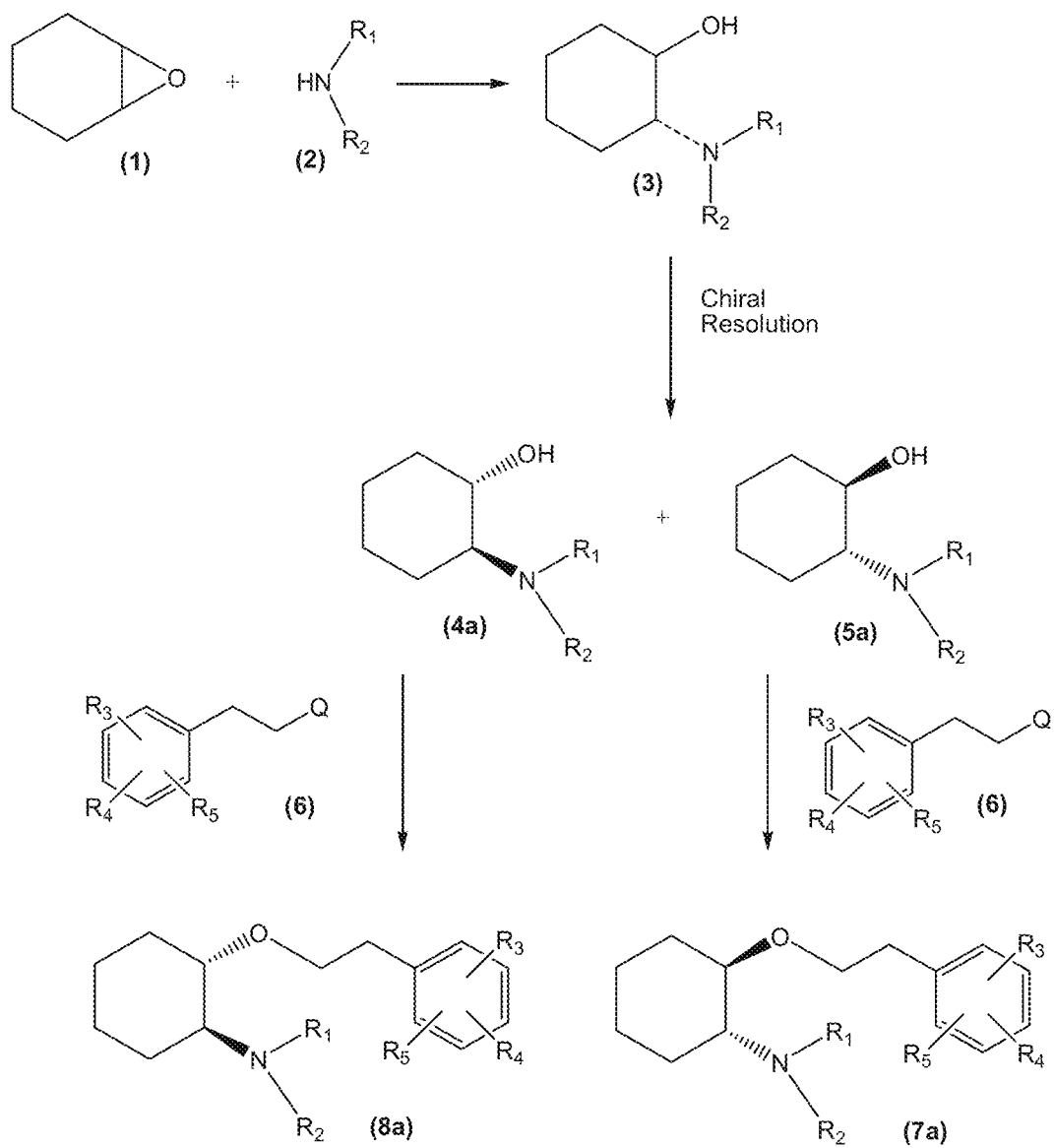
FIG. 1 illustrates a general synthetic scheme that may be employed to prepare a trans-aminocyclohexyl ether compound of formula (7a) or formula (8a).

As noted above, the present invention is directed to aminocyclohexyl ether compounds of formula such as (7), (8), (73), or (74), methods of manufacture thereof, pharmaceutical compositions containing the aminocyclohexyl ether compounds, and various uses for the compounds and compositions. Such uses include the treatment of arrhythmias, ion channel modulation and other uses as described herein.

An understanding of the present invention may be aided by reference to the following definitions and explanation of conventions used herein:

The aminocyclohexyl ether compounds of the invention have an ether oxygen atom at position 1 of a cyclohexane ring, and an amine nitrogen atom at position 2 of the cyclohexane ring, with other positions numbered in corresponding order as shown below in structure ($A^1$):

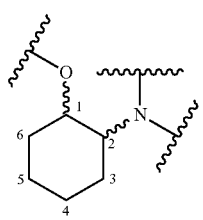

(A$^1$)

The bonds from the cyclohexane ring to the 1-oxygen and 2-nitrogen atoms in the above formula may be relatively disposed in either a cis or trans relationship. Therefore, the stereochemistry of the amine and ether substituents of the cyclohexane ring is either (R,R)-trans or (S,S)-trans for the trans-stereoisomers and is either (R,S)-cis or (S,R)-cis for the cis-stereoisomers.

A wavy bond from a substituent to the central cyclohexane ring indicates that that group may be located on either side of the plane of the central ring as shown on the page in a two dimensional representation such that it may result in a R stereoisomer or a S stereoisomer at the carbon to which the bond is attached if that carbon becomes a chiral center. When a wavy bond is shown intersecting a ring, this indicates that the indicated substituent group may be attached to any position on the ring capable of bonding to the substituent group and that the substituent group may lie above or below the plane of the ring system to which it is bound as shown on the page in a two dimensional representation.

Following the standard chemical literature description practice and as used in this patent, a full wedge bond means above the ring plane as shown on the page in a two dimensional representation, and a dashed wedge bond means below the ring plane as shown on the page in a two dimensional representation; one full bond and one dashed bond (i.e., - - - - - - ) means a trans configuration, whereas two full bonds or two dashed bonds means a cis configuration.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, compounds of the invention containing compounds having the group ($B^1$):

($B^1$)

where the group ($B^1$) is intended to encompass groups wherein any ring atom that could otherwise be substituted with hydrogen, may instead be substituted with either $R_3$, $R_4$ or $R_5$, with the proviso that each of $R_3$, $R_4$ and $R_5$ appears once and only once on the ring. Ring atoms that are not substituted with any of $R_3$, $R_4$ or $R_5$ are substituted with hydrogen. In those instances where the invention specifies that a non-aromatic ring is substituted with one or more functional groups, and those functional groups are shown connected to the non-aromatic ring with bonds that bisect ring bonds, then the functional groups may be present at different atoms of the ring, or on the same atom of the ring, so long as that atom could otherwise be substituted with a hydrogen atom.

The compounds of the present invention contain at least two asymmetric carbon atoms and thus exist as enantiomers and diastereoisomers. For the present invention, the words diastereomer and diastereoisomer and related terms are equivalent and interchangeable. Unless otherwise indicated, the present invention includes all enantiomeric and diastereoisomeric forms of the aminocyclohexyl ether compounds of the invention. Pure stereoisomers, mixtures of enantiomers and/or diastereoisomers, and mixtures of different compounds of the invention are included within the present invention. Thus, compounds of the present invention may occur as racemates, racemic mixtures and as individual diastereoisomers, or enantiomers, unless a specific stereoisomer enantiomer or diastereoisomer is identified, with all isomeric forms being included in the present invention. For the present invention, a racemate or racemic mixture does not imply a 50:50 mixture of stereoisomers only. Other enantiomerically or diastereoiosmerically enriched mixtures of varying ratios of stereoisomers are also contemplated. Unless otherwise noted, the phrase "stereoisomerically substantially pure" generally refers to those asymmetric carbon atoms that are described or illustrated in the structural formulae for that compound.

The definition of stereoisomeric purity (or optical purity or chiral purity) and related terminology and their methods of determination (e.g., Optical rotation, circular dichroism etc.) are well known in the art (see e.g., E. L. Eliel and S. H. Wilen, in Stereochemistry of Organic Compounds; John Wiley & Sons: New York, 1994; and references cited therein). The phrase "stereoisomerically substantially pure" generally refers to the enrichment of one of the stereoisomers (e.g., enantiomers or diastereoisomers) over the other stereoisomers in a sample, leading to chiral enrichment and increase in optical rotation activity of the sample. Enantiomer is one of a pair of molecular species that are mirror images of each other and not superposable. They are 'mirror-image' stereoisomers. Diastereoisomers generally refer to stereoisomers not related as mirror-images. Enantiomer excess (ee) and diastereoisomer excess (de) are terms generally used to refer the stereoisomeric purity (or optical purity or chiral purity) of a sample of the compound of interest. Their definition and methods of determination are well known in the art and can be found e.g., in E. L. Eliel and S. H. Wilen, in Stereochemistry of Organic Compounds; John Wiley & Sons: New York, 1994; and references cited therein. "Stereoselectively making" refers to preparing the compound having enantiomer excess (ee) or diastereoisomer excess (de).

For the present invention, enantiomer excess (ee) or diastereoisomer excess (de) in the range of about 50% to about 100% is contemplated. A preferred range of enantiomer excess (ee) or diastereoisomer excess (de) is about 60% to about 100%. Another preferred range of enantiomer excess (ee) or diastereoisomer excess (de) is about 70% to about 100%. A more preferred range of enantiomer excess (ee) or diastereoisomer excess (de) is about 80% to about 100%. Another more preferred range of enantiomer excess (ee) or diastereoisomer excess (de) is about 85% to about 100%. An even more preferred range of enantiomer excess (ee) or diastereoisomer excess (de) is about 90% to about 100%. Another even more preferred range of enantiomer excess (ee) or diastereoisomer excess (de) is about 95% to about 100%. It is understood that the phrase "about 50% to about 100%" includes but is not limited to all the possible percentage numbers and fractions of a number from 50% to 100%. Similarly, the phrase "about 60% to about 100%" includes but is not limited to all the possible percentage numbers and fractions of a number from 60% to 100%; the phrase "about 70% to about 100%" includes but is not limited to all the possible percentage numbers and fractions of a number from 70% to 100%; the phrase "about 80% to about 100%" includes but is not limited to all the possible percentage numbers and fractions of a number from 80% to 100%; the phrase "about 85% to about 100%" includes all but is not limited to the possible percentage numbers and fractions of a number from 85% to 100%; the phrase "about 90% to about 100%" includes but is not limited to all the possible percentage numbers and fractions of a number from 90% to 100%; the phrase "about 95% to about 100%" includes all but is not limited to the possible percentage numbers and fractions of a number from 95% to 100%.

As an example, and in no way limiting, the generality of the above, a compound designated with the formula

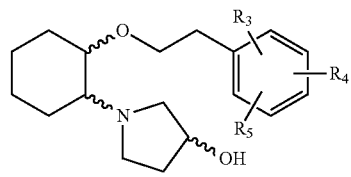

includes at least three chiral centers (the cyclohexyl carbon bonded to the oxygen ($C^1$), the cyclohexyl carbon bonded to the nitrogen ($C^2$), and the pyrrolidinyl carbon bonded to the oxygen ($C^{3'}$)) and therefor has at least eight separate stereoisomers, which are (1R,2R)-2-[(3R)-Hydroxypyrrolidinyl]-1-($R_3$, $R_4$ and $R_5$ substituted phenethoxy)-cyclohexane; (1R,2R)-2-[(3S)-Hydroxypyrrolidinyl]-1-($R_3$, $R_4$ and $R_5$ substituted phenethoxy)-cyclohexane; (1S,2S)-2-[(3R)-Hydroxypyrrolidinyl]-1-($R_3$, $R_4$ and $R_5$ substituted phenethoxy)-cyclohexane; (1S,2S)-2-[(3S)-Hydroxypyrrolidinyl]-1-($R_3$, $R_4$ and $R_5$ substituted phenethoxy)-cyclohexane; (1R,2S)-2-[(3R)-Hydroxypyrrolidinyl]-1-($R_3$, $R_4$ and $R_5$ substituted phenethoxy)-cyclohexane; (1R,2S)-2-[(3S)-Hydroxypyrrolidinyl]-1-($R_3$, $R_4$ and $R_5$ substituted phenethoxy)-cyclohexane; (1S,2R)-2-[(3R)-Hydroxypyrrolidinyl]-1-($R_3$, $R_4$ and $R_5$ substituted phenethoxy)-cyclohexane; and (1S,2R)-2-[(3S)-Hydroxypyrrolidinyl]-1-($R_3$, $R_4$ and $R_5$ substituted phenethoxy)-cyclohexane; and, unless the context make plain otherwise as used in this patent a compound of the formula

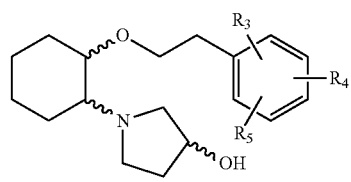

means a composition that includes a component that is either one of the possible pure enantiomeric or diastereisomeric forms of the indicated compound or is a mixture of any two or more of the pure enantiomeric or diastereisomeric forms, where the mixture can include any number of the enantiomeric or diastereisomeric forms in any ratio.

As an example, and in no way limiting the generality of the above, unless the context make plain otherwise as used in this patent a compound designated with the chemical formula (1R,2R)/(1S,2S)-2-[(3R)-Hydroxypyrrolidinyl]-1-(3,4-dimethoxyphenethoxy)-cyclohexane means a composition that includes a component that is either one or both of the two pure enantiomeric/diastereomeric forms of the indicated compound (i.e., (1R,2R)-2-[(3R)-Hydroxypyrrolidinyl]-1-(3,4-dimethoxyphenethoxy)-cyclohexane or (1S,2S)-2-[(3R)-Hydroxypyrrolidinyl]-1-(3,4-dimethoxyphenethoxy)-cyclohexane) or is a mixture of the two pure enantiomeric/diastereomeric forms, where the mixture can include any relative amount of the two enantiomers/diastereomers.

The phrase "independently at each occurrence" is intended to mean (i) when any variable occurs more than one time in a compound of the invention, the definition of that variable at each occurrence is independent of its definition at every other occurrence; and (ii) the identity of any one of two different variables (e.g., $R_1$ within the set $R_1$ and $R_2$) is selected without regard the identity of the other member of the set. However, combinations of substituents and/or variables are permissible only if such combinations result in compounds that do not violate the standard rules of chemical valency.

Certain chemical groups named herein are preceded by the shorthand notation "$C_x$-$C_y$" where x and y indicate the lower and upper, respectively, number of carbon atoms to be found in the indicated chemical group. For example; $C_1$-$C_8$alkyl describes an alkyl group, as defined below, having a total of 1 to 8 carbon atoms, and $C_7$-$C_{12}$aralkyl describes an aralkyl group, as defined below, having a total of 7 to 12 carbon atoms. Occasionally, certain chemical groups named herein are preceded by the shorthand notation "$C_z$" where z indicate the total number of carbons to be found in the indicated chemical group. The total number of carbons in the shorthand notation does not include carbons that may exist in substituents of the group described.

In accordance with the present invention and as used herein, the following terms are defined to have following meanings, unless explicitly stated otherwise:

"Acid addition salts" generally refer to but are not limited to those salts which retain the biological effectiveness and properties of the free bases and which are not biologically or otherwise undesirable, formed with inorganic acids such as but not limited to hydrochloric acid, hydrobromic acid, sulfuric acid, nitric acid, phosphoric acid and the like, or acceptable Lewis acids, or organic acids such as but not limited to acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like, and include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

"Acyl" refers to branched or unbranched hydrocarbon fragments terminated by a carbonyl —(C=O)— group containing the specified number of carbon atoms. Examples include acetyl (Ac) [$CH_3C(=O)$—, a $C_2$acyl] and propionyl [$CH_3CH_2C(=O)$—, a $C_3$acyl].

"Alkanoyloxy" refers to an ester substituent wherein the non-carbonyl oxygen is the point of attachment to the molecule. Examples include propanoyloxy [($CH_3CH_2C(=O)$—O—, a $C_3$ alkanoyloxy] and ethanoyloxy [$CH_3C(=O)$—O—, a $C_2$ alkanoyloxy].

"Aralkanoyloxy" refers to an ester substituent wherein the non-carbonyl oxygen is the point of attachment to the molecule and the ester substituent also comprises an alkylene group wherein one of the points of attachment is to an aryl group. An example of an aralkanoyloxy group is $C_6H_5CH_2C(=O)$—O—, a $C_8$ aralkanoyloxy group.

"Alkoxy" refers to an oxygen (O)-atom substituted by an alkyl group, for example, alkoxy can include but is not limited to methoxy, which may also be denoted as —$OCH_3$, —OMe or a $C_1$ alkoxy.

"Alkoxyalkyl" refers to an alkylene group substituted with an alkoxy group. For example, 2-methoxyethyl [$CH_3OCH_2CH_2$-] 1-methoxyethyl [$CH_3CH(OCH_3)$—] and ethoxymethyl ($CH_3CH_2OCH_2$—] are both $C_3$ alkoxyalkyl groups.

"Aralkoxy" refers to an oxygen (O)-atom substituted by an aralkyl group. An example of an aralkoxy group is $C_6H_5CH_2O$—, a $C_7$ aralkoxy group.

"Alkoxycarbonyl" refers to an ester substituent wherein the carbonyl carbon is the point of attachment to the molecule. Examples include ethoxycarbonyl [$CH_3CH_2OC(=O)$—, a $C_3$ alkoxycarbonyl] and methoxycarbonyl [$CH_3OC(=O)$—, a $C_2$ alkoxycarbonyl].

"Aralkoxycarbonyl" refers to an ester substituent wherein the carbonyl carbon is the point of attachment to the molecule and the ester substituent also comprises an alkylene group wherein one of the points of attachment is to an aryl group. An example of an aralkoxycarbonyl group is $C_6H_5CH_2O$—C(=O)—, a $C_8$ aralkoxycarbonyl group.

"Alkyl" refers to a branched or unbranched hydrocarbon fragment containing the specified number of carbon atoms and having one point of attachment. Examples include n-propyl (a $C_3$ alkyl), iso-propyl (also a $C_3$ alkyl), and t-butyl (a $C_4$ alkyl). Methyl is represented by the symbol Me or $CH_3$.

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$ alkylene].

"Alkylcarboxy" refers to a branched or unbranched hydrocarbon fragment terminated by a carboxylic acid group [—COOH]. Examples include carboxymethyl [HOOC—$CH_2$—, a $C_2$ alkylcarboxy] and carboxyethyl [HOOC—$CH_2CH_2$—, a $C_3$ alkylcarboxy].

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds of the present invention, where phenyl and naphthyl groups are preferred carbocyclic aryl groups. Preferred optional substituents include alkyl, alkoxy, acyl, and halo (such as bromo and fluoro).

"Aralkyl" refers to an alkylene group wherein one of the points of attachment is to an aryl group. An example of an aralkyl group is the benzyl group (Bn) [$C_6H_5CH_2$—, a $C_7$ aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present invention.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio See particularly Section C, Rules for Naming Organic Compounds, B. Fundamental Heterocyclic Systems. Suitable heteroaryls include but not limited to furanyl, thienyl, pyridyl, pyrrolyl, pyrimidyl, pyrazinyl, imidazolyl, and the like.

"Hydroxyalkyl" refers to a branched or unbranched hydrocarbon fragment bearing an hydroxy (—OH) group. Examples include hydroxymethyl (—CH$_2$OH, a C$_1$hydroxyalkyl) and 1-hydroxyethyl (—CHOHCH$_3$, a C$_1$hydroxyalkyl).

"Thioalkyl" refers to a sulfur atom substituted by an alkyl group, for example thiomethyl (CH$_3$S—, a C$_1$thioalkyl).

"Modulating" in connection with the activity of an ion channel means that the activity of the ion channel may be either increased or decreased in response to administration of a compound or composition or method of the present invention. Thus, the ion channel may be activated, so as to transport more ions, or may be blocked, so that fewer or no ions are transported by the channel.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and a pharmaceutically acceptable organic or inorganic acid (acid addition salts) or a pharmaceutically acceptable organic or inorganic base (base addition salts) which retain the biological effectiveness and properties of the compounds of the present invention and which are not biologically or otherwise undesirable. Examples of pharmaceutically acceptable salt include but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002. The compounds of the present invention may be used in either the free base or salt forms, with both forms being considered as being within the scope of the present invention.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Compositions described herein as "containing a compound of the present invention" encompass compositions that may contain more than one compound of the present invention formula.

The synthetic methods/procedures described herein, especially when taken with the general knowledge in the art, provide sufficient guidance to perform the synthesis, isolation, and purification of the compounds of the present invention.

EMBODIMENTS OF THE INVENTION

One embodiment of the method of making compounds of formula (7), as set forth above in the Summary of the Invention, is that embodiment which further comprises optionally protecting the compound of formula (5) and/or the compound of formula (6) before the reaction of compound of formula (5) with the compound of formula (6) and optionally deprotecting the compound of formula (7) after the reaction.

One embodiment of the method of making compounds of formula (7), as set forth above in the Summary of the Invention, is that embodiment wherein the compound of formula (7) is a compound of formula (7a):

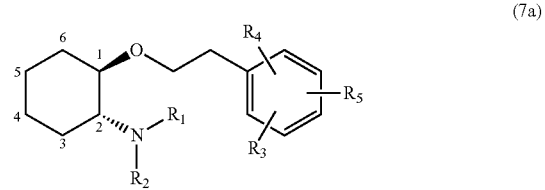

(7a)

or a pharmaceutically acceptable salt, ester, amide, complex, chelate, clathrate, solvate, polymorph, metabolite or prodrug thereof, wherein $R_1$ and $R_2$ are each independently selected from hydrogen, $C_1$-$C_8$alkyl, $C_3$-$C_8$alkoxyalkyl, $C_1$-$C_8$hydroxyalkyl, $C_8$-$C_{12}$aralkoxycarbonyl and $C_7$-$C_{12}$aralkyl; or $R_1$ and $R_2$ are each independently selected from $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached, form a ring denoted by formula (I):

(I)

wherein the ring of formula (I) is formed from the nitrogen as shown as well as three to nine additional ring atoms independently selected from the group consisting of carbon, nitrogen, oxygen, and sulfur; where any two adjacent ring atoms may be joined together by single or double bonds, and where any one or more of the additional carbon ring atoms may be substituted with one or two substituents selected from the group consisting of hydrogen, hydroxy, $C_1$-$C_3$hydroxyalkyl, oxo, $C_2$-$C_4$acyl, $C_1$-$C_3$ alkyl, $C_2$-$C_4$alkylcarboxy, $C_1$-$C_3$alkoxy, $C_7$-$C_{12}$aralkoxy, and $C_1$-$C_{20}$alkanoyloxy, or may be substituted to form a spiro five- or six-membered heterocyclic ring containing one or two heteroatoms selected from the group consisting of carbon, nitrogen, oxygen, and sulfur; or any two adjacent additional carbon ring atoms may be fused to a $C_3$-$C_8$carbocyclic ring, and any one or more of the additional nitrogen ring atoms may be substituted with substituents selected from the group consisting of hydrogen, $C_1$-$C_6$alkyl, $C_2$-$C_4$acyl, $C_2$-$C_4$hydroxyalkyl and $C_3$-$C_8$alkoxyalkyl;

or $R_1$ and $R_2$, when taken together with the nitrogen atom to which they are directly attached, form a bicyclic ring system comprising 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl; and wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —CHF$_2$, —SO$_2$N(R$_8$)R$_9$, —OCF$_3$, C$_2$-C$_7$alkanoyloxy, C$_1$-C$_6$alkyl, C$_1$-C$_6$alkoxy, C$_7$-C$_{12}$aralkoxy, C$_2$-C$_7$alkoxycarbonyl, C$_1$-C$_6$thioalkyl, aryl or —N(R$_6$)R$_7$, where R$_6$, R$_7$, R$_8$, and R$_9$ are each independently selected from hydrogen, acetyl, methanesulfonyl or C$_1$-C$_6$ alkyl;

or R$_3$, R$_4$ and R$_5$ are independently hydrogen, hydroxy or C$_1$-C$_6$ alkoxy; with the proviso that R$_3$, R$_4$ and R$_5$ cannot all be hydrogen at the same time;

and the compound of formula (5) is a compound of formula (5a):

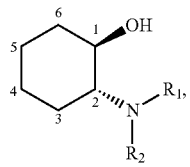

(5a)

wherein R$_1$ and R$_2$ are as defined in the Summary of the Invention.

Another embodiment of the method of making compounds of formula (7) or formula (7a), as set forth above in the Summary of the Invention, is that embodiment wherein the suitable conditions for treating the compound of formula (5) or formula (5a) with the compound of formula (6) comprise activating Q in the presence of an acid.

Another embodiment of the method of making compounds of formula (7) or formula (7a), as set forth above in the Summary of the Invention, is that embodiment wherein the suitable conditions for treating the compound of formula (5) or formula (5a) with the compound of formula (6) comprise activating Q in the presence of a catalytic amount of an acid in an aprotic solvent.

One embodiment of the making of the compounds of formula (7a), as set forth above in the Summary of the Invention, is that embodiment which further comprises a separation step prior to the reaction of the compound of formula (5a) with the compound of formula (6), wherein the separation step comprises separating a mixture of a compound of formula (5a):

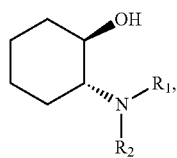

(5a)

wherein R$_1$ and R$_2$ are as defined above, and a compound of formula (4a):

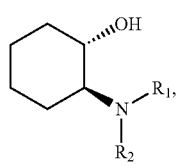

(4a)

wherein R$_1$ and R$_2$ are as defined above, under suitable conditions to yield a compound of formula (5a) in isolation from the compound of formula (4a), wherein the separation step further comprises an optional functionalization step wherein the hydroxy group and/or the —N(R$^1$)R$^2$ group of one or both of the compound of formula (4a) and the compound of formula (5a) are functionalized in a manner in which the resulting functionalized compounds are amenable to resolution; performing resolution under suitable conditions to separate the functionalized compounds; and optionally removing, under suitable conditions, the functional group from the functionalized compounds.

One embodiment of the making of the compounds of formula (8), as set forth above in the Summary of the Invention, is that embodiment which further comprises optionally protecting the compound of formula (4) and/or the compound of formula (6) before the reaction of compound of formula (4) with the compound of formula (6) and optionally deprotecting the compound of formula (8) after the reaction.

One embodiment of the method of making compounds of formula (8), as set forth above in the Summary of the Invention, is that embodiment wherein the compound of formula (8) is a compound of formula (8a):

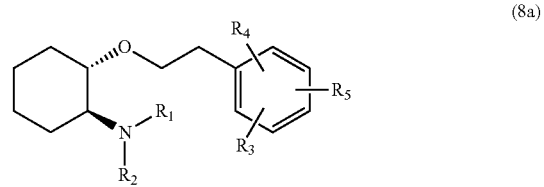

(8a)

or a pharmaceutically acceptable salt, ester, amide, complex, chelate, clathrate, solvate, polymorph, metabolite or prodrug thereof, wherein R$_1$ and R$_2$ are each independently selected from hydrogen, C$_1$-C$_8$alkyl, C$_3$-C$_8$alkoxyalkyl, C$_1$-C$_8$hydroxyalkyl, C$_8$-C$_{12}$aralkoxycarbonyl and C$_7$-C$_{12}$aralkyl; or R$_1$ and R$_2$ are each independently selected from C$_3$-C$_8$alkoxyalkyl, C$_1$-C$_8$hydroxyalkyl, and C$_7$-C$_{12}$aralkyl; or R$_1$ and R$_2$, when taken together with the nitrogen atom to which they are directly attached, form a ring denoted by formula (I):

(I)

wherein the ring of formula (I) is formed from the nitrogen as shown as well as three to nine additional ring atoms independently selected from the group consisting of carbon, nitrogen, oxygen, and sulfur; where any two adjacent ring atoms may be joined together by single or double bonds, and where any one or more of the additional carbon ring atoms may be substituted with one or two substituents selected from the group consisting of hydrogen, hydroxy, C$_1$-C$_3$hydroxyalkyl, oxo, C$_2$-C$_4$acyl, C$_1$-C$_3$ alkyl, C$_2$-C$_4$alkylcarboxy, C$_1$-C$_3$alkoxy, C$_7$-C$_{12}$aralkoxy, and C$_1$-C$_{20}$alkanoyloxy, or may be substituted to form a spiro five- or six-membered heterocyclic ring containing one or two heteroatoms selected from the group consisting of carbon, nitrogen, oxygen, and sulfur; or any two adjacent additional carbon ring atoms may be fused to a $C_3$-$C_8$carbocyclic ring, and any one or more of the additional nitrogen ring atoms may be substituted with substituents selected from the group consisting of hydrogen, $C_1$-$C_6$alkyl, $C_2$-$C_4$acyl, $C_2$-$C_4$hydroxyalkyl and $C_3$-$C_8$alkoxyalkyl;

or $R_1$ and $R_2$, when taken together with the nitrogen atom to which they are directly attached, form a bicyclic ring system comprising 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl; and wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$, where $R_6$, $R_7$, $R_8$, and $R_9$ are each independently selected from hydrogen, acetyl, methanesulfonyl or $C_1$-$C_6$ alkyl;

or $R_3$, $R_4$ and $R_5$ are independently hydrogen, hydroxy or $C_1$-$C_6$ alkoxy; with the proviso that $R_3$, $R_4$ and $R_5$ cannot all be hydrogen at the same time;

and the compound of formula (4) is a compound of formula (4a):

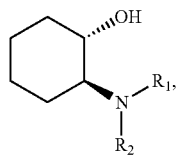

(4a)

wherein $R_1$ and $R_2$ are as defined in the Summary of the Invention.

Another embodiment of the method of making compounds of formula (8) or formula (8a), as set forth above in the Summary of the Invention, is that embodiment wherein the suitable conditions for treating the compound of formula (4) or formula (4a) with the compound of formula (6) comprise activating Q in the presence of an acid.

Another embodiment of the method of making compounds of formula (8) or formula (8a), as set forth above in the Summary of the Invention, is that embodiment wherein the suitable conditions for treating the compound of formula (4) or formula (4a) with the compound of formula (6) comprise activating Q in the presence of a catalytic amount of an acid in an aprotic solvent.

One embodiment of the making of the compounds of formula (8a), as set forth above in the Summary of the Invention, is that embodiment which further comprises a separation step prior to the reaction of the compound of formula (4a) with the compound of formula (6), wherein the separation step comprises separating a mixture of a compound of formula (5a):

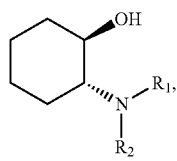

(5a)

wherein $R_1$ and $R_2$ are as defined above, and a compound of formula (4a):

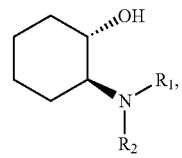

(4a)

wherein $R_1$ and $R_2$ are as defined above, under suitable conditions to yield a compound of formula (4a) in isolation from the compound of formula (5a), wherein the separation step further comprises an optional functionalization step wherein the hydroxy group and/or the —$N(R^1)R^2$ group of one or both of the compound of formula (4a) and the compound of formula (5a) are functionalized in a manner in which the resulting functionalized compounds are amenable to resolution; performing resolution under suitable conditions to separate the functionalized compounds; and optionally removing, under suitable conditions, the functional group from the functionalized compounds.

One embodiment of the making of the compounds of formula (73), as set forth above in the Summary of the Invention, is that embodiment which further comprises optionally protecting the compound of formula (71) and/or the compound of formula (6) before the reaction of compound of formula (71) with the compound of formula (6) and optionally deprotecting the compound of formula (73) after the reaction.

One embodiment of the method of making compounds of formula (73), as set forth above in the Summary of the Invention, is that embodiment wherein the compound of formula (73) is a compound of formula (73a):

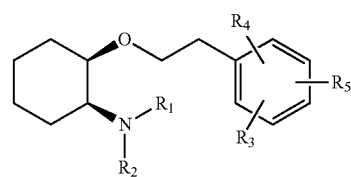

(73a)

or a pharmaceutically acceptable salt, ester, amide, complex, chelate, clathrate, solvate, polymorph, metabolite or prodrug thereof, wherein $R_1$ and $R_2$ are each independently selected from hydrogen, $C_1$-$C_8$alkyl, $C_3$-$C_8$alkoxyalkyl, $C_1$-$C_8$hydroxyalkyl, $C_8$-$C_{12}$aralkoxycarbonyl and $C_7$-$C_{12}$aralkyl; or $R_1$ and $R_2$ are each independently selected from $C_3$-$C_8$alkoxyalkyl, $C_1$-$C_8$hydroxyalkyl, and $C_7$-$C_{12}$aralkyl; or $R_1$ and $R_2$, when taken together with the nitrogen atom to which they are directly attached, form a ring denoted by formula (I):

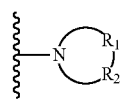

(I)

wherein the ring of formula (I) is formed from the nitrogen as shown as well as three to nine additional ring atoms independently selected from the group consisting of carbon, nitrogen, oxygen, and sulfur; where any two adjacent ring atoms may be joined together by single or double bonds, and where any one or more of the additional carbon ring atoms may be substituted with one or two substituents selected from the group consisting of hydrogen, hydroxy, $C_1$-$C_3$hydroxyalkyl, oxo, $C_2$-$C_4$acyl, $C_1$-$C_3$ alkyl, $C_2$-$C_4$alkylcarboxy, $C_1$-$C_3$alkoxy, $C_7$-$C_{12}$aralkoxy, and $C_1$-$C_{20}$alkanoyloxy, or may be substituted to form a spiro five- or six-membered heterocyclic ring containing one or two heteroatoms selected from the group consisting of carbon, nitrogen, oxygen, and sulfur; or any two adjacent additional carbon ring atoms may be fused to a $C_3$-$C_8$carbocyclic ring, and any one or more of the additional nitrogen ring atoms may be substituted with substituents selected from the group consisting of hydrogen, $C_1$-$C_6$alkyl, $C_2$-$C_4$acyl, $C_2$-$C_4$hydroxyalkyl and $C_3$-$C_8$alkoxyalkyl;

or $R_1$ and $R_2$, when taken together with the nitrogen atom to which they are directly attached, form a bicyclic ring system comprising 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl; and wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, $C_2$-$C_7$alkanoyloxy, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$, where $R_6$, $R_7$, $R_8$, and $R_9$ are each independently selected from hydrogen, acetyl, methanesulfonyl or $C_1$-$C_6$ alkyl;

or $R_3$, $R_4$ and $R_5$ are independently hydrogen, hydroxy or $C_1$-$C_6$ alkoxy; with the proviso that $R_3$, $R_4$ and $R_5$ cannot all be hydrogen at the same time;

and the compound of formula (71) is a compound of formula (71a):

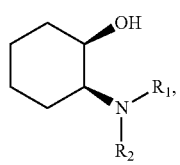

(71a)

wherein $R_1$ and $R_2$ are as defined in the Summary of the Invention.

Another embodiment of the method of making compounds of formula (73) or formula (73a), as set forth above in the Summary of the Invention, is that embodiment wherein the suitable conditions for treating the compound of formula (71) or formula (71a) with the compound of formula (6) comprise activating Q in the presence of an acid.

Another embodiment of the method of making compounds of formula (73) or formula (73a), as set forth above in the Summary of the Invention, is that embodiment wherein the suitable conditions for treating the compound of formula (71) or formula (71a) with the compound of formula (6) comprise activating Q in the presence of a catalytic amount of an acid in an aprotic solvent.

One embodiment of the making of the compounds of formula (73a), as set forth above in the Summary of the Invention, is that embodiment which further comprises a separation step prior to the reaction of the compound of formula (71a) with the compound of formula (6), wherein the separation step comprises separating a mixture of a compound of formula (71a):

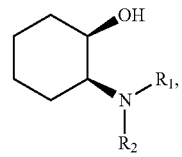

(71a)

wherein $R_1$ and $R_2$ are as defined above, and a compound of formula (72a):

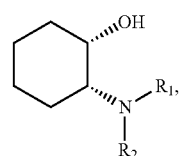

(72a)

wherein $R_1$ and $R_2$ are as defined above, under suitable conditions to yield a compound of formula (71a) in isolation from the compound of formula (72a), wherein the separation step further comprises an optional functionalization step wherein the hydroxy group and/or the —$N(R^1)R^2$ group of one or both of the compound of formula (71a) and the compound of formula (72a) are functionalized in a manner in which the resulting functionalized compounds are amenable to resolution; performing resolution under suitable conditions to separate the functionalized compounds; and optionally removing, under suitable conditions, the functional group from the functionalized compounds.

One embodiment of the making of the compounds of formula (74), as set forth above in the Summary of the Invention, is that embodiment which further comprises optionally protecting the compound of formula (72) and/or the compound of formula (6) before the reaction of compound of formula (72) with the compound of formula (6) and optionally deprotecting the compound of formula (74) after the reaction.

One embodiment of the method of making compounds of formula (74), as set forth above in the Summary of the Invention, is that embodiment wherein the compound of formula (74) is a compound of formula (74a):

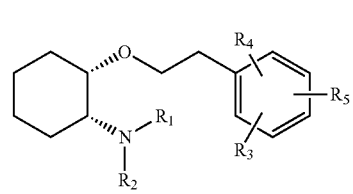

(74a)

or a pharmaceutically acceptable salt, ester, amide, complex, chelate, clathrate, solvate, polymorph, metabolite or prodrug thereof, wherein $R_1$ and $R_2$ are each independently selected from hydrogen, $C_1$-$C_8$alkyl, $C_3$-$C_8$alkoxyalkyl, $C_1$-$C_8$hydroxyalkyl, $C_8$-$C_{12}$aralkoxycarbonyl and $C_7$-$C_{12}$aralkyl; or $R_1$ and $R_2$ are each independently selected from $C_3$-$C_5$alkoxyalkyl, $C_1$-$C_8$hydroxyalkyl, and $C_7$-$C_{12}$aralkyl; or $R_1$ and $R_2$, when taken together with the nitrogen atom to which they are directly attached, form a ring denoted by formula (I):

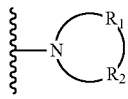

(I)

wherein the ring of formula (I) is formed from the nitrogen as shown as well as three to nine additional ring atoms independently selected from the group consisting of carbon, nitrogen, oxygen, and sulfur; where any two adjacent ring atoms may be joined together by single or double bonds, and where any one or more of the additional carbon ring atoms may be substituted with one or two substituents selected from the group consisting of hydrogen, hydroxy, $C_1$-$C_3$hydroxyalkyl, oxo, $C_2$-$C_4$acyl, $C_1$-$C_3$ alkyl, $C_2$-$C_4$alkylcarboxy, $C_1$-$C_3$alkoxy, $C_7$-$C_{12}$aralkoxy, and $C_1$-$C_{20}$alkanoyloxy, or may be substituted to form a spiro five- or six-membered heterocyclic ring containing one or two heteroatoms selected from the group consisting of carbon, nitrogen, oxygen, and sulfur; or any two adjacent additional carbon ring atoms may be fused to a $C_3$-$C_8$carbocyclic ring, and any one or more of the additional nitrogen ring atoms may be substituted with substituents selected from the group consisting of hydrogen, $C_1$-$C_6$alkyl $C_2$-$C_4$acyl, $C_2$-$C_4$hydroxyalkyl and $C_3$-$C_8$alkoxyalkyl;

or $R_1$ and $R_2$, when taken together with the nitrogen atom to which they are directly attached, form a bicyclic ring system comprising 3-azabicyclo[3.2.2]nonan-3-yl, 2-azabicyclo[2.2.2]octan-2-yl, 3-azabicyclo[3.1.0]hexan-3-yl, and 3-azabicyclo[3.2.0]heptan-3-yl; and wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, $C_2$-$C_7$alkanoyloxy, $C_1$-$C_6$alkoxy, $C_7$-$C_{12}$aralkoxy, $C_2$-$C_7$alkoxycarbonyl, $C_1$-$C_6$thioalkyl, aryl or —$N(R_6)R_7$, where $R_6$, $R_7$, $R_8$, and $R_9$ are each independently selected from hydrogen, acetyl, methanesulfonyl or $C_1$-$C_6$ alkyl;

or $R_3$, $R_4$ and $R_5$ are independently hydrogen, hydroxy or $C_1$-$C_6$ alkoxy; with the proviso that $R_3$, $R_4$ and $R_5$ cannot all be hydrogen at the same time;

and the compound of formula (72) is a compound of formula (72a):

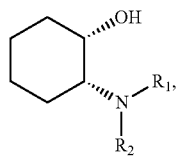

(72a)

wherein $R_1$ and $R_2$ are as defined in the Summary of the Invention.

Another embodiment of the method of making compounds of formula (74) or formula (74a), as set forth above in the Summary of the Invention, is that embodiment wherein the suitable conditions for treating the compound of formula (72) or formula (72a) with the compound of formula (6) comprise activating Q in the presence of an acid.

Another embodiment of the method of making compounds of formula (74) or formula (74a), as set forth above in the Summary of the Invention, is that embodiment wherein the suitable conditions for treating the compound of formula (72) or formula (72a) with the compound of formula (6) comprise activating Q in the presence of a catalytic amount of an acid in an aprotic solvent.

One embodiment of the making of the compounds of formula (74a), as set forth above in the Summary of the Invention, is that embodiment which further comprises a separation step prior to the reaction of the compound of formula (72a) with the compound of formula (6), wherein the separation step comprises separating a mixture of a compound of formula (71a):

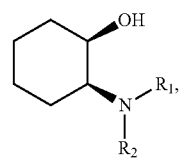

(71a)

wherein $R_1$ and $R_2$ are as defined above, and a compound of formula (72a):

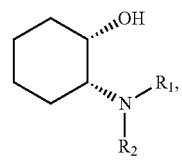

(72a)

wherein $R_1$ and $R_2$ are as defined above, under suitable conditions to yield a compound of formula (72a) in isolation from the compound of formula (71a), wherein the separation step further comprises an optional functionalization step wherein the hydroxy group and/or the —$N(R^1)R^2$ group of one or both of the compound of formula (71a) and the compound of formula (72a) are functionalized in a manner in which the resulting functionalized compounds are amenable to resolution; performing resolution under suitable conditions to separate the functionalized compounds; and optionally removing, under suitable conditions, the functional group from the functionalized compounds.

One embodiment of the method of making the compounds of formulae (7), (8), (73) and (74) is that method wherein the separation step comprises crystallization, kinetic resolution, chemical separation, enzymatic resolution, and/or chromatographic resolution.

Of this embodiment, one embodiment is wherein the optional functionalization step comprises formation of acid addition salts of the mixture of the compound of formula (4) and the compound of formula (5) or the mixture of the compound of formula (71) and the compound of formula (7).

Of this embodiment, another embodiment is wherein the separation step comprises crystallization.

Of this embodiment, another embodiment is wherein the separation step comprises kinetic resolution.

Of this embodiment, another embodiment is wherein the separation step comprises chemical separation via diastereomers.

Of this embodiment, another embodiment is wherein the separation step and/or resolution is enzyme mediated.

Of this embodiment, another embodiment is wherein the separation step comprises chromatographic resolution.

Of the aspects of making the compounds of formula (7), (8), (73) and (74), as set forth above in the Summary of the Invention, one embodiment is that method wherein, independently at each occurrence:

$R_1$ is selected from hydrogen, $C_1$-$C_8$alkyl, $C_8$-$C_{12}$aralkoxycarbonyl and $C_7$-$C_{12}$aralkyl;

$R_2$ is selected from hydrogen, $C_1$-$C_8$alkyl, $C_8$-$C_{12}$aralkoxycarbonyl and $C_7$-$C_{12}$aralkyl;

or $R_1$ and $R_2$, when taken together with the nitrogen atom to which they are directly attached, form a ring denoted by formula (I):

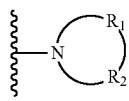

(I)

wherein the ring of formula (I) is formed from the nitrogen as shown as well as three to eight additional ring atoms independently selected from the group consisting of carbon, nitrogen, oxygen, and sulfur; where any two adjacent ring atoms may be joined together by single or double bonds, and where any one or more of the additional carbon ring atoms may be substituted with one or two substituents selected from the group consisting of hydrogen, hydroxy, $C_1$-$C_3$ hydroxyalkyl, oxo, $C_2$-$C_4$acyl, $C_1$-$C_3$alkyl, $C_2$-$C_4$alkylcarboxy, $C_1$-$C_3$alkoxy, $C_7$-$C_{12}$aralkoxy, and $C_1$-$C_{20}$alkanoyloxy, or may be substituted to form a spiro five- or six-membered heterocyclic ring containing one or two heteroatoms selected from the group consisting of carbon, nitrogen, oxygen, and sulfur; and any one or more of the additional nitrogen ring atoms may be substituted with substituents selected from the group consisting of hydrogen, $C_1$-$C_6$alkyl, $C_7$-$C_{12}$aralkyl, $C_2$-$C_4$acyl, $C_2$-$C_4$hydroxyalkyl and $C_3$-$C_8$alkoxyalkyl;

$R_3$, $R_4$ and $R_5$ are independently chlorine, fluorine, hydrogen, hydroxy, hydroxymethyl, methanesulfonamido, nitro, cyano, sulfamyl, trifluoromethyl, —$CHF_2$, —$SO_2N(R_8)R_9$, —$OCF_3$, $C_2$-$C_7$alkanoyloxy, $C_1$-$C_6$alkyl, $C_1$-$C_6$alkoxy, $C_7$-$C_{12}$aralkoxy, $C_2$-$C_7$alkoxycarbonyl, or —$N(R_6)R_7$ where $R_6$, $R_7$, $R_8$, and $R_9$ are independently hydrogen, acetyl, methanesulfonyl or $C_1$-$C_6$ alkyl; or $R_3$, $R_4$ and $R_5$ are independently hydrogen, hydroxy or $C1$-$C6$alkoxy; with the proviso that $R_3$, $R_4$ and $R_5$ cannot all be hydrogen at the same time; and Q is an imidate ester, an O-carbonate, a S-carbonate, an O-sulfonyl derivative, or a phosphate derivative.

Of this embodiment, one embodiment is wherein, independently at each occurrence, the ring of formula (I) is formed from the nitrogen as shown as well as four to five additional ring atoms independently selected from the group consisting of carbon; where any two adjacent ring atoms may be joined together by single or double bonds, and where any one or more of the additional carbon ring atoms may be substituted with one or two substituents selected from the group consisting of hydrogen, hydroxy, oxo, $C_2$-$C_4$acyl, $C_7$-$C_{12}$aralkoxy, and $C_1$-$C_3$alkoxy; and wherein $R_3$, $R_4$ and $R_5$ are independently hydrogen, hydroxy or $C_1$-$C_6$ alkoxy, with the proviso that $R_3$, $R_4$ and $R_5$ cannot all be hydrogen at the same time.

Of the various aspects of the invention as set forth above in the Summary of the Invention and the various embodiments of the invention as set forth above, one embodiment is the method wherein, independently at each occurrence, the ring of formula (I) is:

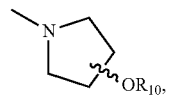

where $R_{10}$ is either hydrogen, or $C_7$-$C_{12}$aralkyl;

wherein at least one of $R_3$, $R_4$ and $R_5$ is $C_1$-$C_6$alkoxy; and wherein Q is a trihaloacetimidate, a pentafluorobenzimidate, an imidazole carbonate derivative, an imidazolethiocarbonate, an O-sulfonyl derivative, a diphenyl phosphate, a diphenylphosphineimidate, or a phosphoroamidate.

Of this embodiment, one embodiment is that method wherein, independently at each occurrence, the ring of formula (I) is:

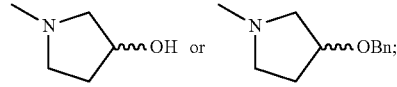

wherein at least two of $R_3$, $R_4$ and $R_5$ are $C_1$-$C_4$alkoxy; and wherein Q is a trichloroacetimidate, a pentafluorobenzimidate, an imidazole carbonate derivative, an imidazolethiocarbonate, an O-sulfonyl derivative, a diphenyl phosphate, a diphenylphosphineimidate, or a phosphoroamidate Of this embodiment, one embodiment is that method wherein, independently at each occurrence, the ring of formula (I) is:

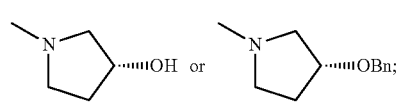

wherein $R_3$ is hydrogen, and $R_4$ and $R_5$ are each $C_1$-$C_4$alkoxy; and wherein Q is a trichloroacetimidate, or a pentafluorobenzimidate.

Of this embodiment, another embodiment is that method wherein, independently at each occurrence, the ring of formula (I) is:

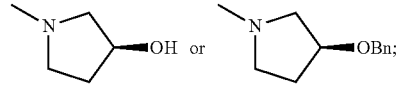

wherein $R_3$ is hydrogen, and $R_4$ and $R_5$ are each $C_1$-$C_4$alkoxy; and wherein Q is a trichloroacetimidate, or a pentafluorobenzimidate.

One embodiment of the invention is that embodiment wherein the aminocyclohexyl ether of formula (7) is:

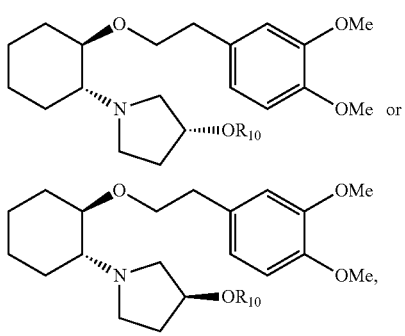

wherein $R_{10}$ is hydrogen or $C_7$-$C_{12}$aralkyl.

Another embodiment of the invention is that embodiment wherein the aminocyclohexyl ether of formula (8) is:

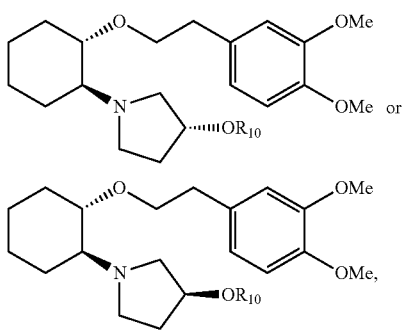

wherein $R_{10}$ is hydrogen or $C_7$-$C_{12}$aralkyl.

Another embodiment of the invention is that embodiment wherein the aminocyclohexyl ether of formula (73) is:

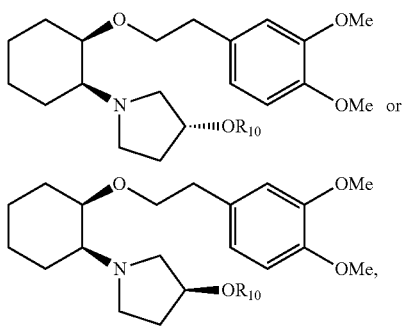

wherein $R_{10}$ is either hydrogen, or $C_7$-$C_{12}$ aralkyl.

Another embodiment of the invention is that embodiment wherein the aminocyclohexyl ether of formula (74) is:

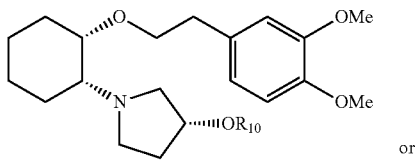

or

-continued

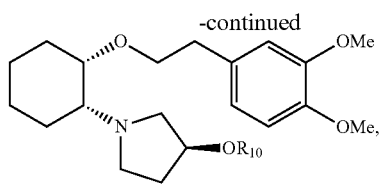

wherein $R_{10}$ is either hydrogen, or $C_7$-$C_{12}$aralkyl.

One embodiment of the invention is wherein the aminocyclohexyl ether of formula (7) is a compound of formula (75):

(75)

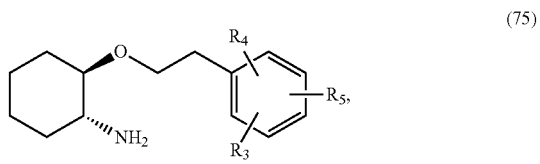

wherein $R_3$, $R_4$ and $R_5$ are the same as defined for compounds of formula (7).

One embodiment of the invention is wherein the aminocyclohexyl ether of formula (8) is a compound of formula (76):

(76)

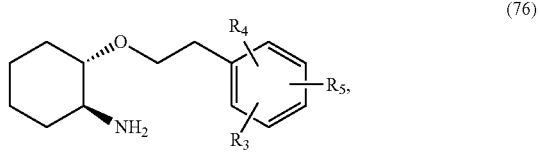

wherein $R_3$, $R_4$ and $R_5$ are the same as defined for compounds of formula (8).

One embodiment of the invention is wherein the aminocyclohexyl ether of formula (73) is a compound of formula (77):

(77)

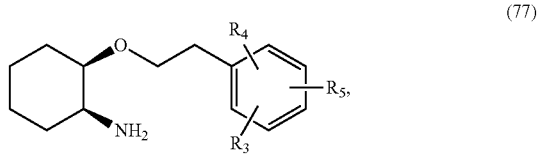

wherein $R_3$, $R_4$ and $R_5$ are the same as defined for compounds of formula (73).

One embodiment of the invention is wherein the aminocyclohexyl ether of formula (74) is a compound of formula (78):

(78)

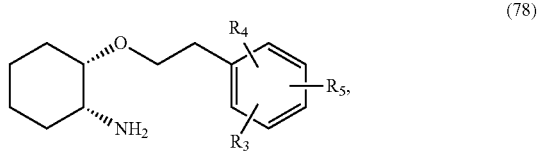

wherein $R_3$, $R_4$ and $R_5$ are the same as defined for compounds of formula (74).

Of these embodiments for compounds of formulae (75), (76), (77) and (78), one embodiment is the method wherein $R_3$, $R_4$ and $R_5$ are independently hydrogen, hydroxy or $C_1$-$C_6$alkoxy, with the proviso that $R_3$, $R_4$ and $R_5$ cannot all be hydrogen at the same time.

Another embodiment of these embodiments for compounds of formulae (75), (76), (77) and (78) is the method wherein $R_3$, $R_4$ and $R_5$ are independently hydrogen, hydroxy or $C_1$-$C_6$ alkoxy, with the proviso that $R_3$, $R_4$ and $R_5$ cannot all be hydrogen at the same time.

Of this embodiment, one embodiment is the method wherein $R_3$ is hydrogen, and $R_4$ and $R_5$ are each $C_1$-$C_4$ alkoxy.

Of this embodiment, one embodiment is the method wherein $R_4$ and $R_5$ are each $C_1$alkoxy at the 3- and 4-carbon position of the phenyl group, respectively.

Of the above embodiments, one embodiment is wherein each Lg is independently chloro or bromo; $R_{11}$ is $C_1$-$C_3$alkyl; $R_{12}$ is $C_2$-$C_3$acyl; and $R_{13}$ is $C_2$-$C_3$acyl.

Of the above embodiments, one embodiment is wherein the reducing reagent for step (b) is Red-Al (Vitride, Sodium aluminum bis(2-methoxyethoxy)hydride. CAS [22722-98-1]).

In one embodiment, the present invention provides a compound of formula (7), or a solvate, pharmaceutically acceptable salt, ester, amide, complex, chelate, stereoisomer, clathrate, stereoisomeric mixture, geometric isomer, crystalline or amorphous form, metabolite, metabolic precursor or prodrug thereof prepared by the method of the present invention:

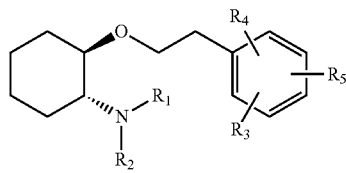

(7)

In one embodiment, the present invention provides a compound of formula (8), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof prepared by the method of the present invention:

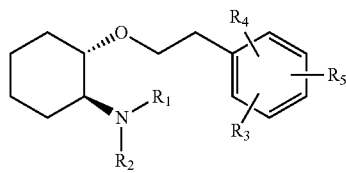

(8)

In one embodiment, the present invention provides a compound of formula (14A), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof prepared by the method of the present invention:

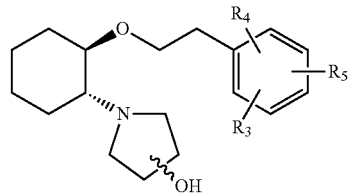

(14A)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14A), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14A), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14A), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14A), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14A), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14A), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14A), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14B), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

(14B)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14B), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14B), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14B), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14B), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14B), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14B), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14B), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14C), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

(14C)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14C), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14C), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14C), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14C), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14C), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14C), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14C), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14D), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

(14D)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14D), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14D), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14D), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14D), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14D), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14D), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14D), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14E), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

(14E)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14E), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14E), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14E), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14E), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14E), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14E), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14E), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14F), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

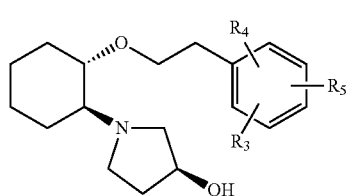

(14F)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14F), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14F), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14F), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14F), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14F), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14F), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14F), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (73), or a solvate, pharmaceutically acceptable salt, ester, amide, complex, chelate, stereoisomer, clathrate, stereoisomeric mixture, geometric isomer, crystalline or amorphous form, metabolite, metabolic precursor or prodrug thereof prepared by the method of the present invention.

In one embodiment, the present invention provides a compound of formula (74), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof prepared by the method of the present invention.

In one embodiment, the present invention provides a compound of formula (14G), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof prepared by the method of the present invention:

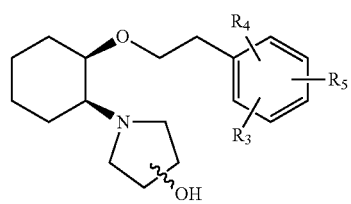

(14G)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14G), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14G), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14G), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14G), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14G), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14G), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14G), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14H), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

(14H)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14H), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14H), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14H), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14H), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14H), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14H), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14H), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14I), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

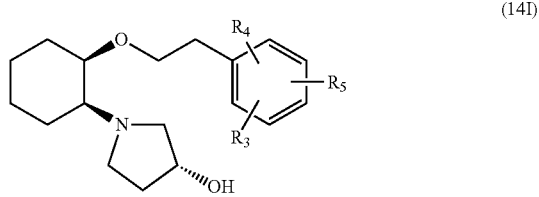

(14I)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14I), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14I), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14I), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14I), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14I), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14I), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14I), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14J), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

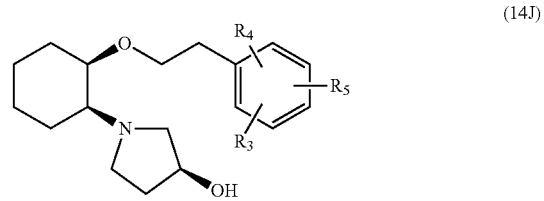

(14J)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14J), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14J), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14J), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14J), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14J), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14J), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14J), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14K), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

(14K)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14K), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14K), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14K), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14K), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14K), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14K), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14K), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound of formula (14L), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, prepared by the method of the present invention:

(14L)

wherein $R_3$, $R_4$ and $R_5$ are independently hydrogen, hydroxy or $C_1$-$C_6$ alkoxy, including isolated enantiomeric, diastereoisomeric and geometric isomers thereof, and mixtures thereof, with the proviso that $R_3$, $R_4$ and $R_5$ cannot all be hydrogen.

In one embodiment, the present invention provides a compound of formula (14L), or a solvate, pharmaceutically acceptable salt thereof, including isolated enantiomeric, diastereoisomeric and geometric isomers thereof, and mixtures, thereof prepared by the method of the present invention.

In one embodiment, the present invention provides a compound of formula (14L), or a solvate, pharmaceutically acceptable salt thereof, prepared by the method of the present invention wherein $R_3$ is hydrogen, $R_4$ and $R_5$ are independently hydroxy or $C_1$-$C_6$ alkoxy, including isolated enantiomeric, diastereoisomeric and geometric isomers thereof, and mixtures thereof.

In one embodiment, the present invention provides a compound of formula (14L), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently hydroxy or $C_1$-$C_4$ alkoxy.

In one embodiment, the present invention provides a compound of formula (14L), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14L), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are independently $C_1$-$C_4$ alkoxy.

In one embodiment, the present invention provides a compound of formula (14L), or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In one embodiment, the present invention provides a compound of formula (14L), or a solvate, pharmaceutically acceptable salt thereof, including isolated enantiomeric, diastereoisomeric and geometric isomers thereof, and mixtures thereof, prepared by the method of the present invention wherein $R_3$ is hydrogen, and $R_4$ and $R_5$ are $C_1$ alkoxy.

In another embodiment, the present invention provides a compound or any salt thereof, or any solvate thereof, or mixture comprising one or more said compounds or any salt thereof, or any solvate thereof, that may be prepared by the method of the present invention, selected from the group consisting of:

| Structure | Chemical name |
|---|---|
| | (1R,2R)/(1S,2S)-2-[(3R)/(3S)-Hydroxypyrrolidinyl]-1-(3,4-dimethoxy-phenethoxy)-cyclohexane |
| | (1R,2R)/(1S,2S)-2-[(3R)-Hydroxypyrrolidinyl]-1-(3,4-dimethoxy-phenethoxy)-cyclohexane |
| | (1R,2R)/(1S,2S)-2-[(3S)-Hydroxy-pyrrolidinyl]-1-(3,4-dimethoxy-phenethoxy)-cyclohexane |
| | (1R,2R)-2-[(3R)-Hydroxy-pyrrolidinyl]-1-(3,4-dimethoxypheneth-oxy)-cyclohexane |
| | (1R,2R)-2-[(3S)-Hydroxy-pyrrolidinyl]-1-(3,4-dimethoxypheneth-oxy)-cyclohexane |
| | (1R,2S)-2-[(3R)-Hydroxy-pyrrolidinyl]-1-(3,4-dimethoxypheneth-oxy)-cyclohexane |
| | (1R,2S)-2-[(3S)-Hydroxy-pyrrolidinyl]-1-(3,4-dimethoxypheneth-oxy)-cyclohexane |
| | (1S,2R)-2-[(3R)-Hydroxy-pyrrolidinyl]-1-(3,4-dimethoxypheneth-oxy)-cyclohexane |
| | (1S,2R)-2-[(3S)-Hydroxy-pyrrolidinyl]-1-(3,4-dimethoxypheneth-oxy)-cyclohexane |
| | (1S,2S)-2-[(3R)-Hydroxy-pyrrolidinyl]-1-(3,4-dimethoxypheneth-oxy)-cyclohexane |
| | (1S,2S)-2-[(3S)-Hydroxy-pyrrolidinyl]-1-(3,4-dimethoxypheneth-oxy)-cyclohexane |
| | (1R,2S)/(1S,2R)-2-[(3R)/(3S)-Hydroxy-pyrrolidinyl]-1-(3,4-dimethoxy-phenethoxy)-cyclohexane |

In another embodiment, the present invention provides a compound, or mixture comprising compounds, or any solvate thereof, selected from the group consisting of:

| Structure | Chemical name |
|---|---|
| ·HCl | (1R,2R)-2-[(3R)-Hydroxy-pyrrolidinyl]-1-(3,4-dimethoxypheneth-oxy)-cyclohexane monohydrochloride |

-continued

| Structure | Chemical name |
|---|---|
| (structure with OCH3, OCH3, pyrrolidine-OH, •HCl) | (1S,2S)-2-[(3R)-Hydroxypyrrolidinyl]-1-(3,4-dimethoxyphenethoxy)-cyclohexane monohydrochloride |
| (structure with OMe, OMe, pyrrolidine-OH, •HCl) | (1R,2R)-2-[(3S)-Hydroxypyrrolidinyl]-1-(3,4-dimethoxyphenethoxy)-cyclohexane monohydrochloride |
| (structure with OCH3, OCH3, pyrrolidine-OH, •HCl) | (1S,2S)-2-[(3S)-Hydroxypyrrolidinyl]-1-(3,4-dimethoxyphenethoxy)-cyclohexane monohydrochloride |

In another embodiment, the present invention provides a composition that includes one or more of the compounds listed above that may be prepared by the method of the present invention, or includes a solvate or a pharmaceutically acceptable salt of one or more of the compounds. The composition may or may not include additional components as is described elsewhere in detail in this patent.

In one embodiment, the present invention provides a compound which is (1R,2R)-2-[(3R)-Hydroxypyrrolidinyl]-1-(3,4-dimethoxyphenethoxy)-cyclohexane free base or any salt thereof, or any solvate thereof, that may be prepared by the method of the present invention.

In one embodiment, the present invention provides a compound which is (1R,2R)-2-[(3S)-Hydroxypyrrolidinyl]-1-(3,4-dimethoxyphenethoxy)-cyclohexane free base or any salt thereof, or any solvate thereof, that may be prepared by the method of the present invention.

In one embodiment, the present invention provides a compound which is (1S,2S)-2-[(3R)-Hydroxypyrrolidinyl]-1-(3,4-dimethoxyphenethoxy)-cyclohexane free base or any salt thereof, or any solvate thereof, that may be prepared by the method of the present invention.

In one embodiment, the present invention provides a compound which is (1S,2S)-2-[(3S)-Hydroxypyrrolidinyl]-1-(3,4-dimethoxyphenethoxy)-cyclohexane free base or any salt thereof, or any solvate thereof, that may be prepared by the method of the present invention.

In one embodiment, the present invention provides a compound which is (1R,2R)-2-[(3R)-Hydroxypyrrolidinyl]-1-(3,4-dimethoxyphenethoxy)-cyclohexane monohydrochloride, or any solvate thereof, that may be prepared by the method of the present invention.

In one embodiment, the present invention provides a compound which is (1R,2R)-2-[(3S)-Hydroxypyrrolidinyl]-1-(3,4-dimethoxyphenethoxy)-cyclohexane monohydrochloride, or any solvate thereof, that may be prepared by the method of the present invention.

In one embodiment, the present invention provides a compound which is (1S,2S)-2-[(3R)-Hydroxypyrrolidinyl]-1-(3,4-dimethoxyphenethoxy)-cyclohexane monohydrochloride, or any solvate thereof, that may be prepared by the method of the present invention.

In one embodiment, the present invention provides a compound which is (1S,2S)-2-[(3S)-Hydroxypyrrolidinyl]-1-(3,4-dimethoxyphenethoxy)-cyclohexane monohydrochloride, or any solvate thereof, that may be prepared by the method of the present invention.

In one embodiment, the present invention provides a compound which is (1R,2S)-2-[(3R)-Hydroxypyrrolidinyl]-1-(3,4-dimethoxyphenethoxy)-cyclohexane free base or any salt thereof, or any solvate thereof, that may be prepared by the method of the present invention.

In one embodiment, the present invention provides a compound which is (1R,2S)-2-[(3S)-Hydroxypyrrolidinyl]-1-(3,4-dimethoxyphenethoxy)-cyclohexane free base or any salt thereof, or any solvate thereof, that may be prepared by the method of the present invention.

In one embodiment, the present invention provides a compound which is (1S,2R)-2-[(3R)-Hydroxypyrrolidinyl]-1-(3,4-dimethoxyphenethoxy)-cyclohexane free base or any salt thereof, or any solvate thereof, that may be prepared by the method of the present invention.

In one embodiment, the present invention provides a compound which is (1S,2R)-2-[(3S)-Hydroxypyrrolidinyl]-1-(3,4-dimethoxyphenethoxy)-cyclohexane free base or any salt thereof, or any solvate thereof, that may be prepared by the method of the present invention.

In one embodiment, the present invention provides a compound which is (1R,2S)-2-[(3R)-Hydroxypyrrolidinyl]-1-(3,4-dimethoxyphenethoxy)-cyclohexane monohydrochloride, or any solvate thereof, that may be prepared by the method of the present invention.

In one embodiment, the present invention provides a compound which is (1R,2S)-2-[(3S)-Hydroxypyrrolidinyl]-1-(3,4-dimethoxyphenethoxy)-cyclohexane monohydrochloride, or any solvate thereof, that may be prepared by the method of the present invention.

In one embodiment, the present invention provides a compound which is (1S,2R)-2-[(3R)-Hydroxypyrrolidinyl]-1-(3,4-dimethoxyphenethoxy)-cyclohexane monohydrochloride, or any solvate thereof, that may be prepared by the method of the present invention.

In one embodiment, the present invention provides a compound which is (1S,2R)-2-[(3S)-Hydroxypyrrolidinyl]-1-(3,4-dimethoxyphenethoxy)-cyclohexane monohydrochloride, or any solvate thereof, that may be prepared by the method of the present invention.

The present invention also provides protonated versions of all of the compounds described in this patent that may be prepared by the method of the present invention. That is, for each compound described in this patent, the invention also includes the quaternary protonated amine form of the compound that may be prepared by the method of the present invention. These quaternary protonated amine form of the compounds may be present in the solid phase, for example in crystalline or amorphous form, and may be present in solution. These quaternary protonated amine form of the compounds may be associated with pharmaceutically acceptable anionic counter ions, including but not limited to those described in for example: "Handbook of Pharmaceutical Salts, Properties, Selection, and Use", P. Heinrich Stahl and Camille G. Wermuth (Eds.), Published by VHCA (Switzerland) and Wiley-VCH (FRG), 2002.

Methods of the Invention

The aminocyclohexyl ether compounds of the present invention contain ether and amino functional groups disposed in a 1,2 arrangement on a cyclohexane ring. Accordingly, the ether and amino functional groups may be disposed in either a cis or trans relationship, relative to one another and the plane of the cyclohexane ring as shown on the page in a two dimensional representation.

The present invention provides synthetic methodology for the preparation of the aminocyclohexyl ether compounds according to the present invention as described herein. The aminocyclohexyl ether compounds described herein may be prepared from aminoalcohols and alcohols by following the general methods described below, and as illustrated in the Figures and disclosures therein. Some general synthetic processes for aminocyclohexyl ethers have been described in WO 99/50225 and references cited therein. Other processes that may be used for preparing compounds of the present invention are described in the following US provisional patent applications: U.S. Ser. No. 60/476,083, U.S. Ser. No. 60/476,447, U.S. Ser. No. 60/475,884, U.S. Ser. No. 60/475,912 and U.S. Ser. No. 60/489,659, and U.S. Ser. No. 10/862,157 and PCT/US2004/18050 and references therein.

Figure 1A:
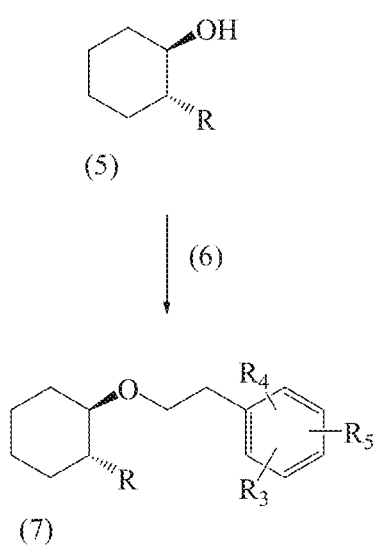
FIG. 1A illustrates a general synthetic methodology that may be employed to prepare a compound of formula (7).

As outlined in FIG. 1A, the preparation of a stereoisomerically substantially pure compound of formula (7) can be carried out by alkylation of the hydroxy group in compound (5) under appropriate conditions with an alkylating reagent such as compound (6), wherein Q represents a good leaving group which on reaction with the hydroxy function on the carbon at the 1-position in (5) will result in the formation of an ether compound (7) such that the stereochemical spatial arrangement of the hydroxy group on the carbon at the 1-position in (5) is retained in that of the ether (7) resulting in the overall retention of the trans-(1R,2R) stereochemical description; and optionally protecting (5) and/or (6) before said reaction, and deprotecting the product after said reaction.

Haloacetimidate (e.g. 2,2,2-trifluoroacetimidate or 2,2,2-trichloroacetimidate) is one example of a compound of formula (6) containing a suitable Q group for the purposes of this invention. For some compounds of the formula (5) and/or the formula (6), it may be necessary to introduce appropriate protection groups prior to this alkylation step being performed. Suitable protecting groups and the corresponding deprotection conditions are set forth in, for example, Greene, "Protective Groups in Organic Chemistry", John Wiley & Sons, New York N.Y. (1991) and references cited therein.

Other examples of suitable Q groups for the compounds of formula (6) are provided below in Table A. (For a review of the application of various examples of Q in the formation of an ether compound with an alcohol see, for example, Toshima K. and Tatsuta K. Chem. Rev. 1993, 93, 1503, Tsuda T., Nakamura S. and Hashimoto S. Tetrahedron Lett. 2003, 44, 6453, Martichonok V. and Whitesides G. M. J. Org. Chem., 1996, 61, 1702 and references cited therein.)

In addition to haloacetimidate (e.g. trihaloacetimidate such as 2,2,2-trifluoroacetimidate or 2,2,2-trichloroacetimidate) and other imidate esters (e.g. pentafluorobenzimidate), other examples of suitable Q groups for the compounds of formula (6), include, but are not limited to, O-carbonates and S-carbonates, including imidazole carbonates and imidazolethiocarbonates. Phosphate examples of a Q group include a diphenyl phosphate, a diphenylphosphineimidate, a phosphoroamidate and a O-sulfonyl group.

TABLE A

Examples of Q

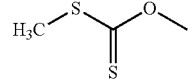

TABLE A-continued

Examples of Q

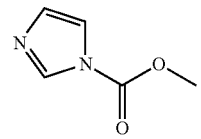

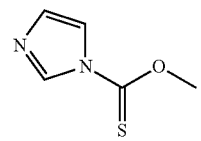

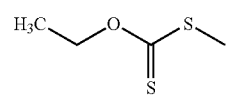

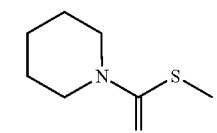

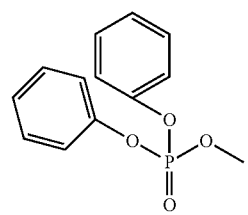 [SMILES: COP(=O)(Oc1ccccc1)Oc1ccccc1]

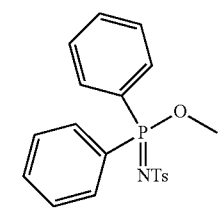

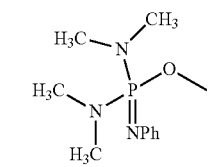

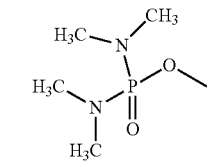

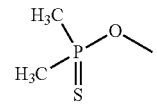

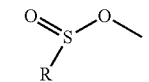

TABLE A-continued

Examples of Q

[structure: enol ether with R, R', R'', OMe]

[structure: 3-methyl-2-methoxy-6-methylpyridine·BF₃]

[structure: 2-methoxypyrimidine·BF₃]

[structure: F₃B–O–S(=O⁺)(R)–OMe]

[structure: 4-methoxy-nitrobenzene N-oxide]

Figure 1B:
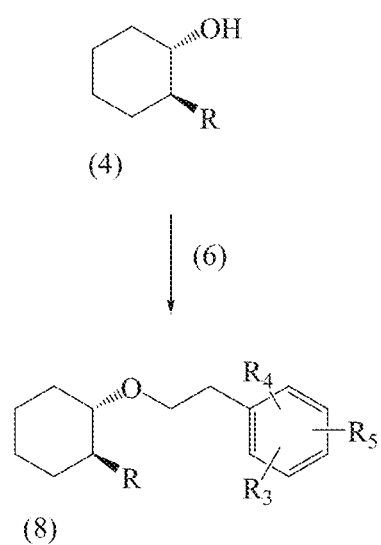
FIG. 1B illustrates a general synthetic methodology that may be employed to prepare a compound of formula (8).

As outlined in FIG. 1B, the preparation of a stereoisomerically substantially pure compound of formula (8) can be carried out by alkylation of the hydroxy group in compound (4) under appropriate conditions with an alkylating reagent such as compound (6), wherein Q represents a good leaving group which on reaction with the hydroxy function on the carbon at the 1-position in (4) will result in the formation of an ether compound (8) such that the stereochemical spatial arrangement of the hydroxy group on the carbon at the 1-position in (4) is persevered in that of the ether (8) resulting in the overall retention of the trans-(1S, 2S) stereochemical description; and optionally protecting (4) and/or (6) before said reaction, and deprotecting the product after said reaction.

It would be appreciated by those skilled in the art that reaction conditions and reagents described above for synthesizing (7) from (5) may be applicable for the preparation of (8) from (4).

The chiral substrates (4a) and (5a) may be obtained by separating a mixture of the two stereoisomers such as the racemate (3) as outlined in FIG. 1. In general, as illustrated in FIG. 1, the racemate (3) can be readily prepared by treatment of cyclohexene oxide (1) with the amine (2) under appropriate conditions well known in the art.

The racemate (3) or other mixture comprises of formulae (4a) and (5a) is then subjected to a resolution process whereby the one or both stereoisomers are separated into products that are in stereoisomerically substantially pure form. In some situations it may be adequate that the resolution process produces compounds of sufficient enrichment in their optical purity for application in the subsequent steps of the synthetic process. Methods for resolution of racemates or other stereoisomeric mixtures are well known in the art (e.g., E. L. Eliel and S. H. Wilen, in *Stereochemistry of Organic Compounds*; John Wiley & Sons: New York, 1994; Chapter 7, and references cited therein). Suitable processes may include but are not limited to separation of stereoisomers by crystallization (e.g. preferential crystallization, preferential crystallization in the presence of additives), asymmetric transformation of racemates, chemical separation (e.g. formation and separation of diastereomers such as diastereomeric salt mixtures or the use of other resolving agents; separation via complexes and inclusion compounds), kinetic resolution (e.g. with titanium tartrate catalyst), enzymatic resolution (e.g., lipase mediated, carbony reductase mediated) and chromatographic separation (e.g., HPLC with chiral stationary phase and/or with simulated moving bed technology, or supercritical fluid chromatography and related techniques) (see e.g., T. J. Ward, Analytical Chemistry, 2002, 2863-2872).

Figure 2:
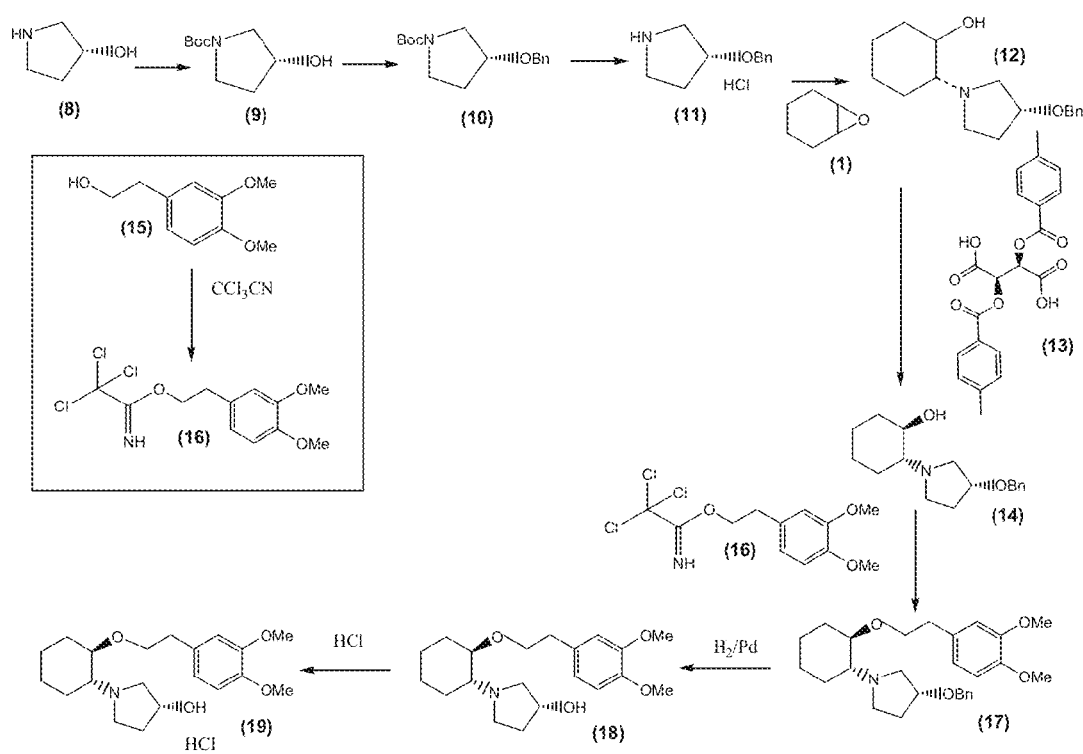
FIG. 2 illustrates a reaction scheme that may be used as a process for preparing a stereoisomerically substantially pure trans-(1R,2R)-aminocyclohexyl ether compound of formula (18) and its HCl salt of formula (19).

As outlined in FIG. 2, the present invention provides a process for preparing a stereoisomerically substantially pure trans-(1R,2R)-aminocyclohexyl ether compound of formula (18) and its HCl salt of formula (19).

The free hydroxy group in compound (14) is alkylated under appropriate conditions with (16) to form compound (17). The 2,2,2-trichloroacetimidate (16) is readily prepared from the corresponding alcohol, 3,4-dimethoxyphenethyl alcohol (15) which is commercially available (e.g., Aldrich), by treatment with trichloroacetonitrile. The alkylation of compound (14) by 2,2,2-trichloroacetimidate (16) can be carried out in the presence of a Brønsted acid (e.g. HBF₄) or Lewis acid such as BF₃OEt₂.

The benzyl (Bn) protection group of compound (17) may be removed by standard procedure (e.g., hydrogenation in the presence of a catalyst under appropriate conditions. Palladium on activated carbon is one example of the catalysts. Other suitable conditions are as described in Greene, "Protective Groups in Organic Chemistry", John Wiley & Sons, New York N.Y. (1991)). The product is a stereoisomerically substantially pure trans-aminocyclohexyl ether compound of formula (18) and is generally formed as the free base. The free base may be converted, if desired, to the monohydrochloride salt by known methodologies, or alternatively, if desired, to other acid addition salts by reaction with an inorganic or organic acids under appropriate conditions. Acid addition salts can also be prepared metathetically by reaction of one acid addition salt with an acid that is stronger than that giving rise to the initial salt.

As shown in FIG. 2, compound (14) can be obtained from racemate (12) by resolution mediated by diastereomeric salt mixtures using e.g. di-O,O-p-toluoyl-L-tartaric acid (13). Various other acids (e.g., such as those described in E. L. Eliel and S. H. Wilen, in *Stereochemistry of Organic Compounds*; John Wiley & Sons: New York, 1994; Chapter 7, and references cited therein) may also be used for the resolution process.

As outlined in FIG. 2, racemate (12) can be readily prepared from 3R-pyrrolidinol (8), which is commercially available (e.g., Aldrich) or may be prepared according to published procedure (e.g., Chem. Ber./Recueil 1997, 130, 385-397). Detials may be found in U.S. Ser. No. 10/862,157 and PCT/US2004/18050 and references therein.

Figure 7:
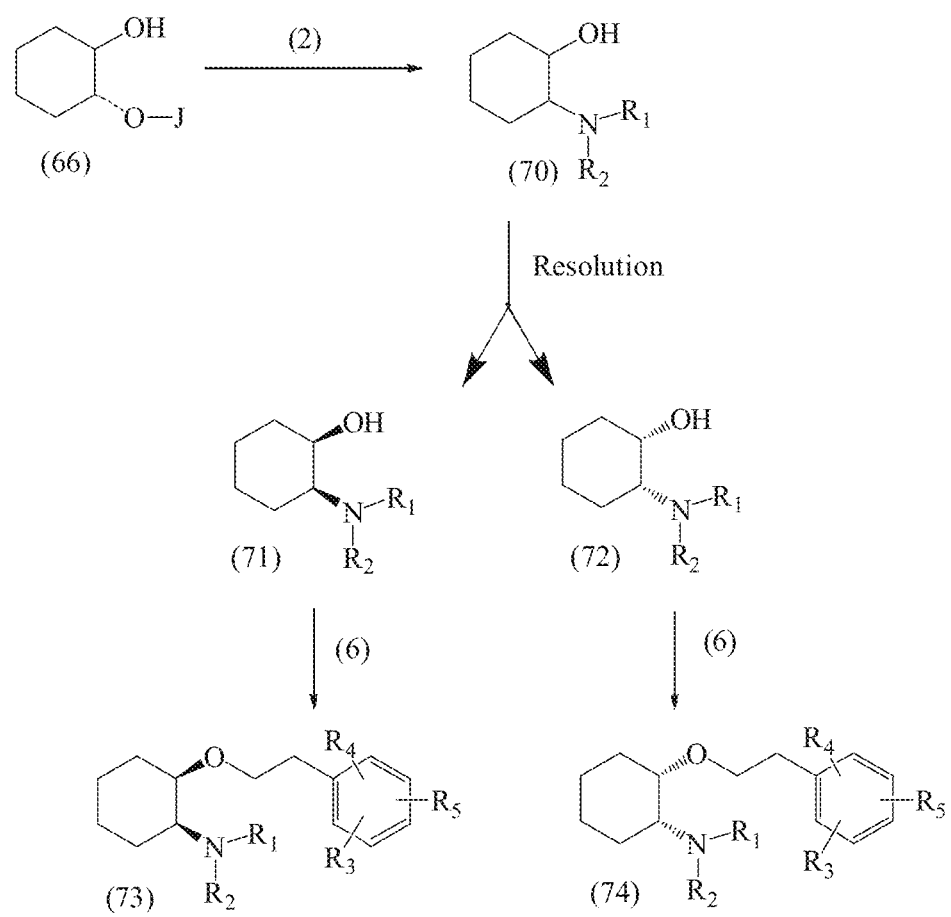
FIG. 7 illustrates a general reaction scheme that may be used as a process for preparing a stereoisomerically substantially pure cis-(1R,2S)-aminocyclohexyl ether compound of formula (73) or a stereoisomerically substantially pure cis-(1S,2R)-aminocyclohexyl ether compound of formula (74).

As outlined in FIG. 7, the present invention provides a process for preparing a stereoisomerically substantially pure cis-(1R,2S)-aminocyclohexyl ether compound of formula (73) or a stereoisomerically substantially pure cis-(1S,2R)-aminocyclohexyl ether compound of formula (74).

In a first step, one of the two hydroxy groups of trans-1, 2-cyclohexane diol is converted under suitable conditions into an activated form as represented by compound (66). An "activated form" as used herein means that the hydroxy group is converted into a good leaving group (—O-J) which on reaction with an appropriate nucleophile (e.g., $HNR_1R_2$, formula (2)) will result in a substitution product (70) with substantial inversion of the stereochemical configuration of the carbon bearing the activated hydroxy group.

The leaving group (—O-J) may be but is not limited to an alkanesulfonate such as a trifluoromethanesulfonate group ($CF_3SO_3$—) or a mesylate group (MsO—), an arenesulfonate such as a benzenesulfonate group ($PhSO_3$—), a mono- or poly-substituted benzenesulfonate group, a mono- or poly-halobenzenesulfonate group, a 2-bromobenzenesulfonate group, a 2,6-dichlorobenzenesulfonate group, a pentafluorobenzenesulfonate group, a 2,6-dimethylbenzenesulfonate group, a tosylate group (TsO—) or a nosylate (NsO—), or other equivalent good leaving groups. The hydroxy group may also be converted into other suitable leaving groups according to procedures well known in the art. The leaving group may be any suitable leaving group on reaction with a nucleophilic reactant with inversion of stereochemical configuration known in the art, including but not limited to compounds disclosed in M. B. Smith and J. March in "March's Advanced Organic Chemistry", Fifth edition, Chapter 10, John Wiley & Sons, Inc., New York, N.Y. (2001). In a typical reaction for the formation of an alkanesulfonate (e.g., a mesylate) or an arenesulfonate (e.g., a tosylate or a nosylate), trans-1,2-cyclohexane diol is treated with a hydroxy activating reagent such as an alkanesulfonyl halide (e.g., mesyl chloride (MsCl)) or an arenesulfonyl halide (e.g., tosyl chloride (TsCl) or nosyl chloride (NsCl)) in the presence of a base, such as pyridine or triethylamine. The reaction is generally satisfactorily conducted at about 0° C., but may be adjusted as required to maximize the yields of the desired product. The hydroxy group may also be converted into other suitable leaving groups according to procedures well known in the art, using any suitable activating agent, including but not limited to those disclosed in M. B. Smith and J. March in "March's Advanced Organic Chemistry", Fifth edition, Chapter 10, John Wiley & Sons, Inc., New York, N.Y. (2001). The addition of other reagents to facilitate for example the formation of monosulfonylates may be advantageously employed (e.g., M. J. Martinelli, et al. "Selective monosulfonylation of internal 1,2-diols catalyzed by di-n-butyltin oxide" Tetrahedron Letters, 2000, 41, 3773). The stereomisomeric mixture (70) comprises of formulae (71) and (72) is then subjected to a resolution process whereby one or both of the two optically active isomers are separated into products that are in stereoisomerically substantially pure form. In some situations it may be adequate that the resolution process produces compounds of formula (71) and/or (72) of sufficient enrichment in their optical purity for application in the subsequent steps of the synthetic process. Methods for resolution of stereomisomeric mixture or racemic mixtures are well known in the art (e.g., E. L. Eliel and S. H. Wilen, in *Stereochemistry of Organic Compounds*; John Wiley & Sons: New York, 1994; Chapter 7, and references cited therein). Suitable processes such as crystallization (e.g. preferential crystallization, preferential crystallization in the presence of additives), asymmetric transformation of racemates, chemical separation (e.g. formation and separation of diastereomers such as diastereomeric salt mixtures or the use of other resolving agents; separation via complexes and inclusion compounds), kinetic resolution (e.g. with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, Analytical Chemistry, 2002, 2863-2872).

In a separate reaction step, alkylation of the free hydroxy group on the carbon at the 1-position in compound of formula (71) to form compound of formula (73) is carried out under appropriate conditions with an alkylating reagent such as compound (6), wherein Q represents a good leaving group which on reaction with the hydroxy function on the carbon at the 1-position in (71) will result in the formation of an ether compound of formula (73) such that the stereochemical spatial arrangement of the hydroxy group on the carbon at the 1-position in (71) is persevered in that of the ether (73) resulting in the overall retention of the cis-(1R,2S) stereochemical description; and optionally protecting (71) and/or (6) before said reaction, and deprotecting the product after said reaction.

Examples of the Q function are as disclosed above. Haloacetimidate (e.g. 2,2,2-trifluoroacetimidate or 2,2,2-trichloroacetimidate) is one example for the Q function. Other examples are shown in Table A above. For some compounds of the formula (71) and/or the formula (6), it may be necessary to introduce appropriate protection groups prior to this alkylation step being performed. Suitable protecting groups and the corresponding deprotection conditions are set forth in, for example, Greene, "Protective Groups in Organic Chemistry", John Wiley & Sons, New York N.Y. (1991) and references cited therein.

It would be appreciated by those skilled in the art that reaction conditions and reagents described above for synthesizing (73) from (71) may be applicable for the preparation of (74) from (72).

Figure 8:
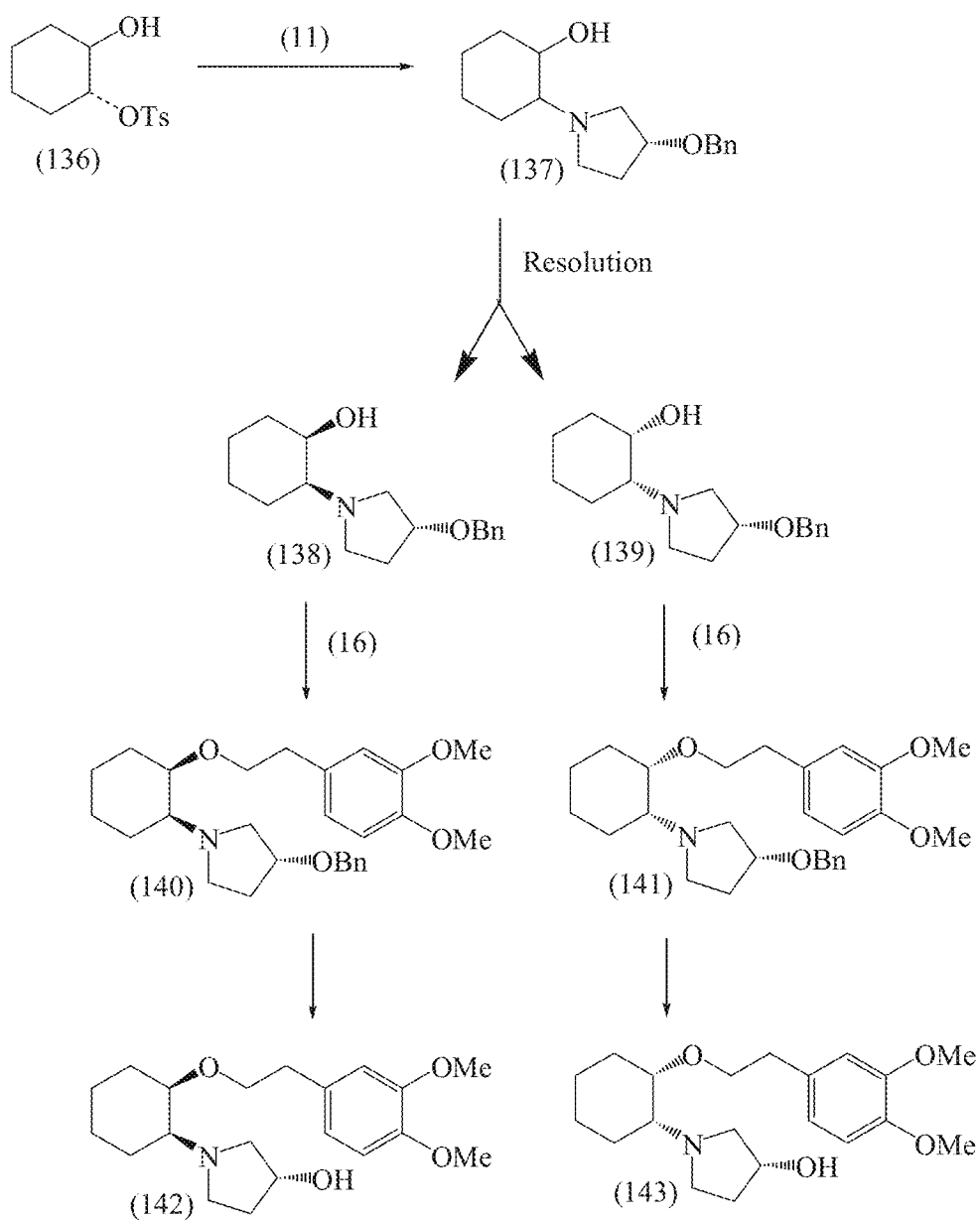
FIG. 8 illustrates a reaction scheme that may be used as a process for preparing a stereoisomerically substantially pure cis-(1R,2S)-aminocyclohexyl ether compound of formula (142) or a stereoisomerically substantially pure cis-(1S,2R)-aminocyclohexyl ether compound of formula (143).

As outlined in FIG. 8, reaction of (136) with (11) will form a stereoisomeric mixture (137). Resolution of (137) by methods such as those described above for (12) will provide stereoisomerically substantially pure (138) and/or (139). Alkylation of (138) with (16) under appropriate conditions will form (140) which on debenzylation by standard procedure (e.g., hydrogenation in the presence of a catalyst under appropriate conditions; palladium on activated carbon is one example of the catalysts) as described above for (17), will yield (142). Similarly, (143) may be prepared from stereoisomerically substantially pure (139).

Figure 9:
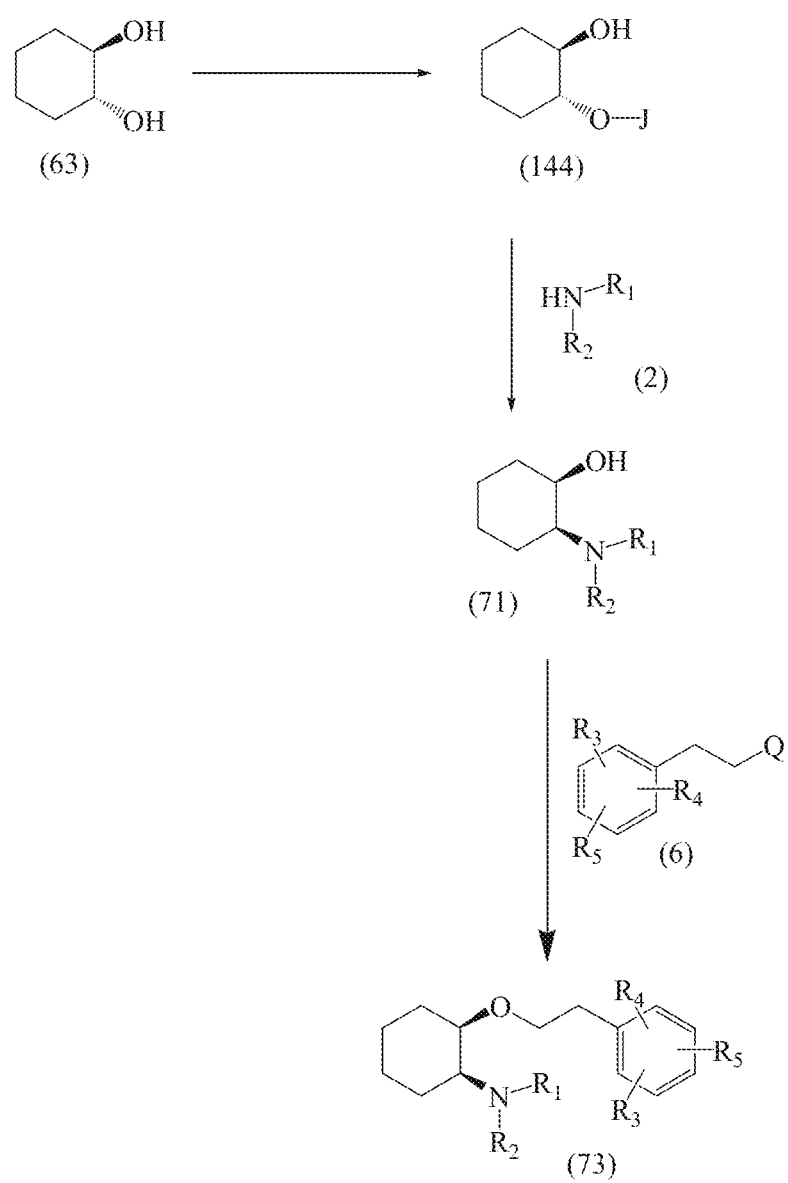
FIG. 9 illustrates a general reaction scheme that may be used as a process for preparing a stereoisomerically substantially pure cis-(1R,2S)-aminocyclohexyl ether compound of formula (73).
Figure 10:
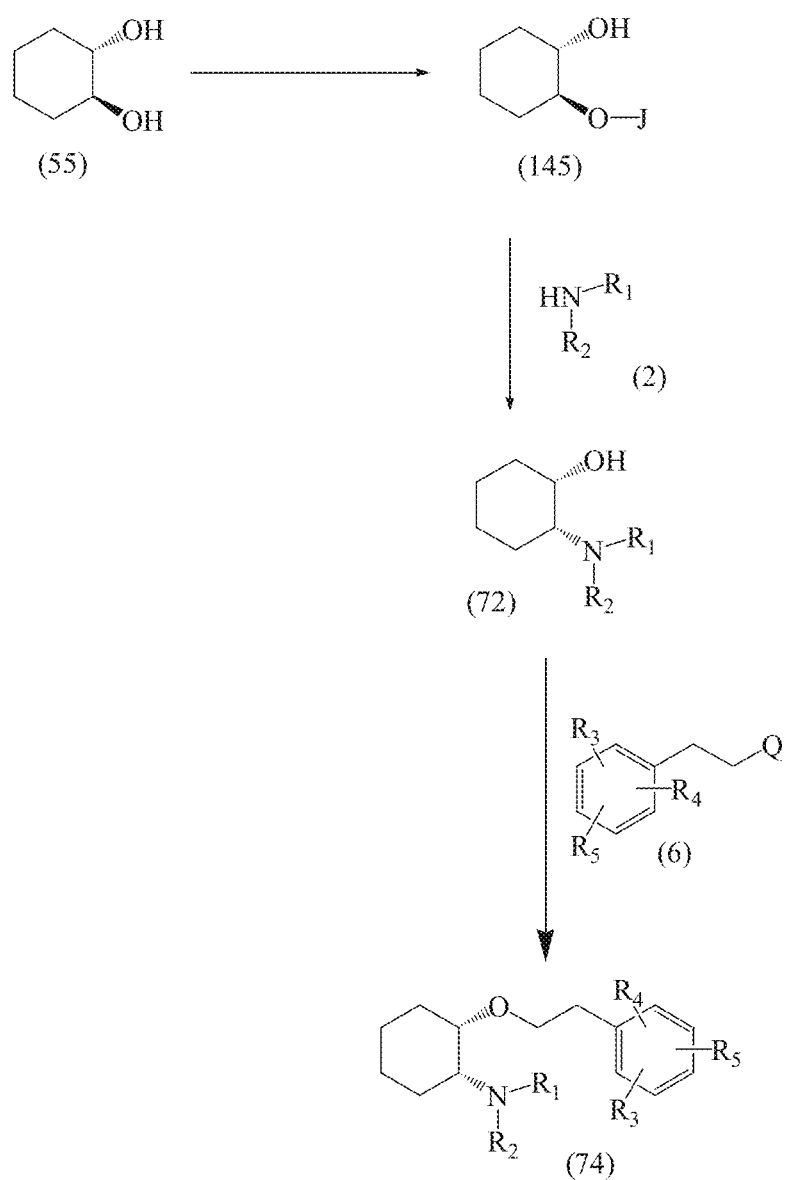
FIG. 10 illustrates a general reaction scheme that may be used as a process for preparing a stereoisomerically substantially pure cis-(1S,2R)-aminocyclohexyl ether compound of formula (74).

As outlined in FIG. 9, chiral substrate (71) for the synthesis of (74) may be prepared in stereoisomerically substantially pure form from (63) using appropriate reaction conditions similar to those described above. The diol (63) is commercially available (e.g. Aldrich), Similarly as outlined in FIG. 10, chiral substrate (72) for the synthesis of (74) may be prepared in stereoisomerically substantially pure form from (55). The latter is commercially available (e.g. Aldrich).

Figure 11:
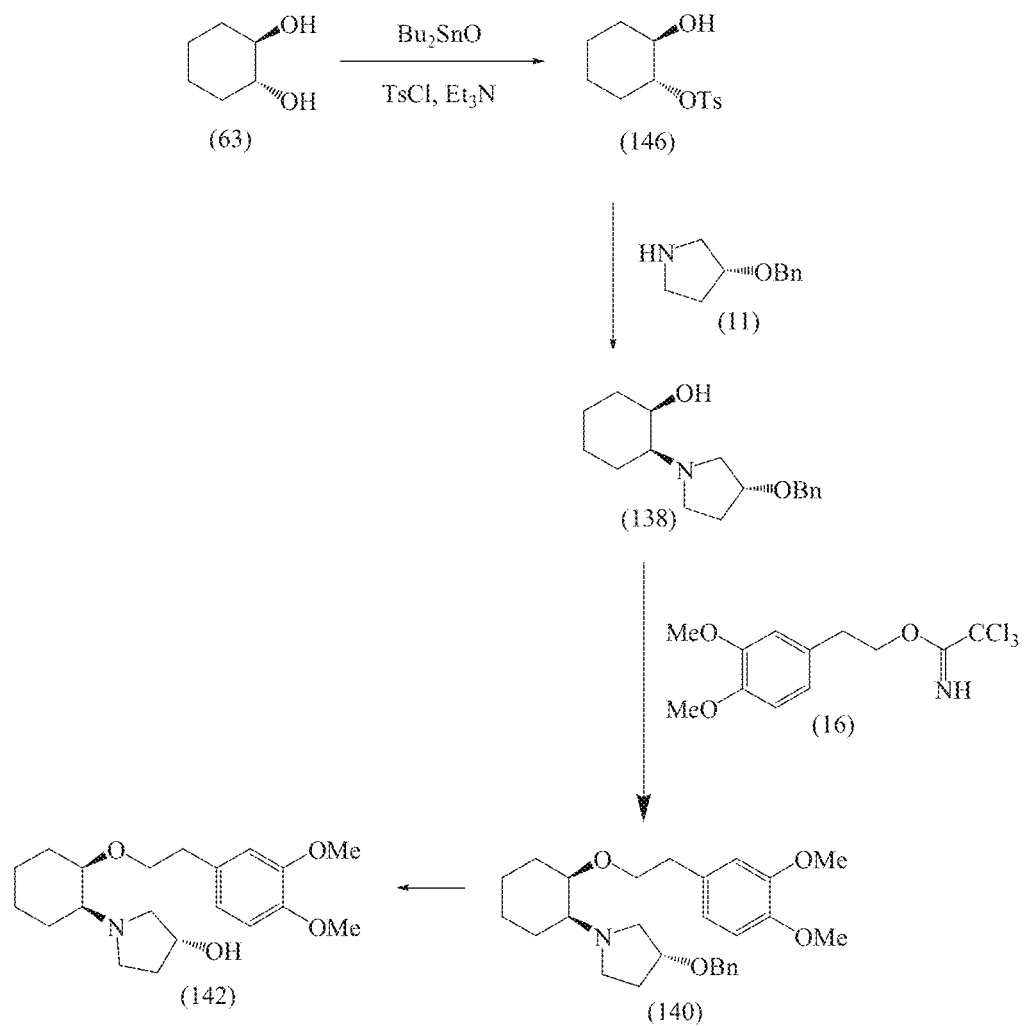
FIG. 11 illustrates a reaction scheme that may be used as a process for preparing a stereoisomerically substantially pure cis-(1R,2S)-aminocyclohexyl ether compound of formula (142).

As outlined in FIG. 11, stereoisomerically substantially pure compound of formula (142) may be prepared from (63) using appropriate reaction conditions similar to those described above.

Figure 12:
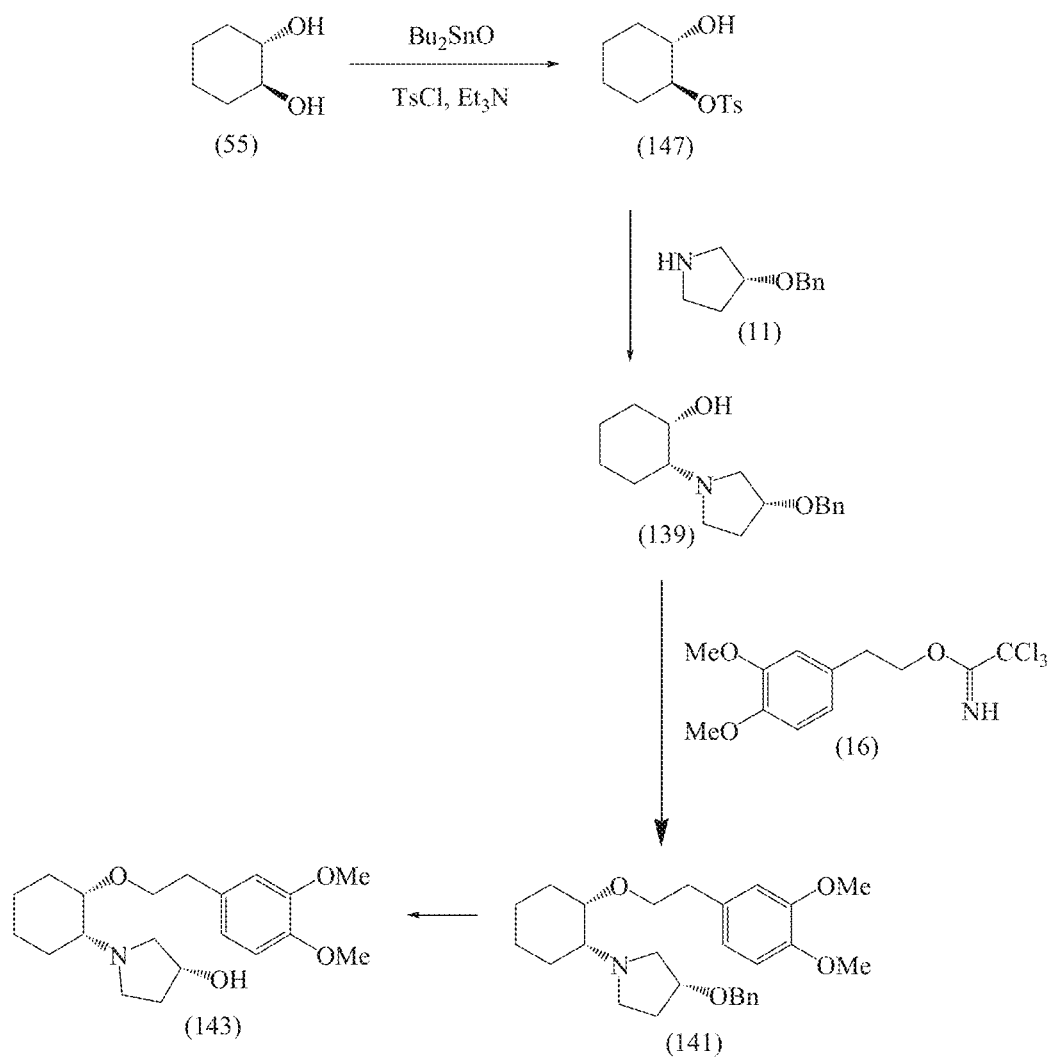
FIG. 12 illustrates a reaction scheme that may be used as a process for preparing a stereoisomerically substantially pure cis-(1S,2R)-aminocyclohexyl ether compound of formula (143).

Similarly as outlined in FIG. 12, stereoisomerically substantially pure compound of formula (143) may be prepared from (55) using appropriate reaction conditions similar to those described above.

Figure 13:
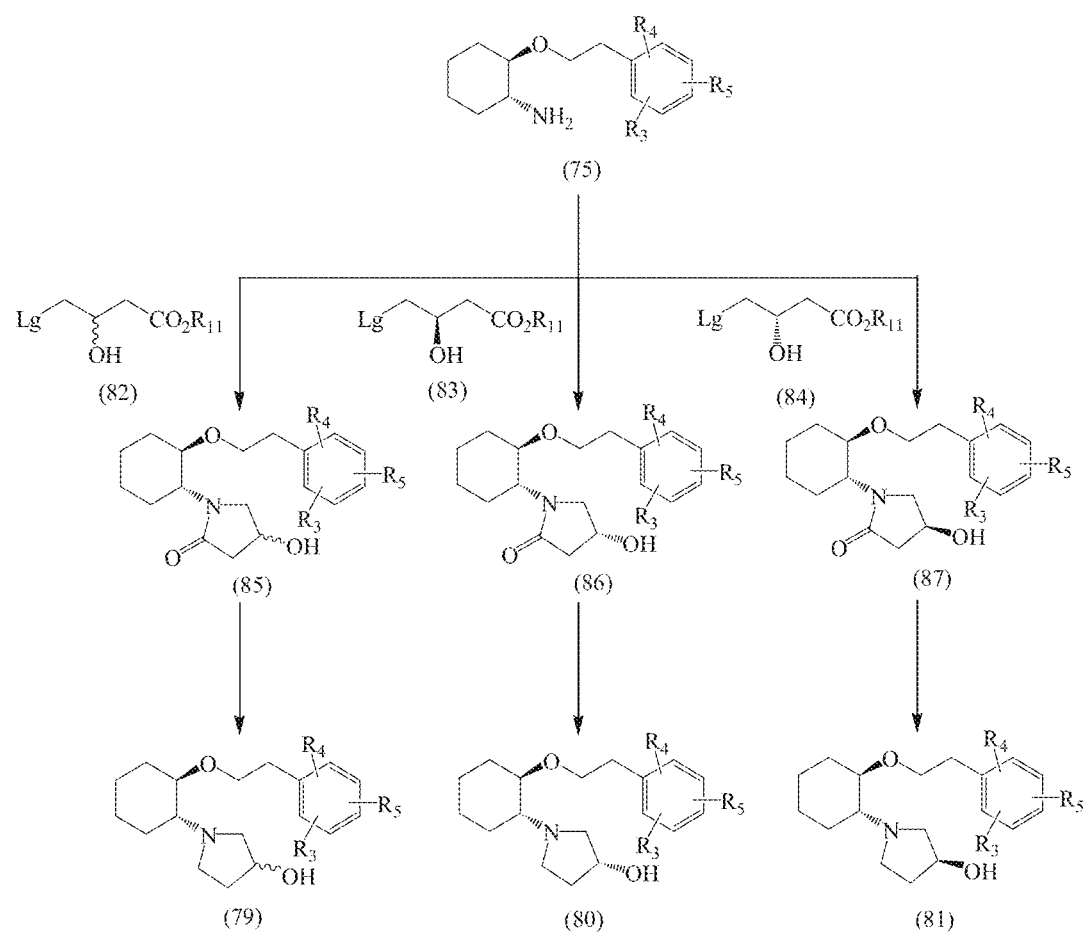
FIG. 13 illustrates a general reaction scheme that may be used as a process for preparing a stereoisomerically substantially pure trans-(1R,2R)-aminocyclohexyl ether compound of formula (79) or formula (80) or formula (81).

As outlined in FIG. 13, treatment of (75) with (82), (83) or (84) will form the intermediate (85), (86) or (87) respectively, which on reduction with for example Red-Al (Vitride, Sodium aluminum bis(2-methoxyethoxy)hydride; CAS [22722-98-1]) will yield (79), (80) or (81) respectively.

Figure 14:
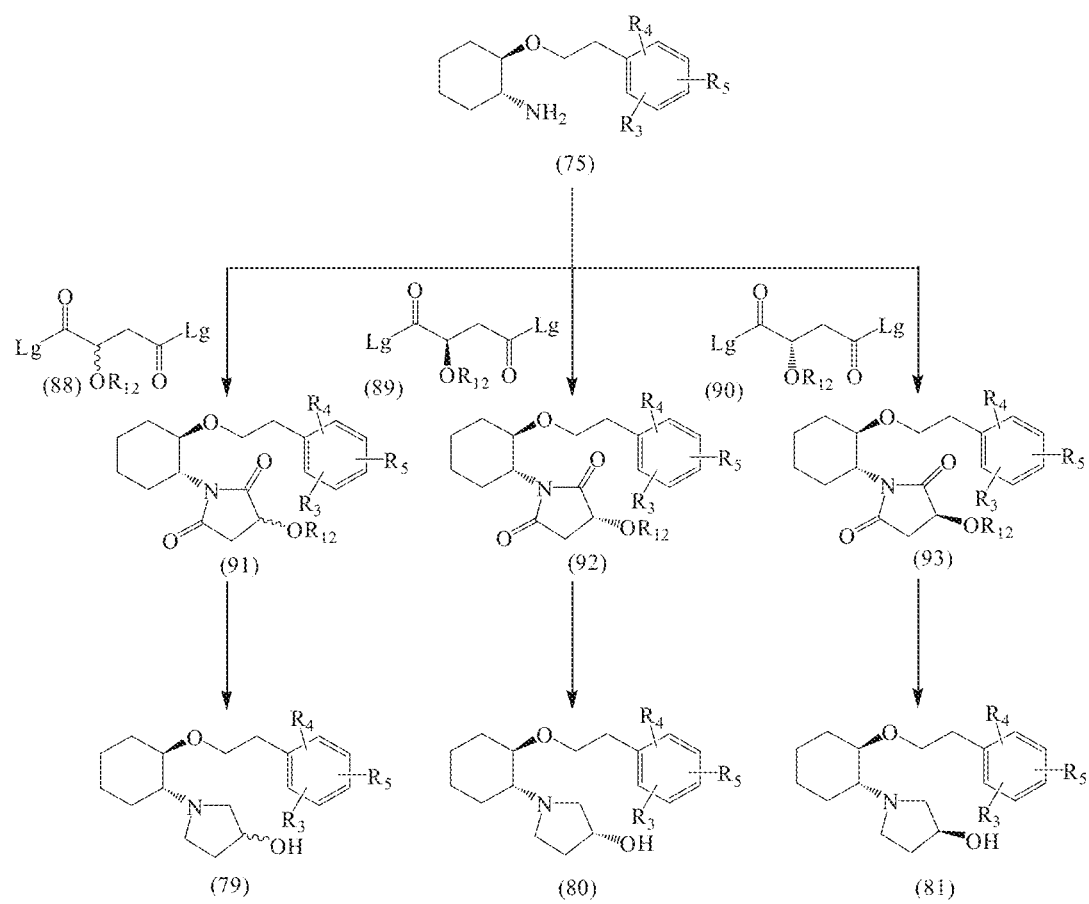
FIG. 14 illustrates a general reaction scheme that may be used as a process for preparing a stereoisomerically substantially pure trans-(1R,2R)-aminocyclohexyl ether compound of formula (79) or formula (80) or formula (81).

FIG. 14 shows a general reaction scheme where treatment of (75) with (88), (89) or (90) will form the intermediate (91), (92) or (93) respectively, which on reduction with for example Red-Al (Vitride, Sodium aluminum bis(2-methoxyethoxy)hydride; CAS [22722-98-1]) will yield (79), (80) or (81) respectively.

Figure 15:
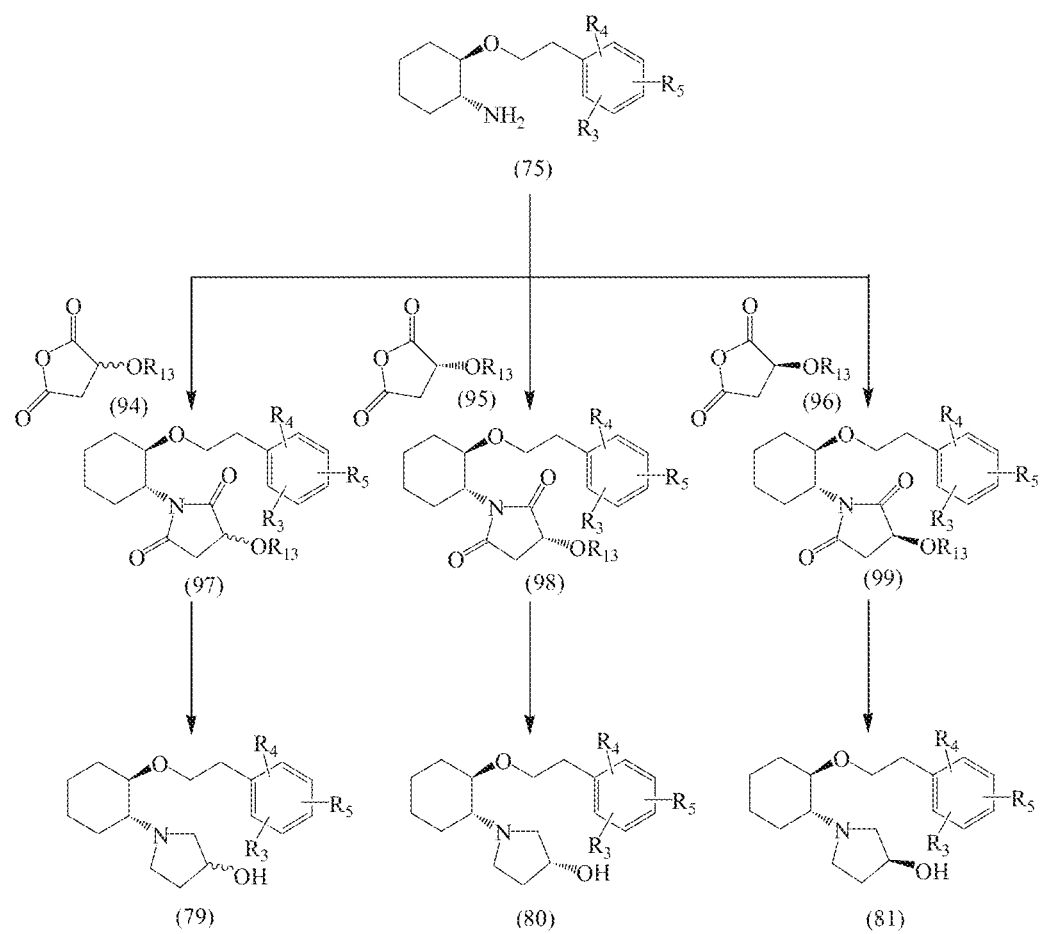
FIG. 15 illustrates a general reaction scheme that may be used as a process for preparing a stereoisomerically substantially pure trans-(1R,2R)-aminocyclohexyl ether compound of formula (79) or formula (80) or formula (81).

As outlined in FIG. 15, reaction of (75) with (94), (95) or (96) will form the intermediate (85), (86) or (87) respectively, which on reduction with for example Red-Al (Vitride, Sodium aluminum bis(2-methoxyethoxy)hydride; CAS [22722-98-1]) will yield (79), (80) or (81) respectively.

Figure 16:
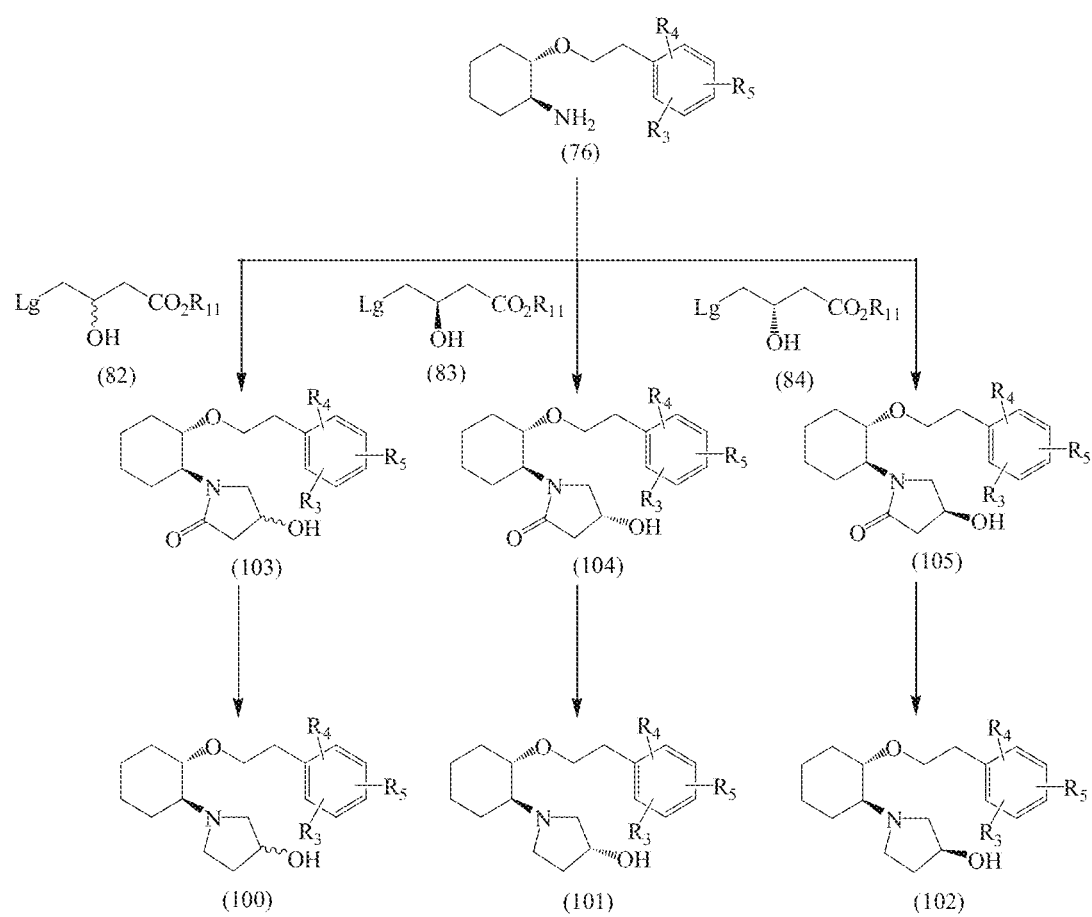
FIG. 16 illustrates a general reaction scheme that may be used as a process for preparing a stereoisomerically substantially pure trans-(1S,2S)-aminocyclohexyl ether compound of formula (100) or formula (101) or formula (102).

It would be appreciated by those skilled in the art that reaction conditions and reagents described above for preparing intermediates (85), (86) or (87) from (75) and (82), (83) or (84) respectively may be applicable for the preparation of (103), (104) or (105) from (76) and (82), (83) or (84) respectively as outlined in FIG. 16. Reduction of (103), (104) or (105) with for example Red-Al (Vitride, Sodium aluminum bis(2-methoxyethoxy)hydride; CAS [22722-98-1]) will yield (100), (101) or (102) respectively.

Figure 17:
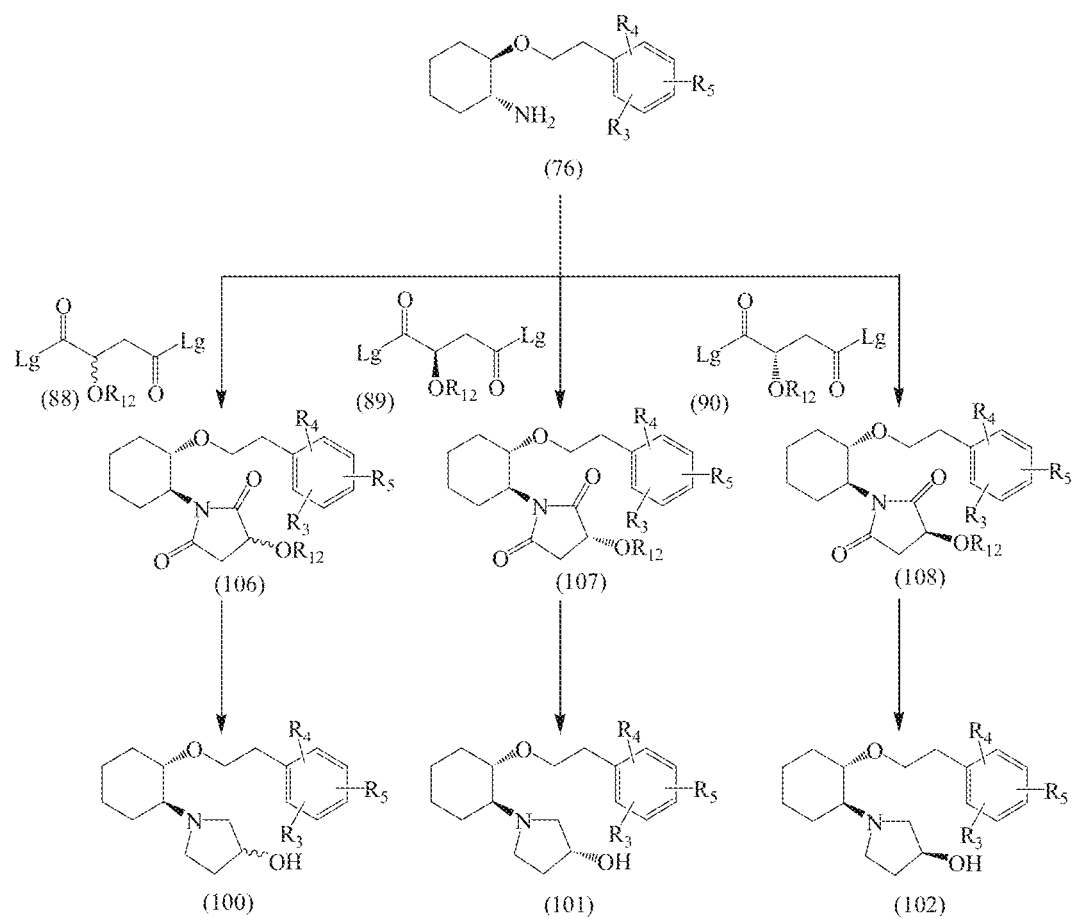
FIG. 17 illustrates a general reaction scheme that may be used as a process for preparing a stereoisomerically substantially pure trans-(1S,2S)-aminocyclohexyl ether compound of formula (100) or formula (101) or formula (102).

Reaction conditions similar to those described for FIG. 14 may be applicable for the general reaction scheme as shown in FIG. 17 for preparing trans-(1S,2S)-aminocyclohexyl ether compound of formula (100) or formula (101) or formula (102) starting from (76).

Figure 18:
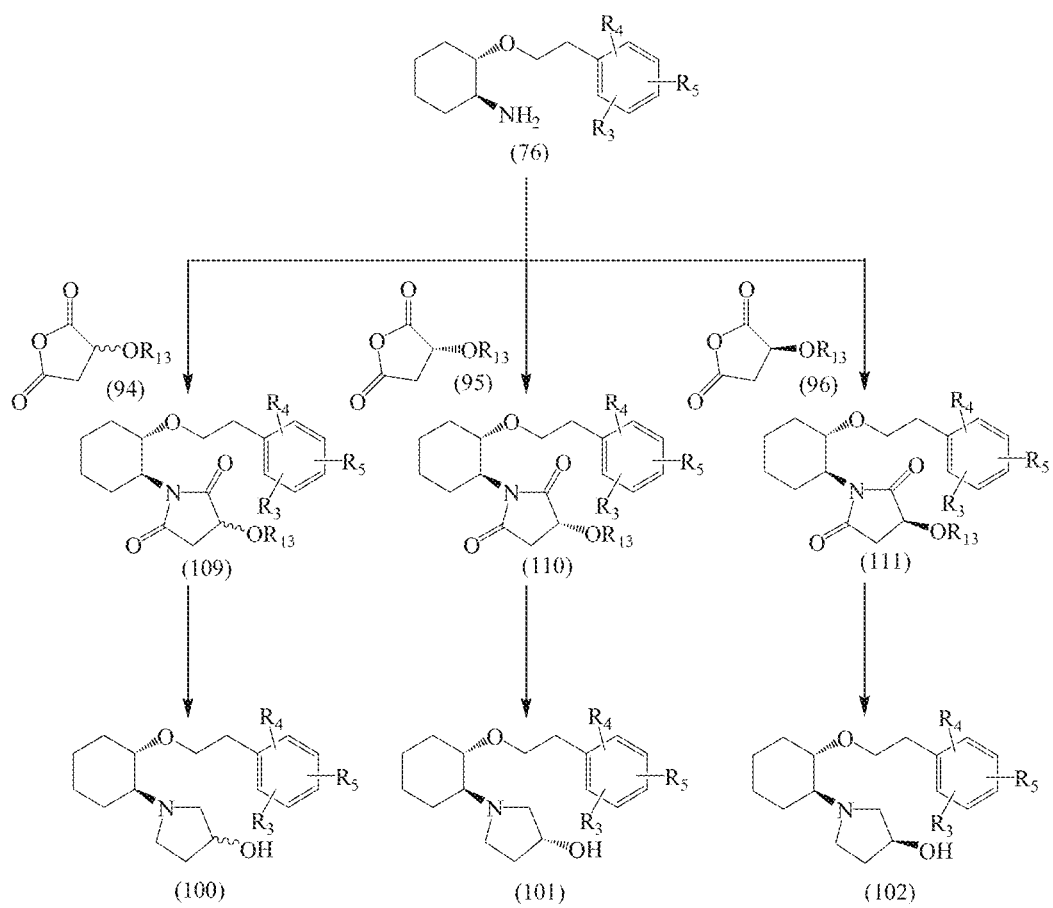
FIG. 18 illustrates a general reaction scheme that may be used as a process for preparing a stereoisomerically substantially pure trans-(1S,2S)-aminocyclohexyl ether compound of formula (100) or formula (101) or formula (102).

Similarly, reaction conditions described for FIG. 15 may be applicable for the general reaction scheme as shown in FIG. 18 for preparing trans-(1S,2S)-aminocyclohexyl ether compound of formula (100) or formula (101) or formula (102) starting from (76).

Figure 19:
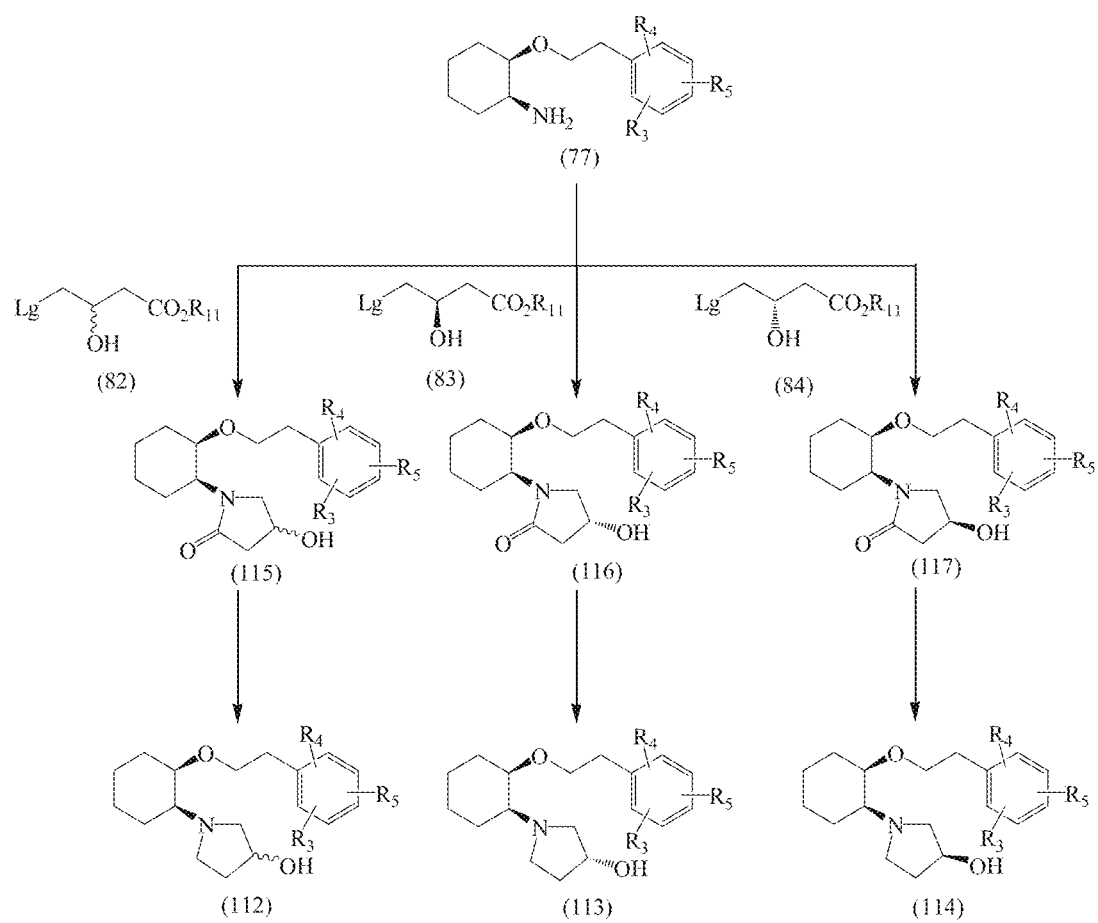
FIG. 19 illustrates a general reaction scheme that may be used as a process for preparing a stereoisomerically substantially pure cis-(1R,2S)-aminocyclohexyl ether compound of formula (112) or formula (113) or formula (114).
Figure 22:
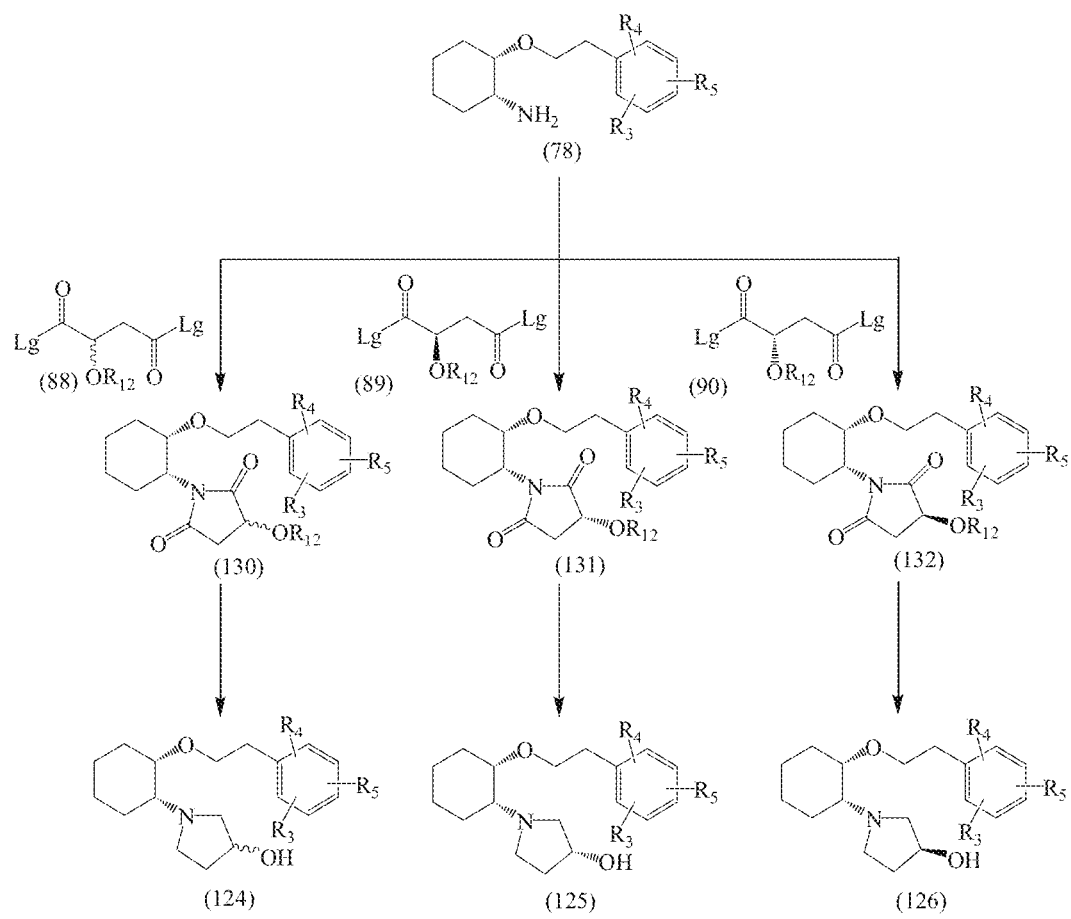
FIG. 22 illustrates a general reaction scheme that may be used as a process for preparing a stereoisomerically substantially pure cis-(1S,2R)-aminocyclohexyl ether compound of formula (124) or formula (125) or formula (126).

It would be appreciated by those skilled in the art that reaction conditions and reagents described above for FIG. 13 or FIG. 16 may be applicable for the general reaction scheme as shown in FIG. 19 for preparing cis-(1R,2S)-aminocyclohexyl ether compound of formula (112) or formula (113) or formula (114) starting from (77); and for the general reaction scheme as shown in FIG. 22 for preparing cis-(1S,2R)-aminocyclohexyl ether compound of formula (124) or formula (125) or formula (126) starting from (78).

Figure 20:
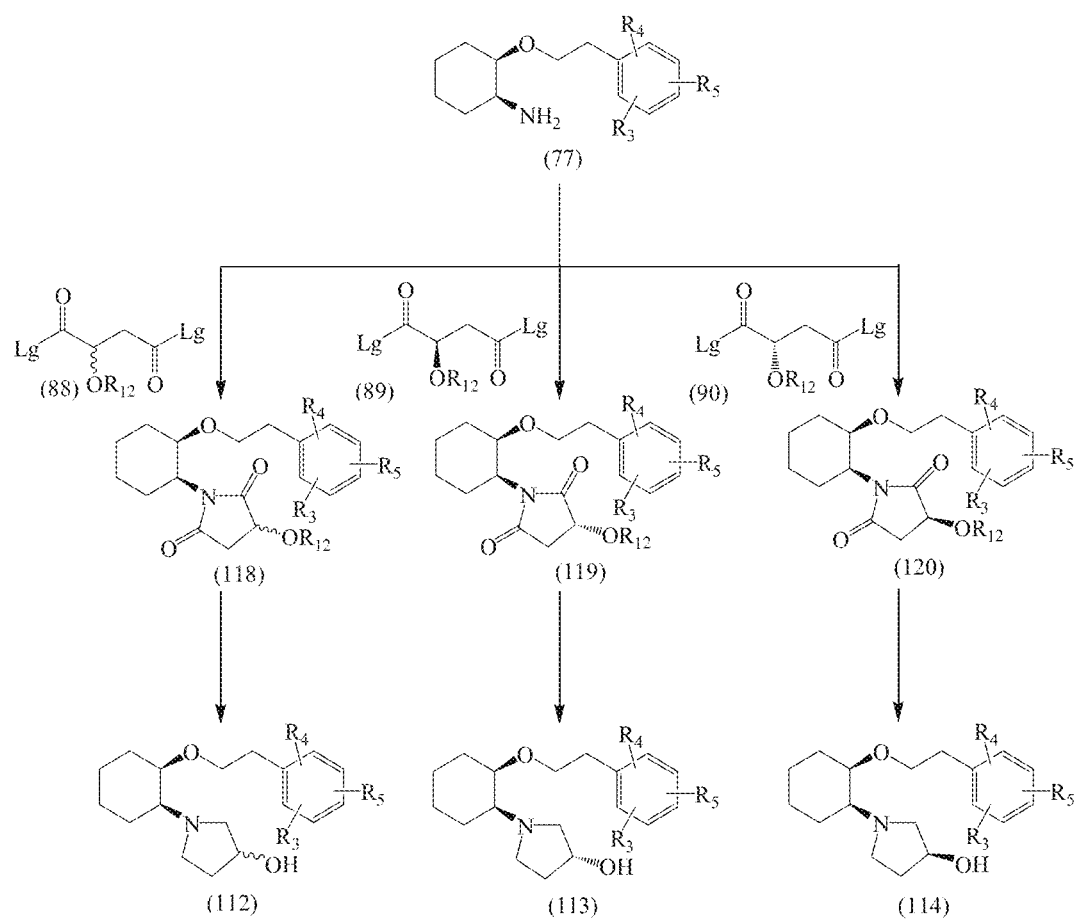
FIG. 20 illustrates a general reaction scheme that may be used as a process for preparing a stereoisomerically substantially pure cis-(1R,2S)-aminocyclohexyl ether compound of formula (112) or formula (113) or formula (114).
Figure 23:
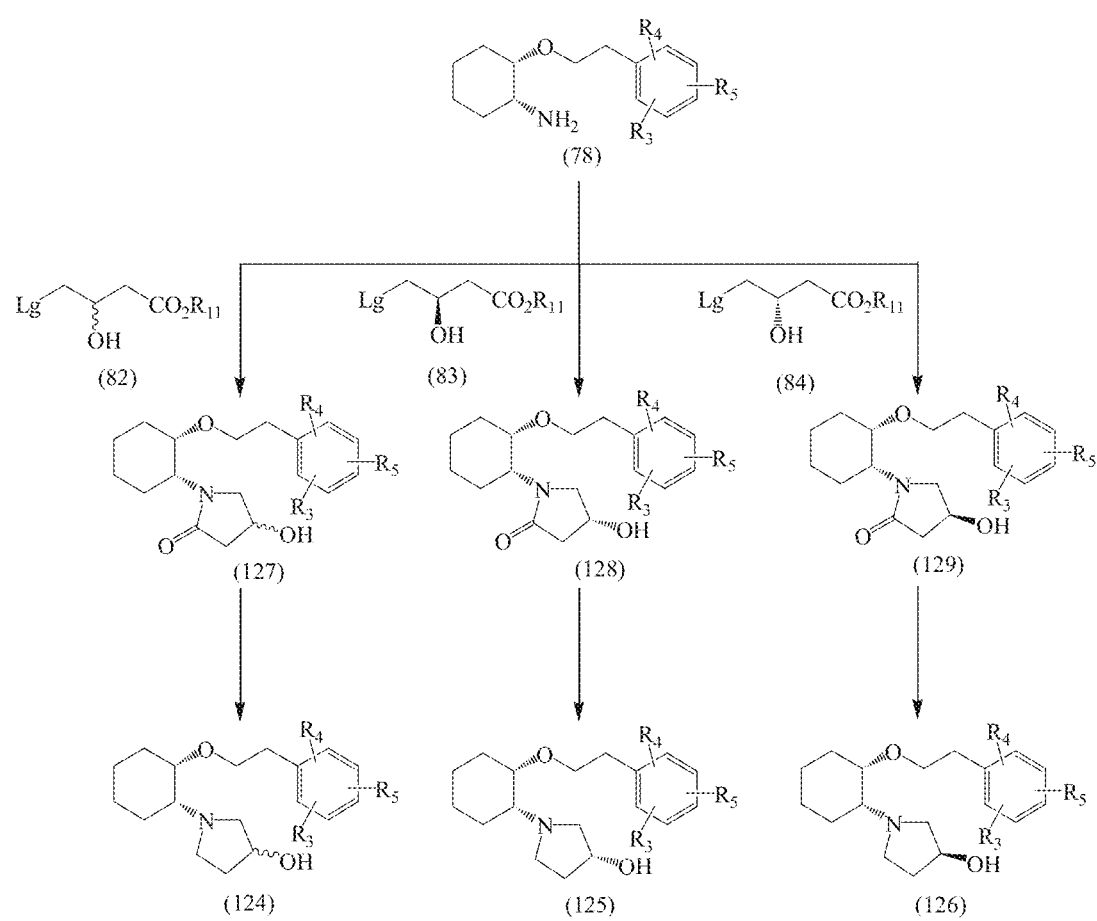
FIG. 23 illustrates a general reaction scheme that may be used as a process for preparing a stereoisomerically substantially pure cis-(1S,2R)-aminocyclohexyl ether compound of formula (124) or formula (125) or formula (126).

Similarly, reaction conditions and reagents described above for FIG. 14 or FIG. 17 may be applicable for the general reaction scheme as shown in FIG. 20 for preparing cis-(1R,2S)-aminocyclohexyl ether compound of formula (112) or formula (113) or formula (114) starting from (77); and for the general reaction scheme as shown in FIG. 23 for preparing cis-(1S,2R)-aminocyclohexyl ether compound of formula (124) or formula (125) or formula (126) starting from (78).

Figure 21:
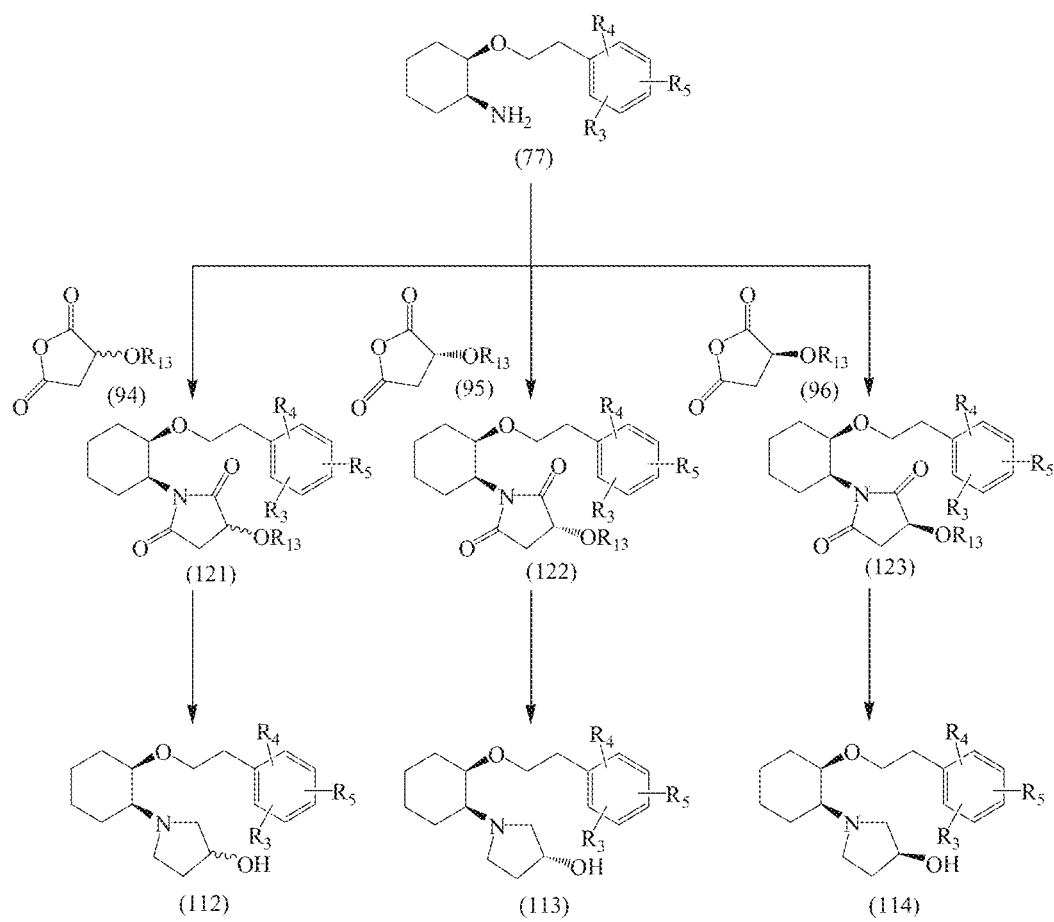
FIG. 21 illustrates a general reaction scheme that may be used as a process for preparing a stereoisomerically substantially pure cis-(1R,2S)-aminocyclohexyl ether compound of formula (112) or formula (113) or formula (114).
Figure 24:
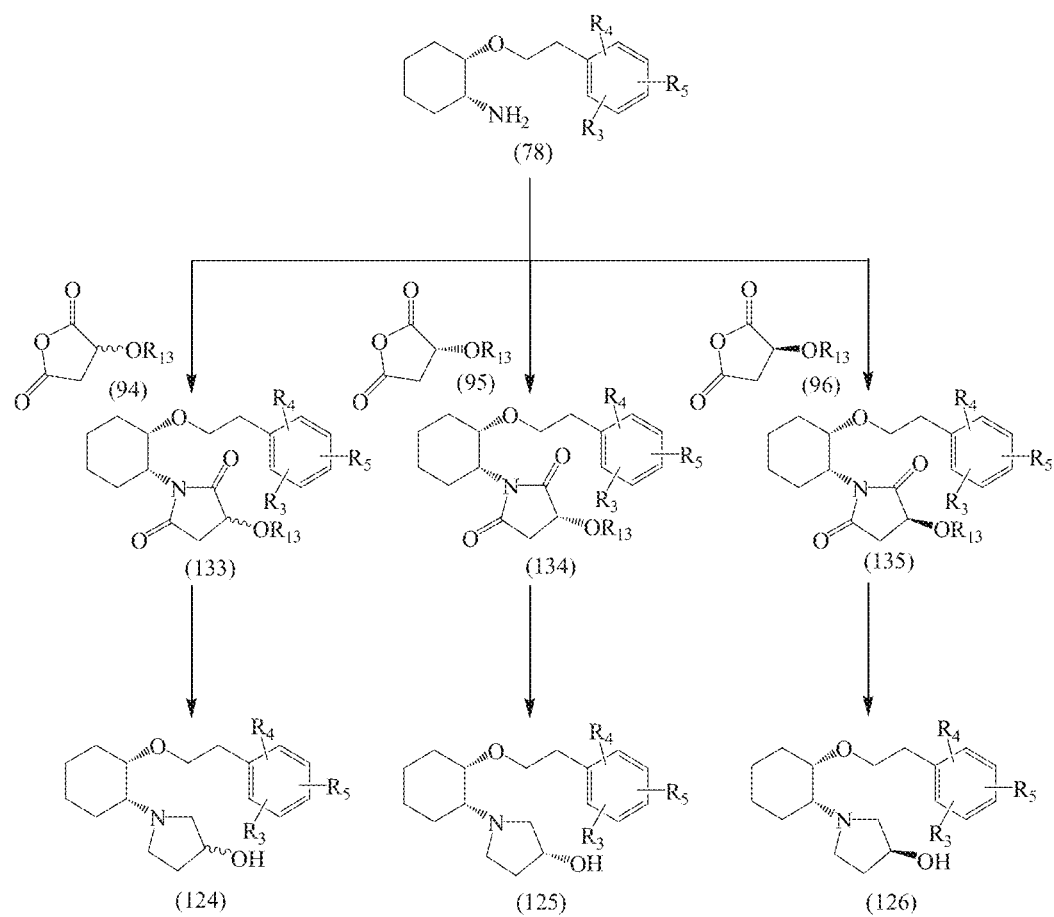
FIG. 24 illustrates a general reaction scheme that may be used as a process for preparing a stereoisomerically substantially pure cis-(1S,2R)-aminocyclohexyl ether compound of formula (124) or formula (125) or formula (126).

Similarly, reaction conditions and reagents described above for FIG. 15 or FIG. 18 may be applicable for the general reaction scheme as shown in FIG. 21 for preparing cis-(1R,2S)-aminocyclohexyl ether compound of formula (112) or formula (113) or formula (114) starting from (77); and for the general reaction scheme as shown in FIG. 24 for preparing cis-(1S,2R)-aminocyclohexyl ether compound of formula (124) or formula (125) or formula (126) starting from (78).

The aminocyclohexyl ether compounds of the present invention may be used for medical applications, including, for example, cardiac arrhythmia, such as atrial arrhythmia and ventricular arrhythmia.

The present invention also encompasses the pharmaceutically acceptable salts, esters, amides, complexes, chelates, clathrates, solvates, crystalline or amorphous forms, metabolites, metabolic precursors or prodrugs of the compounds of the present invention. Pharmaceutically acceptable esters and amides can be prepared by reacting, respectively, a hydroxy or amino functional group with a pharmaceutically acceptable organic acid, such as identified below. A prodrug is a drug which has been chemically modified and may be biologically inactive at its site of action, but which is degraded or modified by one or more enzymatic or other in vivo processes to the parent bioactive form. Generally, a prodrug has a different pharmakokinetic profile than the parent drug such that, for example, it is more easily absorbed across the mucosal epithelium, it has better salt formation or solubility and/or it has better systemic stability (e.g., an increased plasma half-life).

Those skilled in the art recognize that chemical modifications of a parent drug to yield a prodrug include: (1) terminal ester or amide derivatives, which are susceptible to being cleaved by esterases or lipases; (2) terminal peptides, which may be recognized by specific or nonspecific proteases; or (3) a derivative that causes the prodrug to accumulate at a site of action through membrane selection, and combinations of the above techniques. Conventional procedures for the selection and preparation of prodrug derivatives are described in H. Bundgaard, Design of Prodrugs, (1985). Those skilled in the art are well-versed in the preparation of prodrugs and are well-aware of its meaning.

The present invention also encompasses the pharmaceutically acceptable complexes, chelates, metabolites, or metabolic precursors of the compounds of the present invention. Information about the meaning these terms and references to their preparation can be obtained by searching various databases, for example Chemical Abstracts and the U.S. Food and Drug Administration (FDA) website. Documents such as the followings are available from the FDA: Guidance for Industry, "In Vivo Drug Metabolism/Drug Interaction Studies—Study Design, Data Analysis, and Recommendations for Dosing and Labeling", U.S. Department of Health and Human Services, Food and Drug Administration, Center for Drug Evaluation and Research (CDER), Center for Biologics Evaluation and Research (CBER), November 1999. Guidance for Industry, "In Vivo Drug Metabolism/Drug Interaction Studies in the DRUG DEVELOPMENT PROCESS: STUDIES IN VITRO", U.S. Department of Health and Human Services, Food and Drug Administration, Center for Drug Evaluation and Research (CDER), Center for Biologics Evaluation and Research (CBER), April 1997.

The synthetic procedures described herein, especially when taken with the general knowledge in the art, provide sufficient guidance to those of ordinary skill in the art to perform the synthesis, isolation, and purification of the compounds of the present invention. Further, it is contemplated that the individual features of these embodiments and examples may be combined with the features of one or more other embodiments or examples.

As used herein, "treating arrhythmia" refers to therapy for arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral dosage form. Such dosage forms include, but are not limited to, parenteral solutions, tablets, capsules, sustained release implants, and transdermal delivery systems. Generally, oral or intravenous administration is preferred for some treatments. The dosage amount and frequency are selected to create an effective level of the agent without harmful effects. It will generally range from a dosage of from about 0.01 to about 100 mg/kg/day, and typically from about 0.1 to 10 mg/kg where administered orally or intravenously for antiarrhythmic effect or other therapeutic application.

In order to assess whether a compound has a desired pharmacological activity with the present invention, it may be subjected to a series of tests. The precise test to employ will depend on the physiological response of interest. The published literature contains numerous protocols for testing the efficacy of a potential therapeutic agent, and these protocols may be employed with the present compounds and compositions.

For example, in connection with treatment or prevention of arrhythmia, a series of four tests may be conducted. In the first of these tests, a compound of the present invention is given as increasing (doubling with each dose) intravenous infusion every 5 minutes to a conscious rat. The effects of the compound on blood pressure, heart rate and the ECG are measured continuously. Increasing doses are given until a severe adverse event occurs. The drug related adverse event is identified as being of respiratory, central nervous system or cardiovascular system origin. This test gives an indication as to whether the compound is modulating the activity of sodium channels and/or potassium channels, and in addition gives information about acute toxicity. The indices of sodium channel blockade are increasing P-R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. The test provides evidence for direct toxic effects on the myocardium. Additionally, selectivity, potency and efficacy of action of a compound can be ascertained under conditions simulating ischemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions.

All of the foregoing tests are performed using rat tissue. In order to ensure that a compound is not having effects which are only specific to rat tissue, further experiments are performed in dogs and primates. In order to assess possible sodium channel and potassium channel blocking action in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system is assessed.

The effects of a compound on the ECG and responses to electrical stimulation are also assessed in intact, anesthetized monkeys (*Macaca fascicularis*). In this preparation, a blood pressure cannula and ECG electrodes are suitably placed in an anesthetized monkey. In addition, a stimulating electrode is placed onto the right atria and/or ventricle, together with monophasic action potential electrode. As in the tests described above, ECG and electrical stimulation response to a compound reveal the possible presence of sodium and/or potassium channel blockade. The monophasic action potential also reveals whether a compound widens the action potential, an action expected of a potassium channel blocker.

As another example, in connection with the mitigation or prevention of the sensation of pain, the following test may be performed. To determine the effects of a compound of the present invention on an animal's response to a sharp pain sensation, the effects of a slight prick from a 7.5 g weighted syringe fitted with a 23G needle as applied to the shaved back of a guinea pig (*Cavia porcellus*) is assessed following subcutaneous administration of sufficient (50 µl, 10 mg/ml) solution in saline to raise a visible bleb on the skin. Each test is performed on the central area of the bleb and also on its periphery to check for diffusion of the test solution from the point of administration. If the test animal produces a flinch in response to the stimulus, this demonstrates the absence of blockade of pain sensation. Testing can be carried out at intervals for up to 8 hours or more post-administration. The sites of bleb formation are examined after 24 hours to check for skin abnormalities consequent to local administration of test substances or of the vehicle used for preparation of the test solutions.

The following examples are offered by way of illustration and not by way of limitation. In the Examples, and unless otherwise specified, starting materials were obtained from well-known commercial supply houses, e.g., Aldrich Chemical Company (Milwaukee, Wis.), and were of standard grade and purity. "Ether" and "ethyl ether" each refers to diethyl ether; "h." refers to hours; "min." refers to minutes; "GC" refers to gas chromatography; "v/v" refers to volume per volume; and ratios are weight ratios unless otherwise indicated.

General Experimental Procedures

Melting points were determined on a Fisher-Johns apparatus and are uncorrected. NMR spectra were acquired in the indicated solvent on a Brucker AC-200, Varian XL-300, Brucker AV-300 or AV-400. Mass spectra were recorded for EI on a Kratos MS50, for FAB/LSIMS on a Kratos Concept IIHQ and for ES on a Micromass (Waters) Quattro (I) MSMS, connected to a HP 1090 Series 2 LC (Agilent), controlled by Masslynx version 3.3 software. Elemental analyses were performed on an Element Analyzer 1108 by D. & H. Malhow, University of Alberta, Edmonton, AB. Where analyses are indicated only by symbols of the elements, analytical results were within ±0.4% of the theoretical values. Whenever elemental analyses were not available, purity was determined by HPLC and capillary electrophoresis (CE). HPLC analyses were performed using a Gilson HPLC system (Gilson, Middleton, Wis.) with UV detection at 200 nm. A $C_{18}$ column with 150×4.6 mm, 5μ particle size was used. The mobile phase was delivered isocratically or as a gradient at a flow rate of 1 mL/min and consisted of a combination of phosphate buffer (low or high pH) and acetonitrile. Samples were prepared at ~100 μg/mL in mobile phase and 20 μL were injected into the HPLC. Purity was expressed in area %. CE analyses were performed using a P/ACE System MDQ (Beckman Coulter, Fullerton, Calif.). Uncoated silica capillaries with 60 (50 to detector) cm length and 75 μm internal diameter were used. The run buffer used was 100 mM sodium phosphate (pH 2.5). The separation voltage was either 23 or 25 kV (normal polarity) and the capillary cartridge temperature was maintained at 20° C. Samples (~0.5 mg/mL in water) were injected by pressure at 0.5 psi for 6 seconds. Detection was by UV at 200 or 213 nm. Purity was expressed in area %. IR were recorded on a Perkin-Elmer 983G spectrophotometer. Optical rotations were performed by F. Hoffman-La Roche Ltd (CH, Basel). Thin layer chromatography (TLC) was performed on E. Merck, TLC aluminum sheets 20×20 cm, Silica gel 60 $F_{254}$ plates. Flash chromatography was performed on E. M. Science silica gel 60 (70-230 mesh). Dry flash chromatography was performed with Sigma silica gel type H. Chromatotron chromatography (Harisson Research, USA) was performed on 4 mm plate with EM Science silica gel 60P $F_{254}$ with Gypsum or aluminum oxide 60P $F_{254}$ with Gypsum (type E). Preparative HPLC were performed on a Waters Delta Prep 4000 with a cartridge column (porasil, 10 μm, 125 Å, 40 mm×100 mm) GC analyses were performed on a Hewlett Packard HP 6890 equipped with 30 m×0.25 mm×0.25 capillary column HP-35 (crosslinked 35% PH ME siloxane) and a flame-ionization detector. High-boiling solvents (DMF, DMSO) were Sure/Seal™ from Aldrich, and tetrahydrofuran (THF) and ethylene glycol dimethyl ether (DME) were distilled from sodium-benzophenone ketyl. Organic extracts were dried with $Na_2SO_4$ unless otherwise noted. All moisture sensitive reactions were performed in dried glassware under a nitrogen or argon atmosphere.

Biological Activity Data

Assessment of Antiarrhythmic Efficacy

Antiarrhythmic efficacy may be assessed by investigating the effect of a compound on the incidence of cardiac arrhythmias in anesthetized rats subjected to coronary artery occlusion. Rats weighing 200-300 gms are subjected to preparative surgery and assigned to groups in a random block design. In each case, the animal is anesthetized with pentobarbital during surgical preparation. The left carotid artery is cannulated for measurement of mean arterial blood pressure and withdrawal of blood samples. The left jugular vein is also cannulated for injection of drugs. The thoracic cavity is opened and a polyethylene occluder loosely placed around the left anterior descending coronary artery. The thoracic cavity is then closed. An ECG is recorded by insertion of electrodes placed along the anatomical axis of the heart. In a random and double-blind manner, an infusion of vehicle or the compound to be tested is given about 15 min post-surgery. After 5 minutes infusion, the occluder is pulled so as to produce a coronary artery occlusion. ECG, arrhythmias, blood pressure, heart rate and mortality are monitored for 15 minutes after occlusion. Arrhythmias are recorded as ventricular tachycardia (VT) and ventricular fibrillation (VF) and scored according to Curtis, M. J. and Walker, M. J. A., *Cardiovasc. Res.* 22:656 (1988) (see Table 1).

TABLE 1

| Score | Description |
|---|---|
| 0 | 0-49 VPBs |
| 1 | 50-499 VPBs |
| 2 | >499 VPBs and/or 1 episode of spontaneously reverting VT or VF |
| 3 | >1 episode of VT or VF or both (>60 s total combined duration) |
| 4 | VT or VF or both (60-119 s total combined duration) |
| 5 | VT or VF or both (>119 s total combined duration) |
| 6 | fatal VF starting at >15 min after occlusion |
| 7 | fatal VF starting at from 4 min and 14 min 59 s after occlusion |
| 8 | fatal VF starting at from 1 min and 3 min 59 s after occlusion |
| 9 | fatal VF starting <1 min after occlusion | where: VPB = ventricular premature beats
VT = ventricular tachycardia
VF = ventricular fibrillation Rats are excluded from the study if they did not exhibit pre-occlusion serum potassium concentrations within the range of 2.9-3.9 mM. Occlusion is associated with increases in R-wave height and "S-T" segment elevation; and an occluded zone (measured after death by cardiogreen dye perfusion) in the range of 25%-50% of total left-ventricular weight.

Results of the test compounds prepared by the method of the present invention may be expressed as values of a given infusion rate in micromol/kg/min. ($ED_{50}AA$) which will reduce the arrhythmia score in treated animals to 50% of that shown by animals treated only with the vehicle in which the test compound(s) is dissolved.

Measurement of Cardiovascular and Behavioral Effects

Preparative surgery is performed in Sprague Dawley rats weighing 200-300 gm and anaesthetized with 65 mg/kg (i.p.) pentobarbital. The femoral artery and vein are cannulated using polyethylene (PE)-10 tubing. Prior to surgery, this PE-10 tubing had been annealed to a wider gauge (PE-50) tubing for externalization. The cannulated PE-10/PE-50 tubing is passed through a trocar and exteriorised together with three (lead II) limb ECG leads (see below). The trocar is threaded under the skin of the back and out through a small incision at the mid-scapular region. A ground ECG electrode is inserted subcutaneously using a 20 gauge needle with the lead wire threaded through it. To place the other ECG electrodes, a small incision is made in the anterior chest region over the heart and ECG leads are inserted into the subcutaneous muscle layer in the region of the heart using a 20 guage needle. Other ECG leads are inserted into the subcutaneous muscle layer in the region near the base of the neck and shoulder (right side). The animal is returned to a clean recovery-cage with free access to food and water. The treatment and observational period for each animal commenced after a 24-hour recovery period.

A 15 minute-observational period is recorded followed by the intravenous infusion regime of the test compound at an initial dose of 2.0 μmol/kg/min (at 1 ml/hr). This rate is doubled every 5 minutes until one of the following effects is observed:

a) partial or complete convulsions
b) severe arrhythmias
c) bradycardia below 120 beats/minute
d) hypotension below 50 mmHg
e) the dose exceeds 32 times the initial starting dose (i.e. 64 μmol/kg/min).

Blood pressure (BP), heart rate (HR) and ECG variables are continuously recorded while behavioral responses are also monitored and the total accumulative drug dose and drug infusion rate at which the response (such as convulsion, piloerection, ataxia, restlessness, compulsive chewing, lip-smacking, wet dog shake etc.) occurred are recorded.

Blood Samples

Estimates of plasma concentrations of the test compound are determined by removing a 0.5 ml blood sample at the end of the experiment. Blood samples are centrifuged for 5 min at 4600×g and the plasma decanted. Brain tissue samples are also extracted and kept frozen (−20° C.) along with the plasma samples for chemical analysis.

Data Analysis

Electrocardiograph (ECG) parameters: PR, QRS, $QT_1$ (peak of T-wave), $QT_2$ (midpoint of T-wave deflection) and hemodynamic parameters: BP and HR are analyzed using the automated analysis function in LabView (National Instruments) with a customized autoanalysis software (Nortran Pharmaceuticals). The infused dose producing 25% from control ($D_{25}$) for all recorded ECG variables is determined.

Results of the tests can be expressed as $D_{25}$ (micromol/kg) which are the doses required to produce a 25% increase in the ECG parameter measured. The increases in P-R interval and QRS interval indicate cardiac sodium channel blockade while the increase in Q-T interval indicates cardiac potassium channel blockade.

Electrophysiological Test (In Vivo)

This experiment determines the potency of the test compound for its effects on haemodynamic and electrophysiological parameters under non-ischemic conditions.

Methods

Surgical Preparation

Male Sprague-Dawley rats weighing from 250-350 g are used. They are randomly selected from a single group and anesthetized with pentobarbital (65 mg/kg, ip.) with additional anesthetic given if necessary.

The trachea is cannulated and the rat is artificially ventilated at a stroke volume of 10 ml/kg, 60 strokes/minute. The right external jugular vein and the left carotid artery are cannulated for intravenous injections of compounds and blood pressure (BP) recording, respectively.

Needle electrodes are subcutaneously inserted along the suspected anatomical axis (right atrium to apex) of the heart for ECG measurement. The superior electrode is placed at the level of the right clavicle about 0.5 cm from the midline, while the inferior electrode is placed on the left side of the thorax, 0.5 cm from the midline and at the level of the ninth rib.

Two Teflon-coated silver electrodes are inserted through the chest wall using 27G needles as guides and implanted in the epicardium of left ventricle (4-5 mm apart). Square pulse stimulation is provided by a stimulator controlled by a computer. In-house programmed software is used to determine the following: threshold current (iT) for induction of extra systoles, maximum following frequency (MFF), effective refractory period (ERP) and ventricular flutter threshold (VTt). Briefly, iT is measured as the minimal current (in μA) of a square wave stimulus required to capture and pace the heart at a frequency of 7.5 Hz and a pulse width of 0.5 msec; ERP is the minimum delay (in msec) for a second stimulus required to cause an extra systole with the heart entrained at a frequency of 7.5 Hz (1.5×iT and 0.2 msec pulse width), MFF is the maximum stimulation frequency (in Hz) at which the heart is unable to follow stimulation (1.5×iT and 0.2 msec pulse width); VTt is the minimum pulse current (in μA) to evoke a sustained episode of VT (0.2 msec pulse width and 50 Hz) (Howard, P. G. and Walker, M. J. A., *Proc. West. Pharmacol. Soc.* 33:123-127 (1990)).

Blood pressure (BP) and electrocardiographic (ECG) parameters are recorded and analyzed using LabView (National Instruments) with a customized autoanalysis software (Nortran Pharmaceuticals Inc.) to calculate mean BP (mmHg, ⅔ diastolic+⅓ systolic blood pressure), HR (bpm, 60/R-R interval); PR (msec, the interval from the beginning of the P-wave to the peak of the R-wave), QRS (msec, the interval from the beginning of the R-wave due to lack of Q wave in rat ECG, to the peak of the S-wave), QT (msec, the interval from the beginning of the R-wave to the peak of the T-wave).

Experimental Protocol

The initial infusion dose is chosen based on a previous toxicology study of the test compound in conscious rats. This is an infusion dose that did not produce a 10% change from pre-drug levels in haemodynamic or ECG parameters.

The animal is left to stabilize prior to the infusion treatment according to a predetermined random and blind table. The initial infusion treatment is started at a rate of 0.5 ml/hr/300 g (i.e., 0.5 μmol/kg/min) Each infusion dose is doubled (in rate) every 5 minutes. All experiments are terminated at 32 ml/hr/300 g (i.e., 32 μmol/kg/min) Electrical stimulation protocols are initiated during the last two minutes of each infusion level.

Data Analyses

Responses to test compounds are calculated as percent changes from pre-infusion values; this normalization is used to reduce individual variation. The mean values of BP and ECG parameters at immediately before the electrical stimulation period (i.e., 3 min post-infusion) are used to construct cumulative dose-response curves. Data points are fit using lines of best fit with minimum residual sum of squares (least squares; SlideWrite program; Advanced Graphics Software, Inc.). $D_{25}$'s (infused dose that produced 25% change from pre-infusion value) are interpolated from individual cumulative dose-response curves and used as indicators for determining the potency of compounds of the present invention.

Canine Vagal-AF Model

General Methods

Mongrel dogs of either sex weighing 15-49 kg are anesthetized with morphine (2 mg/kg im initially, followed by 0.5 mg/kg IV every 2 h) and α-chloralose (120 mg/kg IV followed by an infusion of 29.25 mg/kg/h; St.-Georges et al., 1997). Dogs are ventilated mechanically with room air supplemented with oxygen via an endotracheal tube at 20 to 25 breaths/minute with a tidal volume obtained from a nomogram. Arterial blood gases are measured and kept in the physiological range ($SAO_2$>90%, pH 7.30-7.45). Catheters are inserted into the femoral artery for blood pressure recording and blood gas measurement, and into both femoral veins for drug administration and venous sampling. Catheters are kept patent with heparinized 0.9% saline solution. Body temperature is maintained at 37-40° C. with a heating blanket.

The heart is exposed via a medial thoracotomy and a pericardial cradle is created. Three bipolar stainless steel, Teflon™-coated electrodes are inserted into the right atria for recording and stimulation, and one is inserted into the left atrial appendage for recording. A programmable stimulator (Digital Cardiovascular Instruments, Berkeley, Calif.) is used to stimulate the right atrium with 2 ms, twice diastolic threshold pulses. Two stainless steel, Teflon™-coated electrodes are inserted into the left ventricle, one for recording and the other for stimulation. A ventricular demand pacemaker (GBM 5880, Medtronics, Minneapolis, Minn.) is used to stimulate the ventricles at 90 beats/minute when (particular during vagal-AF) the ventricular rate became excessively slow. A P23 ID transducer, electrophysiological amplifier (Bloom Associates, Flying Hills, Pa.) and paper recorder (Astromed MT-95000, Toronto, ON, Canada) are used to record ECG leads II and III, atrial and ventricular electrograms, blood pressure and stimulation artefacts. The vagi are isolated in the neck, doubly-ligated and divided, and electrodes inserted in each nerve (see below). To block changes in β-adrenergic effects on the heart, nadolol is administered as an initial dose of 0.5 mg/kg iv, followed by 0.25 mg/kg IV every two hours.

Atrial Fibrillation Model

Drug effects to terminate sustained AF maintained during continuous vagal nerve stimulation are assessed. Unipolar hook electrodes (stainless steel insulated with Teflon™, coated except for the distal 1-2 cm) are inserted via a 21 gauge needle within and parallel to the shaft of each nerve. In most experiments, unipolar stimuli are applied with a stimulator (model DS-9F, Grass Instruments, Quincy, Mass.) set to deliver 0.1 ms square-wave pulses at 10 Hz and a voltage 60% of that required to produce asystole. In some experiments, bipolar stimulation is used. The voltage required to produce asystole ranged from 3-20 volts. Under control conditions, a short burst of rapid atrial pacing (10 Hz, four times diastolic threshold) is delivered to induce AF which is ordinarily sustained for more than 20 minutes. The vagal stimulation voltage is adjusted under control conditions, and then readjusted after each treatment to maintain the same bradycardic effect. AF is defined as rapid (>500 minute under control conditions), irregular atrial rhythm with varying electrogram morphology.

Measurement of Electrophysiological Variables and Vagal Response

Diastolic threshold current is determined at a basic cycle length of 300 ms by increasing the current 0.1 mA incrementally until stable capture is obtained. For subsequent protocols current is set to twice diastolic threshold. Atrial and ventricular ERP is measured with the extrastimulus method, over a range of S1S2 intervals at a basic cycle length of 300 ms. A premature extrastimulus S2 is introduced every 15 basic stimuli. The S1S2 interval is increased in 5 ms increments until capture occurred, with the longest S1S2 interval consistently failing to produce a propagated response defining ERP. Diastolic threshold and ERP are determined in duplicate and averaged to give a single value. These values are generally within 5 ms. The interval from the stimulus artefact and the peak of the local electrogram is measured as an index of conduction velocity. AF cycle length (AFCL) is measured during vagal-AF by counting the number of cycles (number of beats −1) over a 2-second interval at each of the atrial recording sites. The three AFCLs measurements are averaged to obtain an overall mean AFCL for each experimental condition.

The stimulus voltage-heart rate relationship for vagal nerve stimulation is determined under control conditions in most experiments. The vagal nerves are stimulated as described above with various voltages to determine the voltage which caused asystole (defined as a sinus pause greater than 3 seconds). The response to vagal nerve stimulation is confirmed under each experimental condition and the voltage adjusted to maintain the heart rate response to vagal nerve stimulation constant. In cases in which is not possible to produce asystole, vagal nerve stimulation is adjusted to a voltage which allowed two 20-minute episodes of vagal-AF to be maintained under control conditions (see below).

Experimental Protocols

One of the experimental groups studied is summarized in Table 3. Each dog received only one drug at doses indicated in Table 3. The first series of experiments are dose ranging studies, followed by blinded study in which 1-3 doses are given. All drugs are administered IV via an infusion pump, with drug solutions prepared freshly in plastic containers on the day of the experiment. Vagal stimulation parameters are defined under control conditions as described above, and maintenance of AF during 20 minutes of vagal nerve stimulation under control conditions is verified. After the termination of AF, the diastolic threshold and ERP of the atrium and ventricle are determined. Subsequently, these variables are reassessed in the atrium under vagal nerve stimulation. Electrophysiological testing usually took 15-20 minutes. The heart rate response to vagal nerve stimulation is confirmed and the vagal-AF/electrophysiological testing protocol is repeated. A pre-drug blood sample is obtained and vagal-AF reinstituted. Five minutes later, one of the treatments is administered at doses shown in Table 2. The total dose is infused over 5 minutes and a blood sample obtained immediately thereafter. No maintenance infusion is given. If AF terminated within 15 minutes, the electrophysiological measurements obtained under control conditions are repeated and a blood sample is obtained. If AF is not terminated by the first dose (within 15 minutes), a blood sample is obtained and vagal stimulation is discontinued to allow a return to sinus rhythm. The electrophysiological measurements are repeated and a third and final blood sample for this dose is obtained. AF is reinitiated and the vagal-AF/drug infusion/electrophysiological testing protocol is repeated until AF is terminated by the drug.

Statistical Analysis

Group data are expressed as the mean±SEM. Statistical analysis is carried out for effective doses for AFCL, and ERP using a t-test with a Bonferroini correction for multiple comparisons. Drug effects on blood pressure, heart rate, diastolic threshold and ECG intervals are assessed at the median dose for termination of AF. Two tailed tests are used and a $p<0.05$ is taken to indicate statistical significance.

TABLE 2

Experimental Groups and Doses of Drugs

| Drug | Dose range tested (μmol/kg) | Effective doses for terminating AF (μmol/kg) | Mean dose required for termination of AF (μmol/kg) | Median dose required for termination of AF (μmol/kg) |
|---|---|---|---|---|
| Flecainide | 1.25-10 | 4-2.5; 1-10 | 4 ± 2 | 2.5 |

A single drug was administered to each dog over the dose range specified until AF was terminated. The number of dogs in which AF was terminated at each dose is shown (number of dogs-dose, in μmol/kg). The mean±SEM as well as the median dose required to terminate AF is shown. Each dog received only one drug.

Compounds prepared by the method of the present invention may be evaluated by this method. The effectiveness of flecainide as a control in the present study was comparable to that previously reported.

Canine Sterile Pericarditis Model

This model has been used to characterize the mechanisms of AF and atrial flutter (AFL). Waldo and colleagues have found that AF depends on reentry and that the site of termination is usually an area of slowed conduction. This canine model is prepared by dusting the exposed atria with talcum powder followed by "burst" pacing the atria over a period of days after recovery. AF is inducible two days after surgery, however, by the fourth day after surgical preparation; sustainable atrial flutter is the predominant inducible rhythm. The inducibility of AF at day 2 is somewhat variable, such that only 50% of dogs may have sustained AF (generally <60 minutes) for a requisite of 30 minutes. However, the sustainable atrial flutter that evolves by the fourth day is inducible in most preparations. Atrial flutter is more readily "mapped" for purposes of determining drug mechanisms. Inducibility of AF subsides after the fourth day post-surgery, similar to the AF that often develops following cardiac surgery that the sterile pericarditis model mimics. There may be an inflammatory component involved in the etiology of post-surgery AF that would provide a degree of selectivity to an ischaemia or acid selective drug. Similarly, while coronary artery bypass graft (CABG) surgery is performed to alleviate ventricular ischaemia, such patients may also be at risk for mild atrial ischaemia due to coronary artery disease (CAD). While atrial infarcts are rare, there has been an association from AV nodal artery stenosis and risk for AF following CABG surgery. Surgical disruption of the autonomic innervation of the atria may also play a role in AF following CABG.

Methods

Studies are carried out in a canine model of sterile percarditis to determine the potency and efficacy of compounds of the present invention in terminating atrial fibrillation/flutter. Atrial flutter or fibrillation was induced 2 to 4 days after creation of sterile pericarditis in adult mongrel dogs weighing 19 kg to 25 kg. In all instances, the atrial fibrillation or flutter lasted longer than 10 minutes.

Creation of the Sterile Pericarditis Atrial Fibrillation/Flutter Model

The canine sterile pericarditis model is created as previously described. At the time of surgery, a pair of stainless steel wire electrodes coated with FEP polymer except for the tip (O Flexon, Davis and Geck) are sutured on the right atrial appendage, Bachman's bundle and the posteroinferior left atrium close to the proximal portion of the coronary sinus. The distance from each electrode of each pair is approximately 5 mm. These wire electrodes are brought out through the chest wall and exteriorized posteriorly in the interscapular region for subsequent use. At the completion of surgery, the dogs are given antibiotics and analgesics and then are allowed to recover. Postoperative care included administration of antibiotics and analgesics.

In all dogs, beginning on postoperative day 2, induction of stable atrial fibrillation/flutter is attempted in the conscious, non-sedated state to confirm the inducibility and the stability of atrial fibrillation/flutter and to test the efficacy of the drugs. Atrial pacing is performed through the electrodes sutured during the initial surgery. On postoperative day 4, when stable atrial flutter is induced, the open-chest study is performed.

For the open-chest study, each dog is anesthetized with pentobarbital (30 mg/kg IV) and mechanically ventilated with 100% oxygen by use of a Boyle model 50 anesthesia machine (Harris-Lake, Inc.). The body temperature of each dog is kept within the normal physiological range throughout the study with a heating pad. With the dog anesthetized, but before the chest is opened, radiofrequency ablation of the His bundle is performed to create complete atrioventricular (AV) block by standard electrode catheter techniques. This is done to minimize the superimposition of atrial and ventricular complexes during subsequent recordings of unipolar atrial electrograms after induction of atrial flutter. After complete AV block is created, an effective ventricular rate is maintained by pacing of the ventricles at a rate of 60 to 80 beats per minute with a Medtronic 5375 Pulse Generator (Medtronic Inc.) to deliver stimuli via the electrodes sutured to the right ventricle during the initial surgery.

Determination of Stimulus Thresholds and Refractory Periods During Pacing

For the induction of AF/AFL, one of two previously described methods is used: (1) introduction of one or two premature atrial beats after a train of 8 paced atrial beats at a cycle length of 400 ms, 300 ms, 200 ms, or 150 ms, or (2) rapid atrial Pacing for Periods of 1 to 10 seconds at rates incrementally faster by 10 to 50 beats per minute than the spontaneous sinus rate until atrial flutter is induced or there is a loss of 1:1 atrial capture. Atrial pacing is performed from either the right atrial appendage electrodes or the posteroinferior left atrial electrodes. All pacing is performed using stimuli of twice threshold for each basic drive train with a modified Medtronic 5325 programmable, battery-poared stimulator with a pulse width of 1.8 ms.

After the induction of stable atrial fibrillation/flutter (lasting longer than 10 minutes), the atrial fibrillation/flutter cycle length is measured and the initial mapping and analysis are performed to determine the location of the atrial fibrillation/flutter reentrant circuit. Atrial flutter is defined as a rapid atrial rhythm (rate, >240 beats per minute) characterized by a constant beat-to-beat cycle length, polarity, morphology, and amplitude of the recorded bipolar electrograms.

Drug Efficacy Testing Protocol

1. Effective refractory periods (ERPs) are measured from three sites: right atrial appendage (RAA), posterior left atrium (PLA), and Bachman's Bundle (BB), at two basic cycle lengths 200 and 400 ms.

2. Pace induce A-Fib or AFL. This is attempted for one hour. If no arrhythmia is induced, no further study is done on that day.

3. If induced, AF must have been sustained for 10 minutes. Then a waiting period is allowed for spontaneous termination or 20 minutes, whichever came first.

4. AF is then reinduced and 5 minutes is allowed before starting drug infusion.

5. Drug is then infused in a bolus over 5 minutes.

6. If AF terminated with the first dose then a blood sample is taken and ERP measurements are repeated.

7. Five minutes is allowed for the drug to terminate. If there is no termination then the second dose is given over 5 minutes.

8. After termination and ERPs are measured, a second attempt to reinduce AF is tried for a period of ten minutes.

9. If reinduced and sustained for 10 minutes, a blood sample is taken and the study repeated from #3 above.

10. If no reinduction, then the study is over.

Compounds prepared by the method of the present invention may be evaluated by this method.

Assessment of Pain Blockage

CD-1 mice (20-30 g) are restrained in an appropriate holder. A tourniquet is placed at the base of the tail and a solution of the test compound (50 µl, 5 mg/ml) is injected into the lateral tail vein. The tourniquet is removed 10 min after the injection. Suitable dilutions of compound solution are used to obtain an $ED_{50}$ for pain blockade at various times after injection. Pain responses are assessed by pin prick at regular intervals up to 4 hours post injection and the duration of pain blockage is recorded for three animals for each test compound solution. Compounds prepared by the method of the present invention may be evaluated according to the method described.

In Vitro Assessment of Inhibition Activity of ION Channel Modulating Compounds on Different Cardiac Ionic Currents Cell Culture:

The relevant cloned ion channels (e.g., cardiac hH1Na, Kv1.4, Kv1.5, Kv4.2, Kv2.1, HERG etc.) are studied by transient transfection into HEK cells using the mammalian expression vector pCDNA3. Transfections for each channel type are carried out separately to allow individual study of the ion channel of interest. Cells expressing channel protein are detected by cotransfecting cells with the vector pHook-1 (Invitrogen, San Diego, Calif., USA). This plasmid encoded the production of an antibody to the hapten phOX, which when expressed is displayed on the cell surface. Equal concentrations of individual channel and pHook DNA are incubated with 10×concentration of lipofectAce in Modified Eagle's Medium (MEM, Canadian Life Technologies) and incubated with parent HEK cells plated on 25 mm culture dishes. After 3-4 hours the solution is replaced with a standard culture medium plus 20% fetal bovine serum and 1% antimycotic. Transfected cells are maintained at 37C in an air/5% CO2 incubator in 25 mm Petri dishes plated on glass coverslips for 24-48 hours to allow channel expression to occur. 20 min prior to experiments, cells are treated with beads coated with phOX. After 15 min, excess beads are ished off with cell culture medium and cells which had beads stuck to them are used for electrophysiological tests.

Solutions:

For whole-cell recording the control pipette filling solution contained (in mM): KCl, 130; EGTA, 5; MgCl2, 1; HEPES, 10; Na2ATP, 4; GTP, 0.1; and is adjusted to pH 7.2 with KOH. The control bath solution contained (in mM): NaCl, 135; KCl, 5; sodium acetate, 2.8; MgCl2, 1; HEPES, 10; CaCl2, 1; and is adjusted to pH 7.4 with NaOH. The test ion channel modulating compound is dissolved to 10 mM stock solutions in water and used at concentrations from 0.5 and 100 μM.

Electrophysiological Procedures:

Coverslips containing cells are removed from the incubator before experiments and placed in a superfusion chamber (volume 250 μl) containing the control bath solution at 22C to 23C. All recordings are made via the variations of the patch-clamp technique, using an Axopatch 200A amplifier (Axon Instruments, CA). Patch electrodes are pulled from thin-walled borosilicate glass (World Precision Instruments; FL) on a horizontal micropipette puller, fire-polished, and filled with appropriate solutions. Electrodes had resistances of 1.0-2.5 μohm when filled with control filling solution. Analog capacity compensation is used in all whole cell measurements. In some experiments, leak subtraction is applied to data. Membrane potentials have not been corrected for any junctional potentials that arose from the pipette and bath solution. Data are filtered at 5 to 10 kHz before digitization and stored on a microcomputer for later analysis using the pClamp6 software (Axon Instruments, Foster City, Calif.). Due to the high level of expression of channel cDNA's in HEK cells, there is no need for signal averaging. The average cell capacitance is quite small, and the absence of ionic current at negative membrane potentials allowed faithful leak subtraction of data.

Data Analysis:

The concentration-response curves for changes in peak and steady-state current produced by the test compound are computer-fitted to the Hill equation:

$$f=1-1/[1+(IC_{50}/[D])^n] \quad [1]$$

where f is the fractional current (f=Idrug/Icontrol) at drug concentration [D]; $IC_{50}$ is the concentration producing half-maximal inhibition and n is the Hill coefficient.

Compounds of the present invention may be evaluated by this method. The results show that compounds of the present invention tested have different degree of effectiveness in blocking various ion channels. Block is determined from the decrease in peak hH1 $Na^+$ current, or in steady-state Kv1.5 and integrated Kv4.2 current in the presence of drug. To record $Na^+$ current, cells are depolarized from the holding potential of −100 mV to a voltage of −30 mV for 10 ms to fully open and inactivate the channel. To record Kv1.5 and Kv4.2 current, cells are depolarized from the holding potential of −80 mV to a voltage of +60 mV for 200 ms to fully open the channel. Currents are recorded in the steady-state at a range of drug concentrations during stimulation every 4 s. Reduction in peak current ($Na^+$ channel), steady-state current (Kv1.5 channel) or integrated current (Kv4.2) at the test potential of −30 mV ($Na^+$ channel) or +60 mV (Kv1.5 and Kv4.2 channel) is normalized to control current, then plotted against the concentration of test compound. Data are averaged from 4-6 cells. Solid lines are fit to the data using a Hill equation. The activity of compounds prepared by method of the present invention to modulate various ionic currents of interest may be similarly studied.

Assessment of Proarrhythmia (Torsade De Pointes) Risk of Ion Channel

Modulating Compounds in Primates

Method

General Surgical Preparation:

All studies are carried out in male *Macaca fascicularis* weighing from 4 and 5.5 kg. Animals are fasted over night and pre-medicated with ketamine (10 mg/kg im). Both saphenous veins are cannulated and a saline drip instituted to keep the lines patent. Halothane anaesthesia (1.5% in oxygen) is administered via a face mask. Lidocaine spray (10% spray) is used to facilitate intubation. After achieving a sufficient depth of anaesthesia, animals are intubated with a 4 or 5 French endotrachial tube. After intubation halothane is administered via the endotracheal tube and the concentration is reduced to 0.75-1%. Artificial respiration is not used and all animals continue to breathe spontaneously throughout the experiment. Blood gas concentrations and blood pH are measured using a blood gas analyser (AVO OPTI I). The femoral artery is cannulated to record blood pressure.

Blood pressure and a modified lead II ECG are recorded using a MACLAB 4S recording system paired with a Macintosh PowerBook (2400c/180). A sampling rate of 1 kHz is used for both signals and all data is archived to a Jazz disc for subsequent analysis.

Vagal Nerve Stimulation:

Either of the vagi is isolated by blunt dissection and a pair of electrodes inserted into the nerve trunk. The proximal end of the nerve is crushed using a vascular clamp and the nerve is stimulated using square wave pulses at a frequency of 20 Hz with a 1 ms pulse width delivered from the MACLAB stimulator. The voltage (range 2-10 V) is adjusted to give the desired bradycardic response. The target bradycardic response is a reduction in heart rate by half. In cases where a sufficient bradycardic response could not be obtained, 10

µg/kg neostigmine iv is administered. This dose of neostigmine is also given after administration of the test drug in cases where the test drug has vagolytic actions.

Test Compounds:

A near maximum tolerated bolus dose of the test compound, infused (iv) over 1 minute, is used to assess the risk of torsade de pointes caused by each test compound. The actual doses vary slightly depending on the animals' weight. Clofilium, 30µ mol/kg, is used as a positive comparison (control) for these studies. The expectation is that a high dose of drug would result in a high incidence of arrhythmias. The test compounds are dissolved in saline immediately before administration.

Experimental Protocol:

Each animal receives a single dose of a given drug iv. Before starting the experiment, two 30 second episodes of vagal nerve stimulation are recorded. A five minute rest period is allowed from episodes and before starting the experiment. The test solution is administered as an iv bolus at a rate of 5 ml/minute for 1 minute using an infusion pump (total volume 5 ml). ECG and blood pressure responses are monitored continuously for 60 minutes and the occurrence of arrhythmias is noted. The vagal nerve is stimulated for 30 seconds at the following times after injection of the drug: 30 seconds, 2, 5, 10, 15, 20, 25, 30 and 60 minutes.

Blood samples (1 ml total volume) are taken from each treated animal at the following times after drug administration: 30 seconds, 5, 10, 20, 30 and 60 minutes as well as 3, 6, 24 and 48 hours. Blood samples taken up to 60 minutes after drug administration are arterial while those taken after this time are venous. Samples are centrifuged, the plasma decanted and frozen. Samples are kept frozen before analysis of plasma concentration of the drug and potassium.

Statistics:

The effect of drugs on blood pressure, heart rate and ECG intervals are described as the mean±SEM for a group size of "n."

Compounds of the present invention may be evaluated by this method.

Determination of CNS Toxicity

In order to assess the activity of ion channel compounds in vivo it is important to know the maximum tolerated dose. Here CNS toxicity was assessed by investigating the minimum dose of a compound which induces partial or complete convulsions in conscious rats. The procedure avoids using lethality as an end point as well as avoiding unnecessary suffering as the experiment is terminated if this appears likely. Should the drug precipitate a life threatening condition (e.g., severe hypotension or cardiac arrhythmias) the animals are sacrificed via an overdose of pentobarbital.

Rats weighing 200-250 g were anaesthetized with pentobarbital anesthetic and subjected to preparative surgery. The femoral artery was cannulated for measurement of blood pressure and withdrawal of blood samples. The femoral vein was cannulated for injection of drugs. ECG leads were inserted into the subcutaneous muscle layer in the region of the heart and in the region near the base of the neck and shoulder. All cannulae and ECG leads were exteriorized in the mid scalpular region. To alleviate post-operative pain narcotics and local anesthetics were used. Animals were returned to a recovery cage for at least 24 hours before commencing the experiment. Infusion of the compound was then commenced via the femoral vein cannula. The initial rate of infusion was set at 2.0 micromole/kg/min at a rate of 1 ml/hr. The infusion rate was doubled every minute until partial or complete convulsions were observed. The maximum infusion rate used was 64 micromole/kg/min. Rates were continuously monitored and end time an infusion rate noted.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited by the specific embodiments and examples contained in this patent.

The following examples are offered by way of illustration and not by way of limitation. Unless otherwise specified, starting materials and reagents may be obtained from well-known commercial supply houses, e.g., Sigma-Aldrich Fine Chemicals (St. Louis, Mo.), and are of standard grade and purity; or may be obtained by procedures described in the art or adapted therefrom, where suitable procedures may be identified through the Chemical Abstracts and Indices therefor, as developed and published by the American Chemical Society (Washington, D.C.).

Example 1

Synthesis of 2R-(3R-benzyloxy-pyrrolidin-1R-yl)-cyclohexanol (14) from 2-(3-benzyloxy-pyrrolidin-1-yl)-cyclohexanol (12) and L-tartaric acid (13) (FIG. 2)

To a 1 L reaction vessel, L-tartaric acid (13) (17.7 g, 45.9 mmol) dissolved in 500 mL isopropanol was added a solution of 2-(3-benzyloxy-pyrrolidin-1-yl)-cyclohexanol (12) (59.2 g, 182.6 mmol) in 300 mL isopropanol at 20-25° C. The resulting solution was cooled to about 0 to −20° C., and stirring was continued for a further 10 h. The resultant beige coloured suspension was filtered and the crystals were washed two times with isopropanol (50 mL). The crystals were dried at about 30 to 50° C. in vacuo to give an off-white coloured solid (39.0 g, 90.6%). This solid was suspended in $H_2O$ (300 g) and methyl-t-butyl ether (200 mL). The resultant slurry was acidified with 10% HCl (42 mL, 115 mmol) until a pH of about 1 was obtained. The upper organic phase was separated and the lower aqueous phase was washed twice with methyl-t-butyl ether (2×100 mL). The pH of the aqueous phase was adjusted to 10-12 using 32% NaOH (31 mL, 248 mmol) and extracted twice with methyl-t-butyl-ether (200 mL, 100 mL). The combined organic phases were dried over sodium sulphate and the methyl-t-butyl ether was removed in vacuo to provide the product 2-(3-benzyloxy-pyrrolidin-1-yl)-cyclohexanol (14) as a yellow oil (18.95 g, 68.8 mmol.)

Synthesis of 3R-benzyloxy-1R-{2R-[2-(3,4-dimethoxy-phenyl)-ethoxy]-cyclohexyl}-pyrrolidine (17) from 2R-(3R-benzyloxy-pyrrolidin-1R-yl)-cyclohexanol (14) and trichloro-acetic acid 2-(3,4-dimethoxy-phenyl)-ethyl ester (16) (FIG. 2)

$HBF_4$ (60.3 mL, 71.2 g, 0.439 mol) was added dropwise to a solution of 2R-(3R-benzyloxy-pyrrolidin-1R-yl)-cyclohexanol (14) (94.8 g, 0.338 mol) in $CH_2Cl_2$ at about −10 to 10° C., and the mixture was stirred for 15 min at this temperature. To this yellow emulsion a solution of trichloro-acetic acid 2-(3,4-dimethoxy-phenyl)-ethyl ester (16) (121.4 g, 0.372 mol) in CH$_2$Cl$_2$ (520 mL) and diisopropyl ether (520 mL) was added. The resulting brown, turbid mixture was stirred at about −10 to 10° C. for about 15 to 25 h. After addition of saturated NaHCO$_3$ (680 mL), the mixture was stirred for about 20 to 40 min. The organic phase was extracted with 10% H$_3$PO$_4$ (6×210 mL), and then the combined aqueous phases were extracted with CH$_2$Cl$_2$ (2×150 mL). The combined organic phases were washed with 10% H$_3$PO$_4$ (90 mL) and with NaOH (pH 10, 220 mL). Removal of the solvent in vacuo yielded a brown oil (94.5 g,) of (17).

Synthesis of 1R-{2R-[2-(3,4-dimethoxy-phenyl)-ethoxy]-cyclohexyl}-pyrrolidin-3R-ol (18) from 3R-benzyloxy-1R-{ 2R-[2-(3,4-dimethoxy-phenyl)-ethoxy]-cyclohexyl}-pyrrolidine (17) (FIG. 2)

A suspension of 3R-benzyloxy-1R-{2R-[2-(3,4-dimethoxy-phenyl)-ethoxy]-cyclohexyl}-pyrrolidine (17) (94 g) from above reaction and Pd/C (10%, 20.4 g) in methanol (940 mL) and conc. HCl (35.8 g) was hydrogenated for about 2 h at RT. The solvent was removed in vacuo after filtration. The residue was dissolved in H$_2$O (500 mL), the resulting opalescent solution was treated for 15 min with activated charcoal (3 g) at RT, and the mixture was filtered to yield a clear yellow solution, which was washed with CH$_2$Cl$_2$ (2×50 mL). The pH of the aqueous phase was adjusted to >12 by the addition of conc. NaOH (57.6 g). Extraction with methyl-t-butyl ether (3×125 mL) and removal of the solvent in vacuo yielded a yellow oil (45.6 g). Addition of H$_2$O (220 mL) and conc. HCl (11 g) resulted in a clear yellow solution which was then washed with CH$_2$Cl$_2$ (3×20 mL). The aqueous phase was calcified to pH >11 by the addition of conc. NaOH (15.4 g), and the resulting emulsion extracted with methyl-t-butyl ether (3×50 mL). The organic phases were combined, and the solvent was removed in vacuo to yield a yellow oil (38.1 g) of (18).

Synthesis of 1R-{2R-[2-(3,4-dimethoxy-phenyl)-ethoxy]-cyclohexyl}-pyrrolidin-3R-ol hydrochloride (19) from 1R-{2R-[2-(3,4-dimethoxy-phenyl)-ethoxy]-cyclohexyl}-pyrrolidin-3R-ol (18) (FIG. 2)

HCl$_{(g)}$ was bubbled through a solution of 1R-{2R-[2-(3,4-dimethoxy-phenyl)-ethoxy]-cyclohexyl}-pyrrolidin-3R-ol (18) (38.1 g) from the above reaction in isopropanol (150 mL) for 15 min at RT. After the addition of seeding crystals at about 25 to 35° C. the mixture was cooled to about 10° C. and kept at this temperature for 6 h. Filtration, washing of the filter residue with isopropanol (15 mL) and upon drying at about 45° C. in vacuo yielded white crystals of 1R-{2R-[2-(3,4-dimethoxy-phenyl)-ethoxy]-cyclohexyl}-pyrrolidin-3R-ol hydrochloride (19) (37.9 g, HPLC-purity: 99.1%).

Example 2

Figure 3:
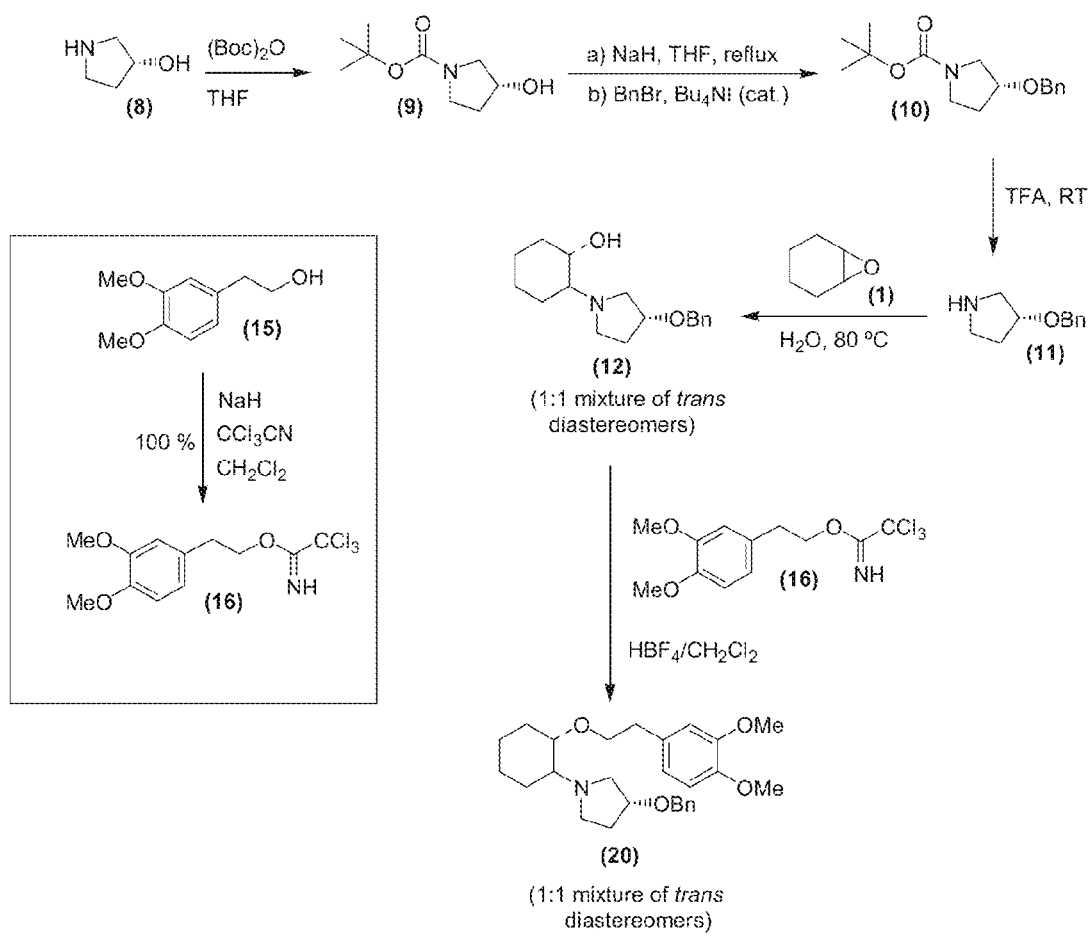
FIG. 3 illustrates a reaction scheme that may be used as a process for preparing a diastereomeric mixture of trans-aminocyclohexyl ether compounds of formula (20).

Synthesis of 3-benzyloxy-1-{2-[2-(3,4-dimethoxy-phenyl)-ethoxy]-cyclohexyl}-pyrrolidine (20) (FIG. 3)

To NaH (0.99 g, 41 mmol, 80% dispersion in mineral oil) in CH$_2$Cl$_2$ (10 mL) was added 2-(3,4-dimethoxy-phenyl)-ethanol (15) (5 g, 27.4 mmol) in CH$_2$Cl$_2$ (20 mL). The reaction mixture was stirred for about 45 min at RT and then cooled to about −5 to 10° C. before addition of trichloro-acetonitrile (5.94 g, 41 mmol). The reaction mixture was stirred for one hour after which the reaction was judged to be complete by TLC and GC. The reaction mixture was then quenched with water (30 mL), the organic layer was separated and the aqueous layer was extracted thrice with CH$_2$Cl$_2$ (3×20 mL). The combined organic layers were dried over anhydr MgSO$_4$ and concentrated in vacuo to yield quantitatively the desired (16) (9 g).

To a cold (about −5 to 10° C.), stirred mixture of 2-(3-benzyloxy-pyrrolidin-1-yl)-cyclohexanol (12) (1.0 g, 3.6 mmol) and (16) (2.4 g, 7.3 mmol, 2 equiv.) in CH$_2$Cl$_2$ (16 mL) was added tetrafluoroboric acid (3.63 mmol, 0.50 mL, Aldrich Cat. #40,006-8). The reaction mixture was allowed to warm to RT and stirred for another 2 h, after which analysis by TLC and GC indicated conversion of the cyclohexanol (12) into the desired product (20). The reaction mixture was quenched with saturated aq. NaHCO$_3$ (25 mL), and the aqueous layer was collected and washed thrice with CH$_2$Cl$_2$ (3×30 mL). The organic layers were combined, dried over Na$_2$SO$_4$ (anhydr) and concentrated under reduced pressure to give a residue, which was dissolved in a mixture of Et$_2$O—CH$_2$Cl$_2$ (95:5, v/v, 52 mL). Subsequently, water (75 mL) was added, and the pH of the aqueous solution was adjusted to pH 0.5 by drop-wise addition of 6 M aq. HCl. The organic layer, which was shown to contain unreacted (16), was discarded. The pH of the aqueous solution was then adjusted to pH 6.3 prior to extraction with Et$_2$O (50 mL). The aqueous layer (pH 6.3) was extracted twice more with Et$_2$O (50 mL), the ether extracts (from extractions conducted at pH 6.3) were combined, and dried over Na$_2$SO$_4$ (anhydr). Concentration under reduced pressure provided a residue, which was then subjected to high vacuum to yield 1.0 g of (20) (69% yield).

Characterization of (20): TLC R$_f$ 0.83 (neutral alumina, EtOAc-hexanes, 1:1, v/v, 0.5% v/v iPrNH$_2$); $^1$H-NMR (300 MHz, CDCl$_3$) δ 7.3 (m, 5H, Ar), 6.75 (d, 3H, Ar), 4.43 (m, 2H, OCH$_2$Ar), 4.05 (m, 1H), 3.83 (2×s, 6H, 2×OCH$_3$), 3.75-1.20 (m, 20H, aliphatic H's); $^{13}$C-NMR (75 MHz, CDCl$_3$, APT) δ 148.66, 147.33, 138.48, 131.99, 128.28, 127.60, 127.44, 120.75, 112.37, 111.15, 79.27, 77.82, 70.87, 69.74, 64.01, 56.86, 55.86, 55.76, 49.81, 36.44, 31.23, 28.76, 26.93, 23.17, 22.83 (unaccounted peaks from an unknown impurity: 58.30, 57.51, 52.76, 49.20, 34.65, 33.23, 25.21, 24.13, 21.30, 18.36).

MS (ES) M$^+$ 440.2 (20) and M$^+$ 276.1 unreacted (12).

Synthesis of 2-(3-benzyloxy-pyrrolidin-1-yl)-cyclohexanol (12) (FIG. 7)

A mixture of (1) (12.5 mL, 120.9 mmol, Aldrich cat. # C10,250-4), (11) (14.3 g, 80.6 mmol) and water (6 mL) was heated at about 80° C. for about 9.5 h, after which GC analysis revealed complete consumption of (11). The reaction mixture was allowed to cool to RT and diluted with water (140 mL). By the addition of 1 M aq HCl (55 mL), the pH was adjusted to 4.6 and the mixture was extracted with Et$_2$O (2×200 mL). After the aqueous layer was adjusted to pH 12.5 by the addition of 40% aq NaOH (NaCl may be added to effect separation into 2 clear layers), the aqueous layer was extracted with Et$_2$O (1×400 mL, 1×200 mL). The combined Et$_2$O extracts (from basic aqueous layer) were dried (Na$_2$SO$_4$ anhydr), and concentrated under reduced pressure and then in vacuo at 55° C. with stirring, to give (12) as an orange oil (15.9 g, 72%) of 96% purity (GC).

Characterization of (12): R$_f$ 0.24 (EtOAc-iPrNH$_2$, 98:2, v/v); $^1$H NMR (200 MHz, CDCl$_3$) δ 7.4-7.2 (m, 5H), 4.5 (s, 2H), 4.2-4.0 (m, 1H), 3.9 (br s, 1H), 3.4-3.2 (m, 1H), 3.0-2.5 (m, 4H), 2.4 (t, J 10 Hz, 1H), 2.2-1.9 (m, 2H), 1.9-1.6 (m, 4H), 1.3-1.1 (m, 4H); $^{13}$C NMR (75 MHz, CDCl$_3$) δ 138.30, 128.35, 127.61, 127.55, 77.98, 77.71, 71.07, 71.01, 70.52, 70.45, 64.96, 64.89, 54.16, 52.74, 46.83, 45.43, 33.24, 31.53, 31.34, 25.20, 24.13, 21.40, 21.33; IR (film) 3450 (broad) cm$^{-1}$.

Example 2a

Figure 4:
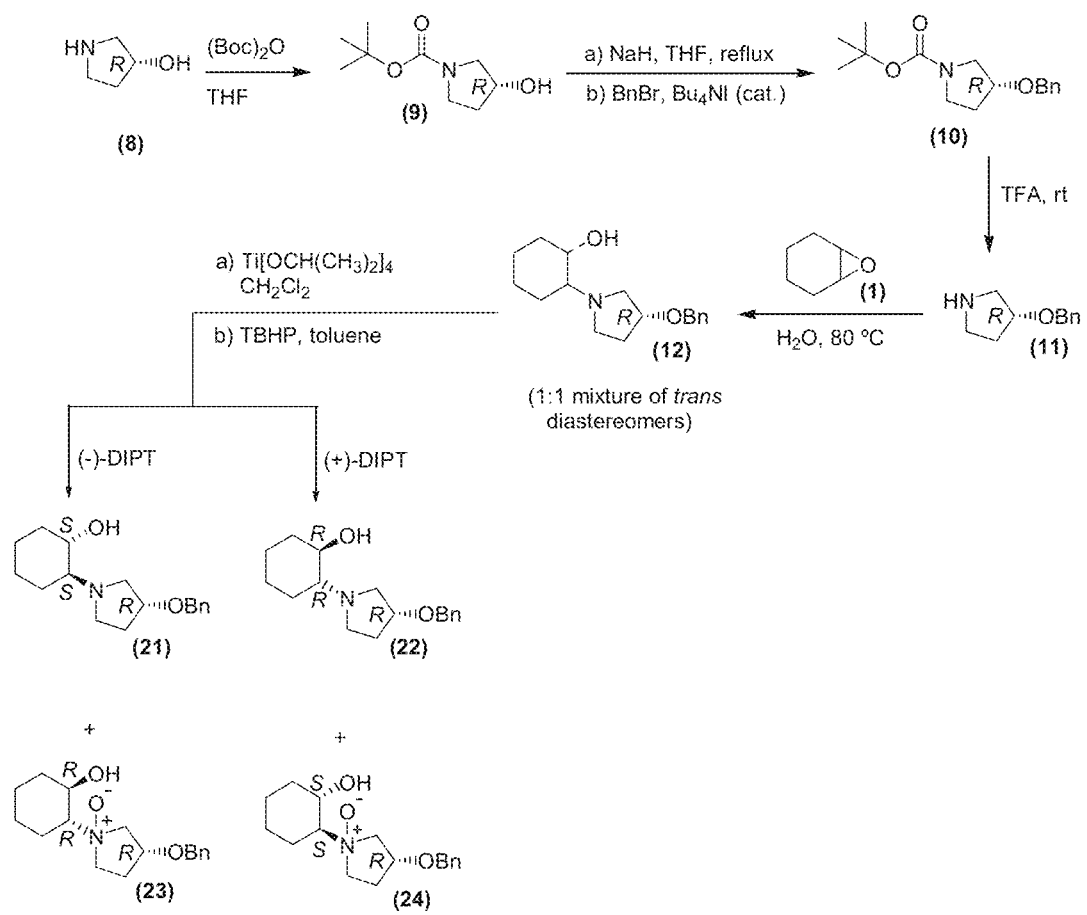
FIG. 4 illustrates a reaction scheme that may be used as a process for preparing a stereoisomerically substantially pure trans-(1R,2R)-aminocyclohexyl alcohol of formula (22) and a stereoisomerically substantially pure trans-(1S,2S)-aminocyclohexyl alcohol of formula (21).

Kinetic Resolution of 2-(3-benzyloxy-pyrrolidin-1-yl)-cyclohexanol (12) (FIG. 4)

A 200-mL, three-necked round-bottomed flask equipped with a Teflon-coated magnetic stir bar was oven-dried and allowed to cool to RT under argon. After the addition of 2-(3-benzyloxy-pyrrolidin-1-yl)-cyclohexanol (12) (3.0 g, 10.9 mmol) and (+)-DIPT (3.06 g, 13.1 mmol, 2.8 mL, Aldrich cat. #22,918-0), the reaction vessel was briefly flushed with Ar. The flask was then successively charged with $CH_2Cl_2$ (80 mL) and $Ti(OiPr)_4$ (6.2 g, 21.8 mmol, 6.5 mL, Aldrich cat. #20,527-3). The reaction mixture was kept by agitation for about 30 min at RT and then cooled to about $-30$ to $-10°$ C. To the solution was added about 0.5 to 0.7 equiv. of tert-butyl hydroperoxide (1.82 mL, 6.5 mmol, 3.6 M solution in toluene) and the resultant mixture was stirred at about $-30$ to $-10°$ C. for 2.5 h. Subsequently, the reaction was quenched by the successive addition of $Et_2O$ (60 mL), water (5 mL), and 40% aq NaOH (5 mL), and the resultant mixture was stirred for about 4.5 h at RT. During this period, the clear yellow mixture became a milky suspension, which was filtered through a 1-inch pad of Celite 545® (Aldrich cat. #41,993-1). The recovered solid was vigorously stirred in refluxing $CHCl_3$ for about 10 min before filtration of the mixture through the Celite pad. The filtrates were combined and concentrated in vacuo to afford a mixture of white and pale yellow solids. Trituration in hexanes (100 mL), filtration and washing with hexanes (100 mL) gave a white solid, which is the optically active N-oxide of 2S-(3R-benzyloxy-pyrrolidin-1S-yl)-cyclohexanol (21) ((24)1.73 g, 56% yield). The hexanes extract was diluted with $Et_2O$ (25 mL), washed with water (ca. 2×5 mL) and dried ($Na_2SO_4$, anhydr). The solvent was evaporated in vacuo to afford 1.35 g (44% yield) of 2R-(3R-benzyloxy-pyrrolidin-1R-yl)-cyclohexanol (22). The diastereomeric excess (de) of (22) was assessed to be 91% by chiral CE in 5% highly sulfated γ-cyclodextrin in 25 mM triethylammonium-phosphate buffer (pH 2.5) and 18 kV reverse polarity.

Characterization of (22): $^1$H-NMR (300 MHz, $CDCl_3$) δ 7.30 (m, 5H, Ar), 4.40 (d, 2H, $OCH_2$), 4.1 (m, 1H, $CHOCH_2$), 3.4 (m, 1H, CHOH), 2.7-2.9 (m, 4H), 2.5 (m, 1H, CHN), 2.1-1.5 (m, 6H), 1.5-1.0 (m, 4H); $^{13}$C-NMR (75 MHz, $CDCl_3$) δ 138.05, 128.34, 127.58, 77.67, 71.06, 70.38, 65.41, 52.93, 47.30, 33.38, 31.16, 25.01, 24.02, 21.90; MS (ES) M$^+$ 276.2 (100%); MS (ES) M$^+$ 276.2 (100%), $[α]_D^{589}$ $-63.7°$ (10, $CHCl_3$).

Similarly, treatment of 2-(3-benzyloxy-pyrrolidin-1-yl)-cyclohexanol (12) (3.0 g, 10.9 mmol) with (−)-DIPT (3.06 g, 13.1 mmol, 2.8 mL, Aldrich Cat. #22,780-3) provided the optically active N-oxide of 2R-(3R-benzyloxy-pyrrolidin-1R-yl)-cyclohexanol (16) ((23)1.88 g, 61% yield) and 1.1 g (36% yield) of the 2S-(3R-benzyloxy-pyrrolidin-1S-yl)-cyclohexanol (21) as an orange oil. The diastereomeric excess (de) of (21) was assessed to be 95% by chiral CE.

Characterization of (21): $^1$H-NMR (300 MHz, $CDCl_3$) δ 7.30 (m, 5H, Ar), 4.5 (d, 2H, $OCH_2$), 4.1 (m, 1H, $CHOCH_2$), 3.4 (m, 1H, CHOH), 2.7-2.9 (m, 4H), 2.5 (m, 1H, CHN), 2.1-1.5 (m, 6H), 1.5-1.0 (m, 4H); $^{13}$C-NMR (75 MHz, $CDCl_3$) δ 138.16, 128.35, 127.58, 77.53, 71.01, 70.38, 65.36, 54.58, 45.74, 33.37, 31.36, 25.08, 24.07, 21.81; MS (ES) M$^+$ 276.2 (100%); $[α]_D^{589}$ $+77.7°$ (10, $CHCl_3$).

Example 3

Figure 5:
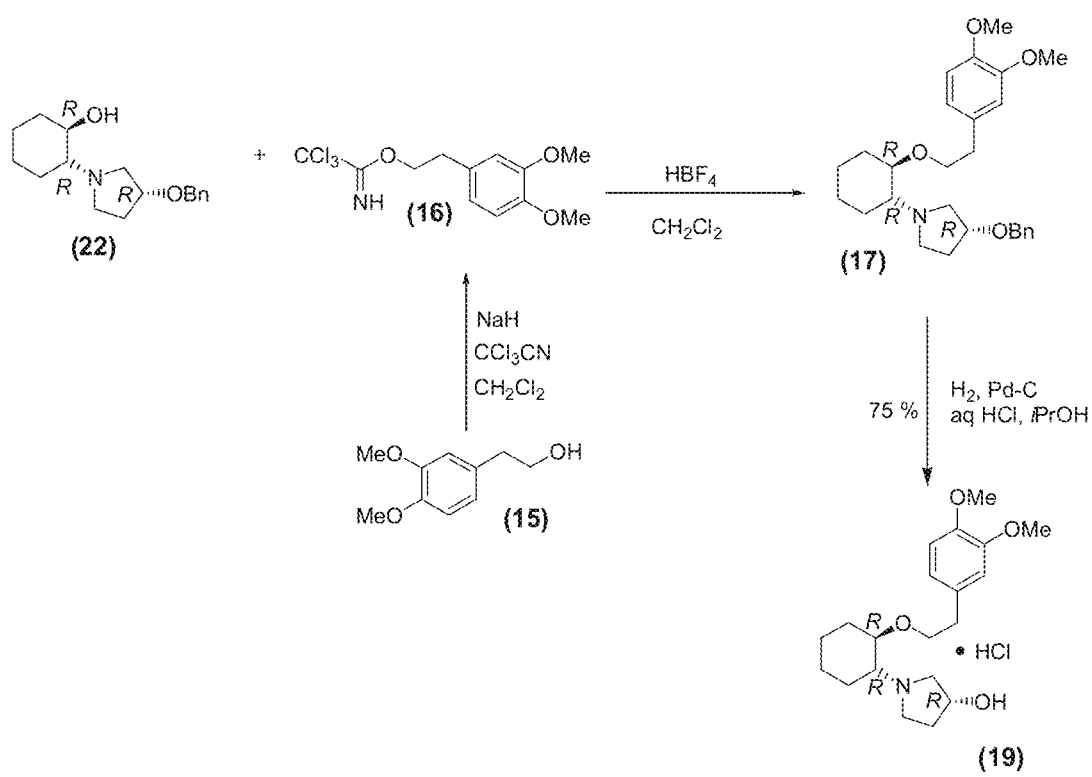
FIG. 5 illustrates a reaction scheme that may be used as a process for preparing a stereoisomerically substantially pure trans-(1R,2R)-aminocyclohexyl ether compound of formula (19).

Synthesis of 3R-benzyloxy-1R-{2R-[2-(3,4-dimethoxy-phenyl)-ethoxy]-cyclohexyl}-pyrrolidine (17) (FIG. 5)

To a cold (about $-5$ to $10°$ C.), stirred mixture of (22) (100 mg, 0.363 mmol) and (16) (0.14 g, 0.44 mmol, 1.2 equiv) in $CH_2Cl_2$ (5 mL) was added tetrafluoroboric acid (0.363 mmol, 27 μL, Aldrich Cat. #40,006-8). The reaction mixture was allowed to warm to RT and stirred for another 2 h, after which analysis by TLC and GC indicated complete consumption of starting materials. The reaction mixture was cooled to about 0° C. and quenched by successive addition of water (3 mL) and 10 M aq NaOH (2 mL). The aqueous layer was washed with $CH_2Cl_2$ (3×5 mL). The organic layers were combined, dried over $Na_2SO_4$ (anhydr) and concentrated under reduced pressure to give a residue, which was dissolved in a mixture of $Et_2O$—$CH_2Cl_2$ (95:5, v/v, 5 mL). Subsequently, water (20 mL) was added, and the pH of the aqueous solution was adjusted to pH 0.5 by dropwise addition of 6 M aq HCl. The organic layer, which was shown to contain unreacted (16), was discarded. The pH of the aqueous solution was then adjusted to about pH 5.5 to 6.8 prior to extraction with $Et_2O$ (20 mL). The aqueous layer was extracted twice more with $Et_2O$ (2×20 mL), the ether extracts (from extractions conducted at about pH 5.5 to 6.8) were combined, and dried over $Na_2SO_4$ (anhydr). Concentration under reduced pressure followed by high vacuum yielded 114 mg of (17) (72% yield). The diastereomeric excess (de) of (17) was assessed to be 92.4% by chiral CE in 5% highly sulfated γ-cyclodextrin in 25 mM triethylammonium-phosphate buffer (pH 2.5) and 18 kV reverse polarity.

Characterization of (17): TLC R$_f$ 0.84 (neutral alumina, EtOAc-hexanes, 1:1, v/v, 0.5% v/v iPrNH$_2$); $^1$H-NMR (300 MHz, $CDCl_3$) δ 7.3 (m, 5H, Ar), 6.75 (d, 3H, Ar), 4.43 (d, 2H, $OCH_2Ar$), 4.05 (m, 1H), 3.83 (d, 6H, 2×$OCH_3$), 3.50 (m, 2H, $OCH_2CH_2$), 3.40 (m, 1H), 3.00-2.50 (m, 4H), 2.35 (m, 2H), 2.46-1.90 (1H, m), 1.86-1.70 (m, 2H), 1.64-1.54 (m, 2H), 1.38-1.18 (m, 6H); $^{13}$C-NMR (75 MHz, $CDCl_3$) δ 148.65, 147.32, 138.42, 131.94, 128.32, 127.61, 120.75, 112.33, 111.09, 79.15, 70.96, 69.74, 57.02, 55.82, 55.41, 50.09, 36.44, 31.20, 28.79, 27.12, 23.18, 22.78; MS (ES) M$^+$440.5.

Synthesis of 1R-{2R-[2-(3,4-dimethoxy-phenyl)-ethoxy]-cyclohexyl}-pyrrolidin-3R-ol hydrochloride (19) (FIG. 5)

(a) To a Parr hydrogenator was added a solution of 3R-benzyloxy-1R-{2R-[2-(3,4-dimethoxy-phenyl)-ethoxy]-cyclohexyl}-pyrrolidine (17) (185 mg, 0.42 mmol) in ethanol (8 mL) and 6 M aq HCl (400 μL). The solution was stirred for 10 min after which 10% Pd-C catalyst (65 mg, Aldrich cat. #20,569-9) was added and the reaction vessel was evacuated and charged with H$_2$ (60 psi). The reaction mixture was agitated under H$_2$ at RT for 5 h, and then filtered through a plug of Celite 545® (Aldrich cat. #41,993-1), which was pre-wetted with ethanol under suction. The Pd-C catalyst was well rinsed with ethanol.

(b) The acidic alcoholic solution was concentrated under reduced pressure azeotropically with toluene to give a residue which is triturated in ethyl acetate with ultrasonication for 15 min to yield the title compound 122.6 mg (75%).

(c) The crude title compound (19) (122.6 mg) was dissolved in ethanol (600 μL) and ethyl acetate was added dropwise (1 mL) and stored at about 3 to 10° C. for about 3 to 5 days. The solvent was pipetted off to leave a white residue. The residual solvent was then evaporated in vacuo to give 18 mg of the title compound. The diastereomeric excess (de) was assessed to be 84.7% (chiral CE in 5% highly sulfated γ-cyclodextrin in 25 mM triethylammonium-phosphate buffer (pH 2.5) and 18 kV reverse polarity) with a chemical purity of 90% (CE in 100 mM phosphate buffer (pH 2.5) and normal polarity at 25 kV).

Characterization of (19): TLC $R_f$ 0.71 (neutral alumina, Et$_2$NH-EtOAc, 1:4, v/v); $^1$H-NMR (300 MHz, CDCl$_3$) δ 6.55 (3H, Ar), 4.10 (1H, m, CHOH), 3.55 (d, 6H, 2×OCH$_3$), 3.50 (m, 2H, OCH$_2$CH$_2$), 3.20 (m, 1H), 3.00-2.50 (m, 4H), 2.35 (m, 2H), 2.25-1.90 (m, 1H), 1.90-1.55 (m, 2H), 1.55-1.25 (m, 2H), 1.25-1.00 (m, 6H); $^{13}$C-NMR (75 MHz, CDCl$_3$) δ 148.89, 147.62, 131.12, 120.57, 112.20, 111.32, 79.07, 69.29, 66.39, 56.37, 55.86, 53.37, 53.25, 35.83, 33.69, 32.34, 30.09, 28.09, 24.26, 22.98; MS (ES) M$^+$ 350; $[\alpha]^{25}_D$ -2.2° (10, CHCl$_3$).

Example 4

Figure 6:
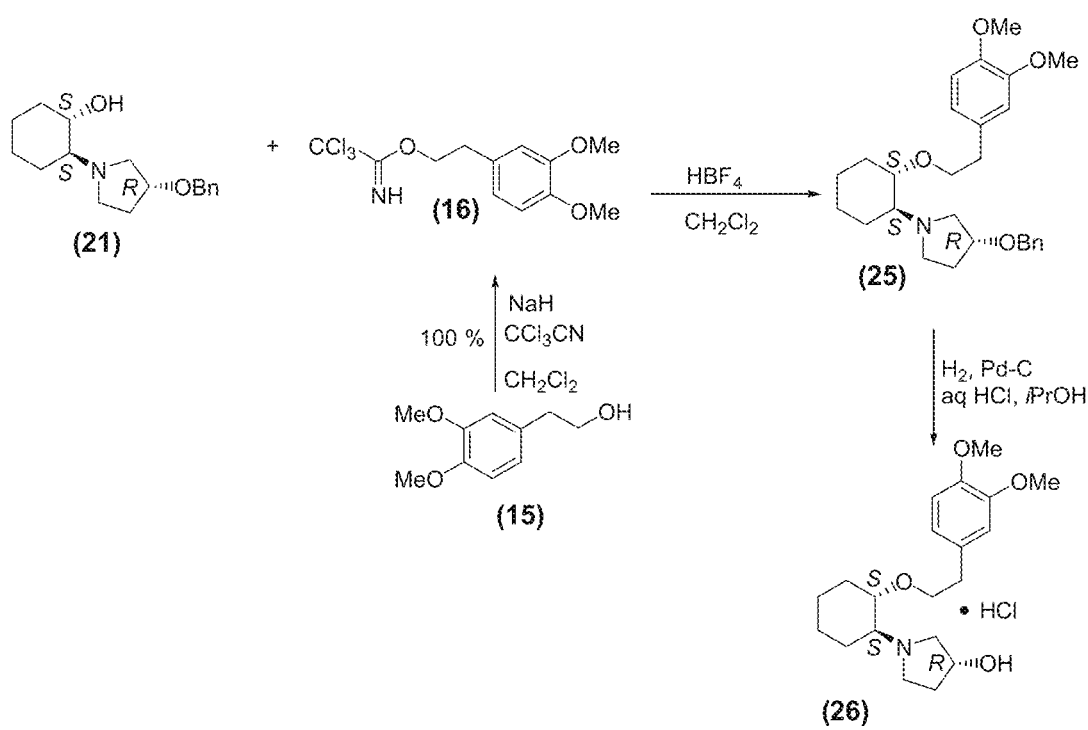
FIG. 6 illustrates a reaction scheme that may be used as a process for preparing a stereoisomerically substantially pure trans-(1S,2S)-aminocyclohexyl ether compound of formula (26).

Synthesis of 3R-benzyloxy-1S-{2S-[2-(3,4-dimethoxy-phenyl)-ethoxy]-cyclohexyl}-pyrrolidine (25) (FIG. 6)

To a cold (about −5 to 10° C.), stirred mixture of 2S-(3R-benzyloxy-pyrrolidin-1S-yl)-cyclohexanol (21) (300 mg, 1.09 mmol) and (16) (0.53 g, 1.6 mmol, 1.5 equiv) in CH$_2$Cl$_2$(10 mL) was added tetrafluoroboric acid (1.09 mmol, 81 μL, Aldrich Cat. #40,006-8). The reaction mixture was allowed to warm to RT and stirred for another 2 h, after which analysis by TLC and GC indicated complete consumption of starting materials. The reaction mixture was cooled to 0° C. and quenched by successive addition of water (3 mL) and 10 M aq NaOH (2 mL). The aqueous layer was washed with CH$_2$Cl$_2$ (3×5 mL). The organic layers were combined, dried over Na$_2$SO$_4$ (anhydr) and concentrated under reduced pressure to give a residue, which was dissolved in a mixture of Et$_2$O—CH$_2$Cl$_2$ (95:5, v/v, 10 mL). Subsequently, water (20 mL) was added, and the pH of the aqueous solution was adjusted to pH 0.4 by dropwise addition of 6M aq HCl. The organic layer, which was shown to contain unreacted (16), was discarded. The pH of the aqueous solution was then adjusted to pH 6.3 prior to extraction with Et$_2$O (20 mL). The aqueous layer (pH 6.3) was extracted twice more with Et$_2$O (2×20 mL), the ether extracts (from extractions conducted at pH 6.3) were combined, and dried over Na$_2$SO$_4$ (anhydr). Concentration under reduced pressure gave a residue, which was subjected to high vacuum to yield 326 mg of (25) (68% yield). The diasteeomeric excess (de) of (25) was assessed to be 95.6% by chiral CE in 5% highly sulfated γ-cyclodextrin in 25 mM triethylammonium-phosphate buffer (pH 2.5) and 18 kV reverse polarity.

Characterization of (25): TLC $R_f$ 0.84 (neutral alumina, EtOAc-hexanes, 1:1, v/v, 0.5% v/v iPrNH$_2$); $^1$H-NMR (300 MHz, CDCl$_3$) δ 7.3 (m, 5H, Ar), 6.75 (d, 3H, Ar), 4.43 (d, 2H, OCH$_2$Ar), 4.05 (m, 1H), 3.83 (d, 6H, 2×OCH$_3$), 3.50 (m, 2H, OCH$_2$CH$_2$), 3.40 (m, 1H), 3.00-2.50 (m, 4H), 2.35 (m, 2H), 2.46-1.90 (1H, m), 1.86-1.70 (m, 2H), 1.64-1.54 (m, 2H), 1.38-1.18 (m, 6H); $^{13}$C-NMR (75 MHz, CDCl$_3$) δ 148.65, 147.31, 138.53, 132.01, 128.27, 127.59, 127.42, 120.73, 112.33, 111.37, 79.21, 77.85, 70.85, 69.76, 57.56, 55.85, 55.75, 49.23, 36.46, 31.21, 28.71, 26.99, 23.09, 22.79; MS (ES) M$^+$ 440.5.

Synthesis of 1S-{2S-[2-(3,4-dimethoxy-phenyl)-ethoxy]-cyclohexyl}-pyrrolidin-3R-ol hydrochloride (26) (FIG. 6)

(a) To a Parr hydrogenator was added a solution of 3R-benzyloxy-1S-{2S-[2-(3,4-dimethoxy-phenyl)-ethoxy]-cyclohexyl}-pyrrolidine (25) (200 mg, 0.46 mmol) in ethanol (8 mL) and 6 M aq HCl(400 μL). The solution was stirred for 10 min after which 10% Pd-C catalyst (65 mg, Aldrich #20,569-9) was added and the reaction vessel was evacuated and charged with H$_2$ (60 psi). The reaction mixture was agitated under H$_2$ at RT for 5 h, and then filtered through a plug of Celite 545® (Aldrich cat. #41,993-1), which was pre-wetted with ethanol under suction to rid air pockets and to ensure efficient charcoal trapping during filtration. The Pd-C catalyst was well rinsed with ethanol.

(b) The acidic alcoholic solution was concentrated under reduced pressure azeotropically with toluene to give a residue which is triturated in ethyl acetate with ultrasonication for 15 min to yield the title compound 131 mg (82%).

(c) The crude title compound (131 mg) was dissolved in ethanol (600 μL) and ethyl acetate was added dropwise (1 mL) and stored in the fridge for 4 days. The solvent was pipetted off to leave a white residue. The residual solvent was then evaporated in vacuo to give 25 mg of the title compound. The diastereomeric excess (de) was assessed to be 91.5% (chiral CE in 5% highly sulfated γ-cyclodextrin in 25 mM triethylammonium-phosphate buffer (pH 2.5) and 18 kV reverse polarity) with a chemical purity of 92% (CE in 100 mM phosphate buffer (pH 2.5) and normal polarity at 25 kV).

Characterization of (26): TLC $R_f$ 0.71 (neutral alumina, Et$_2$NH-EtOAc, 1:4, v/v); $^1$H-NMR (300 MHz, CDCl$_3$) δ 6.52 (3H, Ar), 4.15 (1H, m, CHOH), 3.75 (d, 6H, 2×OCH$_3$), 3.50 (m, 2H, OCH$_2$CH$_2$), 3.25 (m, 1H), 3.00-2.50 (m, 4H), 2.35 (m, 2H), 2.05-1.85 (m, 1H), 1.85-1.65 (m, 2H), 1.65-1.45 (m, 2H), 1.30-1.00 (m, 6H); $^{13}$C-NMR (75 MHz, CDCl$_3$) δ 148.67, 147.16, 131.72, 120.66, 112.19, 110.97, 78.34, 69.75, 68.87, 68.08, 61.37, 56.04, 53.25, 48.56, 36.11, 33.39, 30.39, 26.79, 24.43, 23.42; MS (ES) M$^+$ 350; $[\alpha]^{25}_D$ +0.5° (10, CHCl$_3$).

Example 5a

Figure 42:
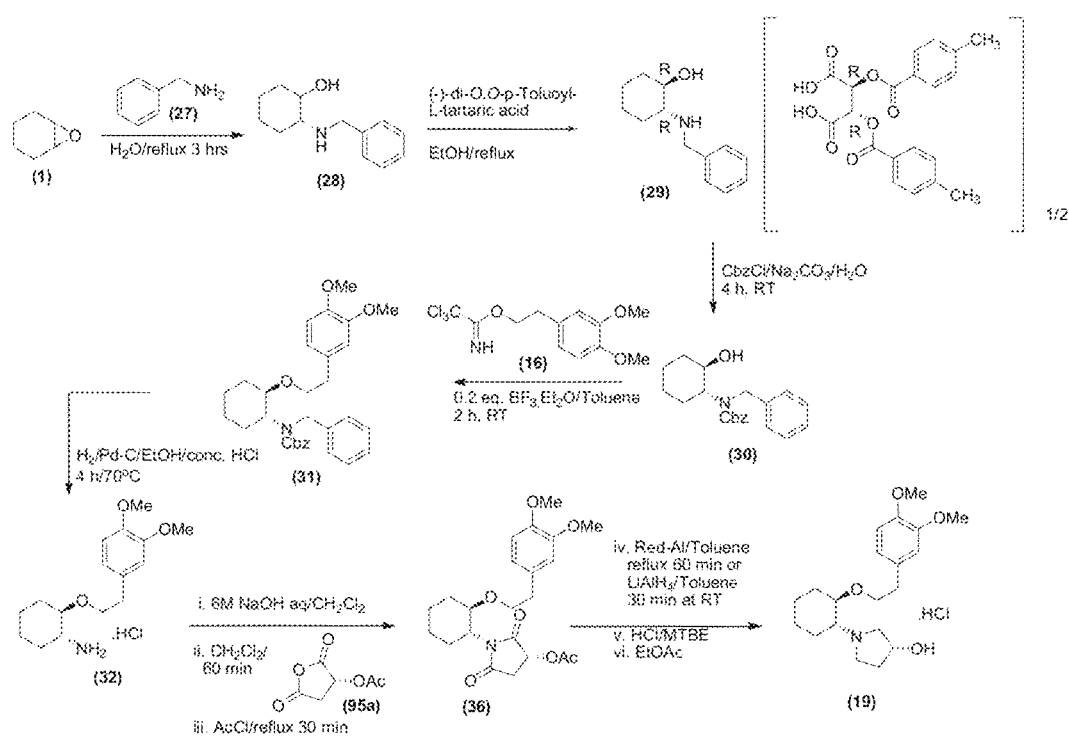
FIG. 42 illustrates a reaction scheme that may be used as a process for preparing a stereoisomerically substantially pure trans-(1R,2R)-aminocyclohexyl ether compound of formula (19).

Preparation of (3R)-1-[(1R,2R)-2-[2-(3,4-Dimethoxyphenyl)ethoxy]cyclohexyl]-3-pyrrolidinol hydrochloride (19) (FIG. 42)

A. Synthesis in General

In general, the synthesis commenced with cyclohexene oxide ring (1) opening by benzylamine (27) in the presence of water to smoothly provide trans-2-benzylaminocyclohexan-1-ol (28) in 96% yield. Resolution of racemic aminoalcohol (28) was accomplished by diastereomeric acid salt crystallization using (−)-di-O,O-p-toluoyl-L-tartaric acid in EtOH affording (1R,2R)-2-benzylaminocyclohexan-1-ol (−)-di-O,O-p-toluoyl-L-hemi-tartrate (29) (51% yield out of theoretical yield, ~96% ee). The tartrate salt was too soluble in MeOH to crystallize out whereas the same tartrate was poorly soluble in iPrOH.

With the desired R,R-aminoalcohol hemi-tartrate (29) in hand, treatment with benzyl chloroformate deactivated the basic nitrogen in giving carbamate (30) in quantitative yield.

Alternatively, isomerically pure (30) may be obtained by resolving racemic (30) using Simulated Moving Bed (SMB) on a Chiralpak AD stationary phase. Subsequent etherification of carbamate (30) proceeded smoothly on reaction with trichloroacetimidate (16) catalyzed by $BF_3.OEt_2$ to afford 4 in good yield (>80%).

In preparation for pyrrolidine ring construction, the N-protective groups were removed by hydrogenolysis ($H_2$, Pd-C, conc HCl, EtOH, 70° C., 4 h) of (31). Alternatively, deprotection of (31) could be performed with ammonium formate and 10% Pd-C in refluxing MeOH as described by Augy-Dorey S, Dalko P, Gero S D, Quiclet-Sire B, Eustache J, Stuetz P, Synthesis of Carbocyclic Analogs of Lipid X. *Tetrahedron*, 1993, 49 (36), 7997-8006. The resultant crude monohydrochloride salt (32) (95.9% ee) was recrystallized from EtOH-$Et_2O$ to provide the enantiomerically pure salt (32) (+99% ee). In accordance with Naylor et al, 4-[(Alkylamino)methyl]furo[3,2-c]pyridines: A New Series of Selective κ-Receptor Agonists. *J. Med. Chem.* 1994, 37, 2138-2144, successive treatment of the corresponding free base of (32) with (R)-(+)-2-acetoxysuccinic anhydride (95a) (Henrot S, Larcheveque M, Petit Y. Aminoacids as chiral synthons: Preparation of enantiomerically pure (R) and (S) malic acids and its application to the synthesis of 3-hydroxy 4-butanolide. *Synthetic Communications* 1986, 16(2), 183-190) and acetyl chloride gave the imido-ether (36), which was used in the next step without further purification. When (32) was neutralized in situ with either triethylamine or sodium carbonate, the N-acylation with (95a) did not proceed as well as when the free base of (32) was isolated prior to condensation with (95a). Furthermore, substitution of acetyl chloride by acetic anhydride for the ring closure failed to provide compound (36).

Reduction of (36) with Red-Al (Alimardanov A R, Barrila M T, Busch F R, Carey J J, Couturier M A, Cui C, *Org Proc Res & Dev* 2004, 8, 834-837), $LiAlH_4$ or borane.THF complex provided (19), after treatment with hydrogen chloride in diethyl ether and trituration in EtOAc. The yield for the reductive step with borane may be as high as 90% and $LiBH_3NMe_2$ could also be used for the reductive step as reported by Pasumansky L, Singaram B, Goralski C T, *Aldrichimica Acta* 2005, 38, 61. HPLC purity for crude (19) was ~80% while assay for crude (19) was only 63%. These results suggest the presence of impurities not detected by LC-UV, such as inorganic material from the reduction and the necessity of optimizing the purification prior to isolation of final API.

Figure 43:
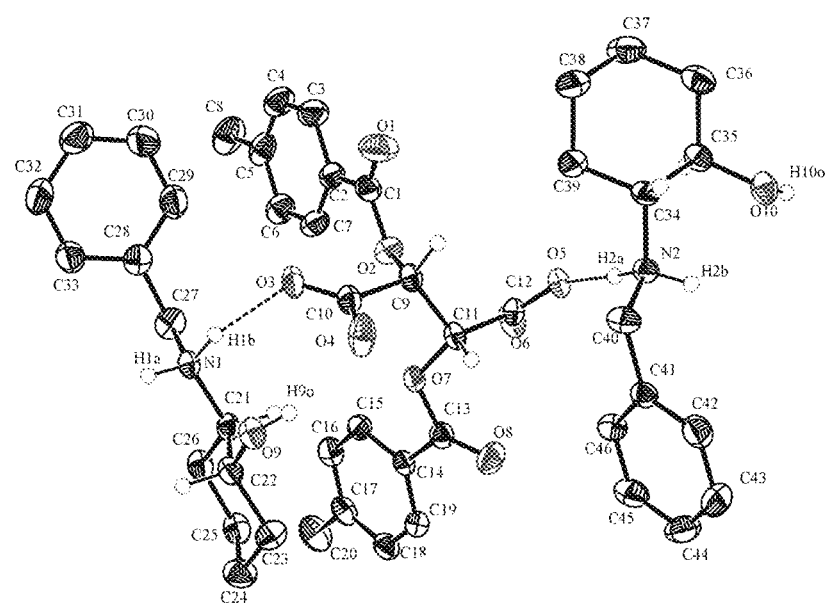
FIG. 43 illustrates an ORTEP Program (Oak Ridge Thermal Ellipsoid Plot Program) representation of (1R,2R)-2-benzylaminocyclohexan-1-ol (−)-di-O,O-p-toluoyl-L-hemitartrate (29a).

To confirm the absolute configuration of (29), an aliquot of the tartrate complex was recrystallized from EtOH to give (1R,2R)-2-benzylaminocyclohexan-1-ol (+99% ee/chiral CE) for X-ray crystallographic diffraction analysis. The ORTEP representation depicted in FIG. 43 clearly shows the desired R,R absolute configuration of (1R,2R)-2-benzylaminocyclohexan-1-ol (−)-di-O,O-p-toluoyl-L-hemi-tartrate (29).

Alternatively, resolution of trans-2-benzylaminocyclohexan-1-ol (28) has been reported using mandelic acid. In particular, in the procedure developed by Dr. Ingo Schiffers under the supervision of Prof. Bolm, Institut für Organische Chemie, RWTH, Aachen, Prof. Pirlet-Str. 1, 52074 Aachen (Germany), a mixture of racemic trans-2-benzylaminocyclohexanol (0.4 mol) and 0.5 equiv mandelic acid in ethyl acetate (760 mL) and EtOH (12 mL) was refluxed until all starting materials were in solution. The flask was then stored at −20° C. overnight and the initial precipitate was filtered, washed successively with ethyl acetate (100 mL), diethyl ether (200 ml) and dried. The first recrystallization was conducted using a (10:1 v/v) mixture of ethyl acetate and ethanol (19 mL per gram of ammonium salt). For the second, third (and if necessary fourth recrystallization), ethyl acetate (22 mL per gram) was used, and ethanol was added at reflux to solubilize residual solids (5-10%). The salt rapidly crystallized when the flask was cooled. For HPLC analysis of the 2-benzylaminocyclohexanol mandelate salt, an aliquot was treated with 1N aq NaOH and extracted with diethyl ether. HPLC conditions: OB-H column, 98:2 v/v heptane/i-propanol, detection at 220 nm, flow 0.5 mL/min; retention times $RT_1$=20.9 min (1S,2S-2-benzylaminocyclohexan-1-ol), $RT_2$=26.9 min (1R,2R-benzylaminocyclohexan-1-ol). The mother liquor of the initial precipitate was washed with 1N aq NaOH and after concentration, the enantiomeric purity (ee) of the residual aminoalcohol was determined. The S,S-isomer could be recovered by crystallization using the enantiomer of mandelic acid (1 equiv).

Figure 44:
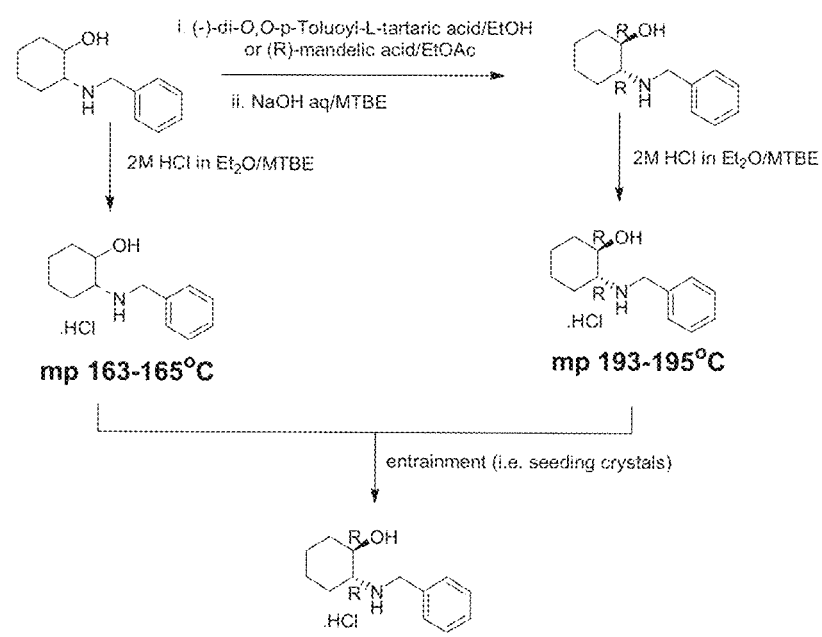
FIG. 44 illustrates a comparison of the melting points of racemic benzylaminocyclohexan-1-ol (28) and the R,R-enantiomer of (28) for subsequent resolution by entrainment.

Another potential way of resolving racemic trans-2-benzylaminocyclohexan-1-ol (28) is by enantioselective crystallization of its monohydrochloride salt. To determine whether crystalline racemic trans-2-benzylaminocyclohexan-1-ol hydrochloride was a true racemate or a conglomerate, the melting points for the monohydrochloride of the racemate and the R,R-enantiomer were compared (FIG. 44). The higher melting point of the 1R,2R-2-benzylaminocyclohexan-1-ol hydrochloride (mp 193-195° C.) compared to that of the racemic hydrochloride (mp 163-165° C.) suggests that the racemic mixture was comprised of conglomerate crystals. A mixture of conglomerate crystals has a decreased melting point compared to that of either enantiomer. For a racemate to form a true conglomerate crystal, the melting point of either enantiomer must be at least 20° C. above the melting point of the crystalline racemate (Anderson N G, "Practical Process Research & Development", Academic Press, 2000, pp 332-333). The mixture may then be resolved by entrainment (Pallavicini M, Bolchi C, Di Pumpo R, Fumagalli L, Moroni B, Valoti E, Demartin F, Resolution of 5-hydroxymethyl-2-oxazolidinone by preferential crystallization and investigations on the nature of the racemates of some 2-oxazolidinone derivatives. Tetrahedron: Asymmetry 2004, 15, 1659-1665).

B. Materials and Methods

Thin-layer chromatography (TLC) was performed on silica gel 60 $F_{254}$ plates purchased from EM Science (cat #5735/7 or #5554/7).

HPLC Methods:
Instrument: Agilent 1100 HPLC
Column: Inertsil ODS-3, 5 □μm, 4.0×250 mm
Column Temp: 23° C.
Injection Volume: 10 μL, in MeCN or MeCN—$H_2O$ (20:80 v/v)
Flow rate: 1.0 mL/min
Detection: 210 nm
Data Acquisition Time: 30 minutes
Needle Wash: 50/50 $H_2O$/MeCN
Mobile Phase A: $KH_2PO_4$ (1.09 g) was dissolved in water (800 mL), and the pH was adjusted to 2.5 by addition of o-phosphoric acid. To this solution was added MeCN (200 mL) and the resultant solution was mixed and filtered.

Mobile Phase B: $KH_2PO_4$ (0.27 g) was dissolved in water (200 mL), and the pH was adjusted to 2.5 by addition of o-phosphoric acid. MeCN (800 mL) was then added to this solution, which was mixed and filtered.

Gradient A:
Run time: 40 minutes

| Time (min) | % A | % B |
|---|---|---|
| 0 | 100 | 0 |
| 30 | 0 | 100 |
| 31 | 100 | 0 |
| 40 | 100 | 0 |

Gradient B:
Run Time: 25 minutes

| Time (min) | % A | % B |
|---|---|---|
| 0 | 100 | 0 |
| 8 | 73.3 | 26.7 |
| 11 | 0 | 100 |
| 20 | 0 | 100 |
| 21 | 100 | 0 |
| 25 | 100 | 0 |

CSK-G Method:
Instrument: Waters 2695 separations module
Flow rate: 2.0 mL/min
Detection: 215 nm
Column Temp: 23° C.
Column: Inertsil ODS-3, 5μ 4.6×150 mm
Injection Volume: 10 μL
Needle Wash: 50/50 Water/MeOH
Sample preparation: 35% Acetonitrile in water
Sample concentration: 1 mg/mL
Data Acquisition Time: 23 minutes
Run Time: 28.1 minutes
Gradient:
Mobile Phase A: Acetonitrile/10 mM sodium octanesulfonate (10:90)
Mobile Phase B: Acetonitrile/10 mM sodium octanesulfonate (90:10)

| Time(min) | % A | % B |
|---|---|---|
| 0 | 82 | 18 |
| 20 | 15 | 85 |
| 23 | 0 | 100 |
| 23.1 | 82 | 18 |
| 28.1 | 82 | 18 |

Chiral CE Methods:
Instrument: Beckman P/ACE System MDQ Capillary Electrophoresis System
Detector: UV set at 200 nm
Cartridge Temperature: 20° C.
Capillary: 60(50) cm bare silica, 75 μm ID
Sample Injection: 0.5 psi 6 s sample, 0.1 psi 10 s run buffer

| PARAMETERS | METHOD A | METHOD B | METHOD C |
|---|---|---|---|
| Run buffer | 5% HS-γ-CD in 25 mM triethylammonium | 5% HS-β-CD in 25 mM triethylammonium | 100 mM HP-β-CD in 10% acetonitrile, phosphate buffer, pH 2.5 |
| | phosphate buffer, pH 2.5 | phosphate buffer, pH 2.5 | 90% CElixir Accelerator Solution B, pH 9.2 |
| Separation | 23 kV, reverse polarity | 20 kV reverse polarity for 25 min followed by 2 psi 3 min push with run buffer | 25 kV, normal polarity |
| Sample Concentration | 1-2 mg/mL | 0.5 mg/mL | 1 mg/mL |
| Sample solvent Rinses | Deionized water 1 min at 20 psi with run buffer | 0.1M HCl At 20 psi: 1 min 0.1M NaOH, 1 min deionized water, 1 min run buffer | Deionized water At 29 psi: 2 min 0.1M NaOH, 2 min deionized water, 1 min CElixir Initiator Solution A, 2 min run buffer |

C. Experimental Procedures

Step 1: Trans-2-Benzylaminocyclohexan-1-ol (28)

A mixture of cyclohexene oxide (1) (19 mL, 0.2 mol, Aldrich cat #C10,280-4) and benzylamine (27) (21 mL, 0.2 mol, Aldrich cat #407712) in water (5 mL) was refluxed for 3 hours. The cooled reaction mixture was partitioned between 4M aq NaOH (100 mL) and methyl t-butyl ether (150 mL). The aqueous layer was further extracted with methyl t-butyl ether (2×100 mL), and the combined organic extracts were dried over anhydrous magnesium sulfate and concentrated in vacuo to give trans-2-benzylaminocyclohexan-1-ol (28) as a low melting point solid (39.4 g, 96% yield); $^1$H-NMR (300 MHz, $CDCl_3$) δ: 7.31-7.22 (m, 5H, Ar), 3.91 (d, J 13 Hz, 1H, $CH_{2a}N$), 3.65 (d, J 13 Hz, 1H, $CH_{2b}N$), 3.18 (dt, J 5 Hz, J 10 Hz, CH), 2.28 (dt, J 5 Hz, J 10 Hz, CH), 2.15-2.10 (m, 1H, CH), 2.00-1.94 (m, 1H, CH), 1.70-1.60 (m, 2H, $CH_2$), 1.31-1.12 (m, 3H, $CH_2$ & CH), 1.03-0.90 (m, 1H, CH); $^{13}$C-NMR (75 MHz, $CDCl_3$) δ: 140.44 (+), 128.31 (−), 128.00 (−), 126.87 (−), 73.62 (−), 62.97 (−), 50.71 (+), 33.35 (+), 30.36 (+), 24.96 (+), 24.28 (+), 19.32 (+).

Step 2: (1R,2R)-2-Benzylaminocyclohexan-1-ol di-O,O-p-toluoyl-L-hemi-tartrate (29)

To a refluxing solution (the residual gummy white solid was separated, discarded and was not characterized) of trans-2-benzylaminocyclohexan-1-ol (28) (41.0 g, 200 mmol) in absolute ethanol (250 mL) was added (5 mL/min) a solution of (−)-di-O,O-p-toluoyl-L-tartaric acid (19.3 g, 50.0 mmol, Aldrich cat #371416) in absolute ethanol (150 mL). The resultant clear yellow solution was then allowed to cool down from 80° C. to room temperature over 7 h with constant agitation, and was seeded with (1R,2R)-2-benzylaminocyclohexan-1-ol (−)-di-O,O-p-toluoyl-L-hemi-tartrate to facilitate crystallization when the reaction mixture had cooled to 70° C. The resultant precipitate was collected, rinsed with absolute EtOH (50 mL), and dried under vacuum and phosphorus pentoxide to give (1R,2R)-2-benzylaminocyclohexan-1-ol (−)-di-O,O-p-toluoyl-L-hemi-tartrate (29) as a white solid (20.3 g, 51% yield). An increased recovery may be achieved by decreasing the volume of EtOH used for resolution by acid salt crystallization; enantiomeric purity: 94.6% ee (for free base, chiral CE method B); the crude hemi-tartrate ((29) (12.2 g) was recrystallized from absolute EtOH (600 mL) to give material (7.30 g) with enhanced optical purity; enantiomeric purity: +99% ee (for free base; chiral CE method B); $[\alpha]_D$ 100.11° (c 1.09, MeOH).

Step 3: (1R,2R)-2[(N-Benzyl-N-benzyloxycarbonyl) amino]cyclohexan-1-ol (30)

To a solution of (1R,2R)-2-benzylaminocyclohexan-1-ol (−)-di-O,O-p-toluoyl-L-hemi-tartrate (29) (15.0 g, 37.6 mmol) and $Na_2CO_3$ (8.0 g, 75 mmol, Aldrich cat #22,353-7) in water (300 mL) was added drop-wise a solution of benzyl chloroformate (5.80 g, 4.80 mL, 33.8 mmol, Aldrich cat #11,993-8) in dichloromethane (100 mL) (dichloromethane could be replaced by toluene, which would eliminate a solvent switch for the next step). Upon completion of the addition, the reaction mixture was stirred for another 2 h. The aqueous layer was collected and extracted with dichloromethane (100 mL), and the combined organic layers were washed with 1M aq HCl (100 mL), dried over anhydrous $MgSO_4$ and concentrated in vacuo to give the carbamate (30) as a colorless oil (13.9 g, quant. yield), which was used without further purification in the next step; $R_f$=0.67 (EOAc-hexanes, 2:1, v/v, +0.5% v/v $iPrNH_2$); $R_t$=15 4 min (HPLC gradient A); MS (ES+) 340.1 $[M+H]^+$.

Step 4A:
3,4-(Dimethoxyphenethoxy)trichloracetimidate (16)

To a reaction flask was charged 3,4-dimethoxyphenethyl alcohol (DMPE, 10 g, Aldrich cat #197653, CAS #7417-21-2) and MTBE (50 mL), and the resultant mixture was stirred at 12° C. (9-15° C.). Solid potassium hydroxide (5.0 g, 1.6 equiv) and methyltributylammonium chloride (75 wt % solution in water; 0.4 g, 0.02 equiv) were successively charged to the reaction flask. Under maximum agitation, trichloroacetonitrile (10.0 g, 1.26 mole equiv, Aldrich cat #T53805, CAS #545-06-2) was charged slowly to the reaction flask via an addition funnel, while the pot temperature was maintained <1° C. Residual trichloroacetonitrile in the addition funnel was rinsed into the flask with MTBE (5 mL). The reaction mixture was agitated at 12° C. (9-15° C.) until the reaction was judged complete (1-4 h) by HPLC analysis (DMPE <1%, E-DMPE ester >96%).

Upon completion of the reaction, the reaction mixture was diluted with MTBE (20 mL) and then cooled to 3° C. (0-6° C.). The MTBE layer was washed with water (3×20 mL) cooled at 3° C. (0-6° C.).

The ratio of the E and Z isomers in the MTBE layer can alternatively be determined by $^1$H-NMR (~1-mL solution is concentrated to dryness, and the residue is analyzed by $^1$H-NMR ($CDCl_3$). The chemical shift of the $CH_2O$ methylene groups is 4.45 ppm for the E isomer and 4.55 ppm in the Z isomer, respectively). If the E isomer is less than 98%, the MTBE layer is washed further with 0.4 M KOH solution.

The MTBE solution was concentrated to dryness under reduced pressure at a maximum bath temperature of 40° C. Ethanol (55 mL) was added to the remaining residue and the mixture was agitated at 25° C. (22-28° C.) until a clear solution was achieved (~30-60 min) The ethanolic solution was cooled to 0° C. (~3 to 3° C.) to allow product crystallization (The E-DMPE ester crystallizes out at 7-10° C.). The slurry was diluted with water (77 mL) and the mixture was agitated at 0° C. (−3 to 3° C.) for ~1 hr. The slurry was filtered and rinsed with cold (0-6° C.) water (36 mL). The wet cake was dried under vacuum at ambient temperature (15-25° C.) until the moisture content (KF) was lower than 0.05% to give the E-DMPE ester (16) as an off-white crystalline solid (90-95% yield) with 99.0+% purity by HPLC); $R_f$=0.33 for 3,4-dimethoxyphenethyl alcohol (EtOAc-hexanes, 1:1 v/v); $R_f$=0.76 for (E)-trichloroacetimidic acid 2-(3,4-dimethoxyphenyl)ethyl ester (16) (EtOAc-hexanes, 1:1 v/v); $^1$H-NMR (300 MHz, $CDCl_3$) δ: 8.22 (br s, 1H, NH), 6.77-6.75 (m, 3H, Ar), 4.42 (t, 2H, J 7 Hz, $CH_2O$), 3.81 & 3.79 (2 s, 6H, 2×$OCH_3$), 2.97 (t, 2H, J 7 Hz, $CH_2$).

Step 4B: (1R,2R)-1-[(N-Benzyl-N-benzyloxycarbonyl)amino]-2-(3,4-dimethoxyphenethoxy)cyclohexane (31)

To a solution of carbamate (30) (10.0 g, 29.5 mmol) in toluene (100 mL) was added sequentially $BF_3.Et_2O$ (0.84 g, 0.75 mL, 5.9 mmol, Aldrich cat #21,660-7) and a solution of trichloroacetimidate (16) (9.62 g, 29.5 mmol, Raylo lot #3022-AL-2P) in toluene (50 mL). The resultant reaction mixture was stirred at room temperature for 2 h, at which point the reaction was judged complete by TLC (EtOAc-hexanes, 1:2 v/v+0.5% v/v $iPrNH_2$; $R_f$ 0.57 for (31)) and subsequently quenched by the addition of water (100 mL). The organic layer was collected and dried over anhydrous magnesium sulfate to yield crude (31) (20.1 g, quant. yield), which was used without further purification in the next step. For the purpose of characterization, an aliquot (1.0 g) of ether (31) was purified by column chromatography on silica gel which was eluted by a mixture of EtOAc-hexanes (1:4, v/v, +0.5% v/v $iPrNH_2$) to provide pure (31) as a colorless oil (0.31 g); $R_f$=0.24 (EtOAc-hexanes, 1:4 v/v, +0.5% v/v $iPrNH_2$); $R_t$=21.9 min (HPLC gradient A); MS (ES+) 504.1 $[M+H]^+$, 526.1 $[M+Na]^+$.

Step 5: (1R,2R)-2-amino-1-(3,4-dimethoxyphenethoxy)cyclohexane monohydrochloride (32)

To a solution of crude ether (31) (20.1 g) in EtOH was added successively concentrated hydrochloric acid (5 mL) and 10% Pd-C(2 g, Aldrich cat #20,569-9). A Parr shaker apparatus, charged successively with this suspension and hydrogen (60 psi), was shaken at 70° C. for 4 h. The reaction mixture was filtered through a bed of Celite 545 (Aldrich cat #4199931), which was rinsed with EtOH (25 mL), and the filtrate was concentrated in vacuo to give the crude monohydrochloride salt (32). The resultant residue was triturated in methyl t-butyl ether (150 mL) and then vigorously stirred for 18 h to give the monohydrochloride salt (32) as an off-white solid (7.68 g, 82% yield over 3 steps); $R_t$=5.7 min (HPLC gradient A); enantiomeric purity: 95.9% ee (for free base, chiral CE method A). For the purpose of characterization, an aliquot of crude (32) was purified by recrystallization from EtOH-MTBE and provided optically pure (32); enantiomeric purity: 99.6% ee (for free base, chiral CE method A); m.p. 135-137° C.; $[\alpha]_D$ −38.53° (c 0.988, $H_2O$); $^1$H-NMR (400 MHz, $D_2O$) δ: 6.88-6.76 (m, 3H, Ar), 3.81 (overlapped dt, J 10 Hz, J 8 Hz, 1H, $CH_2O$), 3.73 (s, 3H, $CH_3O$), 3.71 (s, 3H, $CH_3O$), 3.57 (overlapped dt, J 10 Hz, J 8 Hz, 1H, $CH_2O$), 3.22 (dt, J 10 Hz, J 4.4 Hz, 1H, CHO), 2.88 (dt, J 10 Hz, J 4.4 Hz, 1H, CHN), 2.74 (t, J 7 Hz, 2H, $CH_2$), 2.10-1.62 (m, 4H, aliph), 1.34-0.99 (m, 4H, aliph); $^{13}$C-NMR (100 MHz, $D_2O$) δ: 148.37 (+), 146.94 (+), 132.33 (+), 121.61 (−), 112.81 (−), 112.27 (−), 79.65 (−), 69.76 (+), 56.02/55.95 (−), 54.82 (−), 35.24 (+), 29.66 (+), 28.99 (+), 23.55 (+), 23.36 (+); MS (ES+) 280.2 $[M+H]^+$.

Step 6A: (R)-(+)-2-Acetoxysuccinic anhydride (95a)

A mixture of D-malic acid (10 g, 75 mmol, Major Chemicals Co. Ltd. lot #KS00404) in acetyl chloride (30 mL, Aldrich cat #11,418-9) was heated to 45° C. for 6 h. The excess acetyl chloride was evaporated in vacuo and the residue was taken up in dichloromethane (10-15 mL). The volatiles were removed in vacuo and the residual oil was stored at 4° C. for 18 h. Under cold storage, the oil crystallized, giving rise to (R)-(+)-2-acetoxysuccinic anhydride (95a) as a white solid (11.7 g, quant yield); m.p. 52° C.; $[\alpha]_D$ +23.82° (c 5.44, acetone); $^1$H-NMR (300 MHz, CDCl$_3$) δ: 5.51 (dd, 1H, J 6 Hz, 9 Hz), 3.36 (dd, 1H, J 19 Hz, 9 Hz), 3.00 (dd, 1H, J 19 Hz, 6 Hz), 2.17 (s, 3H); $^{13}$C-NMR (75 MHz, CDCl$_3$) δ: 169.61 (+), 167.66 (+), 166.21 (+), 67.51 (−), 35.10 (+), 20.16 (−).

Step 6B: (3R)-1-[(1R,2R)-2-[2-(3,4-Dimethoxyphenyl)ethoxy]cyclohexyl]-3-pyrrolidinol hydrochloride (19)

(a) (1R,2R)-2-amino-1-(3,4-dimethoxyphenethoxy)cyclohexane hydrochloride (32) (474 mg, 1.50 mmol, 99.4% ee) was partitioned between 6M aq NaOH (1 mL) and dichloromethane (4 mL). The aqueous layer was collected and extracted once more with dichloromethane (4 mL). The combined organic extracts were dried over anhydrous MgSO$_4$ and concentrated in vacuo to give (1R,2R)-2-amino-1-(3,4-dimethoxyphenethoxy)cyclohexane as an orange oil (370 mg, 88% yield).

(b) To a solution of (1R,2R)-2-amino-1-(3,4-dimethoxyphenethoxy)cyclohexane (370 mg) in dichloromethane (4 mL) was added (R)-(+)-2-acetoxysuccinic anhydride (95a) (240 mg, 1.50 mmol). After the resultant solution was stirred at room temperature for 1 h, HPLC analysis (gradient A) showed the appearance of a new major peak ($R_f$=12 5 min) and the absence of starting material ($R_f$=5.7 min) The solvent and volatiles were removed in vacuo.

(c) To the resultant residue was added acetyl chloride (1 mL, 14 mmol, Aldrich cat #11,418-9). The resultant solution was then refluxed for 1 h, after which HPLC analysis (gradient A) revealed the appearance of a new single peak ($R_f$=14.5 min). Subsequently, the cooled (0° C.) reaction mixture was quenched by slow addition of water (3 mL) and was then extracted with toluene (3 mL). The organic layer was collected and dried over anhydrous MgSO$_4$ to give a solution of crude imide (36) in toluene, which was used in the next step without further purification. $R_f$ 0.72 (EtOAc-hexanes, 2:1 v/v, +0.5% v/v iPrNH$_2$).

(d) To a refluxing solution of Red-Al (65 wt % in toluene, 1.86 g, 1.80 mL, 6 mmol, Aldrich cat #19,619-3) in toluene (2 mL) was added dropwise (over 5 min) a solution of crude (36) in toluene (3 mL). After the resultant solution was refluxed for 1 h, TLC analysis (EtOAc-hexanes, 2:1 v/v, +0.5% v/v iPrNH$_2$) revealed the absence of (36) and the appearance of a new polar spot (reduction of (36) with Red-Al at room temperature provided a very complex mixture (HPLC) from which (19) could not be isolated). The cooled (0° C.) reaction mixture was cautiously quenched by addition of 6M aq NaOH (3 mL). After separation of the layers, the organic layer was dried over anhydrous MgSO$_4$ and concentrated in vacuo to give (19) free base as an oil (195 mg, 37% yield). Alternatively, the reduction of (36) was performed using LiAlH$_4$.THF$_2$ 1.0 M in toluene (3 mL, 3 mmol, Aldrich cat #243949) at room temperature. After carefully quenching the reaction by successive addition of water (100 μL), 6M aq NaOH (100 μL) and water (300 μL), the free base of (19) (423 mg, 80% yield) was obtained.

(e) The solution of (19) free base in methyl t-butyl ether (10 mL) was treated with 2M HCl in diethyl ether (2 mL, 2 mmol, Aldrich cat #455180). After the volatiles were removed in vacuo, crude (19) was obtained as a hygroscopic foam. HPLC analysis (gradient A) of this material revealed a major peak ($R_f$=6.5 min).

(f) Crude (19) was triturated in EtOAc (1 mL) to give an off-white solid.

| | |
|---|---|
| Chemical purity | 80 area % (HPLC gradient B). |
| $R_f$ | 6.78 min (HPLC gradient B). |
| Isomeric impurities | 0.15% (3R)-1-[(1S, 2S)-2-[2-(3,4-dimethoxyphenyl)ethoxy]cyclohexyl]-3-Pyrrolidinol hydrochloride, |
| | 1.73% (3S)-1-[(1S, 2S)-2-[2-(3,4-dimethoxyphenyl)ethoxy]cyclohexyl]-3-Pyrrolidinol hydrochloride (chiral CE, method A) |
| | 1.84% (3S)-1-[(1R, 2R)-2-[2-(3,4-dimethoxyphenyl)ethoxy]cyclohexyl]-3-Pyrrolidinol hydrochloride (chiral CE, method C) |
| Wt/wt "as is basis" | 62.9% (HPLC, CSK-G method) |
| MS (ES+) | 350.1 [M + H]$^+$ |

$^1$H-NMR (D$_2$O, 400 MHz) δ: 6.90-6.88 (m, 2H, H-13, H-14), 6.80-6.78 (m, 1H, H-1.5), 4.24 (broad singlet, 1H, H-8), 3.93 (overlapping dt, 1H, J 5.3 Hz, J 10 Hz, H-11), 3.72 & 3.71 (s, 6H, 2×CH$_3$, H-16, H-17), 3.54 (overlapping dt, 1H, J 5.0 Hz, J 9.3 Hz, H-11), 3.30-2.98 (m, 6H, H-1, H-2, H-7, H-10), 2.88-2.64 (m, 2H, H-12), 2.21-2.18 (m, 1H, H-6), 1.95-1.85 (m, 2H, H-3, H-9), 1.70-1.60 (m, 2H, H-4, H-5), 1.28-0.97 (m, 4H, H-3, H-4, H-5, H-6). For the numbering of the protons, refer to the following structure.

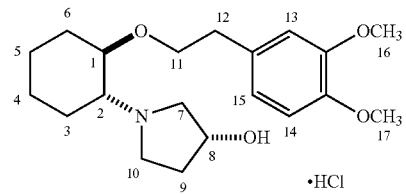

D. Alternate Methods and Reagents

The following alternative methods and reagents may be used to further optimize the steps described above.

Step 1: Preparation of racemic aminoalcohol (28)

i. The aminoalcohol (28) could be the starting material.
ii. Replace methyl t-butyl ether (MTBE) with ethyl acetate.

Step 2: Resolution of trans-2-benzylaminocyclohexanol (28)

i. Reduce the volume of absolute ethanol used and monitor more effectively the cooling process to maximize the recovery and optical purity of the tartrate complex (29).
ii. Recrystallization of the hemi-tartrate (29) could be eliminated.

Step 3: Preparation of carbamate (30)

i. Resolve racemic (30) by simulated moving bed as an economically viable process compared to resolution.

ii. Add benzylchloroformate neat to avoid an additional reaction vessel.
iii. Replace dichloromethane by toluene to avoid a solvent switch before the next step.
iv. Dry azeotropic distillation to provide (30) in toluene ready to use for the next step.

Step 4: Reverse coupling of (30) with (16)

i. Use Lewis acids such as triflic acid or $AlCl_3$ to circumvent the hazard inherent to ether complex such as $BF_3.Et_2O$.
ii. Dry crude material by azeotropic distillation.
iii. Use ethyl acetate or methyl acetate as solvent for the reverse coupling to avoid a solvent switch.
iv. Use a basic wash (e.g., 8% NaOH) to remove undesired trichloracetamide.

Step 5: Hydrogenolysis to give (32)

i. Add anhydrous HCl instead of concentrated HCl
ii. Use MTBE-MeOH crystallization as a mean to increase chemical and optical purity.
iii. Perform hydrogenolysis with ammonium formate in refluxing MeOH.
iv. Isolate amnioether (32) by addition of anhydrous HCl to MeOH followed by addition of a co-solvent such as MTBE. Isolation of (32) after step 5 would allow an upgrade of the material (i.e. chemical and optical purity).
v. Use ethyl acetate as solvent for the hydrogenolysis.

Steps 6a and 6B: De Novo Pyrrolidinol Assembly i. Replace dichloromethane by solvents with similar solubility properties or improved safety such as chlorobenzene, tetrahydrofuran or methyl acetate for the condensation of (32) with (R)-(+)-2-acetoxysuccinic anhydride (95a).
ii. Use acetic anhydride with a catalytic amount of acetyl chloride to achieve ring closure to imido-ether (36) (the same conditions could be used to prepare (R)-(+)-2-acetoxysuccinic anhydride (95a) from D-malic acid) and to remove excess acetic anhydride by an aqueous wash.
iii. Replace Red-Al with borane, generated in situ from sodium borohydride and acetic acid in tetrahydrofuran as reported by Urban et al. (Urban F J, Anderson B G, Orrill S L, Daniels P J. Process Research and Large-Scale Synthesis of a Novel 5,6-Dihydro-(9H)-pyrrazolo[3,4-c]-1,2,4-triazolo[4,3-c]pyridine PDE-IV Inhibitor. Org Proc Res & Dev 2001, 5, 575-580.
iv. Add anhydrous HCl to form the hydrochloride salt (19).
v. Remove undesired diasteromers, namely, (3S)-1-[(1R, 2R)-2-[2-(3,4-dimethoxyphenyl)ethoxy]cyclohexyl]-3-Pyrrolidinol hydrochloride, (3R)-1-[(1S,2S)-2-[2-(3, 4-dimethoxyphenyl)ethoxy]cyclohexyl]-3-Pyrrolidinol hydrochloride, and (3S)-1-[(1S,2S)-2-[2-(3, 4-dimethoxy-phenyl)ethoxy]cyclohexyl]-3-Pyrrolidinol hydrochloride, by recrystallization of (19) from iPrOH-iPrAc (1:1, v/v, ~7 mL/g of substrate).

Example 5b

Figure 45:
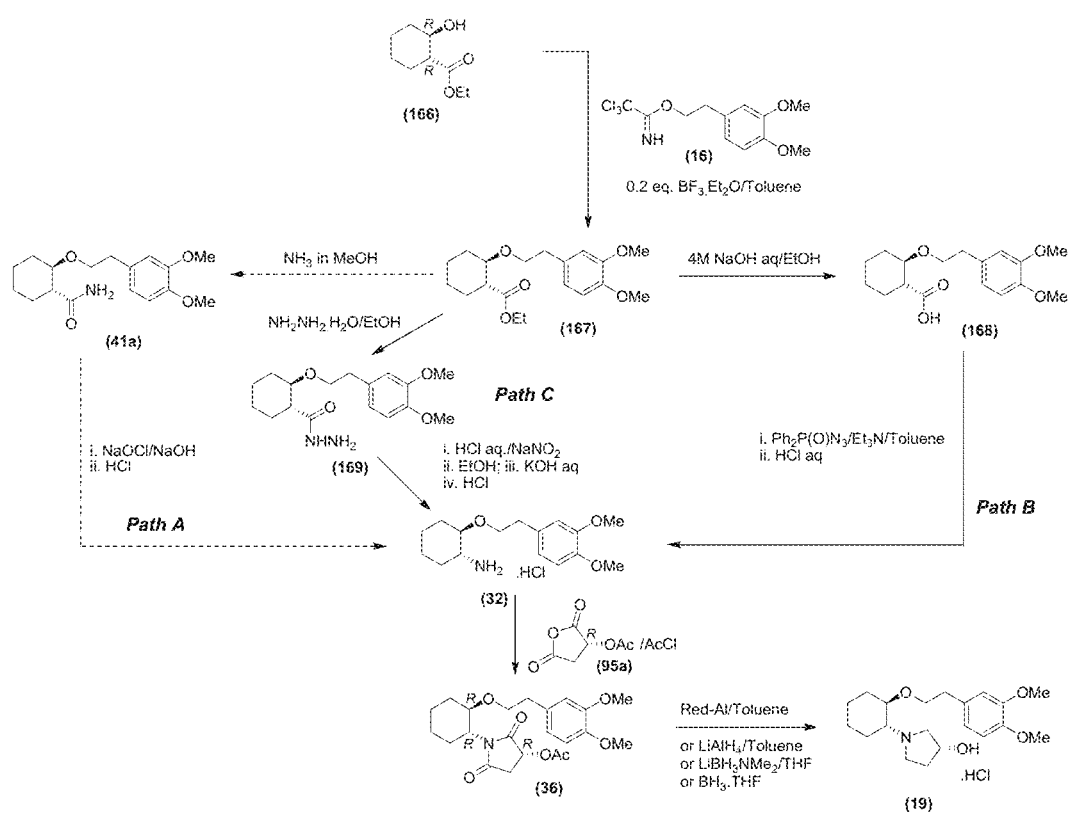
FIG. 45 illustrates a reaction scheme that may be used as a process for preparing a stereoisomerically substantially pure trans-(1R,2R)-aminocyclohexyl ether compound of formula (19).

Alternate Preparation of (1R,2R)-2-amino-1-(3,4-dimethoxyphenethoxy)cyclohexane monohydrochloride (32) (FIG. 45)

Step 1: Ethyl (1R,2R)-2-(3,4-dimethoxyphenethoxy) cyclohexane-1-carboxylate (167)

To ethyl (1R,2R)-2-hydroxycyclohexane-1-carboxylate (166) (1.7 g, 10 mmol) and $BF_3.EtO_2$ (280 mg, 250 μL, 2 mmol) in toluene (10 mL) was added dropwise a solution of 3,4-dimethoxyphenethoxy trichloroacetimidate (16) (3.26 g, 10 mmol) in toluene (15 mL). The resultant solution was stirred at ambient temperature for 2 hrs. The reaction mixture was then quenched with water (10 mL), the organic layer was collected, dried over anhydrous $MgSO_4$ and concentrated in vacuo to give 3.71 g (quant. yield) of ethyl (1R,2R)-2-(3,4-dimethoxyphenethoxy)cyclohexane-1-carboxylic acid (167) which was used without further purification in the next step.

An aliquot of crude 1 was purified by chromatography using a mixture of EtOAc-hexanes (1:4, v/v, +0.5% v/v $iPrNH_2$) to give pure ethyl (1R,2R)-2-(3,4-dimethoxyphenethoxy)cyclohexane-1-carboxylic acid (167); $R_f$: 0.34 (EtOAC-hexanes, 1:1, v/v, +0.5% v/v $iPrNH_2$), $R_t$: 16.35 min (HPLC—method A); $^1$H-NMR (400 MHz, $CDCl_3$) δ: 6.75-6.68 (m, 3H, Ar), 4.04 (q, J 7 Hz, 2H, $CH_2O$), 3.84 (s, 3H, $CH_3O$), 3.81 (s, 3H, $CH_3O$), 3.73 (overlapped dt, J 14 Hz & 9 Hz, 1H, CHO), 3.48 (2 overlapped dt, J 14 Hz & 10 Hz, 2H, $CH_2O$), 2.73 (t, J 7 Hz, 2H, $CH_2$), 2.30 (dt, J 10 Hz & 6 Hz, 1H, CHN), 2.10-1.35 (m, 8H, Aliph), 1.18 (t, J 7 Hz, 3H, $CH_3$); $^{13}$C-NMR (100 MHz, $CDCl_3$) δ: 175.02 (+), 148.58 (+), 147.26 (+), 131.66 (+), 120.63 (−), 112.21 (−), 111.01 (−), 78.90 (−), 69.99 (+), 60.11 (+), 55.82 (−), 55.72 (−), 50.39 (−), 36.16 (+), 30.63 (+), 28.68 (+), 24.65 (+), 24.04 (+), 14.16 (+); MS (ES+) 337.1 $[M+H]^+$, 354.1 $[M+H_2O]^+$.

Step 2a: (1R,2R)-2-(3,4-Dimethoxyphenethoxy) cyclohexane-1-carboxylic acid (168) (path B)

A solution of crude (1R,2R)-2-(3,4-dimethoxyphenethoxy)cyclohexane-1-carboxylic acid (167) (3.71 g, 10 mmol) and 4M NaOH aq (10 mL, 40 mmol) in EtOH (25 mL) was stirred at room temperature for 18 hrs. The reaction mixture was then concentrated in vacuo, the residue was re-dissolved in water (25 mL) and the resultant basic aqueous solution was extracted with diethyl ether (2×25 mL). The aqueous layer was collected, acidified to pH1 with 6M HCl aq and extracted with dichloromethane (2×25 mL). The combined organic extracts were dried over anhydrous $MgSO_4$ and concentrated in vacuo to give 2.29 g of (1R, 2R)-2-(3,4-dimethoxyphenethoxy)cyclohexane-1-carboxylic acid (168) (74% yield; $R_t$: 13.48 min (HPLC—method A); $^1$H-NMR (300 MHz, $CDCl_3$) δ: 7.95 (br s, 1H, $CO_2H$), 6.78-6.69 (m, 3H, Ar), 3.84 (s, 3H, $CH_3O$), 3.82 (s, 3H, $CH_3O$), 3.81 (overlapped dt, J 14 Hz & 7 Hz, 1H, $CH_{2a}O$), 3.57 (dt, J 14 Hz & 7 Hz, 1H, $CH_{2b}O$), 3.52-3.42 (m, 1H, CHO), 2.79 (t, J 7 Hz, 2H, $CH_2$), 2.34 (dt, J 14 Hz & 6 Hz, 1H, CHN), 2.13-1.09 (m, 8H, Aliph); MS (ES+) 307.1 $[M+H]^+$.

Step 3a: (1R,2R)-2-Amino-1-(3,4-dimethoxyphenethoxy)cyclohexane monohydrochloride (32) (path B)

A solution of (1R,2R)-2-(3,4-dimethoxyphenethoxy)cyclohexane-1-carboxylic acid (168) (2.16 g, 7.0 mmol), triethylamine (0.76 g, 1 mL, 7.5 mmol) and diphenylphosphoryl azide (2.34 g, 1.84 mL, 7.5 mmol) in toluene (10 mL) was refluxed for 4 hrs. TLC check in EtOAC-hexanes (1:2, v/v, +0.5% v/v iPrNH$_2$) shows a new non polar spot at R$_f$ 0.7 and no more starting material. The cooled reaction mixture was then quenched with 1M HCl aq (10 mL), the organic layer was collected, dried over anhydrous MgSO$_4$ and concentrated in vacuo. The resultant residue was then treated with 3M HCl aq (10 mL) for 4 hrs at ambient temperature to hydrolyze the isocyanate. The acidic aqueous solution was concentrated in vacuo, the residue was triturated in diethyl ether and the solvent was decanted off. The residue was then recrystallized from EtOH-Et$_2$O to give 0.93 g (42% yield) of (1R,2R)-2-amino-1-(3,4-dimethoxyphenethoxy) cyclohexane monohydrochloride (32); R$_t$: 6.08 min (HPLC—method A); Enantiomeric purity: 98.5% ee & 88% de (chiral CE—method A); $^1$H-NMR (300 MHz, D$_2$O) δ: 6.87-6.73 (m, 3H, Ar), 3.85-3.75 (m, 1H, CH$_{2a}$O), 3.71 (s, 3H, CH$_3$O), 3.69 (s, 3H, CH$_3$O), 3.60-3.50 (m, 1H, CH$_{2b}$O), 3.18 (dt, J 10 Hz & 4.4 Hz, 1H, CHO), 2.85 (dt, J 10 Hz & 4.4 Hz, 1H, CHN), 2.71 (t, J 7 Hz, 2H, CH$_2$), 2.10-0.90 (m, 8H, Aliph); $^{13}$C-NMR (75 MHz, D$_2$O) δ: 148.36 (+), 146.92 (+), 132.34 (+), 121.60 (−), 112.79 (−), 112.28 (−), 79.67 (−), 69.75 (+), 56.00 (−), 55.93 (−), 54.78 (−), 35.19 (+), 29.63 (+), 28.96 (+), 23.51 (+), 23.33 (+); MS (ES+) 280.1 [M+H]$^+$.

Step 1b: (1R,2R)-2-(3,4-Dimethoxyphenethoxy) cyclohexane-1-carboxylic acid hydrazide (169) (path C)

To a solution of crude ethyl (1R,2R)-2-(3,4-dimethoxyphenethoxy)cyclohexane-1-carboxylate (167) (10.0 g, no more than 20 mmol) in EtOH (10 mL) was added dropwise hydrazine.monohydrate (20 mL, 20.6 g, 412 mmol). The resultant mixture was refluxed for 72 hrs. HPLC (method A) showed no more starting material at R$_t$=16.35 min, but a new peak at R$_t$=10.0 min. The cooled reaction mixture was concentrated in vacuo then diethyl ether (150 mL) was added and the resultant mixture was vigorously stirred for 1 hr. The resultant off-white solid was collected and dried under low vacuum in the presence of phosphorus pentoxide to give 6.0 g of (169) (93% yield; R$_t$: 9.8 min (HPLC—method A); $^1$H-NMR (400 MHz, CDCl$_3$) δ: 6.78-6.69 (m, 3H, Ar), 3.85 (s, 3H, CH$_3$O), 3.82 (s, 3H, CH$_3$O), 3.76 (overlapped dt, J 9 Hz & 7 Hz, 1H, CH$_{2a}$O), 3.48 (overlapped dt, J 9 Hz & 7 Hz, 1H, CH$_{2b}$O), 3.38 (dt, J 4 Hz & 10 Hz, 1H, CHO), 2.73 (t, J 7 Hz, 2H, CH$_2$), 2.16-2.12 (m, 1H, CH), 1.98-1.91 (m, 1H, CHN), 1.83-1.66 (m, 3H, Aliph), 1.52 (dq, J 4 Hz & 12.5 Hz, 1H, CH), 1.30-105 (m, 3H, Aliph); $^{13}$C-NMR (100 MHz, CDCl$_3$) δ: 175.26 (+), 148.69 (+), 147.39 (+), 131.32 (+), 120.63 (−), 112.16 (−), 111.14 (−), 78.72 (−), 69.61 (+), 55.85 (−), 55.82 (−), 49.59 (−), 36.02 (+), 30.23 (+), 28.13 (+), 24.67 (+), 24.12 (+); MS (ES+) 323.2 [M+H]$^+$, 345.2 [M+Na]$^+$.

Step 2b: (1R,2R)-2-amino-1-(3,4-dimethoxyphenethoxy)cyclohexane monohydrochloride (32) (path C)

To a solution of (1R,2R)-2-(3,4-dimethoxyphenethoxy) cyclohexane-1-carboxylic acid hydrazide (169) (967 mg, 3.0 mmol) in 1M HCl aq (10 mL) was added dropwise a solution of sodium nitrite (312 mg, 4.5 mmol) in water (3 mL). The resultant mixture was stirred at ambient for 60 min. HPLC monitoring (method A) showed still remaining unreacted starting material 3, added additional sodium nitrite (312 mg, 4.5 mmol) in water (3 mL) and stirred for an additional 60 min. The heterogenous aqueous mixture containing the acyl azide (HPLC—method A, Rt=16.3/16.9 min) was then extracted twice with diethyl ether (2×15 mL). To the combined organic extracts was added EtOH (15 mL) and diethyl ether was removed under reduced pressure. The resultant ethanolic solution was then refluxed for one hour to form the corresponding urethane (HPLC, method A, Rt=14.3 min) Finally, potassium hydroxide 3.0 M aq (10 mL) was added to the ethanolic solution containing the urethane and the mixture was subsequently refluxed for 18 hrs. The reaction mixture was concentrated in vacuo and the residue was taken up with diethyl ether (50 mL). The organic solution was dried over anhydrous MgSO$_4$ and treated with 2.0 M HCl in diethyl ether (4 mL, 4.0 mmol) to give (32) (295 mg, 31% yield); R$_t$: 6.24 min (HPLC—method A); Enantiomeric purity 99.6% ee and +99% de (chiral CE—method A); $^1$H-NMR (400 MHz, D$_2$O) δ: 6.90-6.77 (m, 3H, Ar), 3.86-3.80 (m, 1H, CH$_{2a}$O), 3.73 (s, 3H, CH$_3$O), 3.71 (s, 3H, CH$_3$O), 3.61-3.55 (m, 1H, CH$_{2b}$O), 3.21 (dt, J 10 Hz & 4.4 Hz, 1H, CHO), 2.87 (dt, J 10 Hz & 4.4 Hz, 1H, CHN), 2.74 (t, J 7 Hz, 2H, CH$_2$), 2.10-0.95 (m, 8H, Aliph); $^{13}$C-NMR (100 MHz, D$_2$O) δ: 148.40 (+), 146.97 (+), 132.41 (+), 121.64 (−), 112.86 (−), 112.35 (−), 79.70 (−), 69.77 (+), 56.06 (−), 55.98 (−), 54.81 (−), 35.22 (+), 29.65 (+), 28.98 (+), 23.54 (+), 23.35 (+); MS (ES+) 280.2 [M+H]$^+$.

The compound (32) can then be treated in a manner described above in Example 5a to produce compound (19).

Example 6

Figure 25:
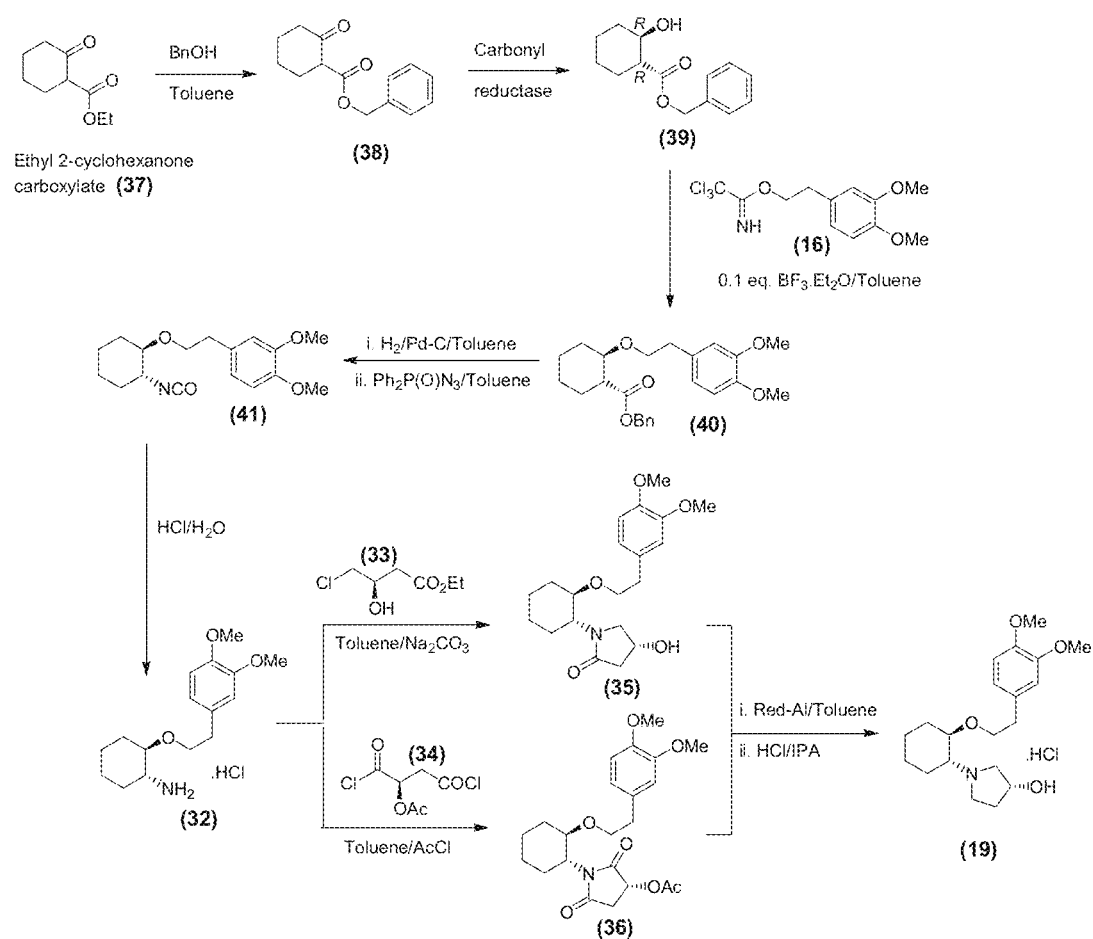
FIG. 25 illustrates a reaction scheme that may be used as a process for preparing a stereoisomerically substantially pure trans-(1R,2R)-aminocyclohexyl ether compound of formula (19).

Asymmetric Reduction of Benzyl 2-Cyclohexanone Carboxylate by Carbonyl Reductase and Curtius Rearrangement (FIG. 25)

Ethyl 2-cyclohexanone carboxylate (37) can be transesterified with benzyl alcohol in toluene (Mottet et al. *J. Org. Chem.* 1999, 64, 1380-1382) to give β-keto ester (38). Asymmetric reduction of β-keto ester (38) with carbonyl reductases (Nakamura et al. *Tetrahedron: Asymmetry* 2003, 14, 2659-2681) would provide chiral β-hydroxy ester (39). Compound (39) will then be coupled with 3,4-dimethoxyphenethoxy trichloroacetimidate (16) in the presence of a catalytic amount of BF$_3$.Et$_2$O complex to give (40). Hydrogenolysis of compound (40) will provide the corresponding carboxylic acid, which will then react with for example diphenylphosphoryl azide to give isocyanate (41) (Nagai, Ukon *Chemical & Pharmaceutical Bulletin* 1975, 23(8), 1841-4; Asunskis et al. *J. Org. Chem.* 1968, 33(3), 1164-1168; Frater et al. *Tetrahedron Lett.* 1984, 25(3), 281-284). Subsequent hydrolysis (Wimalasena et al. *J. Am. Chem. Soc.* 1987, 109(13), 4036-4046; Nakane et al.; *J. Med. Chem.* 1990, 33(9), 2465-2476) will give primary amine (32). Further elaboration of the pyrrolidinol ring can be carried out using the same procedures as previously described in Example 5a.

Example 7

Figure 26:
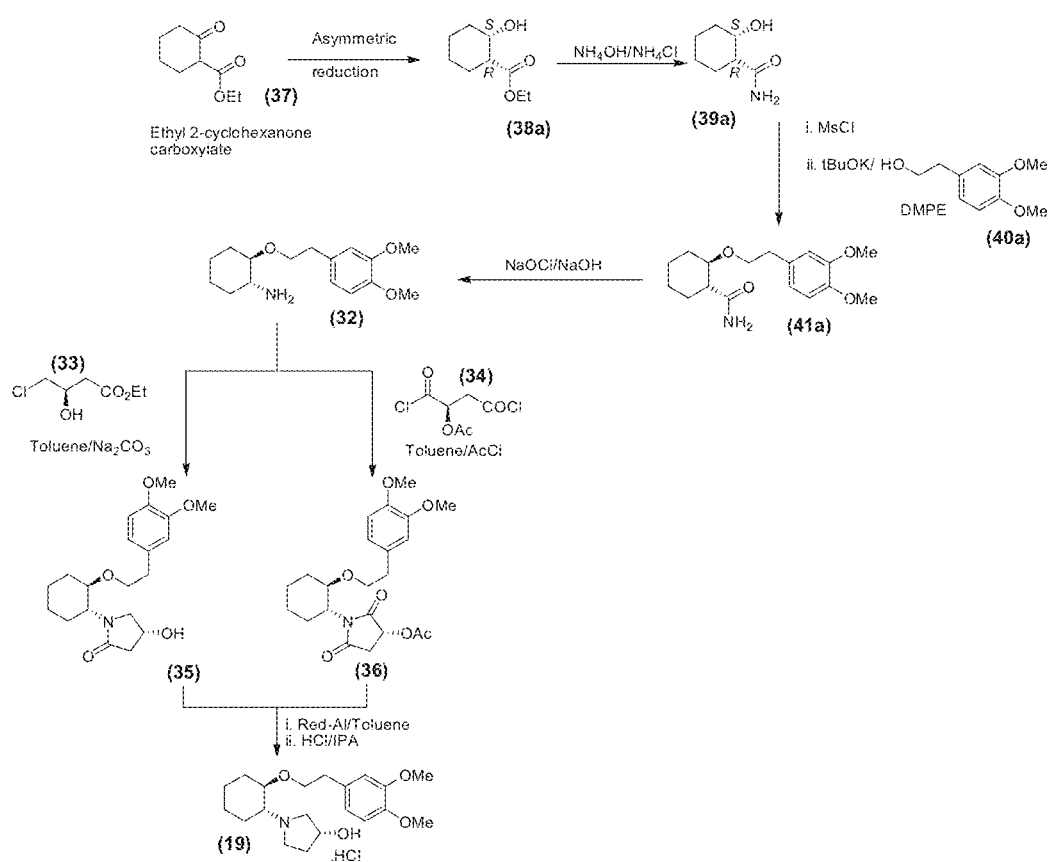
FIG. 26 illustrates a reaction scheme that may be used as a process for preparing a stereoisomerically substantially pure trans-(1R,2R)-aminocyclohexyl ether compound of formula (19).
Figure 27:
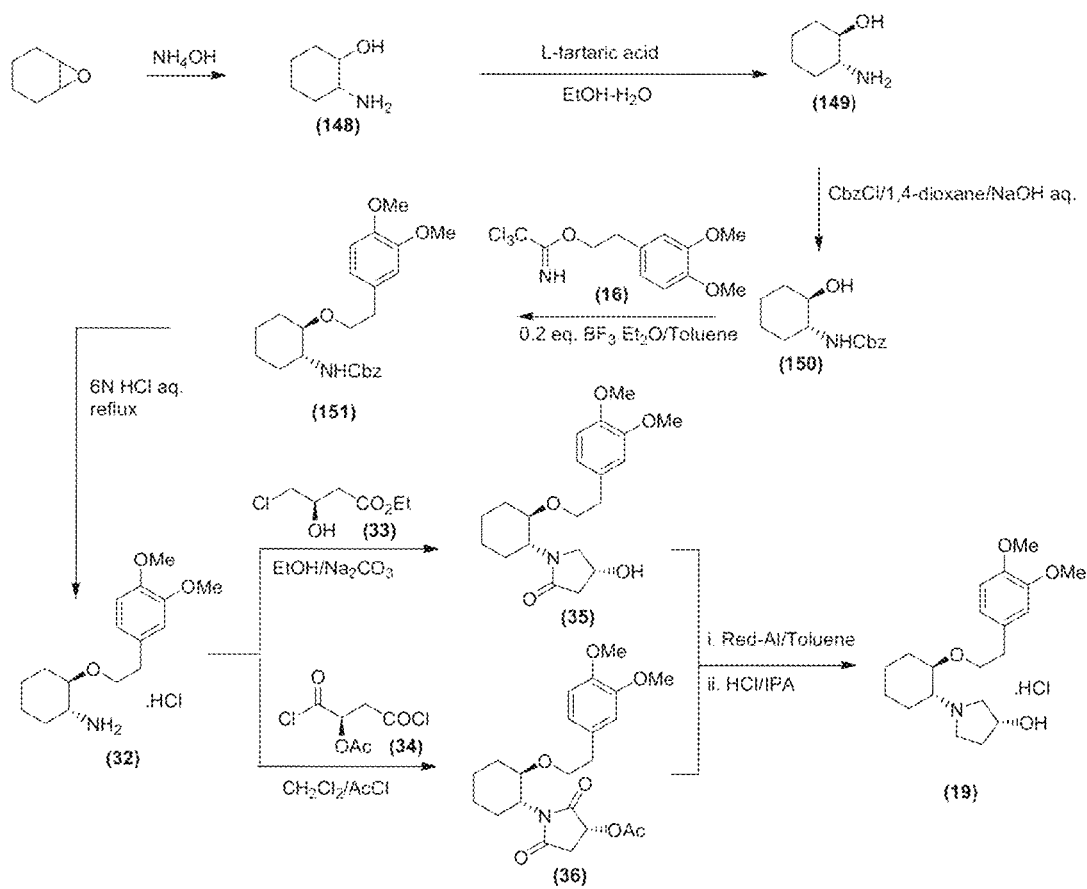
FIG. 27 illustrates a reaction scheme that may be used as a process for preparing a stereoisomerically substantially pure trans-(1R,2R)-aminocyclohexyl ether compound of formula (19).

Asymmetric Reduction of Ethyl 2-Cyclohexanone Carboxylate and Hoffman Rearrangement (FIG. 26)

Asymmetric reduction of ethyl 2-cyclohexanone carboxylate (37) (Yadav et al. *J. Org. Chem.* 2002, 67, 3900-3903; Yadav et al. US 2004/0082043; Miya et al. U.S. Pat. No. 5,215,919; Asako et al. US 2003/0186400) gives ethyl 2-(S)-hydroxycyclohexane-1-(R)-carboxylate (38a). Reaction of ester (38a) with aqueous ammonia and ammonium chloride (Org. Synth. Coll. 1963, Vol. 4, 486) will provide amide (39a). Activation of the hydroxyl group of syn β-hydroxy ester (39a) with mesyl chloride in the presence of triethylamine followed by reaction with the alkoxide of 3,4-dimethoxyphenethoxy alcohol (40a) will give anti carboxamide (41a). Hoffman rearrangement of compound (41a) to (32) (Diehl et al. U.S. Pat. No. 5,032,687; Kleemiss et al. U.S. Pat. No. 5,728,873) can be carried out in the presence of sodium hypochlorite and sodium hydroxide. Further elaboration of the pyrrolidinol ring from primary amine (32) can be carried out using the same procedures as previously described in Example 5a.

Example 8

Figure 32:
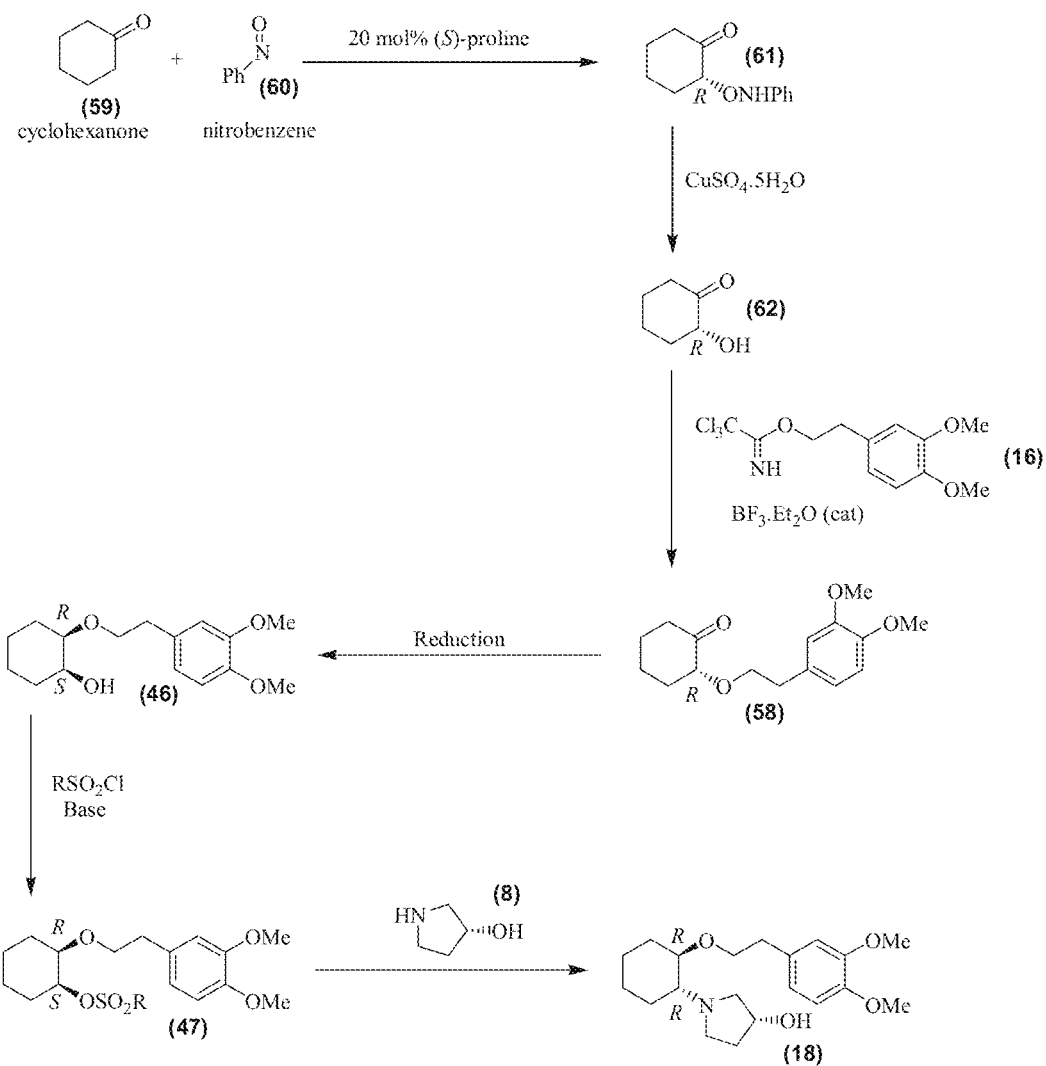
FIG. 32 illustrates a reaction scheme that may be used as a process for preparing a stereoisomerically substantially pure trans-(1R,2R)-aminocyclohexyl ether compound of formula (18).

Resolution of (1R,2R)/(1S,2S)-2-aminocyclohexan-1-ol with L-tartaric acid and reverse coupling (FIG. 32)

Cyclohexene oxide ring opening with ammonium hydroxide (Schlichter and Frahm Arch. Pharm. 1993, 326, 429-436) provided aminoalcohol (148) in 66% yield. The aminoalcohol (148) would then be resolved with L-tartaric acid (Godchot and Mousseron Bull. Soc. Chim. Fr. 1932, 51, 1277-1282) in EtOH—H$_2$O to provide (1R,2R)-2-aminoalcohol (149). The aminoalcohol (149) would then react with benzyl carbamate in 1,4-dioxane in the presence of sodium hydroxide to give compound (150). Compound (150) (1 equivalent) would react with 3,4-dimethoxyphenethoxy trichloroacetimidate (16) (1 equivalent) in the presence of a catalytic amount of BF$_3$.Et$_2$O complex (0.2 equivalents) to give compound (151). Hydrolysis of the carbamate of (151) by reflux in 6N HCl aqueous (Chelucci et al. Synthesis 1990, 1121) would provide compound (32). Further elaboration of the pyrrolidinol ring from primary amine (32) can be carried out using the same procedures as previously described in Example 5a.

Example 9

Figure 28:
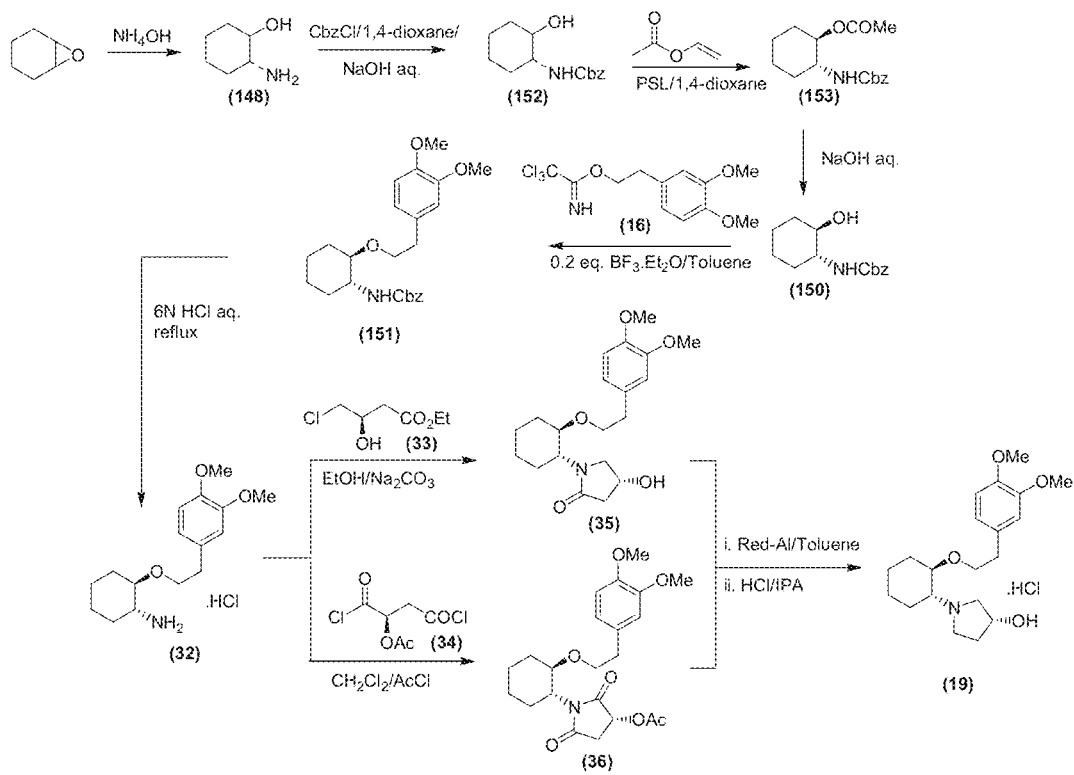
FIG. 28 illustrates a reaction scheme that may be used as a process for preparing a stereoisomerically substantially pure trans-(1R,2R)-aminocyclohexyl ether compound of formula (19).

Enzymatic resolution of (1R,2R)/(1S,2S)-2-aminocyclohexan-1-ol and reverse coupling (FIG. 28)

Cyclohexene oxide ring opening with ammonium hydroxide (Schlichter and Frahm Arch. Pharm. 1993, 326, 429-436) provided aminoalcohol (148) in 66% yield. Compound (148) would then react with benzylchloroformate in 1,4-dioxane in the presence of sodium hydroxide to give compound (152). Treatment of compound (152) with vinyl acetate in the presence of lipase (Ursini et al Synth. Comm. 1999, 29, 1369-1377; Maestro et al. Tetrahedron: Asymmetry, 1997, 8, 3153-3159) would provide compound (153), which after saponification and reverse coupling with trichloroacetamidate (16) in toluene with a catalytic amount of BF$_3$.Et$_2$O would give compound (151). Hydrolysis of the carbamate of (151) by reflux in 6N HCl aqueous (Chelucci et al. Synthesis 1990, 1121) would provide compound (32). Further elaboration of the pyrrolidinol ring from primary amine (32) can be carried out using the same procedures as previously described in Example 5a.

Example 10

Figure 29:
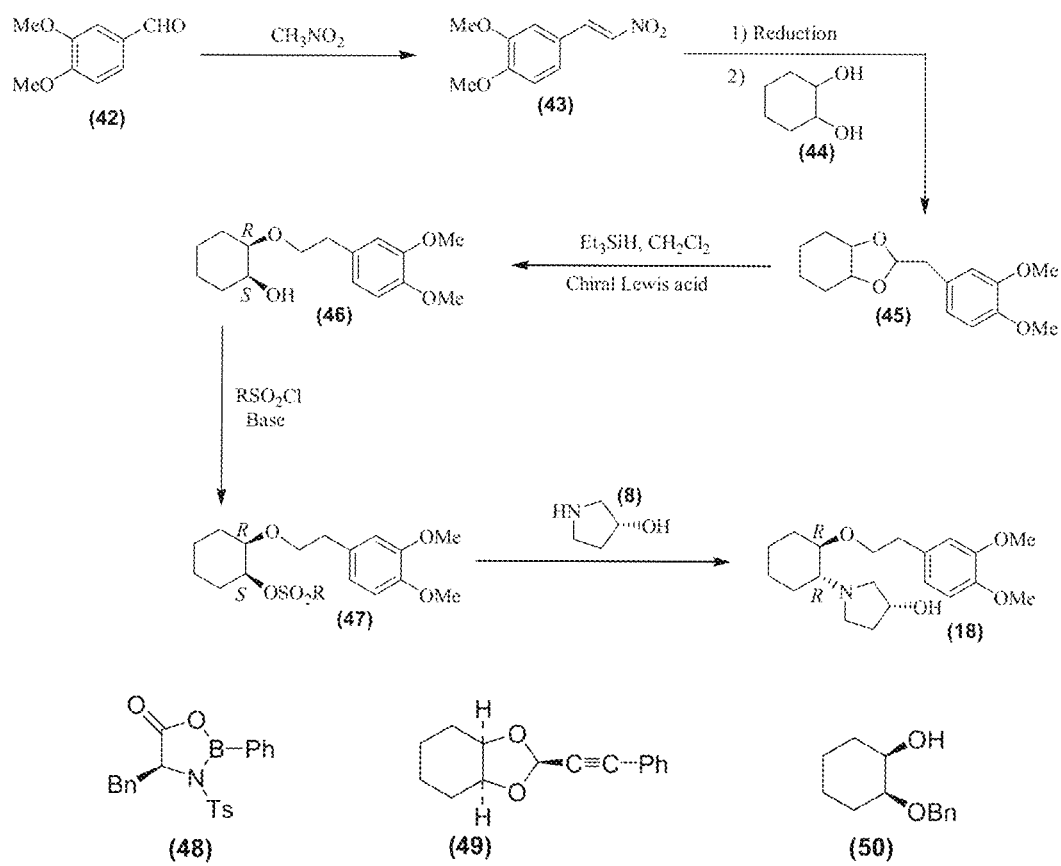
FIG. 29 illustrates a reaction scheme that may be used as a process for preparing a stereoisomerically substantially pure trans-(1R,2R)-aminocyclohexyl ether compound of formula (18).

Hydroxyether Intermediate Via Chiral Acetal Cleavage (FIG. 29)

A key intermediate towards the synthesis of (18) is the formation of compound (46). Compound (46) is synthesized from the corresponding acetal by selective reductive cleavage of the acetal (45) using a chiral Lewis catalyst and triethylsilane. For example, the selective reduction of acetal (45) may provide the ether (46). This is a very concise route towards the synthesis of (46). Racemic acetal (45) can be synthesized from the corresponding 1,2-dimethoxy-4-(2-nitro-vinyl)-benzene (43) by reduction and subsequent addition of cyclohexane-1,2-cis-diol. Compound (43) is synthesized from the readily available 3,4-dimethoxybenzealdehyde, as reported in the literature (Raiford, F. J. Org. Chem. 1944, 9, 170-173. Rao, T. V.; Ravishankar, L.; Lakshny, T. G. K.; Indian J. Chem. 1990, 29, 207-214. Engman, L.; Cava, M. P.; Tetrahedron Lett. 1981, 22, 599-612. Bryce, M. R.; Gardiner, J. M.; Tetrahedron 1988, 44, 599-612. Kubo, A.; Saito, N.; Kawakami, N.; Matsuyama, Y.; Miwa, T.; Synthesis 1987, 9, 824-827. Nachtsheim, C. M.; Frahm, A. W.; Arch. Pharm. 1989, 322, 187-197. Koaukulla, R. P. K.; Trivedi, G. K.; Vora, J. D.; Mathur, H. H.; Synth. Commun. 1994, 24, 819-832. Tasker, A. S.; Sorensen, B. K.; Jae, H-S.; Winn, M.; Geldern, T. W.; von. J. Med. Chem. 1997, 40, 322-330. Varma, R. S.; Dahiya, R.; Kumar, S.; Tetrahedron Lett. 1997, 39, 5131-5134. Liu, J-T.; Yao, C-F.; Tetrahedron Lett. 2001, 42, 6147-6150).

As reported in the following literature references there are precedent in other reactions including the desymmetrization of acetal (49) with Me$_2$C=C(OSiMe$_3$)OEt catalyzed by the chiral acid (48) as a route to compound (50) (Kinguasa, M.; Harada, T.; Oku, A. J. Am. Chem. Soc. 1997, 119, 9067). The conversion of the alcohol (46) into the activated sulfonate (47) should be possible using sulfonyl chloride under basic conditions. Nucleophilic displacement under S$_N$2 condition using 3-(R)-pyrrolidinol (8) should give the desired compound (18).

Example 11

Figure 30:
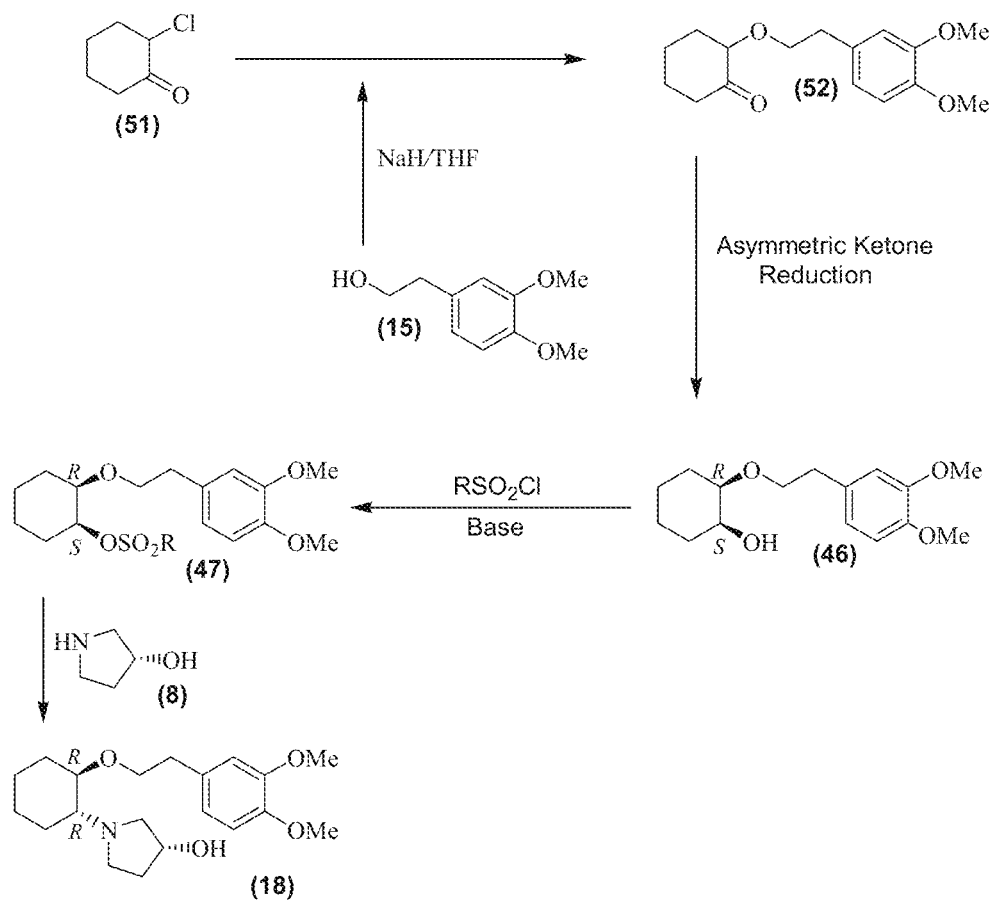
FIG. 30 illustrates a reaction scheme that may be used as a process for preparing a stereoisomerically substantially pure trans-(1R,2R)-aminocyclohexyl ether compound of formula (18).

Hydroxyether Intermediate Via Asymmetric Keto-Ether Reduction (4-5 Steps) (FIG. 30)

2-Chlorocyclohexanone (51), which is commercially available, is readily transformed into the corresponding keto-ether (52) by reacting with the sodium alkoxide ion of 3,4-dimethoxyphenethyl alcohol. Asymmetric reduction using the chiral ruthenium catalyst under Noyori's reaction conditions (Ohkmura T.; Ooka H.; Yamakawa, M.; Ikariya, T.; Noyori, R. J. Org. Chem. 1996, 61, 4872) should give compound (46). There is the literature reference on similar substrate such as 2-methyoxyxyxlohexanone (53). The hydrogenation of this compound under Noyori's reaction conditions proceeded very smoothly to give (1R,2S)-2-methoxycyclohexanol (54) in high yield with excellent enantiomeric excess (Matsumoto, T.; Murayama, T.; Mitushashi, S.; Miura, T. Tetrahedron Lett. 1999, 40, 5043-5046).

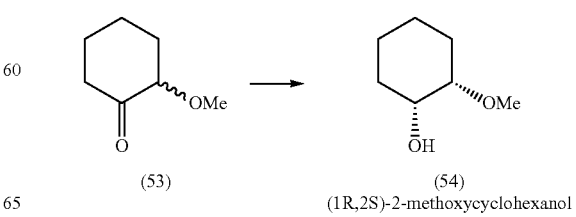

Example 12

Figure 31:
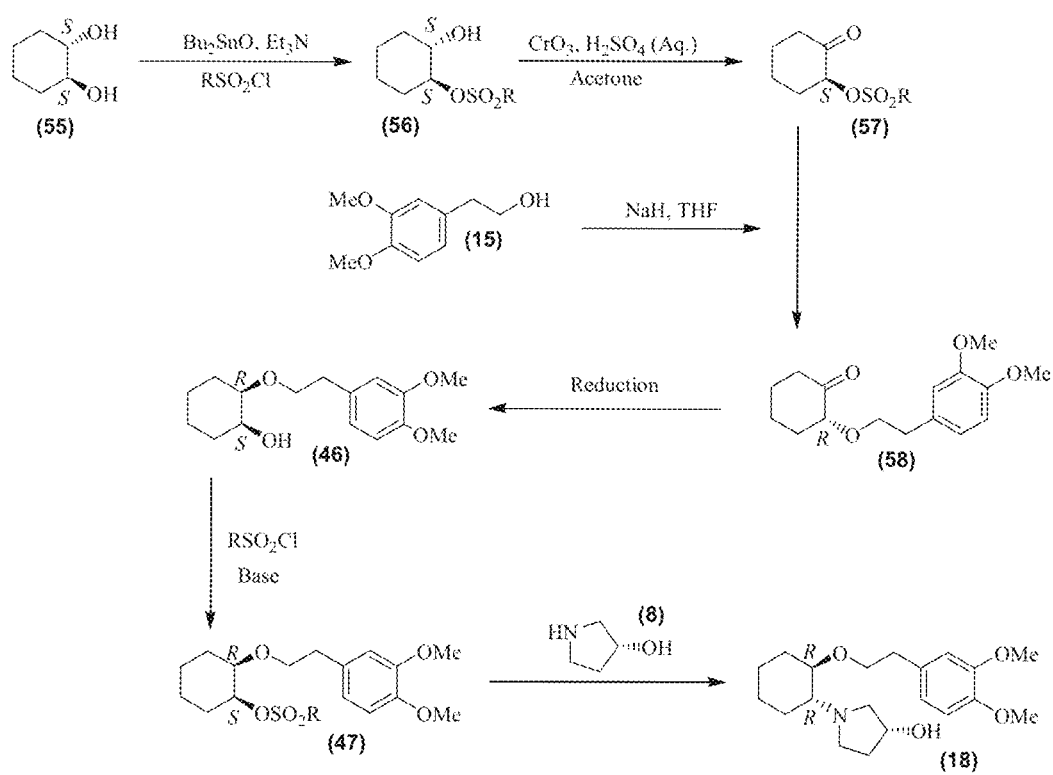
FIG. 31 illustrates a reaction scheme that may be used as a process for preparing a stereoisomerically substantially pure trans-(1R,2R)-aminocyclohexyl ether compound of formula (18).

Hydroxyether Intermediate Via Ketone Reduction: Remote Assistance by α-Ether Group (FIG. 31)

This route is based on the stereoselective reduction of compound (58) by bulky reducing agents such as lithium tri-sec-butylborohydride (L-Selectride), lithium trisiamylboronhydride (LS-Selectride), NB-enantride, and (R) or (S)-Alpine hydride (Brown, H. C.; Krishnamurthy, S. *Tetrahedron* 1979, 33, 567-607. Daverio, P.; Zanda, M. *Tetrahedron: Asymmetry* 2001, 12, 2225-2259.). All of these bulky reducing agents are commercially available. Compound (58) can be synthesized according to process illustrated in FIG. 31 using commercially available trans-cyclohexane-(1S,2S)-diol. Reduction of compound (58) with a bulky reducing agent allows the deliver of the hydride from the opposite side of the ether group, resulting in the formation of compound (46). Activation of hydroxyl-ether (46) with a sulfonyl derivative, followed by nucleophilic displacement with 3-(R)-pyrrolidinol (8) should afford (18).

Example 13

Hydroxyether Intermediate Via Chiral α-Hydroxy Cyclohexanone (FIG. 32)

This route is based on the ability of (S)-proline to catalyzed the α-oxyamination of cyclohexanone (59). When cyclohexanone is treated with nitrobenzene in the presence of a catalytic amount of (S)-proline (20 mol %) in chloroform at RT, resulting in the formation of α-aminooxylated cyclohexanone (61) in 91% yield and greater than 99% ee (Momiyama, N.; Yamamoto, H. *J. Am Chem. Soc.* 2003, 125, 6038-6039. Brown, S. P.; Brochu, M. P.; Sinz, C. J.; MacMillan, D. W. C. *J. Am. Chem. Soc.* 2003, 125, 10808-10809). The ketone (61) can be readily deprotected with $CuSO_4$ to afford the corresponding α-hydroxy ketone (62) and α,α'-dihydroxy ketone adducts in >90% yield without loss of enantioselectivity.

Example 14

Figure 33:
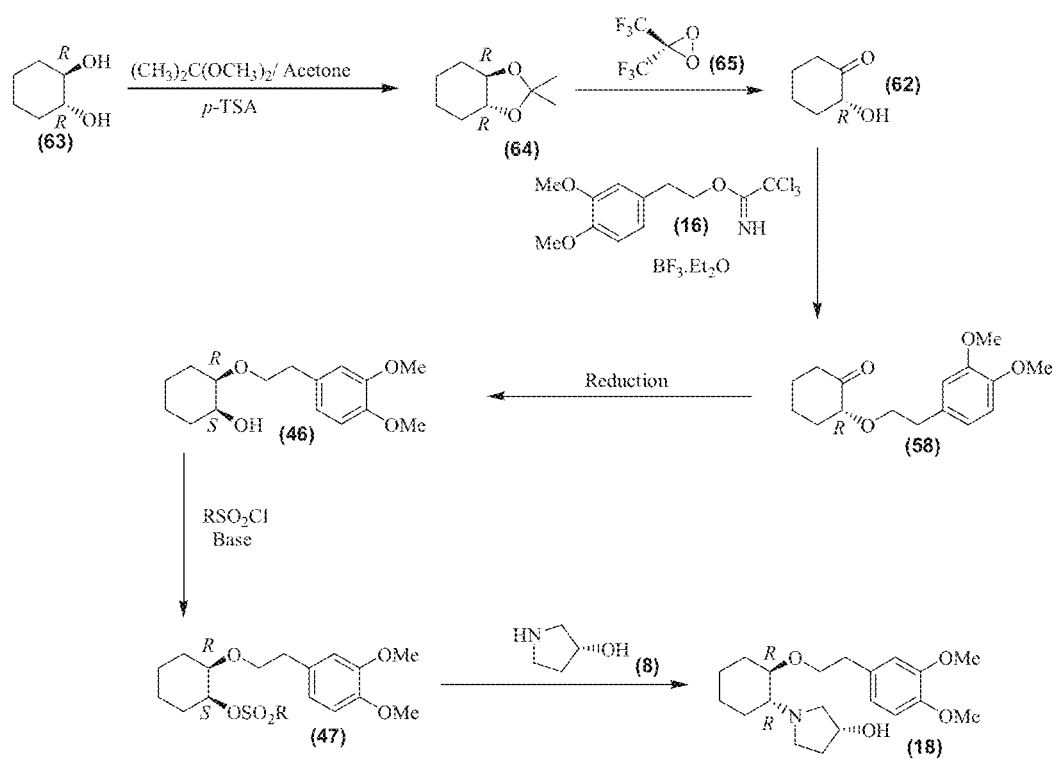
FIG. 33 illustrates a reaction scheme that may be used as a process for preparing a stereoisomerically substantially pure trans-(1R,2R)-aminocyclohexyl ether compound of formula (18).

Hydroxyether Intermediate Via Selective Oxidation of O-Isopropylidene of Trans-Cyclohexane-(1R,2R)-Diol (FIG. 33)

This route is based on the selective oxidation of O-isopropylidene of trans-cyclohexane-(1R,2R)-diol (64) into the corresponding homochiral 2-hydroxy-ketone (62) by 3,3-bis-trifluoromethyl-dioxirane (65). This transformation has been reported (Curci, R.; D'Accolti, L.; Dinoi, A.; Fusco, C.; Rosa, A. Tetrahedron Lett. 1996, 37, 115-118. D'Accolti.; Detomaso, A.; Fusco, C.; Rosa, A.; Curci, R. *J. Org. Chem.* 1993, 58, 3600. Murray, R. W.; Jeyaraman, R. *J. Org. Chem.* 1985, 50, 2847-2853. Adam, W.; Chan, Y-Y.; Cremer, D.; Gauss, J.; Scheutzow, D.; Schindler, M. *J. Org. Chem.* 1987, 52, 2800-2803. Mello, R.; Fiorentino, M.; Sciacovelli, O.; Curci, R.; *J. Org. Chem,* 1988, 53, 3891-3893. Cassidei, L.; Fiorentino, M.; Mello, R.; Sciacovelli, O.; Curci, R. *J. Org. Chem.* 1987, 52, 699-700. Mello, R.; Fiorention, M.; Fusco, C.; Curci, R. *J. Am. Chem. Soc.* 1989, 111, 6749-6757), and the oxidation of the isopropylidene derivative into the 2-hydroxy ketone occurs in high yield (98%), as well as high retention of optical purity. Compound (62) is then reacted with the trichloroaetimidate derivative of 3,4-dimethoxyphenethyl alcohol under Lewis acid conditions to give the corresponding keto-ether (58), which upon reduction with a bulky lithium or boron reducing agent should afford compound (46). Activation of the hydroxyl function group with a sulfonyl derivative, followed by nucleophilic displacement with 3-(R)-pyrrolidinol (8) will afford (18).

Example 15

Figure 34:
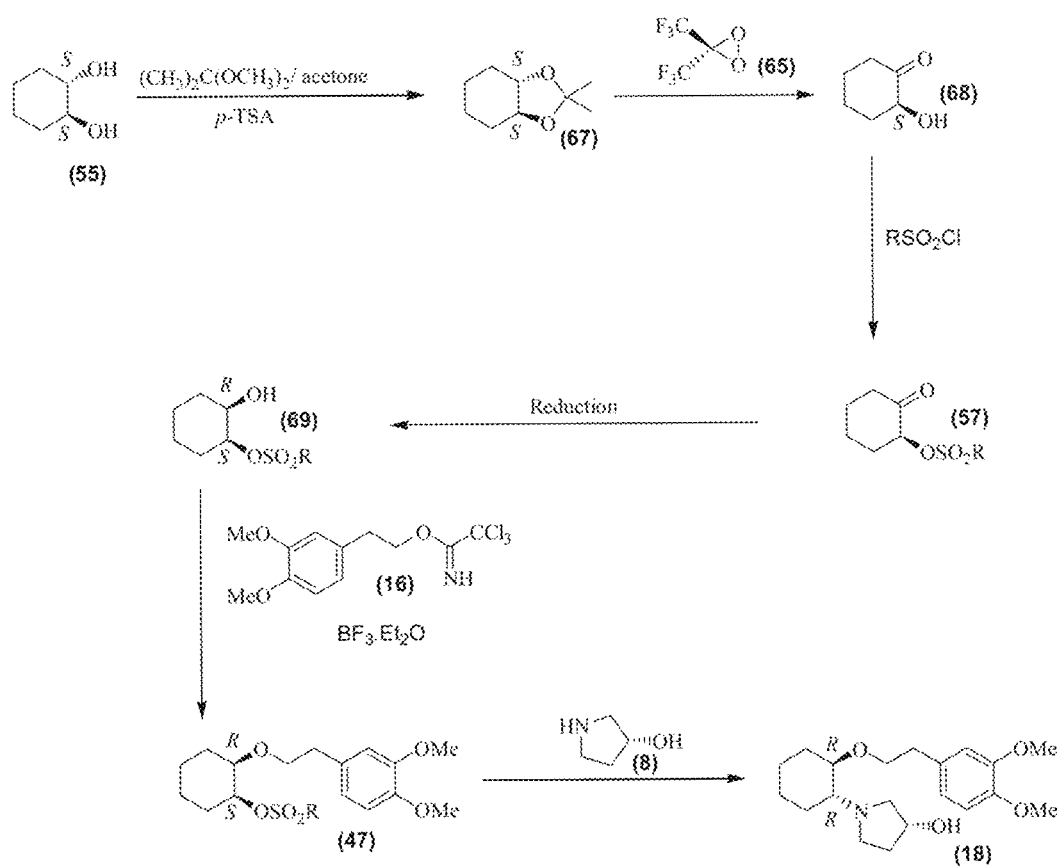
FIG. 34 illustrates a reaction scheme that may be used as a process for preparing a stereoisomerically substantially pure trans-(1R,2R)-aminocyclohexyl ether compound of formula (18).

Hydroxyether Intermediate Via Selective Oxidation of O-Isopropylidene of Trans-Cyclohexane-(1S,2S)-Diol (FIG. 34)

This route is based on the selective oxidation of O-isopropylidene of trans-cyclohexane-(1S,2S)-diol (67) into the corresponding homochiral 2-hydroxy-ketone (68) by 3,3-bis-trifluoromethyl-dioxirane (65). The transformation has been reported for the hydroxyether intermediate via selective oxidation of 0-isopropylidene of trans-cyclohexane-(1R,2R)-diol-(Curci, R.; D'Accolti, L.; Dinoi, A.; Fusco, C.; Rosa, A. Tetrahedron Lett. 1996, 37, 115-118. D'Accolti.; Detomaso, A.; Fusco, C.; Rosa, A.; Curci, R. *J. Org. Chem.* 1993, 58, 3600. Murray, R. W.; Jeyaraman, R. *J. Org. Chem.* 1985, 50, 2847-2853. Adam, W.; Chan, Y-Y.; Cremer, D.; Gauss, J.; Scheutzow, D.; Schindler, M. *J. Org. Chem.* 1987, 52, 2800-2803. Mello, R.; Fiorentino, M.; Sciacovelli, O.; Curci, R.; *J. Org. Chem,* 1988, 53, 3891-3893. Cassidei, L.; Fiorentino, M.; Mello, R.; Sciacovelli, O.; Curci, R. *J. Org. Chem.* 1987, 52, 699-700. Mello, R.; Fiorention, M.; Fusco, C.; Curci, R. *J. Am. Chem. Soc.* 1989, 111, 6749-6757), and the oxidation of the isopropylidene derivative into the 2-hydroxy ketone occurs in high yield (98%), as well as high retention of optical purity. Compound (68) is then reacted with sulfonyl chloride to give compound (57). Reduction of the ketone (57) gives alcohol (69). Compound (69) reacts with the trichloroaetimidate derivative of 3,4-dimethoxyphenethyl alcohol under Lewis acid conditions to give the activated sulfonate (47). Nucleophilic displacement with 3-(R)-pyrrolidinol (8) of the activated sulfonate (47) will afford (18).

Example 16

Figure 35:
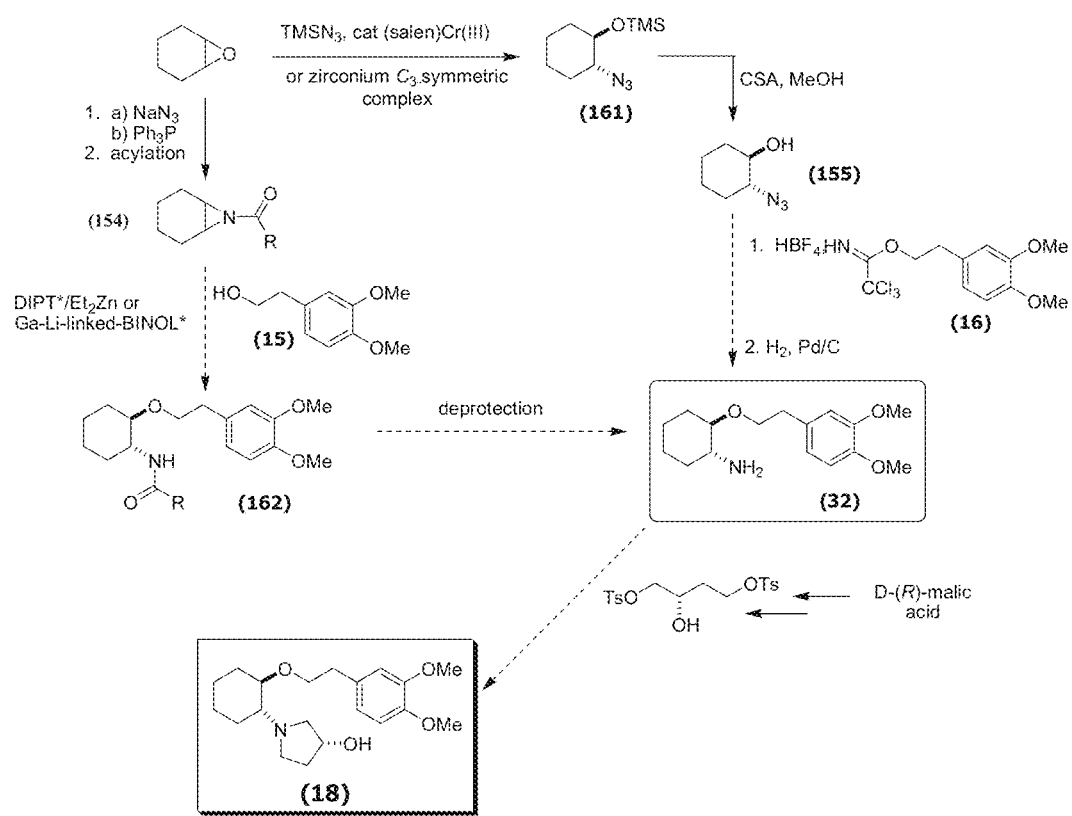
FIG. 35 illustrates a reaction scheme that may be used as a process for preparing a stereoisomerically substantially pure trans-(1R,2R)-aminocyclohexyl ether compound of formula (18).
Figure 36:
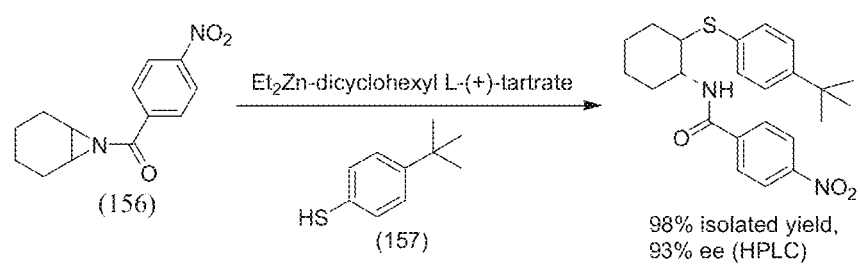
FIG. 36 illustrates a reaction scheme that may be used as a process for asymmetric ring opening of symmetrical N-acylaziridines.

FIG. 35 shows two additional routes starting from cyclohexene oxide (1) to reach the advanced precursor of (18), i.e. 2-aminoether (32). One approach relies on a chiral zinc complex directing attack of 3,4-dimethoxyphenethanol (15) stereoselectively on N-acylaziridine (154) to form (162) (Christoffers J, Schulze Y, Pickardt J. *Tetrahedron* 2001, 57, 1765-1769). Oguni et al. have reported excellent enantioselectivities for asymmetric ring opening of symmetrical N-acylaziridines (156) catalyzed by such zinc complexes, but using thiols (157) as nucleophiles (see FIG. 36) (Hayashi M, Ono K, Hoshimi H, Oguni N. *Tetrahedron* 1996, 52(23), 7817-7832) Chiral boron-based Lewis acids may be another alternative since boron trifluoride etherate has been shown to mediate opening of 2-substituted N-acylaziridines by alcohols (Bodenan J, Chanet-Ray J, Vessiere R. *Synthesis* 1991, 288-292). It may be worthwhile to try the chiral Ga-Li-linked-BINOL complex, (Matsunaga S, Das J, Roels J, Vogl E M, Yamamoto N, Iida T, Yamaguchi K, Shibasaki M. *J Am Chem Soc* 2000, 122, 2252-2260.) In any case, use of the more activated N-alkyoxycarbonylaziridine to promote ring opening may be required.

Another way to access 2-aminoether (32) involves successive etherification of chiral 2-azidocyclohexanol (155) with trichloroacetimidate (16) and hydrogenolytic azide reduction. Azidocyclohexanol (155) (Schaus S E, Larrow J F, Jacobsen E N. *J Org Chem* 1997, 62, 4197-4199). may be obtained in two steps from cyclohexene oxide through an asymmetric ring opening catalyzed by either Jacobsen's (salen)Cr(III) (85% ee, 97% GC purity, 99% isolated yield) ((a) Martinez L E, Leighton J L, Carsten D H, Jacobsen E N, *J. Amer. Chem. Soc.* 1995, 117, 5897-5898. (b) Jacobsen E N, *Acc. Chem. Res.* 2000, 33, 421-431). or Nugent's zirconium $C_3$-symmetrical complex (93% ee, 86% yield), (McCleland B W, Nugent W A., Finn M G. *J. Org. Chem.* 1998, 63, 6656-6666), and subsequent cleavage of the silyl ether. Elaboration of the resultant 2-aminoether (32) into (18) is described above.

Example 17

Figure 37:
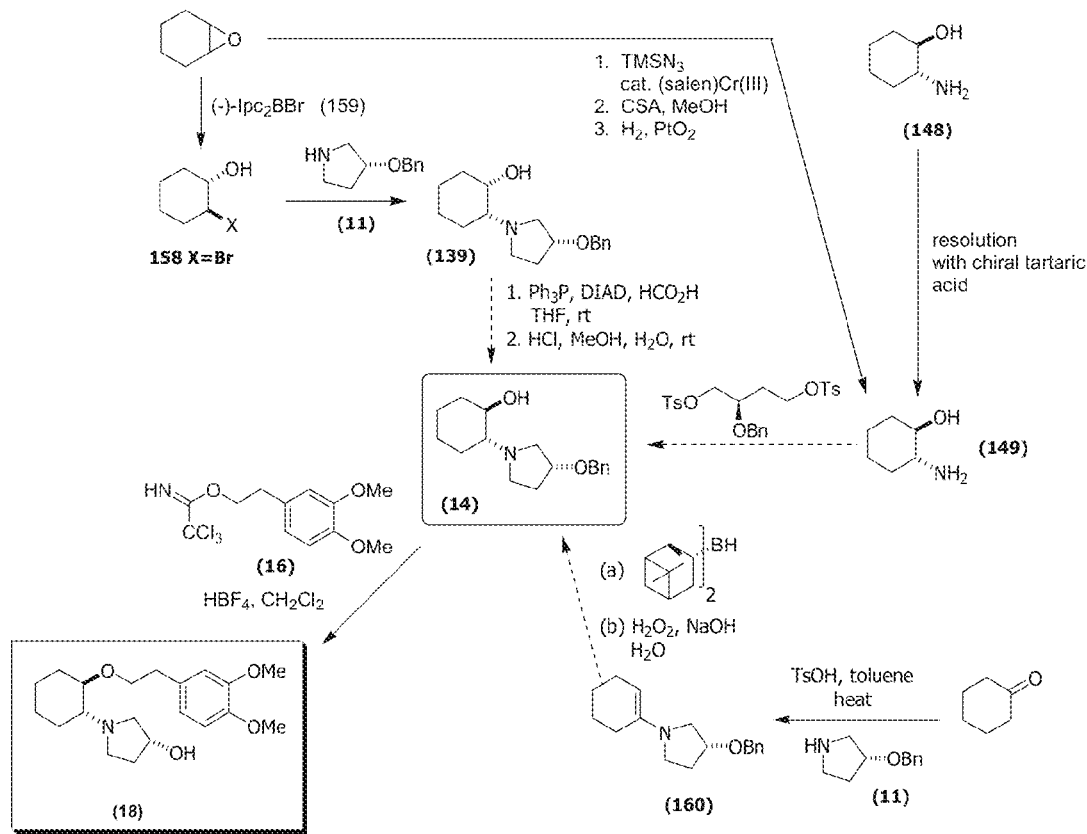
FIG. 37 illustrates a reaction scheme that may be used as a process for preparing a stereoisomerically substantially pure trans-(1R,2R)-aminocyclohexyl ether compound of formula (18).

The three approaches shown in FIG. 37 may offer efficient ways to obtain (14), which could then be subjected to etherification with 3,4-dimethoxyphenethanol (15) activated as the trichloroacetimidate (16), to give (18). In the first approach, optically enriched bromohydrin (158) (84% ee) can be obtained in good recoveries (82% isolated yield) by treatment of cyclohexene oxide with B-bromodiisopinocampheylborane [(a) Joshi N N, Srebnik M, Brown H C. *J. Amer. Chem. Soc.* 1988, 110, 6246-6248. (b) Srebnik M, Joshi N N, Brown H C. *Israel J. Chem.* 1989, 29, 229-237.] Displacement by the pyrrolidine (11) and subsequent inversion of the configuration at the hydroxyl under Mitsunobu conditions (Anderson N G, Lust D A, Colapret K A, Simpson J H, Malley M F, Gougoutas J Z. *J Org Chem* 1996, 61, 7955-7958.) would give chiral aminoalcohol 4RRR.

In the second approach (FIG. 37), aminoalcohol (14) could be obtained from pyrrolidine elaboration of known chiral intermediate (149), which can be prepared in 3 steps from cyclohexene oxide using Jacobsen chemistry [(a) Martinez L E, Leighton J L, Carsten D H, Jacobsen E N, *J. Amer. Chem. Soc.* 1995, 117, 5897-5898. (b) Jacobsen E N, *Acc. Chem. Res.* 2000, 33, 421-431] (see FIG. 35) or from resolution of racemic 2-aminocyclohexanol (148) using chiral tartaric acid [Godchot, Mousseron. *Bull Soc Chem* 1932, 51, 1277].

Example 18

Figure 38:
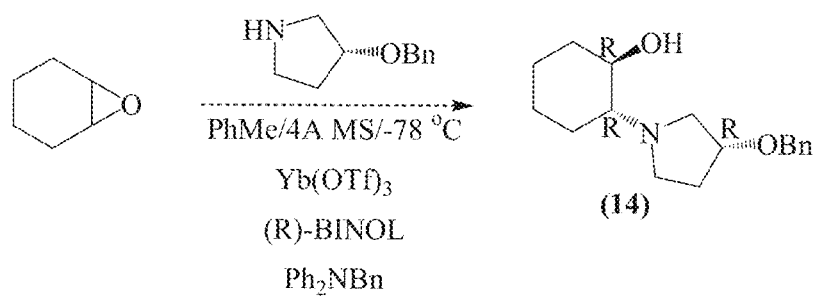
FIG. 38 illustrates a reaction scheme that may be used as a process for preparing a compound of formula (14).

FIG. 38 shows a method that may be used to prepare (14) enantioselectively by treating (1) with (11) under conditions analogous to those reported for other amines in Tetrahedron: Asymmetry 1998, 9, 1747-1752.

Example 19

Figure 39:
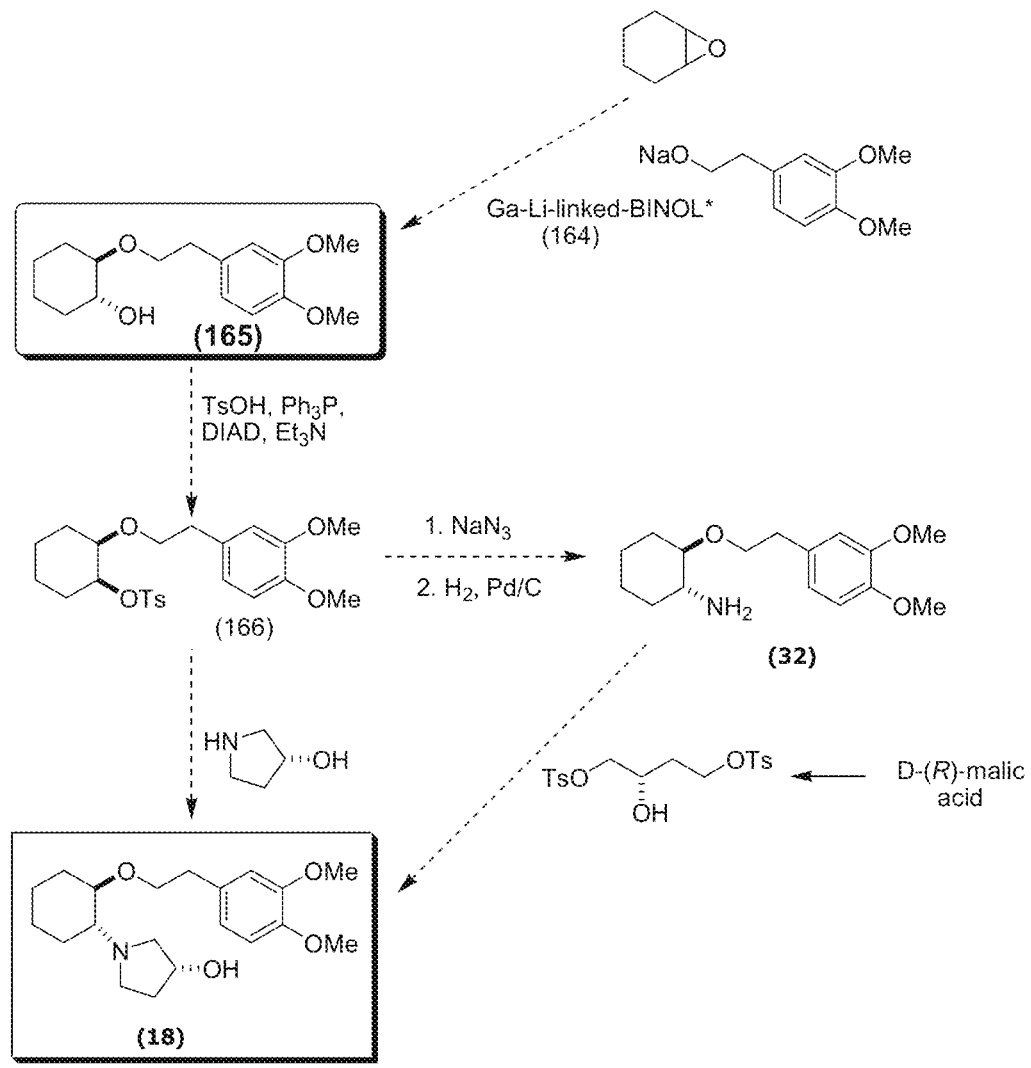
FIG. 39 illustrates a reaction scheme that may be used as a process for preparing a stereoisomerically substantially pure trans-(1R,2R)-aminocyclohexyl ether compound of formula (18).
Figure 40:
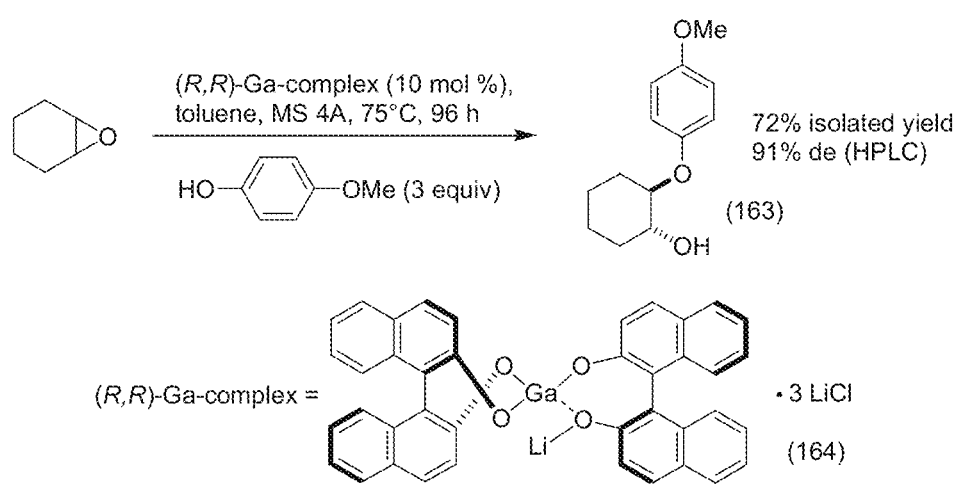
FIG. 40 illustrates a reaction scheme that may be used as a process for stereodifferentiation of oxirane carbons by a phenol.
Figure 41:
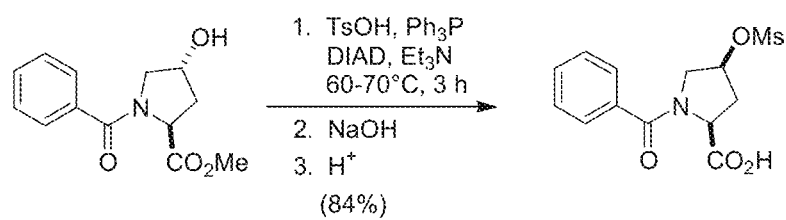
FIG. 41 illustrates a reaction scheme that may be used as a process for clean inversion of a secondary alcohol.

FIG. 39 depicts access to (18) via chiral hydroxyether (165), cyclohexene oxide (1) as commercial raw material. Hydroxyether (165) may be prepared by employing a chiral Lewis acid that directs attack of sodium 3,4-dimethoxyphenethoxide selectively at one of the two oxirane carbons in cyclohexene oxide. Shibasaki et al. have reported stereodifferentiation of these oxirane carbons by a phenol in effecting a ring-opening catalyzed by a chiral Ga-Li-linked-BINOL complex (FIG. 40) [Matsunaga S, Das J, Roels J, Vogl E M, Yamamoto N, Iida T, Yamaguchi K, Shibasaki M. *J Am Chem Soc* 2000, 122, 2252-2260]. Subsequent installation of either the intact pyrrolidine ring or a nitrogen-bearing nucleophile that can be elaborated into the pyrrolidine ring can be carried out by a double inversion at the hydroxyl-substituted carbon in (165). This may be accomplished via a one-pot sulfonation under Mitsunobu conditons [Anderson N G, Lust D A, Colapret K A, Simpson J H, Malley M F, Gougoutas J Z. *J Org Chem* 1996, 61, 7955-7958.]. As depicted in FIG. 42, Anderson et al have reported clean inversion of a secondary alcohol on multikilogram scale into either the mesylate or tosylate in excellent isolated yields (>80%).

What is claimed is:

1. A method for stereoselectively making an aminocyclohexyl ether of the following formula (79), formula (80) or formula (81):

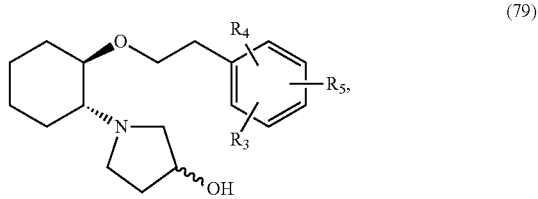

(79)

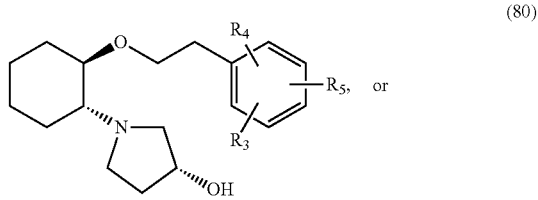

(80)

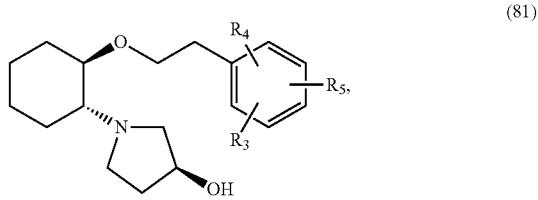

(81)

wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, $C_2$-$C_7$alkanoyloxy, $C_1$-$C_6$alkoxy, $C_7$-$C_{12}$aralkoxy, $C_2$-$C_7$alkoxycarbonyl, $C_1$-$C_6$thioalkyl, aryl or $N(R_6)R_7$ where $R_6$, $R_7$, $R_8$, and $R_9$, are each independently hydrogen, acetyl, methanesulfonyl or $C_1$-$C_6$alkyl;

or $R_3$, $R_4$ and $R_5$ are independently hydrogen, hydroxy or $C_1$-$C_6$alkoxy; with the proviso that $R_3$, $R_4$ and $R_5$ cannot all be hydrogen at the same time, which method comprises:

(a) reacting a compound of formula (75):

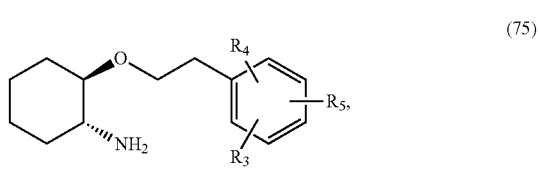

(75)

where $R_3$, $R_4$ and $R_5$ are as defined above, with a compound of formula (82), a compound of formula (83) or a compound of formula (84):

(82)

-continued

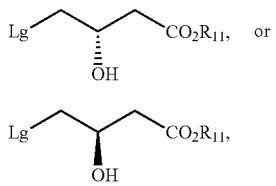
(83)

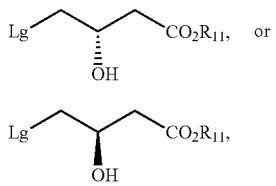
(84)

wherein each Lg is independently a leaving group and each $R_{11}$ is $C_1$-$C_6$alkyl, under suitable conditions to form a compound of formula (85), a compound of formula (86) or a compound of formula (87), respectively:

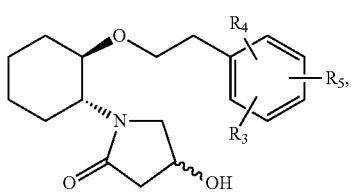
(85)

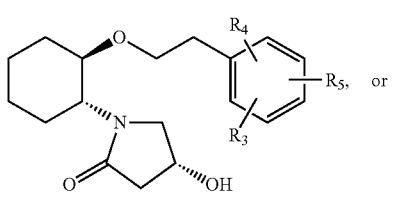
(86)

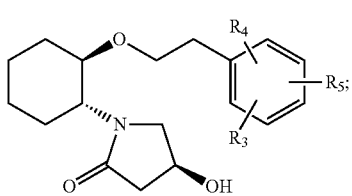
(87)

or reacting a compound of formula (75) with a compound of formula (88), a compound of formula (89) or a compound of formula (90):

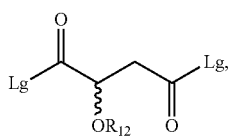
(88)

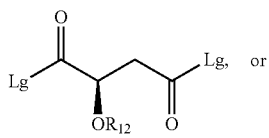
(89)

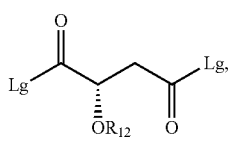
(90)

wherein each Lg is independently a leaving group and each $R_{12}$ is $C_2$-$C_4$acyl or $C_7$-$C_{12}$aralkyl, under suitable conditions to form a compound of formula (91), a compound of formula (92) or a compound of formula (93), respectively:

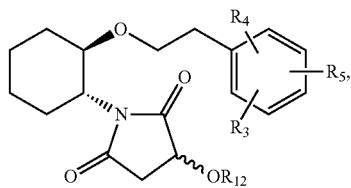
(91)

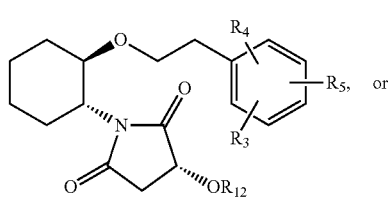
(92)

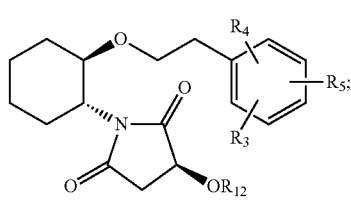
(93)

or reacting a compound of formula (75) with a compound of formula (94), a compound of formula (95) or a compound of formula (96):

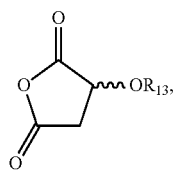
(94)

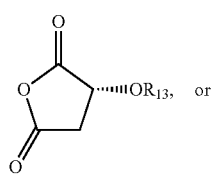
(95)

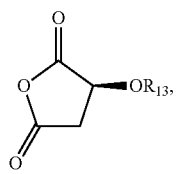
(96)

wherein each $R_{13}$ is $C_2$-$C_4$acyl or $C_7$-$C_{12}$aralkyl, under suitable conditions to form a compound of formula (97), a compound of formula (98) or a compound of formula (99), respectively;

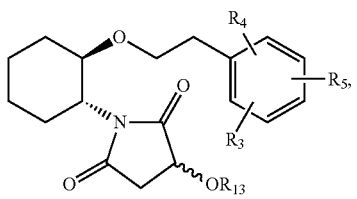
(97)

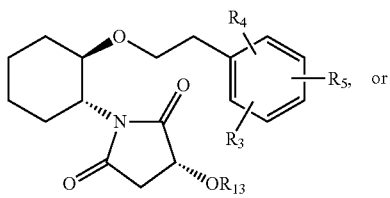
(98)

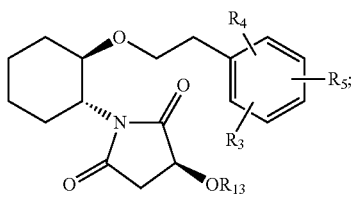
(99)

and (b) reducing the compound of formula (85), the compound of formula (91) or the compound of formula (97) formed in step (a) under suitable conditions to form a compound of formula (79) as set forth above; or reducing the compound of formula (86), the compound of formula (92) or the compound of formula (98) formed in step (a) under suitable conditions to form a compound of formula (80) as set forth above; or reducing the compound of formula (87), the compound of formula (93) or the compound of formula (99) formed in step (a) under suitable conditions to form a compound of formula (81) as set forth above.

2. The method of claim 1 wherein $R_3$, $R_4$ and $R_5$ are independently hydrogen, hydroxy or $C_1$-$C_6$ alkoxy, with the proviso that $R_3$, $R_4$ and $R_5$ cannot all be hydrogen at the same time.

3. The method of claim 2 wherein $R_3$ is hydrogen, and $R_4$ and $R_5$ are each $C_1$-$C_4$ alkoxy.

4. The method of claim 3 wherein $R_4$ and $R_5$ are each $C_1$alkoxy at the S- and 4-carbon position of the phenyl group, respectively.

5. The method of claim 1 wherein each Lg is independently chloro or bromo; $R_{11}$ is $C_1$-$C_3$alkyl; $R_{12}$ is $C_2$-$C_3$acyl; and $R_{13}$ is $C_2$-$C_3$acyl.

6. The method of claim 1 wherein the reducing reagent for step (b) is Red-Al.

7. A method for stereoselectively making an aminocyclohexyl ether of the following formula (100), formula (101) or formula (102):

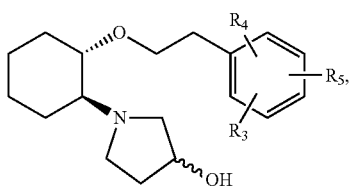
(100)

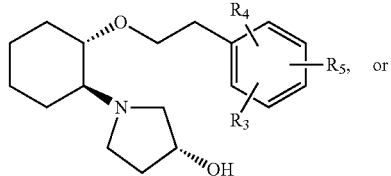
(101)

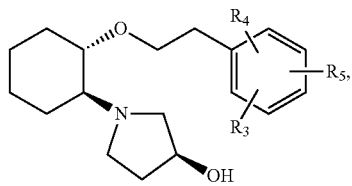
(102)

wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —CHF$_2$, —SO$_2$N(R$_8$)R$_9$, C$_2$-C$_2$alkanoyloxy, C$_1$-C$_6$alkoxy, C$_7$-C$_{12}$aralkoxy, C$_2$-C$_2$alkoxycarbonyl, C$_1$-C$_6$thioalkyl, aryl or N(R$_6$)R$_7$ where R$_6$, R$_7$, R$_8$, and R$_9$, are each independently hydrogen, acetyl, methanesulfonyl or C$_1$-C$_6$alkyl;

or $R_3$, $R_4$ and $R_5$ are independently hydrogen, hydroxy or $C_1$-$C_6$alkoxy; with the proviso that $R_3$, $R_4$ and $R_5$ cannot all be hydrogen at the same time, which method comprises:

(a) reacting a compound of formula (76):

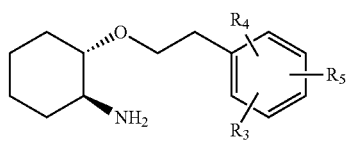
(76)

where $R_3$, $R_4$ and $R_5$ are as defined above, with a compound of formula (82), a compound of formula (83) or a compound of formula (84):

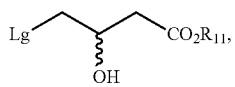
(82)

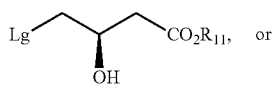
(83)

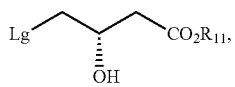
(84)

wherein each Lg is independently a leaving group and each $R_{11}$ is $C_1$-$C_6$alkyl, under suitable conditions to form a compound of formula (103), a compound of formula (104) or a compound of formula (105), respectively:

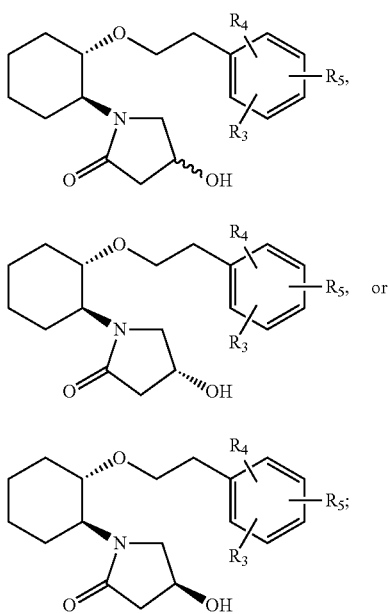

(103)

(104)

(105)

or reacting a compound of formula (76) with a compound of formula (88), a compound of formula (89) or a compound of formula (90):

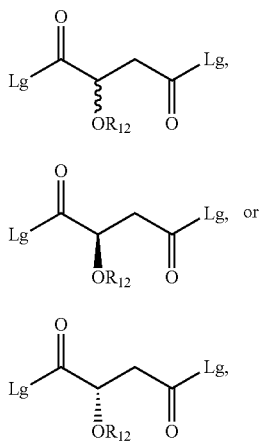

(88)

(89)

(90)

wherein each Lg is independently a leaving group and each $R_{12}$ is $C_2$-$C_4$acyl or $C_7$-$C_{12}$aralkyl, under suitable conditions to form a compound of formula (106), a compound of formula (107), or a compound of formula (108), respectively:

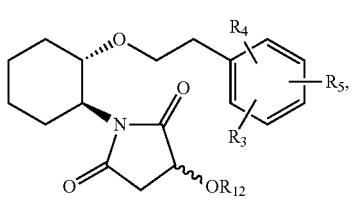

(106)

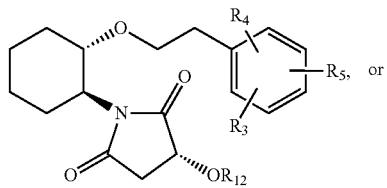

(107)

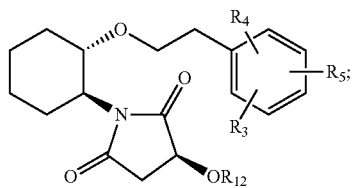

(108)

or reacting a compound of formula (76) with a compound of formula (94), a compound of formula (95) or a compound of formula (96):

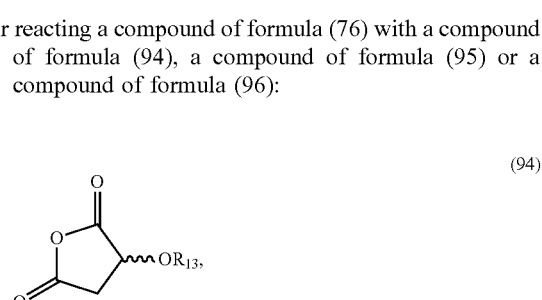

(94)

(95)

(96)

wherein each $R_{13}$ is $C_2$-$C_4$acyl or $C_7$-$C_{12}$aralkyl, under suitable conditions to form a compound of formula (109), a compound of formula (110) or a compound of formula (111), respectively:

(109)

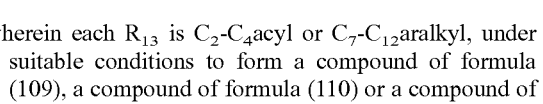

(110)

-continued

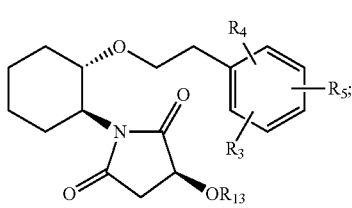
(111)

and (b) reducing the compound of formula (103), the compound of formula (106) or the compound of formula (109) formed in step (a) under suitable conditions to form a compound of formula (100) as set forth above; or reducing the compound of formula (104), the compound of formula (107) or the compound of formula (110) formed in step (a) under suitable conditions to form a compound of formula (101) as set forth above; or reducing the compound of formula (105), the compound of formula (108) or the compound of formula (111) formed in step (a) under suitable conditions to form a compound of formula (102) as set forth above.

8. The method of claim 7 wherein $R_3$, $R_4$ and $R_5$ are independently hydrogen, hydroxy or $C_1$-$C_6$ alkoxy, with the proviso that $R_3$, $R_4$ and $R_5$ cannot all be hydrogen at the same time.

9. The method of claim 8 wherein $R_3$ is hydrogen, and $R_4$ and $R_5$ are each $C_1$-$C_4$ alkoxy.

10. The method of claim 9 wherein $R_4$ and $R_5$ are each $C_1$alkoxy at the S- and 4-carbon position of the phenyl group, respectively.

11. The method of claim 7 wherein each Lg is independently chloro or bromo; $R_{11}$ is $C_1$-$C_3$alkyl; $R_{12}$ is $C_2$-$C_3$acyl; and $R_{13}$ is $C_2$-$C_3$acyl.

12. The method of claim 7 wherein the reducing reagent for step (b) is Red-Al.

13. A method for stereoselectively making an aminocyclohexyl ether of the following formula (112), formula (113) or formula (114):

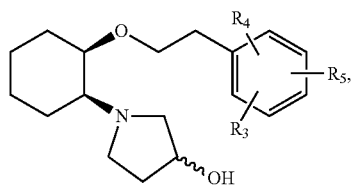
(112)

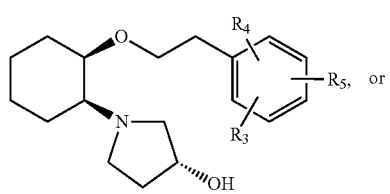
(113)

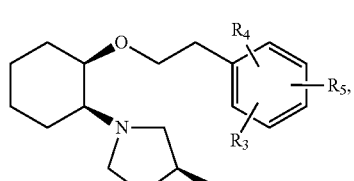
(114)

wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —$CHF_2$, —$SO_2N(R_8)R_9$, $C_2$-$C_2$alkanoyloxy, $C_1$-$C_6$alkoxy, $C_7$-$C_{12}$aralkoxy, $C_2$-$C_2$alkoxycarbonyl, $C_1$-$C_6$thioalkyl, aryl or $N(R_6)R_7$ where $R_6$, $R_7$, $R_8$, and $R_9$, are each independently hydrogen, acetyl, methanesulfonyl or $C_1$-$C_6$alkyl;

or $R_3$, $R_4$ and $R_5$ are independently hydrogen, hydroxy or $C_1$-$C_6$alkoxy; with the proviso that $R_3$, $R_4$ and $R_5$ cannot all be hydrogen at the same time;

which method comprises:

(a) reacting a compound of formula (77):

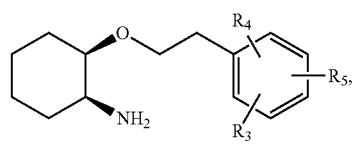
(77)

where $R_3$, $R_4$ and $R_5$ are as defined above, with a compound of formula (82), a compound of formula (83) or a compound of formula (84):

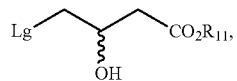
(82)

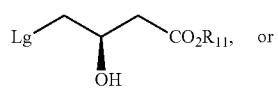
(83)

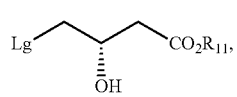
(84)

wherein each Lg is independently a leaving group and each $R_{11}$ is $C_1$-$C_6$alkyl, under suitable conditions to form a compound of formula (115), a compound of formula (116) or a compound of formula (117), respectively:

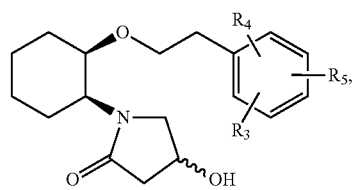
(115)

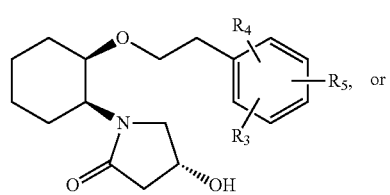
(116)

-continued

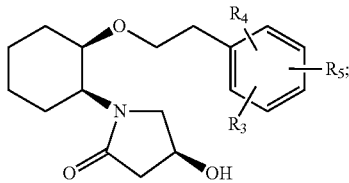
(117)

or reacting a compound of formula (77) with a compound of formula (88), a compound of formula (89) or a compound of formula (90):

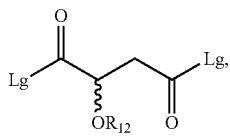
(88)

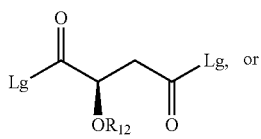
(89)

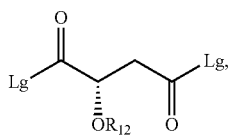
(90)

wherein each Lg is independently a leaving group and each $R_{12}$ is $C_2$-$C_4$acyl or $C_7$-$C_{12}$aralkyl, under suitable conditions to form a compound of formula (118), a compound of formula (119), or a compound of formula (120), respectively:

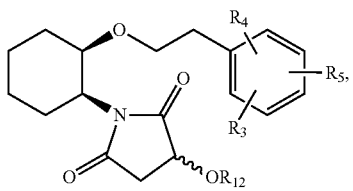
(118)

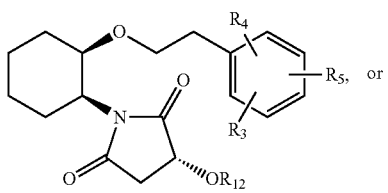
(119)

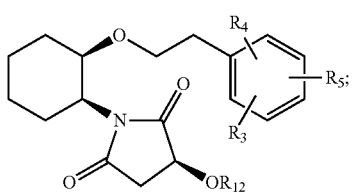
(120)

or reacting a compound of formula (77) with a compound of formula (94), a compound of formula (95) or a compound of formula (96):

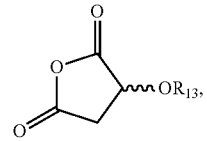
(94)

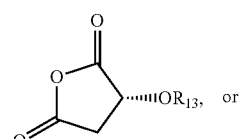
(95)

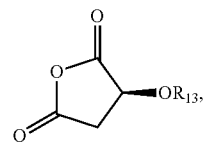
(96)

wherein each $R_{13}$ is $C_2$-$C_4$acyl or $C_7$-$C_{12}$aralkyl, under suitable conditions to form a compound of formula (121), a compound of formula (122) or a compound of formula (123), respectively:

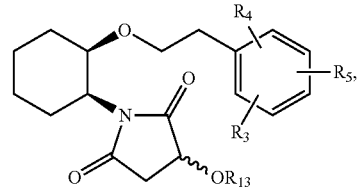
(121)

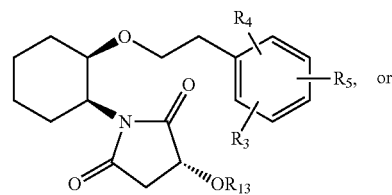
(122)

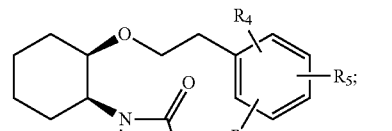
(123)

and (b) reducing the compound of formula (115), the compound of formula (118) or the compound of formula (121) formed in step (a) under suitable conditions to form a compound of formula (112) as set forth above; or reducing the compound of formula (116), the compound of formula (119) or the compound of formula (122) formed in step (a) under suitable conditions to form a compound of formula (113) as set forth above; or reducing the compound of formula (117), the compound of formula (120) or the compound of formula (123)

formed in step (a) under suitable conditions to form a compound of formula (113) as set forth above.

14. The method of claim 13 wherein $R_3$, $R_4$ and $R_5$ are independently hydrogen, hydroxy or $C_1$-$C_6$ alkoxy, with the proviso that $R_3$, $R_4$ and $R_5$ cannot all be hydrogen at the same time.

15. The method of claim 14 wherein $R_3$ is hydrogen, and $R_4$ and $R_5$ are each $C_1$-$C_4$ alkoxy.

16. The method of claim 15 wherein $R_4$ and $R_5$ are each $C_1$alkoxy at the S- and 4-carbon position of the phenyl group, respectively.

17. The method of claim 13 wherein each Lg is independently chloro or bromo; $R_{11}$ is $C_1$-$C_3$alkyl; $R_{12}$ is $C_2$-$C_3$acyl; and $R_{13}$ is $C_2$-$C_3$acyl.

18. The method of claim 13 wherein the reducing reagent for step (b) is Red-Al.

19. A method for stereoselectively making an aminocyclohexyl ether of the following formula (124), formula (125) or formula (126):

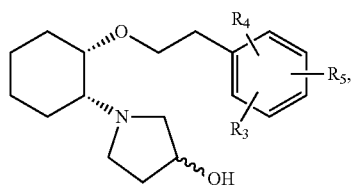
(124)

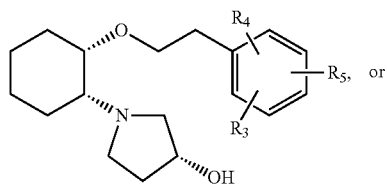
(125)

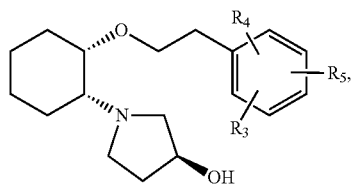
(126)

wherein $R_3$, $R_4$ and $R_5$ are independently bromine, chlorine, fluorine, carboxy, hydrogen, hydroxy, hydroxymethyl, methanesulfonamido, nitro, cyano, sulfamyl, trifluoromethyl, —CHF$_2$, —SO$_2$N(R$_8$)R$_9$, $C_2$-$C_2$alkanoyloxy, $C_1$-$C_6$alkoxy, $C_7$-$C_{12}$aralkoxy, $C_2$-$C_2$alkoxycarbonyl, $C_1$-$C_6$thioalkyl, aryl or N(R$_6$)R$_7$ where $R_6$, $R_7$, $R_8$, and $R_9$, are each independently hydrogen, acetyl, methanesulfonyl or $C_1$-$C_6$alkyl;

or $R_3$, $R_4$ and $R_5$ are independently hydrogen, hydroxy or $C_1$-$C_6$alkoxy; with the proviso that $R_3$, $R_4$ and $R_5$ cannot all be hydrogen at the same time, which method comprises:
(a) reacting a compound of formula (78):

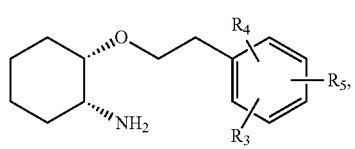
(78)

where $R_3$, $R_4$ and $R_5$ are as defined above, with a compound of formula (82), a compound of formula (83) or a compound of formula (84):

(82)

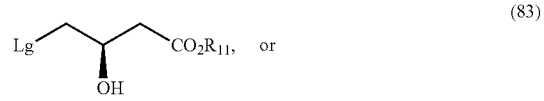
(83)

(84)

wherein each Lg is independently a leaving group and each $R_{11}$ is $C_1$-$C_6$alkyl, under suitable conditions to form a compound of formula (127), a compound of formula (128) or a compound of formula (129), respectively:

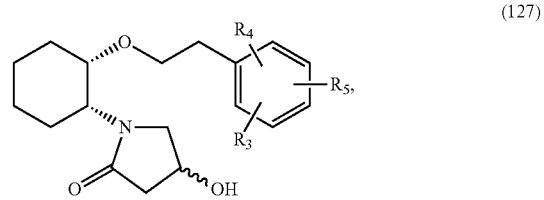
(127)

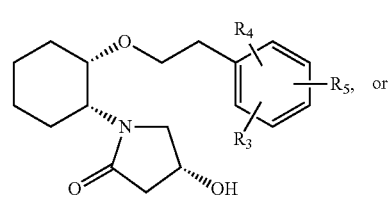
(128)

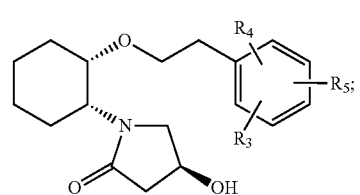
(129)

or reacting a compound of formula (78) with a compound of formula (88), a compound of formula (89) or a compound of formula (90):

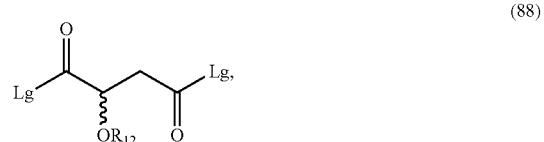
(88)

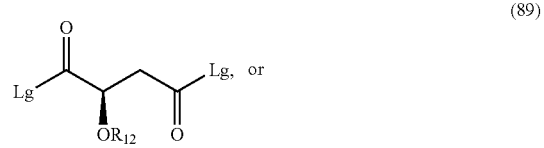
(89)

-continued (90)

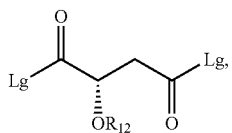

wherein each Lg is independently a leaving group and each $R_{12}$ is $C_2$-$C_4$acyl or $C_7$-$C_{12}$aralkyl, under suitable conditions to form a compound of formula (130), a compound of formula (131), or a compound of formula (132), respectively:

(130)

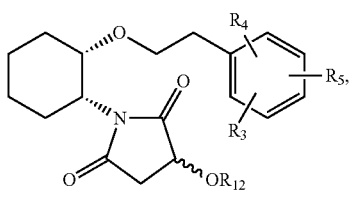

(131)

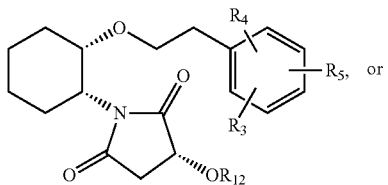

(132)

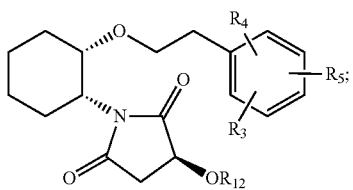

or reacting a compound of formula (78) with a compound of formula (94), a compound of formula (95) or a compound of formula (96):

(94)

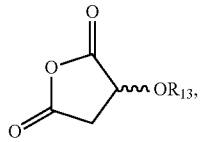

(95)

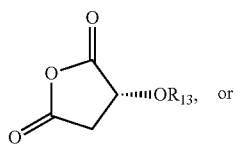

(96)

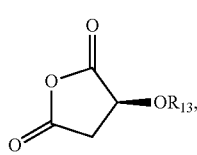

wherein each $R_{13}$ is $C_2$-$C_4$acyl or $C_7$-$C_{12}$aralkyl, under suitable conditions to form a compound of formula (133), a compound of formula (134) or a compound of formula (135), respectively:

(133)

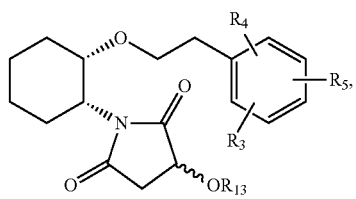

(134)

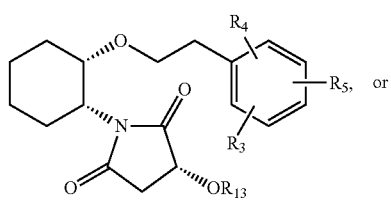

(135)

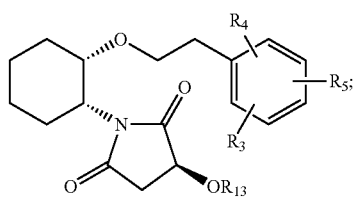

and (b) reducing the compound of formula (127), the compound of formula (130) or the compound of formula (133) formed in step (a) under suitable conditions to form a compound of formula (124) as set forth above; or reducing the compound of formula (128), the compound of formula (131) or the compound of formula (134) formed in step (a) under suitable conditions to form a compound of formula (125) as set forth above; or reducing the compound of formula (129), the compound of formula (132) or the compound of formula (135) formed in step (a) under suitable conditions to form a compound of formula (126) as set forth above.

20. The method of claim 19 wherein $R_3$, $R_4$ and $R_5$ are independently hydrogen, hydroxy or $C_1$-$C_6$ alkoxy, with the proviso that $R_3$, $R_4$ and $R_5$ cannot all be hydrogen at the same time.

21. The method of claim 20 wherein $R_3$ is hydrogen, and $R_4$ and $R_5$ are each $C_1$-$C_4$ alkoxy.

22. The method of claim 21 wherein $R_4$ and $R_5$ are each $C_1$alkoxy at the S- and 4-carbon position of the phenyl group, respectively.

23. The method of claim 19 wherein each Lg is independently chloro or bromo; $R_{11}$ is $C_1$-$C_3$alkyl; $R_{12}$ is $C_2$-$C_3$acyl; and $R_{13}$ is $C_2$-$C_3$acyl.

24. The method of claim 19 wherein the reducing reagent for step (b) is Red-Al.

* * * * *